US011566075B2

(12) United States Patent
Bicknell et al.

(10) Patent No.: US 11,566,075 B2

(45) Date of Patent: Jan. 31, 2023

(54) ANTIBODIES AND RELATED MOLECULES AND USES THEREOF

(71) Applicants: Cancer Research Technology Limited, London (GB); The University of Birmingham, Birmingham (GB)

(72) Inventors: Roy Bicknell, Birmingham (GB); Steven Lee, Birmingham (GB)

(*) Notice: Subject to any disclaimer, the term of this patent is extended or adjusted under 35 U.S.C. 154(b) by 253 days.

(21) Appl. No.: 16/085,192

(22) PCT Filed: Mar. 14, 2017

(86) PCT No.: PCT/GB2017/050689

§ 371 (c)(1),
(2) Date: Sep. 14, 2018

(87) PCT Pub. No.: WO2017/158339

PCT Pub. Date: Sep. 21, 2017

(65) Prior Publication Data

US 2019/0085082 A1 Mar. 21, 2019

(30) Foreign Application Priority Data

Mar. 15, 2016 (GB) ..................................... 1604378

(51) Int. Cl.

| | |
|---|---|
| ***C07K 16/28*** | (2006.01) |
| ***G01N 33/574*** | (2006.01) |
| ***A61K 47/68*** | (2017.01) |
| ***A61P 35/00*** | (2006.01) |
| ***A61K 49/08*** | (2006.01) |
| ***A61K 51/10*** | (2006.01) |
| *A61K 39/00* | (2006.01) |

(52) U.S. Cl.

CPC ...... *C07K 16/2851* (2013.01); *A61K 47/6803* (2017.08); *A61K 47/6849* (2017.08); *A61K 49/085* (2013.01); *A61K 51/10* (2013.01); *A61P 35/00* (2018.01); *G01N 33/574* (2013.01); *A61K 2039/505* (2013.01); *C07K 2317/622* (2013.01); *C07K 2317/70* (2013.01); *C07K 2317/73* (2013.01); *C07K 2317/76* (2013.01); *C07K 2319/03* (2013.01); *C07K 2319/33* (2013.01); *G01N 2333/4724* (2013.01)

(58) Field of Classification Search

None

See application file for complete search history.

(56) References Cited

FOREIGN PATENT DOCUMENTS

| | | | |
|---|---|---|---|
| WO | WO-2011027132 A1 * | 3/2011 | ............. A61P 19/02 |
| WO | 2013/092001 | 6/2013 | |
| WO | 2013/187556 | 12/2013 | |

OTHER PUBLICATIONS

Almagro & Fransson, Frontiers in Bioscience 2008; 13:1619-33.*

De Genst et al., Developmental and Comparative Immunology, 2006, 30:187-98.*

Ward et al. (Nature, 1989, 341:544-546).*

Barthelemy et al. (Journal of Biological Chemistry, 2008, 283:3639-3654).*

Choi et al., 2011, Molecular BioSystems, 2011,7:3327-3334.*

(Continued)

*Primary Examiner* — Brad Duffy

(74) *Attorney, Agent, or Firm* — McDonnell Boehnen Hulbert & Berghoff, LLP

(57) ABSTRACT

The present invention relates to an isolated antibody, which selectively binds to CLEC14A, wherein said antibody (a) comprises at least one heavy chain variable region that comprises three CDRs and at least one light chain variable region that comprises three CDRs, wherein said heavy chain variable region comprises: (i) a variable heavy (VH) CDR1 that has the amino acid sequence of SEQ ID NO. 105, preferably of SEQ ID NO: 2 or 42; (ii) a VH CDR2 that has the amino acid sequence of SEQ ID NO. 106, preferably of SEQ ID NO: 3 or 43; and/or (iii) a VH CDR3 that has the amino acid sequence of SEQ ID NO. 107, preferably of SEQ ID NO: 4 or 44; and/or wherein said light chain variable region comprises: (iv) a variable light (VL) CDR1 that has the amino acid sequence of SEQ ID NO. 108, preferably of SEQ ID NO: 6 or 46; (v) a VL CDR2 that has the amino acid sequence of SEQ ID NO. 109, preferably of SEQ ID NO: 7 or 47; and/or (vi) a VL CDR3 that has the amino acid sequence of SEQ ID NO. 1 10, preferably of SEQ ID NO: 8 or 48; or (b) comprises at least one heavy chain variable region that comprises three CDRs and at least one light chain variable region that comprises three CDRs, wherein said heavy chain variable region comprises: (i) a variable heavy (VH) CDR1 that has the amino acid sequence of SEQ ID NO: 22; (ii) a VH CDR2 that has the amino acid sequence of SEQ ID NO: 23; and/or (iii) a VH CDR3 that has the amino acid sequence of SEQ ID NO: 24; and/or wherein said light chain variable region comprises: (iv) a variable light (VL) CDR1 that has the amino acid sequence of SEQ ID NO: 26; (v) a VL CDR2 that has the amino acid sequence of SEQ ID NO: 27; and/or (vi) a VL CDR3 that has the amino acid sequence of SEQ ID NO: 28; or (c) is an antibody which can compete with antibody (a) or (b) for binding to CLEC14A. The invention further provides chimeric antigen receptors, nucleic acid molecules encoding the antibodies of the invention or the chimeric antigen receptors, vectors, cells and methods/uses of the antibodies and chimeric antigen receptors.

10 Claims, 31 Drawing Sheets

Specification includes a Sequence Listing.

(56) References Cited

OTHER PUBLICATIONS

Griffiths et al. (The EMBO Journal, 1993, 12:725-734).*
Klimka et al., British Journal of Cancer, 2000, 83:252-260.*
Beiboer et al. (Journal of Molecular Biology, 2000, 296:833-849).*
Lippincott-Schwartz (Current Protocols in Cell Biology, 16.0.1-16.0.2, 2002).*
Zhuang et al., "Abstract LB-256: Immunotherapy using genetically modified T lymphocytes to target CLEC14A on the tumor vasculature", Proceedings of the AACR Annual Meeting 2014, (Oct. 1, 2014), URL: http://cancerres.aacrjournals.org/content/74/19_Supplement/LB-256, (Dec. 18, 2015), XP055237609.
Noy P J et al., "Blocking CLEC14A-MMRN2 binding inhibits sprouting angiogenesis and tumour growth", ONCOGENE, (Mar. 9, 2015), vol. 34, No. 47, pp. 5821-5831.
Pearson W R, "An Introduction to Sequence Similarity ("Homology") Searching," Current Protocol Bioinformatics, Jun. 2013, author's manuscript (0 3: doi: 10.1002/0471250953.bi0301s42).
Miura M et al., "Identification and angiogenic role of the novel tumor endothelial marker CLEC14A," Oncogene, Dec. 31, 2012, vol. 31, pp. 293-305.

* cited by examiner

```
CLEC14A   MRPAFALCLLWQALWPGPGGGEHPTADRAGCSASGACYSLHHATMKRQAAEEACILRGGA 60
CD141     MLGVLVLGALALAGLGFPAPAEPQPGGSQ--CVEHDCFALYPGPATFLNASQICDGLRGH 58
          *  .:.*  *  *    *. .*  ...    ...  *::*: .. .   *.: *    *
CLEC14A   LSTVRAGAELRAVLALLRAGPGPGGGSKDLLFWVALERRRSHCTLENE-PLRGFSWLSSD 119
CD141     LMTVRSSVAADVISLLLNGDGGVGRRR----LWIGLQLPPGCGDPKRLGPLRGFQWVTGD 114
          * ***:..   .:  **... * *       :*:.*:   .    :.  *****.*::.*
CLEC14A   PGGLESDTLQWVEEPQRSCTARRCAVLQATGGVEPAG--WKEMRCHLRANGYLCKY 173
CD141     -NNTSYSRWARLDLNGAPLCGPLCVAVSAAEATVPSEPIWEEQQCEVKADGFLCEF 169
           .. . .    ::    .  .  *..: *: .. *:   *:* :*.::*:*:**:::* .
```

Amino acid alignment of CLEC14A CTLD and CD141 CTLD

FIG. 19
tCD34
F2A
scFv
CD28
CD28 signal
CD3ζ
tCD34
F2A
scFv
CD8
4 1BB signal
CD3ζ
tCD34
F2A
scFv
CD8
OX40 signal
CD3ζ
tCD34
F2A
scFv
CD28
CD28 signal
4 1BB signal
CD3ζ
tCD34
F2A
scFv
CD28
CD28 signal
OX40 signal
CD3ζ
tCD34
F2A
scFv
CD8
4 1BB signal
OX40 signal
CD3ζ

ANTIBODIES AND RELATED MOLECULES AND USES THEREOF

This application is a national stage application under 35 U.S.C. § 371 of International Application No. PCT/GB2017/050689, filed Mar. 14, 2017, which claims the benefit of priority from Great Britain Application No. GB 1604378.8, filed Mar. 15, 2016, and Great Britain Application No. GB 1612534.6, filed Jul. 19, 2016. The disclosures of all of the above applications are incorporated by reference herein in their entireties.

The present invention relates generally to the field of antibodies, CLEC14A biology and related therapies, such as chimeric antigen receptors (CARs). More particularly, it provides antibodies that bind to CLEC14A and CARs against the antigen CLEC14A and their expression in immune effector cells to target cells expressing CLEC14A. Such anti-CLEC14A antibodies and immune effector cells have therapeutic uses in diseases and conditions associated with CLEC14A. For instance, the invention provides products for inhibiting angiogenesis and combating diseases associated with unwanted angiogenesis, such as cancer. The antibodies of the invention may also find diagnostic utilities in monitoring or predicting tumour growth and progression e.g. by imaging neovasculature. The antibody-based compositions and methods of the invention also extend to the use of immunoconjugates and other therapeutic combinations, kits and methods. The invention further provides nucleic acid molecules encoding such antibodies and CARs and vectors containing them which may be used to modify host cells, e.g. immune effector cells, to express the antibodies or CARs. In particular, the CARs of the invention comprise an antigen-binding domain derived from the antibodies of the invention.

CLEC14A (also called Epidermal Growth Factor Receptor 5 (EGFR5)) is a single-pass transmembrane glycoprotein that belongs to the vascular restricted C-type lectin family 14, whose other members include CD248/TEM1/Endosialin, Thrombomodulin and CD93. It is a single pass type I transmembrane protein of 490 amino acids (aa) in length, containing a signal peptide (aa 1-21), extracellular region (aa 22-398), transmembrane domain (aa 399-421) and a cytoplasmic domain (aa 422-490). The extracellular region has one C-type lectin-like domain (aa 22-173) and an epidermal growth factor-like region (aa 245-287). Human and mouse CLEC14A proteins show 67% amino acid sequence identity with even greater sequence conservation within the C-type lectin and epidermal growth factor-like domains. Available data on CLEC14A suggests that manipulation of CLEC14A levels or function, e.g. using blocking antibodies, can regulate endothelial migration (WO2011/027132).

Endothelial cells form a single cell layer that lines all blood vessels and regulates exchanges between the blood stream and the surrounding tissues. New blood vessels develop from the walls of existing small vessels by the outgrowth of endothelial cells in a process called angiogenesis. Endothelial cells even have the capacity to form hollow capillary tubes when isolated in culture. Once the vascular system is fully developed, endothelial cells of blood vessels normally remain quiescent with no new vessel formation, with the exception of the formation of new blood vessels in natural wound healing. However, some tumours attract a new blood supply by secreting factors that stimulate nearby endothelial cells to construct new capillary sprouts. Angiogenesis plays a major role in the progression of solid tumours and is widely recognised as a rate-limiting process in the growth of solid tumours. Tumours that fail to attract a blood supply are severely limited in their growth. Thus, the ability to inhibit inappropriate, undesirable or unwanted angiogenesis may be useful in the treatment of solid tumours.

The development of new blood vessels is essential for both local tumour progression and the development of distant metastases. Indeed, the growth and survival of tumours is dependent on their ability to obtain a blood supply and damage inflicted on the tumour endothelium has been shown to effectively eradicate tumours. Tumour angiogenesis involves the degradation of the basement membrane by activated tissue or circulating endothelial precursors, proliferation and migration of endothelial cells, interaction with the extracellular matrix, morphological differentiation, cell adherence and vascular tube formation. Inhibition of tumour angiogenesis is thus a target for anti-tumour therapies, employing either angiogenesis inhibitors alone or in combination with standard cancer treatments. However, targeting anti-tumour agents to the site of angiogenesis depends upon the identification of specific markers of tumour angiogenesis. The endothelium plays a central role in many physiological and pathological processes and it is known to be an exceptionally active transcriptional site. Approximately 1,000 distinct genes are expressed in an endothelial cell, although many of them are not endothelial cell specific.

CLEC14A has been identified as a tumour endothelial marker (WO 2011/027132). CLEC14A is highly expressed on the surface of endothelial cells lining the vasculature of many common human cancers (including breast, liver, prostate, pancreatic, bladder and ovarian carcinomas) but in the vasculature of healthy tissue expression is low or undetectable. It is induced under conditions of low shear stress, such as occur in the ill-formed vessels of tumour tissue, and interacts with MMRN2 within the extracellular matrix. It mediates filipodia formation and endothelial migration, plays a role in sprouting angiogenesis and promotes tumour growth in mice. Thus, blocking or inhibiting CLEC14A function or activity is expected to result in the inhibition of angiogenesis, particularly tumour angiogenesis. Accordingly, there is a need for agents that inhibit or block CLEC14A function or activity and agents that target cells, particularly tumour cells (e.g. tumour vasculature), expressing CLEC14A.

Immunotherapy using antibodies, particularly monoclonal antibodies, has emerged in recent years as a safe and selective method for treating various diseases, including cancer. Antibodies have also been found to be effective in various diagnostic and prognostic analyses, both in vitro and in vivo as well as ex vivo. However, not all antibodies that are capable of binding to a particular antigen are effective in therapy. Thus, there is a need and desire for antibodies that can bind specifically to CLEC14A, particularly for antibodies that bind to different epitopes to previously characterised CLEC14A antibodies, and that may also be therapeutically effective and/or capable of blocking or inhibiting the function or activity of CLEC14A, e.g. for use in inhibiting angiogenesis, particularly tumour angiogenesis, e.g. for use in treating cancer.

Therapies involving the expression of Chimeric Antigen Receptors (CARs) in T-cells or other immune effector cells, e.g. NK cells, have also been developed in recent years. CARs, now widely known and described in the art, are fusion proteins comprising an antigen binding domain, typically but not always derived from an antibody, linked to the signaling domain of the T-cell Receptor (TcR) complex (or equivalent), and can be used to direct T-cells or other immune effector cells against a tumour if a suitable antigen binding domain or antibody is selected.

A CAR construct generally comprises an antigen binding domain, optionally a hinge domain, which functions as a spacer to extend the antigen binding domain away from the plasma membrane of the immune effector cell on which it is expressed, a transmembrane domain, an intracellular signalling domain (e.g. the signalling domain from the zeta chain of the CD3 molecule (CD3ζ) of the TcR complex, or an equivalent) and optionally one or more co-stimulatory domains which may assist in signalling or functionality of the cell expressing the CAR. The different domains may be linked directly or by linkers. A variety of options are available for these different domains and linkers. Accordingly, there is a desire for CARs that can target cells, particularly tumour cells, expressing CLEC14A, e.g. for use in inhibiting angiogenesis, particularly tumour angiogenesis, e.g. for use in treating cancer.

The present inventors have generated antibodies (known herein as CRT-2 and CRT-3) that bind specifically and effectively to CLEC14A. Furthermore, as discussed in more detail in the Examples, the inventors have determined that said antibodies may have useful therapeutic properties, both alone and in combination with a cytotoxic drug (e.g. as an antibody drug conjugate (also known as an immunoconjugate)). Notably the inventors have characterised the antigen binding domains of said antibodies and determined that said domains, and more particularly the variable regions (VL and VH chains) of said domains, may provide an effective CAR for use in adoptive cell transfer therapy against cells expressing CLEC14A. As will be described in more detail below, in more particular embodiments the CAR may comprise an antigen binding domain based on, or comprising, the VL and VH chains of the antibodies of the invention, specifically based on the hypervariable regions or CDRs (complementarity determining regions) thereof, in combination with a "signalling tail" comprising combinations of hinge, transmembrane, co-stimulatory and intracellular signalling domains.

Accordingly, in one aspect, the present invention provides an antibody, particularly an isolated antibody, which selectively binds to CLEC14A, wherein said antibody:

(a) comprises at least one heavy chain variable region that comprises three CDRs and at least one light chain variable region that comprises three CDRs, wherein said heavy chain variable region comprises:

(i) a variable heavy (VH) CDR1 that has the amino acid sequence of SEQ ID NO. 105, preferably of SEQ ID NO: 2 or 42, or a sequence substantially homologous to any of the foregoing SEQ ID NOs having one, two, three or four amino acid substitutions, additions and/or deletions;

(ii) a VH CDR2 that has the amino acid sequence of SEQ ID NO. 106, preferably of SEQ ID NO: 3 or 43, or a sequence substantially homologous to any of the foregoing SEQ ID NOs having one, two, three or four amino acid substitutions, additions and/or deletions; and/or (iii) a VH CDR3 that has the amino acid sequence of SEQ ID NO. 107, preferably of SEQ ID NO: 4 or 44, or a sequence substantially homologous to any of the foregoing SEQ ID NOs having one, two, three or four amino acid substitutions, additions and/or deletions; and/or wherein said light chain variable region comprises:

(iv) a variable light (VL) CDR1 that has the amino acid sequence of SEQ ID NO. 108, preferably of SEQ ID NO: 6 or 46, or a sequence substantially homologous to any of the foregoing SEQ ID NOs having one, two, three or four amino acid substitutions, additions and/or deletions;

(v) a VL CDR2 that has the amino acid sequence of SEQ ID NO. 109, preferably of SEQ ID NO: 7 or 47, or a sequence substantially homologous to any of the foregoing SEQ ID NOs having one, two, three or four amino acid substitutions, additions and/or deletions; and/or (vi) a VL CDR3 that has the amino acid sequence of SEQ ID NO. 110, preferably of SEQ ID NO: 8 or 48, or a sequence substantially homologous to any of the foregoing SEQ ID NOs having one, two, three or four amino acid substitutions, additions and/or deletions; or (b) comprises at least one heavy chain variable region that comprises three CDRs and at least one light chain variable region that comprises three CDRs, wherein said heavy chain variable region comprises:

(i) a variable heavy (VH) CDR1 that has the amino acid sequence of SEQ ID NO: 22 or a sequence substantially homologous thereto having one, two, three or four amino acid substitutions, additions and/or deletions;

(ii) a VH CDR2 that has the amino acid sequence of SEQ ID NO: 23 or a sequence substantially homologous thereto having one, two, three or four amino acid substitutions, additions and/or deletions; and/or (iii) a VH CDR3 that has the amino acid sequence of SEQ ID NO: 24 or a sequence substantially homologous thereto having one, two, three or four amino acid substitutions, additions and/or deletions; and/or wherein said light chain variable region comprises:

(iv) a variable light (VL) CDR1 that has the amino acid sequence of SEQ ID NO: 26 or a sequence substantially homologous thereto having one, two, three or four amino acid substitutions, additions and/or deletions;

(v) a VL CDR2 that has the amino acid sequence of SEQ ID NO: 27 or a sequence substantially homologous thereto having one, two, three or four amino acid substitutions, additions and/or deletions; and/or (vi) a VL CDR3 that has the amino acid sequence of SEQ ID NO: 28 or a sequence substantially homologous thereto having one, two, three or four amino acid substitutions, additions and/or deletions; or (c) is an antibody which can compete with antibody (a) or (b) for binding to CLEC14A.

In some embodiments, the invention provides an antibody, particularly an isolated antibody, which selectively binds to CLEC14A, wherein said antibody:

(a) comprises at least one heavy chain variable region that comprises three CDRs and at least one light chain variable region that comprises three CDRs, wherein said heavy chain variable region comprises:

(i) a variable heavy (VH) CDR1 that has the amino acid sequence of SEQ ID NO. 105, particularly of SEQ ID NO: 2 or 42;

(ii) a VH CDR2 that has the amino acid sequence of SEQ ID NO. 106, particularly of SEQ ID NO: 3 or 43; and/or (iii) a VH CDR3 that has the amino acid sequence of SEQ ID NO. 107, particularly of SEQ ID NO: 4 or 44; and/or wherein said light chain variable region comprises:

(iv) a variable light (VL) CDR1 that has the amino acid sequence of SEQ ID NO. 108, particularly of SEQ ID NO: 6 or 46;

(v) a VL CDR2 that has the amino acid sequence of SEQ ID NO. 109, particularly of SEQ ID NO: 7 or 47; and/or (vi) a VL CDR3 that has the amino acid sequence of SEQ ID NO. 110, particularly of SEQ ID NO: 8 or 48; or (b) is an antibody which can compete with antibody (a) for binding to CLEC14A.

Thus, in some embodiments the antibody (a) has a VH domain of SEQ ID NO: 1 or 41 and/or a VL domain of SEQ ID NO: 5 or 45; or (b) is an antibody which can compete with antibody (a) for binding to CLEC14A. For instance, the antibody may comprise at least one heavy chain variable region that comprises three CDRs and at least one light chain variable region that comprises three CDRs, wherein said heavy chain variable region comprises (i) a VH CDR1 that has the amino acid sequence of SEQ ID NO. 105, particularly of SEQ ID NO: 2 or 42 or a sequence substantially homologous thereto;

(ii) a VH CDR2 that has the amino acid sequence of SEQ ID NO. 106, particularly of SEQ ID NO: 3 or 43 or a sequence substantially homologous thereto; and/or (iii) a VH CDR3 that has the amino acid sequence of SEQ ID NO. 107, particularly of SEQ ID NO: 4 or 44 or a sequence substantially homologous thereto; and/or wherein said light chain variable region comprises:

(iv) a VL CDR1 that has the amino acid sequence of SEQ ID NO. 108, particularly of SEQ ID NO: 6 or 46 or a sequence substantially homologous thereto;

(v) a VL CDR2 that has the amino acid sequence of SEQ ID NO. 109, particularly of SEQ ID NO: 7 or 47 or a sequence substantially homologous thereto; and/or (vi) a VL CDR3 that has the amino acid sequence of SEQ ID NO. 110, particularly of SEQ ID NO: 8 or 48 or a sequence substantially homologous thereto.

Thus, in some embodiments, the antibody of the invention comprises one or more of the CDRs selected from the group consisting of SEQ ID NOs: 2, 3, 4, 6, 7, 8, 42, 43, 44, 46, 47 and 48 or a sequence substantially homologous to any one of the foregoing SEQ ID NOs.

Thus, in some preferred embodiments, the antibody comprises two or more of the heavy chain CDRs of SEQ ID NOs: 2, 3 and 4, or sequences substantially homologous to any one of the foregoing SEQ ID NOs. In particularly preferred embodiments, the antibody comprises three of the heavy chain CDRs of SEQ ID NOs: 2, 3 and 4, or sequences substantially homologous to any one of the foregoing SEQ ID NOs.

Thus, in some preferred embodiments, the antibody comprises two or more of the heavy chain CDRs of SEQ ID NOs: 42, 43 and 44, or sequences substantially homologous to any one of the foregoing SEQ ID NOs. In particularly preferred embodiments, the antibody comprises three of the heavy chain CDRs of SEQ ID NOs: 42, 43 and 44, or sequences substantially homologous to any one of the foregoing SEQ ID NOs.

In additional or alternative embodiments, the antibody comprises two or more of the light chain CDRs of SEQ ID NOs: 6, 7 and 8 or sequences substantially homologous to any one of the foregoing SEQ ID NOs. In particularly preferred embodiments, the antibody comprises three of the light chain CDRs of SEQ ID NOs: 6, 7 and 8, or sequences substantially homologous to any one of the foregoing SEQ ID NOs.

In additional or alternative embodiments, the antibody comprises two or more of the light chain CDRs of SEQ ID NOs: 46, 47 and 48 or sequences substantially homologous to any one of the foregoing SEQ ID NOs. In particularly preferred embodiments, the antibody comprises three of the light chain CDRs of SEQ ID NOs: 46, 47 and 48, or sequences substantially homologous to any one of the foregoing SEQ ID NOs.

Thus, in some embodiments, the antibody comprises three of the heavy chain CDRs of SEQ ID NOs: 2, 3 and 4, or sequences substantially homologous to any one of the foregoing SEQ ID NOs. and three of the light chain CDRs of SEQ ID NOs: 6, 7 and 8, or sequences substantially homologous to any one of the foregoing SEQ ID NOs.

In some embodiments, the antibody comprises three of the heavy chain CDRs of SEQ ID NOs: 42, 43 and 44, or sequences substantially homologous to any one of the foregoing SEQ ID NOs. and three of the light chain CDRs of SEQ ID NOs: 6, 7 and 8, or sequences substantially homologous to any one of the foregoing SEQ ID NOs.

In some embodiments, the antibody comprises three of the heavy chain CDRs of SEQ ID NOs: 2, 3 and 4, or sequences substantially homologous to any one of the foregoing SEQ ID NOs. and three of the light chain CDRs of SEQ ID NOs: 46, 47 and 48, or sequences substantially homologous to any one of the foregoing SEQ ID NOs.

In some embodiments, the antibody comprises three of the heavy chain CDRs of SEQ ID NOs: 42, 43 and 44, or sequences substantially homologous to any one of the foregoing SEQ ID NOs. and three of the light chain CDRs of SEQ ID NOs: 46, 47 and 48, or sequences substantially homologous to any one of the foregoing SEQ ID NOs.

In some embodiments, the antibody comprises a heavy chain that comprises the amino acid sequence of SEQ ID NO: 1 or 41 or a sequence substantially homologous thereto and/or a light chain that comprises the amino acid sequence of SEQ ID NO: 5 or 45 or a sequence substantially homologous thereto.

In some embodiments, the antibody is a single chain fragment variant (scFv). Thus, in some aspects, the antibody comprises the amino acid sequence SEQ ID NO: 9, 49, 50 or 51 or a sequence substantially homologous thereto.

Whilst not wishing to be bound by theory, it is hypothesised that the antibody defined in part (a) above is capable of binding to an epitope in the C-type lectin domain of CLEC14A (residues 22-173 of CLEC14A). (It will be appreciated that different alignment programs may predict an alternative positioning of domains within CLEC14A. Thus, the C-type lectin domain may more particularly be located at residues 22-175 of CLEC14A, 23-173 or 23-175 of CLEC14A or 32-173 or 32-175, depending on the alignment used). In particular, it is thought the antibody binds to an epitope within residues 22-96, e.g. 32-96 and/or residues 109-175, e.g. 109-173 of CLEC14A. Thus, in some embodiments, the antibody does not bind to residues 97-108 of CLEC14A. Whether or not the antibody binds to any of these epitopes or regions can be assessed using standard techniques in the art, including the binding assays described herein such as ELISA.

In preferred embodiments, the antibody which can compete with the antibody defined in part (a) above can bind to substantially the same epitope as the antibody defined in part (a) above. Thus, in some embodiments, the antibody which can compete with the antibody defined in part (a) above can bind to an epitope within residues 22-96, e.g. 32-96 and/or residues 109-175, e.g. 109-173 of CLEC14A. Notably, unless specified the amino acid numbering discussed herein relates to the amino acid sequence of human CLEC14A, set forth in SEQ ID NO. 52.

In alternative embodiments, the present invention provides an antibody, particularly an isolated antibody, which selectively binds to CLEC14A, wherein said antibody:

(a') comprises at least one heavy chain variable region that comprises three CDRs and at least one light chain variable region that comprises three CDRs, wherein said heavy chain variable region comprises:

(i) a variable heavy (VH) CDR1 that has the amino acid sequence of SEQ ID NO: 22;

(ii) a VH CDR2 that has the amino acid sequence of SEQ ID NO: 23; and/or (iii) a VH CDR3 that has the amino acid sequence of SEQ ID NO: 24; and/or wherein said light chain variable region comprises:

(iv) a variable light (VL) CDR1 that has the amino acid sequence of SEQ ID NO: 26;

(v) a VL CDR2 that has the amino acid sequence of SEQ ID NO: 27; and/or (vi) a VL CDR3 that has the amino acid sequence of SEQ ID NO: 28; or (b') is an antibody which can compete with antibody (a') for binding to CLEC14A.

Thus, in some embodiments the antibody (a') has a VH domain of SEQ ID NO: 21 and/or a VL domain of SEQ ID NO: 25; or (b') is an antibody which can compete with antibody (a') for binding to CLEC14A. For instance, the antibody may comprise at least one heavy chain variable region that comprises three CDRs and at least one light chain variable region that comprises three CDRs, wherein said heavy chain variable region comprises (i) a VH CDR1 that has the amino acid sequence of SEQ ID NO: 22 or a sequence substantially homologous thereto;

(ii) a VH CDR2 that has the amino acid sequence of SEQ ID NO: 23 or a sequence substantially homologous thereto; and/or (iii) a VH CDR3 that has the amino acid sequence of SEQ ID NO: 24 or a sequence substantially homologous thereto; and/or wherein said light chain variable region comprises:

(iv) a VL CDR1 that has the amino acid sequence of SEQ ID NO: 26 or a sequence substantially homologous thereto;

(v) a VL CDR2 that has the amino acid sequence of SEQ ID NO: 27 or a sequence substantially homologous thereto; and/or (vi) a VL CDR3 that has the amino acid sequence of SEQ ID NO: 28 or a sequence substantially homologous thereto.

In some embodiments, the antibody of the invention comprises one or more of the CDRs selected from the group consisting of SEQ ID NOs: 22, 23, 24, 26, 27, and 28, or a sequence substantially homologous to any one of the foregoing SEQ ID NOs.

The in some preferred embodiments, the antibody comprises two or more of the heavy chain CDRs of SEQ ID NOs: 22, 23 and 24, or sequences substantially homologous to any one of the foregoing SEQ ID NOs. In particularly preferred embodiments, the antibody comprises three of the heavy chain CDRs of SEQ ID NOs: 22, 23 and 24, or sequences substantially homologous to any one of the foregoing SEQ ID NOs.

In additional or alternative embodiments, the antibody comprises two or more of the light chain CDRs of SEQ ID NOs: 26, 27 and 28 or sequences substantially homologous to any one of the foregoing SEQ ID NOs. In particularly preferred embodiments, the antibody comprises three of the light chain CDRs of SEQ ID NOs: 26, 27 and 28, or sequences substantially homologous to any one of the foregoing SEQ ID NOs.

Thus, in some embodiments, the antibody comprises three of the heavy chain CDRs of SEQ ID NOs: 22, 23 and 24, or sequences substantially homologous to any one of the foregoing SEQ ID NOs. and three of the light chain CDRs of SEQ ID NOs: 26, 27 and 28, or sequences substantially homologous to any one of the foregoing SEQ ID NOs.

In some embodiments, the antibody comprises a heavy chain that comprises the amino acid sequence of SEQ ID NO: 21 or a sequence substantially homologous thereto and/or a light chain that comprises the amino acid sequence of SEQ ID NO: 25 or a sequence substantially homologous thereto.

In some embodiments, the antibody is a single chain fragment variant (scFv). Thus, in some aspects, the antibody comprises the amino acid sequence SEQ ID NO: 29 or a sequence substantially homologous thereto.

Whilst not wishing to be bound by theory, it is hypothesised that the antibody defined in part (a') above does not bind to an epitope in the C-type lectin domain of CLEC14A (e.g. to residues 22-173 of CLEC14A). In particular, it is thought the antibody may bind to an epitope within the region of the sushi-like domain of CLEC14A (residues 174-244) which is proximal to the C-type lectin domain e.g. within residues 174-210, 174-200, 174-190.

In preferred embodiments, the antibody which can compete with the antibody defined in part (a') above can bind to substantially the same epitope as the antibody defined in part (a') above. Thus, in some embodiments, the antibody which can compete with the antibody defined in part (a') above can bind to an epitope within the region between the C-type lectin domain and the sushi-like domain of CLEC14A. Whether or not the antibody binds to any of these epitopes or regions can be assessed using standard techniques in the art, including the binding assays described herein such as ELISA.

The term "competing antibodies", as used herein, refers to antibodies that bind to about, substantially or essentially the same, or even the same, epitope as a "reference antibody". "Competing antibodies" include antibodies with overlapping epitope specificities. Competing antibodies are thus able to effectively compete with a reference antibody for binding to CLEC14A. Preferably, the competing antibody can bind to the same epitope as the reference antibody. Alternatively viewed, the competing antibody preferably has the same epitope specificity as the reference antibody.

"Reference antibodies" as used herein are antibodies which can bind to an epitope of CLEC14A (e.g. the extracellular domain of CLEC14A, preferably human CLEC14A) and which have one or more of the CDR sequences are defined herein, preferably a VH and a VL domain as defined herein.

The identification of one or more competing antibodies is a straightforward technical matter in view of the provision of the antibodies of the invention, i.e. reference antibodies (CRT-2 and CRT-3). As the identification of competing antibodies is determined in comparison to a reference antibody, it will be understood that actually determining the epitope to which either or both antibodies bind is not in any way required in order to identify a competing antibody. However, epitope mapping can be performed using standard techniques, if desired.

By way of example, the following methods for the identification and definition of epitopes are mentioned herein. The amino acid sequence of CLEC14A is known, so synthetic peptides may be used for epitope mapping, e.g. using the Pepscan assay. Site directed mutagenesis is also a powerful tool in epitope mapping and can be used to evaluate the role of single amino acids in immune complex formation. Protein footprinting relies on the fact that the epitope is protected from cleavage when bound as an antibody-antigen complex. Enzyme linked immunosorbent assay (ELISA) and haemaglutination and slot-blotting may also be used in epitope mapping. Crystallisation of the antigen with the antibody may be used to map a non-linear epitope. Protocols for carrying out such methods are widely available and the skilled person will be aware of suitable alternative methods of epitope mapping.

The identification of competing antibodies can be readily determined using any one of variety of immunological screening assays in which antibody competition can be assessed. All such assays are routine in the art and each of U.S. Pat. Nos. 6,342,219, 6,524,583, 7,056,509, 6,887,468, 6,342,221, 6,676,941, 6,703,020 and 6,416,758 are specifically incorporated herein by reference for purposes of supplementing the present teaching concerning how to identify competing antibodies.

For example, where the test antibodies to be examined are obtained from different source animals, or are even of a different isotype, a simple competition assay may be employed in which the reference and test antibodies are admixed (or pre-adsorbed) and applied to CLEC14A-containing composition, preferably cells expressing CLEC14A, phage displaying CLEC14A, or biochips containing immobilised CLEC14A. Protocols based upon ELISAs are particularly suitable for use in such simple competition studies.

In certain embodiments, one would pre-mix the reference antibodies (e.g. CRT2 or CRT3 as defined herein) with varying amounts of the test antibodies (e.g., 1:10, 1:100 or 1:1000) for a period of time prior to applying to an antigen composition. In other embodiments, the reference and varying amounts of test antibodies can simply be admixed during exposure to the antigen composition. In any event, by using species or isotype secondary antibodies one will be able to detect only the bound reference antibodies, the binding of which will be reduced by the presence of a test antibody that "competes" for binding.

In conducting an antibody competition study between a reference antibody and any test antibody (irrespective of species or isotype), one may first label the reference (e.g. CRT-2 or CRT-3) with a detectable label, such as, e.g., biotin or an enzymatic or radioactive label to enable subsequent identification. In these cases, one would pre-mix or incubate the labelled reference antibodies with the test antibodies to be examined at various ratios (e.g., 1:10, 1:100 or 1:1000) and (optionally after a suitable period of time) then assay the reactivity of the labelled reference antibodies and compare this with a control value in which no potentially competing test antibody was included in the incubation.

The assay may be any one of a range of immunological assays based upon antibody binding, and the reference antibodies would be detected by means of detecting their label, e.g., using streptavidin in the case of biotinylated antibodies or by using a chromogenic substrate in connection with an enzymatic label (such as 3,3'5,5' tetramethylbenzidine (TMB) substrate with peroxidase enzyme) or by simply detecting a radioactive label. An antibody that competes with the reference antibodies for binding to CLEC14A will be able to effectively or significantly reduce reference antibody binding to CLEC14A, as evidenced by a reduction in bound label.

The reactivity of the (labelled) reference antibodies in the presence of a completely irrelevant antibody would be the control high value. The control low value would be obtained by incubating the labelled reference (e.g., CRT-2 or CRT-3) antibodies with unlabeled antibodies of exactly the same type, when competition would occur and reduce binding of the labelled antibodies. In a test assay, a significant reduction in labelled antibody reactivity in the presence of a test antibody is indicative of a test antibody that "competes" with the labelled antibody for binding to CLEC14A.

A significant reduction is a "reproducible", i.e., consistently observed, reduction in binding. A "significant reduction" in terms of the present application is defined as a reproducible reduction (in binding of the reference antibody to CLEC14A in an ELISA) of at least about 20%, more preferably at least about 25, 30, 35, 40, 45, 50, 55, 60 or 65%, even more preferably at least about 70%, about 75% or about 80% at any ratio between about 1:10 and about 1:100. Antibodies with even more stringent competing activities will exhibit a reproducible reduction (in binding of the reference antibody to CLEC14A in an ELISA or other suitable assay) of at least about 82%, about 85%, about 88%, about 90%, about 92% or about 95% or so at any ratio between about 1:10 and about 1:100. Complete or near-complete competition, such as exhibiting a reproducible reduction in binding of the reference antibody to CLEC14A of about 99%, about 98%, about 97% or about 96% or so, although by no means required to practice the invention, is certainly not excluded.

The method described above is only one example of a suitable competition assay. The skilled person will be aware of other suitable methods and variations. An alternative competition assay is described below.

Before the alternative competition assay is performed using flow cytometry, some quantities of the tested antibody should be labelled, e.g. by biotinylation. The functionality (retention of the cell-binding properties) of the biotinylated product and the minimal concentration of the biotinylated antibody of the invention (Ab1) that gives sub-maximal binding against a fixed number of CLEC14A+ cells is determined. A total of $10^6$ cells are harvested from exponentially growing cultures and incubated with various antibody concentrations for a suitable period of time at a suitable temperature, e.g. 1 hr at 4° C. The cells are washed and incubated with a suitable detection antibody for a suitable period of time at a suitable temperature, e.g. an additional hour at 4° C. After washing, the cells are analyzed by flow cytometry. For each test antibody, a saturation curve is generated from the data by plotting median fluorescence intensity (MFI) against the antibody concentration.

For the alternative competition assay, CLEC14A+ cells may be prepared as above and treated in duplicate with a mixture of fixed concentration of labelled (biotinylated) antibody (bio-Ab1) and increasing concentrations of non-labelled competitive antibody. The fixed concentration is the minimal concentration of antibody that generates reasonable fluorescence signal against a fixed number of tumour cells as determined above. Ideally, this fixed concentration in nM should be below the affinity of the treated antibody at equilibrium (Kd). In this case the described method can be used for estimation of affinities of competitive antibodies. The antibody mixture is incubated with target cells for a suitable period of time at a suitable temperature, e.g. 1 hr at 4° C. The cells are washed and the cell binding of biotinylated antibody is revealed by incubation with FITC-labelled streptavidin. After subtracting the background fluorescence (PBS-5% FCS) from the median fluorescence reading for each test sample (bio-Ab1+Ab2), the percentage of inhibition is calculated for each Ab2 concentration "c" according to the formula:

$$\%\ \text{inhibition}=(1-\text{MFI bio-}Ab1+Ab2''c''/\text{MFI bio-}Ab1)\times 100$$

As noted above, competing antibodies may comprise one or more CDRs that are substantially homologous to the CDR amino acid sequences disclosed herein. With regard to CDR sequences, the term "substantially homologous" is intended to mean sequences that have 1, 2, 3 or 4 substitutions, deletions or additions relative to the CDR sequences disclosed herein, preferably 1, 2, 3 or 4 substitutions. In some embodiments, said substitutions may be conservative or non-conservative amino acid substitutions, or a mixture thereof.

Thus, in some embodiments, substantially homologous sequences may be sequences containing up to 1, 2 or 3, preferably up to 1 or 2, altered amino acids in one or more of the CDR regions disclosed herein. In some preferred embodiments, said amino acid substitutions are conservative amino acid substitutions.

In all embodiments, the antibodies containing substantially homologous sequences retain the ability to bind CLEC14A.

Preferred antibodies of the invention comprise at least one heavy chain variable region that comprises three CDRs and at least one light chain variable region that comprises three CDRs. Exemplary and preferred sequences for these CDRs are described herein.

As used herein, the succinct term "CLEC14A", unless otherwise specifically stated or made clear from the scientific terminology, means C-type lectin domain family member 14 A (also known as Epidermal Growth Factor Receptor 5 (EGFR5)).

CLEC14A may be free CLEC14A, e.g. recombinant or purified CLEC14A, but preferably it is present in a native form, e.g. on the surface of a cell.

The antibodies of the invention can also bind to fragments of CLEC14A, in particular fragments comprising or consisting of the extracellular domain, or can bind to entities comprising CLEC14A or fragments of CLEC14A. Indeed, as described above, the epitopes of the antibodies of the invention are thought to be located in the extracellular domain of CLEC14A.

"CLEC14A" may also refer to any form of CLEC14A, particularly as CLEC14A is conserved across mammalian species. The antibodies or antibody fragments of the invention may thus bind to human, monkey (e.g. cynomolgus monkey), cow (bovine), mouse, rat, hamster, ferret, guinea pig and/or rabbit CLEC14A, for example. Preferably, the antibodies or antibody fragments of the invention will bind at least to human CLEC14A. Thus, unless stated otherwise, any reference herein to "CLEC14A" may be read to mean "human CLEC14A". In certain preferred embodiments, the antibodies or antibody fragments of the invention will bind at least to human and monkey (e.g. cynomologus monkey) CLEC14A. In other preferred embodiments the antibodies or antibody fragments of the invention will bind at least to human and mouse CLEC14A. In other preferred embodiments the antibodies or antibody fragments of the invention will bind at least to human, monkey and mouse CLEC14A. In other preferred embodiments the antibodies or antibody fragments of the invention will bind at least to human, monkey, guinea pig and mouse CLEC14A.

As used herein, the term "that binds to CLEC14A" or "anti-CLEC14A" in the context of antibodies or antibody fragments of the present invention, means antibodies or antibody fragments that are capable of one or more of the following; preferably, of more than one of the following; and most preferably, of all of the following:

(a) binding to CLEC14A expressed on the surface of a cell, e.g. as assessed by flow cytometry or immunohistochemistry;

(b) binding to a conformationally dependent (e.g. non-linear) CLEC14A epitope, e.g. as assessed by binding to CLEC14A in a Western blot under non-reducing conditions;

(c) binding to free CLEC14A; e.g. recombinantly expressed CLEC14A, on a solid support, e.g. as assessed by ELISA assay or BIAcore assay; and/or (d) binding at least to human CLEC14A, more preferably to human and monkey CLEC14A or to human and mouse CLEC14A, most preferably to human, monkey and mouse CLEC14A.

Preferred antibodies or antibody fragments of the present invention may also be capable of localizing to tumours upon administration to an animal with a tumour.

In the context of binding to CLEC14A+ cells, it should be understood that the antibodies of the present invention bind to CLEC14A+ cells and do not significantly bind to CLEC14A− cells.

The term "do not significantly bind to CLEC14A− cells" should be understood such that any binding of the antibody to CLEC14A− cells does not prohibit the use of said antibody for therapeutic or diagnostic purposes. Thus, by "insignificant" binding to CLEC14A− cells is meant that the binding of the antibody to CLEC14A− cells is weaker than its binding to one or more CLEC14A+ cells. Some cross-reaction with normal cells may thus occur, but this level of binding can be considered to be "background" binding. For therapeutic or diagnostic purposes the main consideration is that the antibody must bind more strongly to one or more types of CLEC14A+ cells than to any CLEC14A− cell with which the antibody may come into contact during the therapeutic or diagnostic application.

The antibody of the invention may be referred to as "CLEC14A-specific". The term "CLEC14A-specific" should be interpreted such that the binding of the antibody to CLEC14A expressing cells is specific enough to allow the use of said antibody for therapeutic or diagnostic purposes. The skilled person can easily determine if any given antibody is CLEC14A-specific by comparing the binding strength to the target CLEC14A+ cell with the binding strength to one or more types of CLEC14A− cells, e.g. wild-type (i.e. not transformed with CLEC14A) HUVEC cells or HEK293T cells.

The skilled person will be aware that binding to CLEC14A+ cells compared to CLEC14A− cells may be assessed by any suitable means known in the art, such as using flow cytometry. Similarly, species cross-reactivity may be assayed using known methods.

Other preferred properties include the absence of significant toxicity in vivo when the antibodies of the invention are administered and the absence of significant other side effects in vivo.

By "CLEC14A+ cells" is meant cells which express CLEC14A on their surface, preferably at least substantially in its wild-type conformation. CLEC14A+ cells may be naturally positive for CLEC14A, or they may be transformants which express recombinant CLEC14A.

The terms "antibody" and "immunoglobulin", as used herein, refer broadly to any immunological binding agent or molecule that comprises an antigen binding domain, including polyclonal and monoclonal antibodies. Depending on the type of constant domain in the heavy chains, whole antibodies are assigned to one of five major classes: IgA, IgD, IgE, IgG, and IgM and the antibodies of the invention may be in any one of these classes. Several of these are further divided into subclasses or isotypes, such as IgG1, IgG2, IgG3, IgG4, and the like. The heavy-chain constant domains that correspond to the difference classes of immunoglobulins are termed α, δ, ε, γ, and μ respectively. The subunit structures and three-dimensional configurations of different classes of immunoglobulins are well known.

Generally, where whole antibodies rather than antigen binding regions (i.e. antibody fragments) are used in the invention, IgG and/or IgM are preferred because they are the most common antibodies in the physiological situation and because they are most easily made in a laboratory setting. IgG1 antibodies are particularly preferred.

The "light chains" of mammalian antibodies are assigned to one of two clearly distinct types: kappa (κ) and lambda (λ), based on the amino acid sequences of their constant domains and some amino acids in the framework regions of their variable domains. There is essentially no preference to the use of κ or λ light chain constant regions in the antibodies of the present invention.

As will be understood by those in the art, the immunological binding reagents encompassed by the term "antibody" extend to all antibodies and antigen binding fragments thereof, including whole antibodies, dimeric, trimeric and multimeric antibodies; bispecific antibodies; chimeric antibodies; recombinant and engineered antibodies, and fragments thereof.

The term "antibody" is thus used to refer to any antibody-like molecule that has an antigen binding region, and this term includes antibody fragments that comprise an antigen binding domain such as Fab', Fab, F(ab')2, single domain antibodies (DABs), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa(lambda) bodies (scFv-CL fusions); Bispecific T-cell Engager (BiTE) (scFv-scFv tandems to attract T cells); dual variable domain (DVD)-Ig (bispecific format); small immunoprotein (SIP) (kind of minibody); SMIP ("small modular immunopharmaceutical" scFv-Fc dimer; DART (ds-stabilized diabody "Dual Affinity ReTargeting"); small antibody mimetics comprising one or more CDRs and the like.

The techniques for preparing and using various antibody-based constructs and fragments are well known in the art (see Kabat et al., 5th Ed. Public Health Service, National Institutes of Health, Bethesda, Md., 647-669, 1991, specifically incorporated herein by reference). Diabodies, in particular, are further described in WO 93/11161; whereas linear antibodies are further described in Zapata et al. (*Protein Eng.,* 8(10):1057-1062, 1995).

Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art.

The antibodies or antibody fragments can be produced naturally or can be wholly or partially synthetically produced. Thus the antibody may be from any appropriate source, for example recombinant sources and/or produced in transgenic animals or transgenic plants, or in eggs using the IgY technology. Thus, the antibody molecules can be produced in vitro or in vivo.

Preferably, the antibody or antibody fragment comprises an antibody light chain variable region (VL) that comprises three CDR domains and an antibody heavy chain variable region (VH) that comprises three CDR domains. Said VL and VH generally form the antigen binding site.

An "Fv" fragment is the minimum antibody fragment that contains a complete antigen-recognition and binding site. This region has a dimer of one heavy chain and one light chain variable domain in tight, non-covalent association. It is in this configuration that the three hypervariable regions (CDRs) of each variable domain interact to define an antigen-binding site on the surface of the VH-VL dimer. Collectively, the six hypervariable regions (CDRs) confer antigen-binding specificity to the antibody.

However, it is well documented in the art that the presence of three CDRs from the light chain variable domain and three CDRs from the heavy chain variable domain of an antibody is not necessary for antigen binding. Thus, constructs smaller than the above classical antibody fragment are known to be effective.

For example, camelid antibodies have an extensive antigen binding repertoire but are devoid of light chains. Also, results with single domain antibodies comprising VH domains alone or VL domains alone show that these domains can bind to antigen with acceptably high affinities. Thus, three CDRs can effectively bind antigen. Furthermore, it is also known that a single CDR, or two CDRs, can effectively bind antigen.

Notably, it is known that two CDRs can effectively bind antigen, and even confer superior properties than possessed by the parent antibody. For example, it has been shown that two CDRs from a parent antibody (a VH CDR1 and a VL CDR3 region) may retain the antigen recognition properties of the parent molecule but have a superior capacity to penetrate tumours. Joining these CDR domains with an appropriate linker sequence (e.g., from VH FR2) to orientate the CDRs in a manner resembling the native parent antibody produced even better antigen recognition. Therefore, it is known in the art that it is possible to construct antigen binding antibody mimetics comprising two CDR domains (preferably one from a VH domain and one from a VL domain, more preferably, with one of the two CDR domains being a CDR3 domain) orientated by means of an appropriate framework region to maintain the conformation found in the parent antibody.

Thus, although preferred antibodies of the invention might comprise six CDR regions (three from a light chain and three from a heavy chain), antibodies with fewer than six CDR regions and as few as one or two CDR regions are encompassed by the invention. In addition, antibodies with CDRs from only the heavy chain or light chain are also contemplated. In this regard, the invention further provides an antibody which selectively binds to CLEC14A, which comprises at least one of (i) a VH CDR1 that has the amino acid sequence of SEQ ID NO: 2 or 42 or a sequence substantially homologous thereto;

(ii) a VH CDR2 that has the amino acid sequence of SEQ ID NO: 3 or 43 or a sequence substantially homologous thereto; and/or (iii) a VH CDR3 that has the amino acid sequence of SEQ ID NO: 4 or 44 or a sequence substantially homologous thereto; and/or (iv) a VL CDR1 that has the amino acid sequence of SEQ ID NO: 6 or 46 or a sequence substantially homologous thereto;

(v) a VL CDR2 that has the amino acid sequence of SEQ ID NO: 7 or 47 or a sequence substantially homologous thereto; and/or (vi) a VL CDR3 that has the amino acid sequence of SEQ ID NO: 8 or 48 or a sequence substantially homologous thereto.

Further provided is an antibody which selectively binds to CLEC14A and which comprises at least one of (i) a VH CDR1 that has the amino acid sequence of SEQ ID NO: 22 or a sequence substantially homologous thereto;

(ii) a VH CDR2 that has the amino acid sequence of SEQ ID NO: 23 or a sequence substantially homologous thereto; and/or (iii) a VH CDR3 that has the amino acid sequence of SEQ ID NO: 24 or a sequence substantially homologous thereto; and/or (iv) a VL CDR1 that has the amino acid sequence of SEQ ID NO: 26 or a sequence substantially homologous thereto;

(v) a VL CDR2 that has the amino acid sequence of SEQ ID NO: 27 or a sequence substantially homologous thereto; and/or (vi) a VL CDR3 that has the amino acid sequence of SEQ ID NO: 28 or a sequence substantially homologous thereto.

Preferred antibodies of the invention that bind to CLEC14A comprise at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO: 2 or 42 or a sequence substantially homologous thereto, (b) a VH CDR2 that has the amino acid sequence of SEQ ID NO: 3 or 43 or a sequence substantially homologous thereto, and (c) a VH CDR3 that has the amino acid sequence of SEQ ID NO: 4 or 44 or a sequence substantially homologous thereto; or (d) a variable heavy (VH) CDR1 that has the amino acid sequence of SEQ ID NO: 22 or a sequence substantially homologous thereto, (e) a VH CDR2 that has the amino acid sequence of SEQ ID NO: 23 or a sequence substantially homologous thereto, and (f) a VH CDR3 that has the amino acid sequence of SEQ ID NO: 24 or a sequence substantially homologous thereto.

Preferred light chain CDR regions for use in conjunction with the specified heavy chain CDR regions are described elsewhere herein. However, other light chain variable regions that comprise three CDRs for use in conjunction with the heavy chain variable regions of the invention are also contemplated. Appropriate light chain variable regions which can be used in combination with the heavy chain variable regions of the invention and which give rise to an antibody which binds CLEC14A can be readily identified by a person skilled in the art.

For example, a heavy chain variable region of the invention can be combined with a single light chain variable region or a repertoire of light chain variable regions and the resulting antibodies tested for binding to CLEC14A. It would be expected that a reasonable number of such combinations of heavy chain variable regions of the invention with different light chain variable regions would retain the ability to bind CLEC14A.

Similar methods could be used to identify alternative heavy chain variable regions for use in combination with preferred light chain variable regions of the invention.

In certain embodiments, the antibody or antibody fragment comprises all or a portion of a heavy chain constant region, such as an IgG1, IgG2, IgG3, IgG4, IgA1, IgA2, IgE, IgM or IgD constant region. Preferably, the heavy chain constant region is an IgG1 heavy chain constant region, or a portion thereof. Furthermore, the antibody or antibody fragment can comprise all or a portion of a kappa light chain constant region or a lambda light chain constant region, or a portion thereof. All or part of such constant regions may be produced naturally or may be wholly or partially synthetic. Appropriate sequences for such constant regions are well known and documented in the art. When a full complement of constant regions from the heavy and light chains is included in the antibodies of the invention, such antibodies are typically referred to herein as "full length" antibodies or "whole" antibodies.

Antibodies containing an Fc region are preferred for certain uses, particularly therapeutic uses in vivo.

In preferred embodiments the antibodies of the invention are monoclonal antibodies, which may be humanised or human monoclonal antibodies. In this regard, human or humanised antibodies generally have at least three potential advantages for use in human therapy. First, the human immune system should not recognize the antibody as foreign. Second, the half-life in the human circulation will be similar to naturally occurring human antibodies, allowing smaller and less frequent doses to be given. Third, because the effector portion is human, it will interact better with the other parts of the human immune system.

Thus, the specific antibodies disclosed in the Examples may be "humanised" in known ways, for example by inserting the CDR regions of said mouse antibodies into the framework of human antibodies. Humanised antibodies can be made using the techniques and approaches described in Verhoeyen et al (1988) Science, 239, 1534-1536, and in Kettleborough et al, (1991) Protein Engineering, I4(7), 773-783. In some instances, Fv framework residues of the human immunoglobulin are replaced by corresponding non-human residues. In general, the humanised antibody will contain variable domains in which all or most of the CDR regions correspond to those of a non-human immunoglobulin, and framework regions which are substantially or completely those of a human immunoglobulin consensus sequence.

Completely human antibodies may be produced using recombinant technologies. Typically large libraries comprising billions of different antibodies are used. In contrast to the previous technologies employing chimerisation or humanisation of e.g. murine antibodies this technology does not rely on immunisation of animals to generate the specific antibody. Instead the recombinant libraries comprise a huge number of pre-made antibody variants wherein it is likely that the library will have at least one antibody specific for any antigen. Thus, in the context of the present invention, a competing antibody having the desired binding characteristics can be identified using such libraries. In order to find the good binder in a library in an efficient manner, various systems where phenotype i.e. the antibody or antibody fragment is linked to its genotype i.e. the encoding gene has been devised. The most commonly used such system is the so called phage display system where antibody fragments are expressed, displayed, as fusions with phage coat proteins on the surface of filamentous phage particles, while simultaneously carrying the genetic information encoding the displayed molecule (McCafferty et al, 1990, Nature 348: 552-554). Phage displaying antibody fragments specific for a particular antigen may be selected through binding to the antigen in question. Isolated phage may then be amplified and the gene encoding the selected antibody variable domains may optionally be transferred to other antibody formats, such as e.g. full-length immunoglobulin, and expressed in high amounts using appropriate vectors and host cells well known in the art. Alternatively, the "human" antibodies can be made by immunising transgenic mice which contain, in essence, human immunoglobulin genes (Vaughan et al (1998) Nature Biotechnol. 16, 535-539).

The "human" and "humanised" antibodies of the invention may include amino acid residues not encoded by human sequences, e.g., mutations introduced by random or site directed mutations in vitro, for example mutations introduced by in vitro cloning or PCR. Particular examples of such mutations are mutations that involve conservative substitutions or other mutations (non-conservative substitutions, additions and/or deletions) in a small number of residues of the antibody, e.g., in up to 5, 4, 3, 2 or 1 of the residues of the antibody, preferably e.g., in up to 5, 4, 3, 2 or 1 of the residues making up one or more of the CDRs of the antibody. Certain examples of such "human" and "humanised" antibodies include antibodies and variable regions that have been subjected to standard modification techniques to reduce the amount of potentially immunogenic sites.

Thus, the "human" and "humanised" antibodies of the invention include sequences derived from and related to sequences found in humans, but which may not naturally exist within the human antibody germline repertoire in vivo. In addition, the human and humanised antibodies of the present invention include proteins comprising human consensus sequences identified from human sequences, or sequences substantially homologous to human sequences.

In addition, the human and humanised antibodies of the present invention are not limited to combinations of VH, VL, CDR or FR regions that are themselves found in combination in human antibody molecules. Thus, the human and humanised antibodies of the invention can include or correspond to combinations of such regions that do not necessarily exist naturally in humans.

In some embodiments, the human antibodies may be fully human antibodies. "Fully human" antibodies, as used herein, are antibodies comprising "human" variable region domains and/or CDRs, as defined above, without substantial non-human antibody sequences or without any non-human antibody sequences. For example, antibodies comprising human variable region domains and/or CDRs "without substantial non-human antibody sequences" are antibodies, domains and/or CDRs in which only up to 5, 4, 3, 2 or 1 amino acids are amino acids that are not encoded by human antibody sequences. Thus, "fully human" antibodies are distinguished from "humanised" antibodies, which are based on substantially non-human variable region domains, e.g., mouse variable region domains, in which certain amino acids have been changed to better correspond with the amino acids typically present in human antibodies.

The "fully human" antibodies of the invention may be human variable region domains and/or CDRs without any other substantial antibody sequences, such as being single chain antibodies. Alternatively, the "fully human" antibodies of the invention may be human variable region domains and/or CDRs integral with or operatively attached to one or more human antibody constant regions. Certain preferred fully human antibodies are IgG antibodies with the full complement of IgG constant regions.

In other embodiments, "human" antibodies of the invention will be part-human chimeric antibodies. "Part-human chimeric" antibodies, as used herein, are antibodies comprising "human" variable region domains and/or CDRs operatively attached to, or grafted onto, a constant region of a non-human species, such as rat or mouse. Such part-human chimeric antibodies may be used, for example, in pre-clinical studies, wherein the constant region will preferably be of the same species of animal used in the pre-clinical testing. These part-human chimeric antibodies may also be used, for example, in ex vivo diagnostics, wherein the constant region of the non-human species may provide additional options for antibody detection.

The term "fragment" as used herein refers to fragments of biological relevance, e.g., fragments that contribute to antigen binding, e.g., form part of the antigen binding site, and/or contribute to the inhibition or reduction in function or activity of the CLEC14A antigen. Certain preferred fragments comprise a heavy chain variable region (VH domain) and/or a light chain variable region (VL domain) of the antibodies of the invention. Other preferred fragments comprise one or more of the heavy chain CDRs of the antibodies of the invention (or of the VH domains of the invention), or one or more of the light chain CDRs of the antibodies of the invention (or of the VL domains of the invention). Certain preferred fragments are at least 5 amino acids in length and comprise at least one CDR region, preferably a CDR3 region, more preferably a heavy chain CDR3 region.

In embodiments where the antibodies of the invention comprise a fragment of any of the defined sequences (for example comprising a fragment of SEQ ID NO: 1, 5, 21, 25, 41 or 45), e.g., are antibodies comprising VH and/or VL domains of the invention, or are antibodies comprising one or more CDRs of the invention, then these regions/domains are generally separated within the antibody so that each region/domain can perform its biological function and so that the contribution to antigen binding is retained. Thus, the VH and VL domains are preferably separated by appropriate scaffold sequences/linker sequences and the CDRs are preferably separated by appropriate framework regions such as those found in naturally occurring antibodies and/or effective engineered antibodies. Thus, the VH, VL and individual CDR sequences of the invention are preferably provided within or incorporated into an appropriate framework or scaffold to enable antigen binding. Such framework sequences or regions may correspond to naturally occurring framework regions, FR1, FR2, FR3 and/or FR4, as appropriate to form an appropriate scaffold, or may correspond to consensus framework regions, for example identified by comparing various naturally occurring framework regions. Alternatively, non-antibody scaffolds or frameworks, e.g., T cell receptor frameworks can be used.

Appropriate sequences that can be used for framework regions are well known and documented in the art and any of these may be used. Preferred sequences for framework regions are one or more (i.e. one, two, three or four) of the framework regions making up the VH and/or VL domains of the invention, i.e., one or more of the framework regions found within SEQ ID NOs. 1, 5, 21, 25, 41 or 45 or framework regions substantially homologous thereto, and in particular framework regions that allow the maintenance of antigen specificity, for example framework regions that result in substantially the same or the same 3D structure of the antibody.

In the context of framework regions of the antibodies of the invention, the term "substantially homologous" includes sequences having at least 60%, 65%, 70% or 75%, preferably at least 80%, and even more preferably at least 85%, 90%, 95%, 96%, 97%, 98% or 99%, sequence identity to the amino acid sequences disclosed herein. Substantially homologous sequences of the invention thus include single or multiple base or amino acid alterations (additions, substitutions, insertions or deletions) to the sequences of the invention. At the amino acid level preferred substantially homologous sequences contain only up to 1, 2, 3, 4 or 5, preferably up to 1, 2 or 3, more preferably up to 1 or 2, altered amino acids, in one or more of the framework regions and/or one or more of the CDRs making up the sequences of the invention. Said alterations can be with conservative or non-conservative amino acids, or a mixture thereof. Preferably said alterations are conservative amino acid substitutions.

Thus, for instance, the antibody of the invention may comprise an antigen binding domain comprising a VH sequence having an amino acid sequence as shown in SEQ ID NO. 1, or an amino acid sequence having at least 60% sequence identity thereto, and a VL sequence having an amino acid sequence as shown in SEQ ID NO. 5, or an amino acid sequence having at least 60% sequence identity thereto, preferably with the proviso that the CDR sequences of SEQ ID NOs. 2, 3, 4, 6, 7 and 8 are retained (i.e. are not modified or altered).

In some embodiments, the antibody of the invention may comprise an antigen binding domain comprising a VH sequence having an amino acid sequence as shown in SEQ ID NO. 41, or an amino acid sequence having at least 60% sequence identity thereto, and a VL sequence having an amino acid sequence as shown in SEQ ID NO. 45, or an amino acid sequence having at least 60% sequence identity thereto, preferably with the proviso that the CDR sequences of SEQ ID NOs. 42, 43, 44, 46, 47 and 48 are retained (i.e. are not modified or altered).

In yet other embodiments, the antibody of the invention may comprise an antigen binding domain comprising a VH sequence having an amino acid sequence as shown in SEQ ID NO. 21, or an amino acid sequence having at least 60% sequence identity thereto, and a VL sequence having an amino acid sequence as shown in SEQ ID NO. 25, or an amino acid sequence having at least 60% sequence identity thereto, preferably with the proviso that the CDR sequences of SEQ ID NOs. 22, 23, 24, 26, 27 and 28 are retained (i.e. are not modified or altered).

In still further embodiments, the antibody of the invention may be an scFv comprising an amino acid sequence as shown in SEQ ID NO. 9, or an amino acid sequence having at least 60% sequence identity thereto with the proviso that the CDR sequences of SEQ ID NOs. 2, 3, 4, 6, 7 and 8 are retained (i.e. are not modified or altered).

In some embodiments, the antibody of the invention may be an scFv comprising an amino acid sequence as shown in SEQ ID NO. 49 or an amino acid sequence having at least 60% sequence identity thereto with the proviso that the CDR sequences of SEQ ID NOs. 42, 43, 44, 6, 7 and 8 are retained (i.e. are not modified or altered). In some embodiments, the antibody of the invention may be an scFv comprising an amino acid sequence as shown in SEQ ID NO. 50 or an amino acid sequence having at least 60% sequence identity thereto with the proviso that the CDR sequences of SEQ ID NOs. 2, 3, 4, 46, 47 and 48 are retained (i.e. are not modified or altered).

In some embodiments, the antibody of the invention may be an scFv comprising an amino acid sequence as shown in SEQ ID NO. 51 or an amino acid sequence having at least 60% sequence identity thereto with the proviso that the CDR sequences of SEQ ID NOs. 42, 43, 44, 46, 47 and 48 are retained (i.e. are not modified or altered).

In other embodiments, the antibody of the invention may be an scFv comprising an amino acid sequence as shown in SEQ ID NO. 29, or an amino acid sequence having at least 60% sequence identity thereto with the proviso that the CDR sequences of SEQ ID NOs. 22, 23, 24, 26, 27 and 28 are retained (i.e. are not modified or altered).

It will be understood, therefore, that in such embodiments, the CDR sequences of the antibodies are retained or substantially retained (i.e. they may optionally be modified within the constraints set out above, e.g. substitution, addition or deletion of 1 to 4 amino acids, such that the binding specificity of the antibody is retained (e.g. unaltered)).

The term "substantially homologous" also includes modifications or chemical equivalents of the amino acid of the present invention that perform substantially the same function as the proteins or nucleic acid molecules of the invention in substantially the same way. For example, any substantially homologous antibody (or the substantially homologous nucleic acid encoding it) should retain the ability to bind to CLEC14A as described above. Preferably, any substantially homologous antibody should retain the functional capabilities of the antibody, e.g. as defined elsewhere herein. Preferably, any substantially homologous antibody should retain the ability to specifically bind to the same epitope of CLEC14A as recognized by the antibody in question, for example, the same epitope recognized by the CDR domains of the invention or the VH and VL domains of the invention as described herein. Binding to the same epitope/antigen can be readily tested by methods well known and described in the art, e.g., using binding assays, e.g., a competition assay. Retention of other functional properties can also readily be tested by methods well known and described in the art.

Thus, a person skilled in the art will appreciate that binding assays can be used to test whether "substantially homologous" antibodies have the same binding specificities as the antibodies and antibody fragments of the invention, for example, binding assays such as ELISA assays or BIAcore assays can readily be used to establish whether such "substantially homologous" antibodies can bind to CLEC14A. As outlined above, a competition binding assay can be used to test whether "substantially homologous" antibodies retain the ability to specifically bind to substantially the same epitope of CLEC14A as recognized by the antibodies of the invention.

Substantially homologous sequences of proteins of the invention include, without limitation, conservative amino acid substitutions, or for example alterations that do not affect the VH, VL or CDR domains of the antibodies, e.g., include scFv antibodies where a different linker sequence is used or antibodies where tag sequences or other components are added that do not contribute to the binding of antigen, or alterations to convert one type or format of antibody molecule or fragment to another type or format of antibody molecule or fragment (e.g., conversion from Fab to scFv or vice versa), or the conversion of an antibody molecule to a particular class or subclass of antibody molecule (e.g., the conversion of an antibody molecule to IgG or a subclass thereof, e.g., IgG1 or IgG3).

A "conservative amino acid substitution", as used herein, is one in which the amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., glycine, cysteine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Homology may be assessed by any convenient method. However, for determining the degree of homology between sequences, computer programs that make multiple alignments of sequences are useful, for instance Clustal W. If desired, the Clustal W algorithm can be used together with BLOSUM 62 scoring matrix and a gap opening penalty of 10 and gap extension penalty of 0.1, so that the highest order match is obtained between two sequences wherein at least 50% of the total length of one of the sequences is involved in the alignment. Other methods to calculate the percentage identity between two amino acid sequences are generally art recognized and include, for example, those described in Computational Molecular Biology, Lesk, e.d. Oxford University Press, New York, 1988, Biocomputing: Informatics and Genomics Projects.

Generally, computer programs will be employed for such calculations. Programs that compare and align pairs of sequences, like ALIGN, FASTA, gapped BLAST, BLASTP, BLASTN, or GCG are also useful for this purpose. Furthermore, the Dali server at the European Bioinformatics institute offers structure-based alignments of protein sequences.

By way of providing a reference point, sequences according to the present invention having 70%, 75%, 80%, 85%, 90%, 95%, 96%, 97%, 98% or 99% homology, sequence identity etc. may be determined using the ALIGN program with default parameters (for instance available on Internet at the GENESTREAM network server, IGH, Montpellier, France).

In addition, although preferred antibodies of the invention are made up of VH, VL or CDRs of the invention, it should be noted that the antibodies of the invention also encompass one or more VH, VL or CDRs of the invention in combination with other VH, VL or CDRs not of the invention, provided that the CLEC14A binding properties or anti-CLEC14A properties of the antibodies of the invention as outlined herein are still present.

The term "heavy chain complementarity determining region" ("heavy chain CDR") as used herein refers to regions of hypervariability within the heavy chain variable region (VH domain) of an antibody molecule. The heavy chain variable region has three CDRs termed heavy chain CDR1, heavy chain CDR2 and heavy chain CDR3 from the amino terminus to carboxy terminus. The heavy chain variable region also has four framework regions (FR1, FR2, FR3 and FR4 from the amino terminus to carboxy terminus). These framework regions separate the CDRs.

The term "heavy chain variable region" (VH domain) as used herein refers to the variable region of a heavy chain of an antibody molecule.

The term "light chain complementarity determining region" ("light chain CDR") as used herein refers to regions of hypervariability within the light chain variable region (VL domain) of an antibody molecule. Light chain variable regions have three CDRs termed light chain CDR1, light chain CDR2 and light chain CDR3 from the amino terminus to the carboxy terminus. The light chain variable region also has four framework regions (FR1, FR2, FR3 and FR4 from the amino terminus to carboxy terminus). These framework regions separate the CDRs.

The term "light chain variable region" (VL domain) as used herein refers to the variable region of a light chain of an antibody molecule.

It should be noted that the Kabat nomenclature is followed herein, where necessary, in order to define the positioning of the CDRs (Kabat et al., 1991 (supra), specifically incorporated herein by reference).

In some embodiments, the antibodies of the present invention, e.g. in IgG format, may have a high binding affinity for CLEC14A, i.e., have a $K_d$ in the range of $1\times10^{-8}$ M or $1\times10^{-9}$ M or less. Importantly, antibodies with such an affinity are in the established range that has been shown to be useful for therapy. Preferably, the antibodies of the invention, e.g. in IgG format, have a binding affinity for CLEC14A that corresponds to a $K_d$ of less than 30 nM, 20 nM, 15 nM or 10 nM, more preferably of less than 10, 9.5, 9, 8.5, 8, 7.5, 7, 6.5, 6, 5.5, 5, 4.5, 4, 3.5, 3, 2.5, 2, 1.5 or 1 nM, most preferably less than 0.9, 0.8, 0.7, 0.6, 0.5, 0.4, 0.3, 0.2 or 0.1 nM.

Any appropriate method of determining $K_d$ may be used. However, preferably the $K_d$ is determined by testing various concentrations of the test antibody against various concentrations of antigen (CLEC14A) in vitro to establish a saturation curve, for example using the Lineweaver-Burk method, or by using commercially available binding model software, such as the 1:1 binding model in the BIAcore 1000 Evaluation software.

With regard to determinations of $K_d$ values, the skilled person will appreciate that apparent $K_d$ values derived from binding experiments using cells expressing a target (e.g. CLEC14A) cannot be considered to be an absolute indication of affinity, because the experimental conditions will affect the apparent binding affinity. For example, the levels of expression of CLEC14A may vary depending on the conditions under which the cells are cultured, as well as differing between different cell types. It is consequently best to compare apparent $K_d$ values obtained within one set of experiments and it may not always be appropriate to compare $K_d$ values obtained in one set of experiments with $K_d$ values obtained in a different set of experiments, particularly if the experimental conditions varied significantly.

Alternatively, the off-rate and the antibody half-life on the surface of the CLEC14A-positive cell can be determined by performing the cell surface retention assay (Adams et al., 1998, Br J Cancer 77: 1405-12; Le Gall et al., 1999, FEBS Lett 453: 164-8). The Le Gall method allows more appropriate mimicking the real situation in human patient under the treatment conditions.

In some embodiments, antibodies of the invention may bind to both human CLEC14A and monkey CLEC14A. Such cross-reactivity between species and in particular between humans and species commonly used as pre-clinical animal models may be an advantage as it allows a more effective translation from pre-clinical studies to clinical use. For example, having an antibody which cross reacts with the native CLEC14A present in the particular animal model used means that the results in this model are more likely to reflect the situation in a human patient, thereby allowing a more accurate assessment of for example dosing to be made and an increased likelihood of identifying any potentially relevant or problematic side effects.

For example, the ability of an antibody of the invention to bind to both human CLEC14A and monkey CLEC14A means that such antibodies can be tested in preclinical toxicity studies to assess adverse side effects of the treatment and to find appropriate tolerated dosages.

In addition, the ability to bind both human CLEC14A and mouse CLEC14A means that the results shown by such antibodies of the invention in mouse models, e.g. mouse syngeneic models using immunocompetent mice, are more likely to be representative of the activity of the antibodies in human subjects. The reason for this is that antibodies which can bind to human CLEC14A but not mouse CLEC14A will bind to CLEC14A expressed by the human tumour cells in the mouse model but will not be able to bind to endogenous murine CLEC14A. This is of course unlike the situation in a human patient, in which CLEC14A expressed by the tumour and endogenous CLEC14A would be present.

In preferred embodiments, antibodies of the invention bind to human and monkey CLEC14A and/or to human and mouse CLEC14A with similar affinities, e.g. with a $K_d$ of 10 nM or less or 5 nM or less, more preferably 3 nM or less or 2 nM or less, most preferably 1 nM or less.

By "similar affinity" is also meant that the binding affinity of the antibody for human CLEC14A and for one or more of the other species of interest (e.g. monkey or mouse) is comparable, e.g. is not more than a factor of 20 different. More preferably the difference between the binding affinities is less than a factor of 15, more preferably less than a factor of 10, most preferably less than a factor of 5, 4, 3 or 2.

However, in other embodiments the antibodies of the present invention may not bind to monkey CLEC14A and/or they may not bind to mouse CLEC14A.

In light of this invention, therefore, a range of anti-CLEC14A antibodies can be made and used in a variety of embodiments, including in the treatment of any of the disorders discussed elsewhere herein, particularly disorders or conditions involving undesired or unwanted angiogenesis, particularly tumour angiogenesis, e.g. for use in treating cancer.

A person skilled in the art will appreciate that the proteins and polypeptides of the invention, such as the light and heavy CDRs, the light and heavy chain variable regions, antibodies, antibody fragments, and immunoconjugates (described in more detail below), may be prepared in any of several ways well known and described in the art, but are most preferably prepared using recombinant methods.

Thus, in a further embodiment the invention provides a nucleic acid molecule encoding an antibody of the invention as described herein or parts or fragments thereof, or nucleic acid molecules substantially homologous thereto. Thus, in some embodiments, the invention provides a nucleic acid molecule comprising one or more sequences selected from SEQ ID NOs. 12, 13, 14, 16, 17 and 18 or one or more sequences selected from SEQ ID NOs. 32, 33, 34, 36, 37 and 38 or one or more sequences selected from SEQ ID NOs. 55, 56, 57, 59, 60 and 61 (i.e. encoding the CDRs described above). In some embodiments, the invention provides a nucleic acid molecule comprising a sequence selected from SEQ ID NOs. 11 and 15 or a sequence selected from SEQ ID NOs: 31 and 35 or a sequence selected from SEQ ID NOs: 54 and 58 (i.e. encoding the variable chains described above). In some embodiments, the invention provides a nucleic acid molecule comprising a sequence selected from SEQ ID NOs: 19, 39, 62, 63 and 64 (i.e. encoding the scFv polypeptides described above).

In some embodiments, the nucleic acid molecules encoding the antibody of the invention may be substantially homologous to the nucleic acid molecules exemplified herein. Thus, in some embodiments the nucleic acid molecule may encode a polypeptide comprising an antigen binding domain comprising a VH sequence as described herein, wherein said nucleic acid molecule comprises a nucleotide sequence set forth in SEQ ID NO. 11, 31 or 54 or nucleotide sequence having at least 60% sequence identity thereto, preferably with the proviso that the nucleotide sequences encoding the CDR sequences of SEQ ID NOs. 2, 3 and 4 or 22, 23 and 24 or 42, 43 and 44 are retained, e.g. the nucleotide sequences comprise SEQ ID NOs: 12, 13 and 14 or 32, 33 and 34 or 55, 56 and 57.

Thus, in some embodiments the nucleic acid molecule may encode a polypeptide comprising an antigen binding domain comprising a VL sequence as described herein, wherein said nucleic acid molecule comprises a nucleotide sequence set forth in SEQ ID NO. 15, 35 or 58 or nucleotide sequence having at least 60% sequence identity thereto, preferably with the proviso that the nucleotide sequences encoding the CDR sequences of SEQ ID NOs. 6, 7 and 8 or 26, 27 and 28 or 46, 47 and 48 are retained, e.g. the nucleotide sequences comprise SEQ ID NOs: 16, 17 and 18 or 36, 37 and 38 or 59, 60 and 61.

In still further embodiments, the nucleic acid molecule may encode a polypeptide comprising an scFv as described herein, wherein said nucleic acid molecule comprises a nucleotide sequence set forth in SEQ ID NO. 19, 39, 49, 50 or 51 or nucleotide sequence having at least 60% sequence identity thereto, preferably with the proviso that the nucleotide sequences encoding the CDR sequences of SEQ ID NOs. 2, 3, 4, 6, 7 and 8 or 22, 23, 24, 26, 27 and 28, or 42, 43, 44, 6, 7 and 8 or 2, 3, 4, 46, 47 and 48 or 42, 43, 44, 46, 47 and 48 are retained, e.g. the nucleotide sequences comprise SEQ ID NOs: 12, 13, 14, 16, 17 and 18 or 32, 33, 34, 36, 37 and 38 or 55, 56, 57, 16, 17 and 18 or 12, 13, 14, 59, 60 and 61 or 55, 56, 57, 59, 60 and 61.

Thus, fragments of the antibodies of the invention as defined herein, or sequences substantially homologous thereto, or nucleic acid molecules comprising sequences encoding such fragments form a yet further aspect of the invention.

Nucleic acid fragments encoding the light and heavy chain variable regions of the antibodies of the invention can be derived or produced by any appropriate method, e.g., by cloning or synthesis. Such sequences could, for example, be prepared by cloning appropriate sequences from e.g., human germ line genes and then making any necessary modifications to the germ line sequences to obtain the sequences of the invention using methods well known and described in the art. An alternative and more efficient method would be to synthesize the appropriate light or heavy chain variable region sequence as overlapping primers, and use primer extension to obtain the full sequence. This full sequence could then be amplified via PCR with primers containing appropriate restriction sites for further cloning and manipulation, e.g., for cloning into an appropriate expression vector. Five to seven overlapping primers per variable region are normally sufficient, thereby making this technique very efficient and precise.

Once nucleic acid fragments encoding the light and heavy chain variable regions of the antibodies of the invention have been obtained, these fragments can be further manipulated by standard recombinant DNA techniques, for example to convert the variable region fragments into full length antibody molecules with appropriate constant region domains, or into particular formats of antibody fragment discussed elsewhere herein, e.g., Fab fragments, scFv fragments, etc. Typically, or as part of this further manipulation procedure, the nucleic acid fragments encoding the antibody molecules of the invention are generally incorporated into an appropriate expression vector in order to facilitate production of the antibodies of the invention.

The term "nucleic acid sequence" or "nucleic acid molecule" as used herein refers to a sequence of nucleoside or nucleotide monomers composed of naturally occurring bases, sugars and intersugar (backbone) linkages. The term also includes modified or substituted sequences comprising non-naturally occurring monomers or portions thereof. The nucleic acid sequences of the present invention may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The nucleic acid molecules may be double stranded or single stranded. The nucleic acid molecules may be wholly or partially synthetic or recombinant.

The term "substantially homologous" as used herein in connection with a nucleic acid sequence includes sequences having at least 60%, 65%, 70% or 75%, preferably at least 80%, and even more preferably at least 85%, 90%, 95%, 96%, 97%, 98% or 99%, sequence identity to the nucleic acid sequence disclosed. Substantially homologous sequences of the invention thus include single or multiple base alterations (additions, substitutions, insertions or deletions) to the sequences of the invention.

The substantially homologous nucleic acid sequences also include nucleotide sequences that hybridize to the nucleic acid sequences disclosed (or their complementary sequences), e.g., hybridize to nucleotide sequences encoding one or more of the light chain or heavy chain CDRs of the invention, the light or heavy chain variable regions of the invention, or the antibodies of the invention (or hybridize to their complementary sequences), under at least moderately stringent hybridization conditions.

By "at least moderately stringent hybridization conditions" it is meant that conditions are selected that promote selective hybridization between two complementary nucleic acid molecules in solution. Hybridization may occur to all or a portion of a nucleic acid sequence molecule. The hybridizing portion is typically at least 15 (e.g., 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(% (G+C)−600/l), or similar equation). Accordingly, the parameters in the wash conditions that determine hybrid stability are sodium ion concentration and temperature. In order to identify molecules that are similar, but not identical, to a known nucleic acid molecule, a 1% mismatch may be assumed to result in about a 1° C. decrease in Tm. For example, if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm−5° C. based on the above equation, followed by a wash of 0.2×SSC/0.1% SDS at 60° C. Moderately stringent hybridization conditions include a washing step in 3×SSC at 42° C. By way of further example, sequences that "hybridize" are those sequences binding (hybridizing) under non-stringent conditions (e.g., 6×SSC, 50% formamide at room temperature) and washed under conditions of low stringency (e.g., 2×SSC, room temperature, more preferably 2×SSC, 42° C.) or conditions of higher stringency (e.g., 2×SSC, 65° C.) (where SSC=0.15M NaCl, 0.015M sodium citrate, pH 7.2).

It is understood, however, that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1-6.3.6 and in: Sambrook et al., Molecular Cloning, a Laboratory Manual, Cold Spring Harbor Laboratory Press, 1989, Vol. 3.

Generally speaking, sequences that hybridize under conditions of high stringency are preferred, as are sequences which, but for the degeneracy of the code, would hybridize under high stringency conditions.

Nucleotide sequences which are degenerate variants of the nucleotide sequences defined herein are further encompassed by the invention. It will be appreciated that due to the degeneracy of the genetic code, that multiple nucleotide sequences may encode a single amino acid sequence. In this regard, such degenerate sequences form part of the present invention. In connection with this, it may be desirable to codon optimise a nucleotide sequence of the invention for expression in a particular host organism or cell (e.g. for expression in a human or a mouse). This may involve the modification of the nucleotide sequences of the invention so that codons are selected (from those that encode a particular amino acid), which are preferentially expressed in a particular host cell/organism. Such a procedure is well known in the art and generally may not alter the encoded amino acid sequence. Codon optimised versions of the nucleotide sequences of the invention are thus further encompassed by the invention. Particularly, polynucleotide sequences comprising the codon optimised sequences of SEQ ID Nos 101-104 are encompassed by the present invention. Variants of SEQ ID Nos 101-104 are further encompassed, wherein said variants have at least 60% identity to a sequence of SEQ ID Nos 101-104 and encode an antibody or a portion thereof which is capable of binding to CLEC14A. In this regard, SEQ ID Nos 101 and 103 are codon optimised sequences for expression in a human host or cell and SEQ ID Nos 102 and 104 are codon optimised sequences for expression in a murine host or cell, where SEQ ID Nos 101-104 encode a scFv of the invention. Particularly, SEQ ID Nos 101 and 102 represent codon optimised sequences for human and murine expression, respectively, of SEQ ID NO. 19 and SEQ ID Nos 103 and 104 represent codon optimised sequences for human and murine expression, respectively, of SEQ ID NO. 39.

The antibody and nucleic acid molecules of the invention are generally "isolated" or "purified" molecules insofar as they are distinguished from any such components that may be present in situ within a human or animal body or a tissue sample derived from a human or animal body. The sequences may, however, correspond to or be substantially homologous to sequences as found in a human or animal body. Thus, the term "isolated" or "purified" as used herein in reference to nucleic acid molecules or sequences and proteins or polypeptides, e.g., antibodies, refers to such molecules when isolated from, purified from, or substantially free of their natural environment, e.g., isolated from or purified from the human or animal body (if indeed they occur naturally), or refers to such molecules when produced by a technical process, i.e., includes recombinant and synthetically produced molecules.

Thus, when used in connection with a nucleic acid molecule, such terms may refer to a nucleic acid substantially free of material with which it is naturally associated such as other nucleic acids/genes or polypeptides. These terms may also refer to a nucleic acid substantially free of cellular material or culture medium when produced by recombinant DNA techniques, or substantially free of chemical precursors, or other chemicals when chemically synthesized. An isolated or purified nucleic acid may also be substantially free of sequences that naturally flank the nucleic acid (i.e., sequences located at the 5' and 3' ends of the nucleic acid) from which the nucleic acid is derived or sequences that have been made to flank the nucleic acid (e.g., tag sequences or other sequence that have no therapeutic value) by, for example, genetic engineering.

Thus, when used in connection with a protein or polypeptide molecule such as light chain CDRs 1, 2 and 3, heavy chain CDRs 1, 2 and 3, light chain variable regions, heavy chain variable regions, and antibodies of the invention, including full length antibodies, the term "isolated" or "purified" typically refers to a protein substantially free of cellular material or other proteins from the source from which it is derived. In some embodiments, particularly where the protein is to be administered to humans or animals, such isolated or purified proteins are substantially free of culture medium when produced by recombinant techniques, or chemical precursors or other chemicals when chemically synthesized. Such isolated or purified proteins may also be free of flanking sequences such as those described above for the isolated nucleic acid molecules.

As mentioned above, the inventors have determined that the antigen binding domains of the antibodies of the invention, and more particularly the variable regions (VL and VH chains) of said domains, may provide an effective CAR for use in adoptive cell transfer therapy against cells, particularly tumour cells (e.g. tumour vasculature), expressing CLEC14A.

Accordingly, the present invention further provides a nucleic acid molecule encoding a chimeric antigen receptor (CAR) directed against the antigen CLEC14A, wherein said CAR when expressed on the surface of an immune effector cell is capable of binding to the antigen CLEC14A expressed on a target cell surface and comprises an antigen binding domain comprising:

(1) (a) a VH CDR sequence comprising:

(i) a VH CDR1 that has the amino acid sequence of SEQ ID NO: 2 or 42; and/or (ii) a VH CDR2 that has the amino acid sequence of SEQ ID NO: 3 or 43; and/or (iii) a VH CDR3 that has the amino acid sequence of SEQ ID NO: 4 or 44; and/or (b) a VL CDR sequence comprising:

(i) a VL CDR1 that has the amino acid sequence of SEQ ID NO: 6 or 46; and/or (ii) a VL CDR2 that has the amino acid sequence of SEQ ID NO: 7 or 47; and/or (vi) a VL CDR3 that has the amino acid sequence of SEQ ID NO: 8 or 48; and/or one or more sequences substantially homologous to the SEQ ID NOs set forth in (a) or (b); or (2) (a) a VH CDR sequence comprising:

(i) a VH CDR1 that has the amino acid sequence of SEQ ID NO: 22; and/or (ii) a VH CDR2 that has the amino acid sequence of SEQ ID NO: 23; and/or (iii) a VH CDR3 that has the amino acid sequence of SEQ ID NO: 24; and/or (b) a VL CDR sequence comprising:

(i) a VL CDR1 that has the amino acid sequence of SEQ ID NO: 26; and/or (ii) a VL CDR2 that has the amino acid sequence of SEQ ID NO: 27; and/or (iii) a VL CDR3 that has the amino acid sequence of SEQ ID NO: 28; and/or one or more sequences substantially homologous to the SEQ ID NOs set forth in (a) or (b).

In some embodiments, the CAR comprises more than one CDR, e.g. 2, 3, 4, 5 or 6 CDRs. Accordingly, in some embodiments the CAR may comprise a VH sequence comprising one, two or three CDRs and/or a VL sequence comprising one, two or three CDRs. Thus, in some embodiments, the invention provides a nucleic acid molecule encoding a CAR directed against the antigen CLEC14A, wherein said CAR when expressed on the surface of an immune effector cell is capable of binding to the antigen CLEC14A expressed on a target cell surface and comprises an antigen binding domain comprising a VH sequence and a VL sequence each comprising three CDR sequences, wherein:

(1) said VH sequence comprises:

(i) a VH CDR1 that has the amino acid sequence of SEQ ID NO: 2 or 42;

(ii) a VH CDR2 that has the amino acid sequence of SEQ ID NO: 3 or 43; and/or (iii) a VH CDR3 that has the amino acid sequence of SEQ ID NO: 4 or 44; and/or wherein said VL sequence comprises:

(iv) a VL CDR1 that has the amino acid sequence of SEQ ID NO: 6 or 46;

(v) a VL CDR2 that has the amino acid sequence of SEQ ID NO: 7 or 47; and/or (vi) a VL CDR3 that has the amino acid sequence of SEQ ID NO: 8 or 48; or one or more sequences substantially homologous to the SEQ ID NOs set forth in (1) (i)-(1) (vi); or (2) said VH sequence comprises:

(i) a VH CDR1 that has the amino acid sequence of SEQ ID NO: 22;

(ii) a VH CDR2 that has the amino acid sequence of SEQ ID NO: 23; and/or (iii) a VH CDR3 that has the amino acid sequence of SEQ ID NO: 24; and/or wherein said VL sequence comprises:

(iv) a VL CDR1 that has the amino acid sequence of SEQ ID NO: 26;

(v) a VL CDR2 that has the amino acid sequence of SEQ ID NO: 27; and/or (vi) a VL CDR3 that has the amino acid sequence of SEQ ID NO: 28; or one or more sequences substantially homologous to the SEQ ID NOs set forth in (2) (i)-(2) (vi).

In a preferred embodiment, a substantially homologous sequence has 1, 2 or 3 amino acid substitutions, additions or deletions in said CDRs. Alternatively viewed, one or more of said CDR sequences may optionally be modified by substitution, addition or deletion of 1 to 3 amino acids. In a particularly preferred embodiment, said amino acid substitutions are conservative substitutions.

The CDR sequences in (1) are, or correspond to, the CDR sequences contained in the VH sequences of SEQ ID NOs. 1 and 41 and the VL sequences of SEQ ID NOs. 5 and 45. The CDR sequences in (2) are, or correspond to, the CDR sequences contained in the VH and VL sequences of SEQ ID NOs. 21 and 25 respectively. SEQ ID NOs. 1, 41, 5 and 45 and SEQ ID NOs. 21 and 25 represent the amino acid sequences of the VH and VL regions of antibodies described above respectively (SEQ ID NOs. 11, 54, 15 and 58 and SEQ ID NOs: 31 and 35 represent the nucleotide sequences encoding said amino acid sequences).

In a preferred embodiment, the CAR comprises at least CDR3 of the respective VH and VL sequences, e.g. SEQ ID NOs: 4 and 8, SEQ ID NOs: 44 and 48 or SEQ ID NOs: 24 and 28 (preferably unmodified sequences). In a particularly preferred embodiment, the CAR comprises at least two of the CDRs of the respective VH and VL sequences, e.g. at least two of SEQ ID NOs: 2, 3 and 4 (i.e. at least 2 and 3, 2 and 4, or 3 and 4) or at least two of SEQ ID NOs: 42, 43 and 44 (i.e. at least 42 and 43, 42 and 44, or 43 and 44) and at least two of SEQ ID NOs: 6, 7 and 8 (i.e. at least 6 and 7, 6 and 8, or 7 and 8) or at least two of SEQ ID NOs: 46, 47 and 48 (i.e. at least 46 and 47, 46 and 48, or 47 and 48), or combinations thereof, or at least two of SEQ ID NOs: 22, 23 and 24 (i.e. at least 22 and 23, 22 and 24, or 23 and 24) and at least two of SEQ ID NOs: 26, 27 and 28 (i.e. at least 26 and 27, 26 and 28, or 27 and 28). Preferably said at least two CDRs are unmodified. In a particularly preferred embodiment, the CAR comprises all of the CDRs of the respective VH and VL sequences, i.e. SEQ ID NOs: 2-4 and 6-8, or 42-44 and 46-48, or SEQ ID NOs: 22-24 and 26-28, preferably wherein said CDRs are unmodified.

More particularly, the CAR when expressed on the surface of an immune effector cell is capable of directing the immune effector cell against a target cell expressing CLEC14A. In other words, the immune cell is capable of directing its effect or function, e.g. its cytotoxic activity, against a said target cell, particularly a target cancer cell, e.g. an endothelial cell in a blood vessel, particularly an endothelial cell in a blood vessel in a tumour.

As is known in the art, and described elsewhere herein, the VL and VH chains of an antibody each comprise 3 CDRs separated by framework regions which act as a scaffold for the CDRs. Thus, the VL and VH sequences of a CAR of the invention comprise the CDR sequences of the VL and VH sequences of the antibodies of the invention separated by framework regions. The framework regions may be those of the VL and VH chains of the antibodies of the invention, but need not be. Thus, the framework regions of the VL and VH chains of the antibodies may be modified, which includes that they may be substituted (thus the amino acid sequence of the framework regions may be modified and/or substituted), e.g. they may be humanised, as described elsewhere herein.

In one particular embodiment, the invention provides a nucleic acid molecule encoding a chimeric antigen receptor (CAR) directed against the antigen CLEC14A, wherein said CAR when expressed on the surface of an immune effector cell is capable of binding to the antigen CLEC14A expressed on a target cell surface and comprises an antigen binding domain comprising the VH sequence of SEQ ID NO. 1 or 41 or an amino acid sequence having at least 95% sequence identity thereto, and/or the VL sequence of SEQ ID NO. 5 or 45 or an amino acid sequence having at least 95% sequence identity thereto.

In a further embodiment, the invention provides a nucleic acid molecule encoding a chimeric antigen receptor (CAR) directed against the antigen CLEC14A, wherein said CAR when expressed on the surface of an immune effector cell is capable of binding to the antigen CLEC14A expressed on a target cell surface and comprises an antigen binding domain comprising the VH sequence of SEQ ID NO. 21 or an amino acid sequence having at least 95% sequence identity thereto, and the VL sequence of SEQ ID NO. 25 or an amino acid sequence having at least 95% sequence identity thereto.

In other embodiments, the framework regions of the VL and VH sequences are modified, and the CAR may comprise an antigen binding domain comprising a VH sequence having an amino acid sequence as shown in SEQ ID NO. 1 or 41, or an amino acid sequence having at least 60% sequence identity thereto, and/or a VL sequence having an amino acid sequence as shown in SEQ ID NO. 5 or 45, or an amino acid sequence having at least 60% sequence identity thereto, preferably with the proviso that the CDR sequences of SEQ ID NOs. 2, 3, 4, 6, 7 and 8 and/or SEQ ID NOs. 42, 43, 44, 46, 47 and 48 are retained (i.e. are not modified or altered).

In yet other embodiments, the framework regions of the VL and VH sequences are modified, and the CAR may comprise an antigen binding domain comprising a VH sequence having an amino acid sequence as shown in SEQ ID NO. 21, or an amino acid sequence having at least 60% sequence identity thereto, and/or a VL sequence having an amino acid sequence as shown in SEQ ID NO. 25, or an amino acid sequence having at least 60% sequence identity thereto, preferably with the proviso that the CDR sequences of SEQ ID NOs. 22, 23, 24, 26, 27 and 28 are retained (i.e. are not modified or altered).

It will be understood, therefore, that in such embodiments, the CDR sequences of the antibodies are retained or substantially retained (i.e. they may optionally be modified within the constraints set out above, e.g. substitution, addition or deletion of 1 to 3 amino acids, such that the binding specificity of the antibody is retained (e.g. unaltered)).

The antigen binding domain is extracellular (i.e. when the CAR is expressed on an immune effector cell). The CAR thus comprises an extracellular domain comprising an antigen binding domain comprising the antibody-based VL and VH sequences as defined above. As will be described in more detail below, the extracellular domain may also comprise a signal sequence, more particularly a plasma membrane targeting sequence, and especially a plasma membrane targeting sequence based on the VL chain.

The nucleic acid molecule of the invention may be used to prepare immune effector cells (more particularly modified immune effector cells) directed against cells expressing CLEC14A. Such (modified) immune effector cells express the CAR on their cell surface and are capable of recognising, or binding to, a target cell expressing CLEC14A, e.g. an endothelial cell in a blood vessel, particularly an endothelial cell in a blood vessel in a tumour. Accordingly, the nucleic acid molecule is such that an immune effector cell expressing said CAR (i.e. the CAR encoded by the nucleic acid molecule) is capable of effector activity (e.g. cytotoxic activity) against (e.g. killing) a target cell expressing CLEC14A. A modified immune effector cell is accordingly a genetically modified or engineered immune effector cell, or alternatively expressed an immune effector cell which has been transduced with a nucleic acid molecule of the invention.

In the method of generating a CLEC14A-specific immune effector cell, the immune effector cell which is modified by introduction of the nucleic acid molecule of the invention may be obtained from a subject to be treated (e.g. a subject with a tumour). After modification of the immune effector cell, and optionally in vitro expansion, the modified immune effector cells expressing the CAR may be re-introduced (i.e. administered) to the subject. Thus, autologous immune effector cells may be used in the therapeutic compositions, methods and uses of the invention, discussed further below. Alternatively, heterologous (i.e. donor or allogeneic, or syngeneic or xenogeneic) immune effector cells may be used.

An immune effector cell may be any immune cell capable of an immune response against a target cell expressing CLEC14A. More particularly, the immune effector cell is capable of abrogating, damaging or deleting a target cell, i.e. of reducing, or inhibiting, the viability of a target cell, preferably killing a target cell (in other words rendering a target cell less or non-viable). The immune effector cell is thus preferably a cytotoxic immune effector cell.

The term “cytotoxic” is synonymous with “cytolytic” and is used herein to refer to a cell capable of inducing cell death by lysis or apoptosis in a target cell.

The term “immune effector cell” as used herein includes not only mature or fully differentiated immune effector cells but also precursor (or progenitor) cells therefor, including stem cells (more particularly haemopoietic stem cells, HSC), or cells derived from HSC. An immune effector cell may accordingly be a T-cell, NK cell, NKT cell, neutrophil, macrophage, or a cell derived from HSCs contained within the CD34+ population of cells derived from a haemopoietic tissue, e.g. from bone marrow, cord blood, or blood e.g. mobilised peripheral blood, which upon administration to a subject differentiate into mature immune effector cells. As will be described in more detail below, in preferred embodiments, the immune effector cell is a T-cell or an NK cell. Primary cells, e.g. cells isolated from a subject to be treated or from a donor subject may be used, optionally with an intervening cell culture step (e.g. to expand the cells) or other cultured cells or cell lines (e.g. NK cell lines such as the NK92 cell line).

The term “directed against the antigen CLEC14A” is synonymous with “specific for CLEC14A” or “anti-CLEC14A”, that is it means simply that the CAR is capable of binding specifically to CLEC14A. In particular, the antigen binding domain of the CAR is capable of binding specifically to CLEC14A (more particularly when the CAR is expressed on the surface of an immune effector cell). Specific binding may be distinguished from non-specific binding to a non-target antigen (in this case an antigen other than CLEC14A). Thus, an immune effector cell expressing the CAR according to the present invention is redirected to bind specifically to and exhibit cytotoxicity to (e.g. kill) a CLEC14A-expressing target cell. Alternatively expressed, the immune effector cell is modified to redirect cytotoxicity towards target cells expressing CLEC14A.

In an embodiment, specific binding to CLEC14A may mean that the antigen binding domain (or CAR comprising the antigen binding domain) binds to or associates with CLEC14A (or more particularly a target cell expressing CLEC14A on its cell surface) with an affinity or Ka (i.e. equilibrium association constant) of greater than or equal to about $10^5\ M^{-1}$, e.g. at least $10^6\ M^{-1}$, $10^7\ M^{-1}$, or $10^8\ M^{-1}$.

The binding of the antigen binding domain of the CAR to its target antigen on the surface of the target cell delivers an activation stimulus to the CAR-containing cell, resulting in induction of effector cell signalling pathways. Binding to target antigen may thereby trigger proliferation, cytokine production, phagocytosis, lytic activity and/or production of molecules that can mediate cell death of the target cell in an MHC-independent manner. Although CARs comprising an intracellular domain comprising solely a signalling domain from CD3ζ or FcRγ may deliver a potent signal for immune cell activation and effector function they may not be sufficient to elicit signals that promote immune effector cell survival and expansion in the absence of a concomitant co-stimulatory signal. Accordingly, it may be preferred for the CAR to contain one or more co-stimulatory signalling domains.

A CAR of the invention thus generally comprises 3, 4, or preferably 5, domains as follows:

(1) an antigen binding domain, capable of binding specifically to CLEC14A, that comprises VH and VL sequences based or derived from SEQ ID NOs. 1 and 5 or 41 and 45 or 21 and 25 as defined above;

(2) optionally a hinge domain that extends the antigen binding domain away from the surface of the immune effector cell;

(3) a transmembrane domain that anchors the CAR to the effector cell and links the extracellular domain comprising the antigen binding domain to the intracellular signalling domain;

(4) an intracellular domain comprising a signalling domain; and optionally or preferably;

(5) one or more co-stimulatory signalling domains.

The CAR may further comprise (6) a signal sequence (i.e. a targeting domain), and in particular a sequence which targets the CAR to the plasma membrane of the immune effector cell. This will generally be positioned next to or close to the antigen binding domain, generally upstream of the antigen binding domain, at the end of the CAR molecule/construct.

It can thus be seen that the CAR may comprise an extracellular domain comprising the antigen binding domain and signal sequence, if present, linked via an optional hinge domain and transmembrane domain to an intracellular domain which comprises one or more signalling domains. In one aspect, the intracellular domain, or the optional hinge, transmembrane and intracellular domains, may be viewed as a “signalling tail” in the CAR construct. The order of the domains in the CAR construct is thus, N-terminal to C-terminal: extracellular domain-optional hinge domain-transmembrane domain-intracellular domain. Within the extracellular and intracellular domains the separate domains may be arranged in any order. Preferably however the order is signal sequence-antigen binding domain in the extracellular domain. In one embodiment, in the intracellular domain the order may be co-stimulatory domain(s)-intracellular signalling domain(s). In another embodiment, the order may be intracellular signalling domain(s)-co-stimulatory domain(s).

In the CAR of the present invention the “antigen binding domain”, which is derived from the variable region sequences of the antibody of the invention, may be provided in various formats, as long as it comprises the VL and VH sequences as defined above. It may accordingly be, or may correspond to, a natural or synthetic antibody sequence. Accordingly, the nucleotide sequence encoding the antigen binding domain in the nucleic acid molecules of the invention may be derived from, or may correspond to a natural sequence or may encode a genetically engineered product. Thus the antigen binding domain may be (or more precisely may correspond to) a fragment of an antibody of the invention comprising the variable region (the antibody light chain and heavy chain variable regions; the VL and VH regions), e.g. a Fv or Fab or $Fab_2$ or the light and heavy chain variable regions can be joined together in a single chain and in either orientation (e.g., VL-VH or VH-VL). The VL and/or VH sequences may be modified, as discussed above. In particular the framework regions may be modified (e.g. substituted, for example to humanise the antigen binding domain).

In a preferred embodiment, the binding domain is a single chain antibody (scFv) derived from the antibody of the invention, e.g. based on or derived from SEQ ID NO. 9, 29, 49, 50 or 51.

In one preferred embodiment the VL and VH are linked together by a linker sequence. More precisely this may be referred to as a “variable region linker sequence”, which is an amino acid sequence that connects a heavy chain variable region to a light chain variable region and provides a spacer function compatible with interaction of the two sub-binding domains so that the resulting polypeptide retains a specific binding affinity to the same target molecule as an antibody that comprises the same light and heavy chain variable regions. The linker sequence may be used to provide for appropriate spacing and conformation of the molecule.

Thus, in one embodiment the scFv comprises the VH sequence of SEQ ID NO. 1 or 41 or a sequence having at least 95% sequence identity thereto linked to the VL sequence of SEQ ID NO.5 or 45 or a sequence having at least 95% sequence identity thereto, preferably in the order VL-VH.

In a further embodiment the scFv comprises the VH sequence of SEQ ID NO. 21 or a sequence having at least 95% sequence identity thereto linked to the VL sequence of SEQ ID NO.25 or a sequence having at least 95% sequence identity thereto, preferably in the order VL-VH.

In another embodiment, the scFv comprises the VH sequence of SEQ ID NO. 1 or 41 or a sequence having at least 60% sequence identity thereto linked to the VL sequence of SEQ ID NO.5 or 45 or a sequence having at least 60% sequence identity thereto, preferably in the order VL-VH. As noted above, this is subject to the proviso that the CDR sequences remain as defined above, and preferably to the proviso that the CDR sequences are unaltered.

In a further embodiment, the scFv comprises the VH sequence of SEQ ID NO. 21 or a sequence having at least 60% sequence identity thereto linked to the VL sequence of SEQ ID NO.25 or a sequence having at least 60% sequence identity thereto, preferably in the order VL-VH. As noted above, this is subject to the proviso that the CDR sequences remain as defined above, and preferably to the proviso that the CDR sequences are unaltered.

More preferably, the VL sequence is linked to VH by a linker sequence. The linker sequence may be between 1-30, more preferably 1-25, 1-22 or 1-20, amino acids long. The linker may be a flexible linker. Suitable linkers can be readily selected and can be of any of a suitable length, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids or longer.

Exemplary flexible linkers include glycine polymers (G)n, glycine-serine polymers, where n is an integer of at least one, glycine-alanine polymers, alanine-serine polymers, and other flexible linkers known in the art. Glycine and glycine-serine polymers are relatively unstructured, and therefore may be able to serve as a neutral tether between domains of fusion proteins such as the CARs described herein. In a representative embodiment the linker sequence may be $(G_4S)_3$ (SEQ ID NO. 65).

Thus in a representative embodiment the nucleic acid molecule of the invention may comprise a nucleotide sequence encoding the amino acid sequence of SEQ ID NO. 9, comprising in order the VH of SEQ ID NO.1, the linker of SEQ ID NO.65 and the VL of SEQ ID NO.5, or a sequence having at least 95% sequence identity thereto.

In another representative embodiment the nucleic acid molecule of the invention may comprise a nucleotide sequence encoding the amino acid sequence of SEQ ID NO. 49, comprising in order the VH of SEQ ID NO. 41, the linker of SEQ ID NO.65 and the VL of SEQ ID NO.5, or a sequence having at least 95% sequence identity thereto.

In yet another representative embodiment the nucleic acid molecule of the invention may comprise a nucleotide sequence encoding the amino acid sequence of SEQ ID NO. 50, comprising in order the VH of SEQ ID NO. 1, the linker of SEQ ID NO.65 and the VL of SEQ ID NO.45, or a sequence having at least 95% sequence identity thereto.

In still another representative embodiment the nucleic acid molecule of the invention may comprise a nucleotide sequence encoding the amino acid sequence of SEQ ID NO. 51, comprising in order the VH of SEQ ID NO. 41, the linker of SEQ ID NO.65 and the VL of SEQ ID NO.45, or a sequence having at least 95% sequence identity thereto.

In a representative embodiment, the nucleic acid molecule of the invention may comprise a nucleotide sequence encoding the amino acid sequence of SEQ ID NO.10, comprising the VH of SEQ ID NO.1 and the VL of SEQ ID NO.5, or a sequence having at least 95% sequence identity thereto. Thus, the nucleic acid molecule of the invention may comprise a nucleotide sequence comprising SEQ ID NO. 20, or a sequence having at least 95% sequence identity thereto.

In another representative embodiment, the nucleic acid molecule of the invention may comprise a nucleotide sequence encoding the amino acid sequence of SEQ ID NO. 30, comprising the VH of SEQ ID NO.21 and the VL of SEQ ID NO.25, or a sequence having at least 95% sequence identity thereto. Thus, the nucleic acid molecule of the invention may comprise a nucleotide sequence comprising SEQ ID NO. 40, or a sequence having at least 95% sequence identity thereto.

In some embodiments, the VH and VL regions may be encoded by nucleotide sequences comprising the nucleotide sequences of SEQ ID NOs. 11 and 15, respectively, or nucleotide sequences having at least 95% nucleotide sequence identity thereto.

In some embodiments, the VH and VL regions may be encoded by nucleotide sequences comprising the nucleotide sequences of SEQ ID NOs. 54 and 58 respectively, or nucleotide sequences having at least 95% nucleotide sequence identity thereto.

In some embodiments, the VH and VL regions may be encoded by nucleotide sequences comprising the nucleotide sequences of SEQ ID NOs. 31 and 35 respectively, or nucleotide sequences having at least 95% nucleotide sequence identity thereto.

In another embodiment, the VH and VL regions may be encoded by nucleotide sequences comprising the nucleotide sequences of SEQ ID NOs. 11 and 15 respectively or SEQ ID NOs. 54 and 58, respectively, or nucleotide sequences having at least 60% nucleotide sequence identity thereto. As above, this is subject to the proviso that the CDR sequences encoded by the nucleotide sequences remain as defined above, and preferably to the proviso that the CDR sequences are unaltered.

In yet another embodiment, the VH and VL regions may be encoded by nucleotide sequences comprising the nucleotide sequences of SEQ ID NOs. 31 and 35 respectively, or nucleotide sequences having at least 60% nucleotide sequence identity thereto. As above, this is subject to the proviso that the CDR sequences encoded by the nucleotide sequences remain as defined above, and preferably to the proviso that the CDR sequences are unaltered.

The VL and VH sequences may, if desired, be humanised by modifying one or more of the framework regions to correspond to at least one human framework region. A "human framework region" refers to a wild type (i.e., naturally occurring) framework region of a human immunoglobulin variable region, an altered framework region of a human immunoglobulin variable region with less than about 50% (e.g., preferably less than about 45%, 40%, 30%, 25%, 20%, 15%, 10%, 5%, or 1%) of the amino acids in the region deleted or substituted (e.g., with one or more amino acid residues of a non-human immunoglobulin framework region at corresponding positions), or an altered framework region of a nonhuman immunoglobulin variable region with less than about 50% (e.g., less than 45%, 40%, 30%, 25%, 20%, 15%, 10%, or 5%) of the amino acids in the region deleted or substituted (e.g., at positions of exposed residues and/or with one or more amino acid residues of a human immunoglobulin framework region at corresponding positions) so that, in one aspect, immunogenicity is reduced.

Thus, in a particular embodiment, the framework regions of the VH sequences of SEQ ID NOs. 1, 21 and 41 and the VL sequences of SEQ ID NOs. 5, 25 and 45 may be modified (more specifically the amino acid sequences of the framework regions may be modified), whilst retaining, or substantially retaining, the amino acid sequences of the CDRs.

Accordingly, in another embodiment, the framework regions of the VH sequences in the CAR have at least 60% amino acid sequence identity to the framework regions of SEQ ID NOs. 1, 21 and 41 and/or the framework regions of the VL sequences in the CAR have at least 60% amino acid sequence identity to the framework regions of SEQ ID NOs. 5, 25 and 45.

As noted above, the CAR, and more particularly the extracellular domain thereof, may also comprise a signal sequence (or targeting domain). Such a sequence will generally be provided at the N-terminal end of the molecule (construct) and may function to, co-translationally or post-translationally, direct transfer of the molecule. In particular, the signal sequence may be a sequence which targets the CAR to the plasma membrane of the immune effector cell. This may be linked directly or indirectly (e.g. via a linker sequence) to the antigen binding domain, generally upstream of the antigen binding domain, at the N-terminal end of the CAR molecule/construct. The linker sequence may be a linker as described in connection with the variable region linker above. In one embodiment the signal sequence is linked directly to the N-terminal end of the antigen binding domain, e.g. to the N-terminal end of the VL sequence.

The antigen binding domain of the CAR is optionally followed by a hinge domain. The hinge region in a CAR is generally between the transmembrane domain and the antigen binding domain. In certain embodiments, a hinge region is an immunoglobulin hinge region and may be a wild type immunoglobulin hinge region or an altered wild type immunoglobulin hinge region, for example a truncated hinge region. Other exemplary hinge regions which may be used include the hinge region derived from the extracellular regions of type 1 membrane proteins such as CD8α, CD4, CD28 and CD7, which may be wild-type hinge regions from these molecules or may be altered. Preferably the hinge region is, or is derived from, the hinge region of human CD8α, CD4, CD28 or CD7. The hinge region is alternatively (and interchangeably) referred to as a spacer or spacer region.

An "altered wild type hinge region" or "altered hinge region" or "altered spacer" refers to (a) a wild type hinge region with up to 30% amino acid changes (e.g. up to 25%, 20%, 15%, 10%, or 5% amino acid changes e.g. substitutions or deletions), (b) a portion of a wild type hinge region that is at least 10 amino acids (e.g., at least 12, 13, 14 or 15 amino acids) in length with up to 30% amino acid changes (e.g., up to 25%, 20%, 15%, 10%, or 5% amino acid changes, e.g. substitutions or deletions), or (c) a portion of a wild type hinge region that comprises the core hinge region (which may be 4, 5, 6, 7, 8, 9, 10, 11, 12, 13, 14, or 15, or at least 4, 5, 6, 7, 8, 9, 10, 11, 12, 13, 14, or 15 amino acids in length). When an altered wild type hinge region is interposed between and connecting the CLEC14A-specific binding domain and another region (e.g., a transmembrane domain) in the chimeric antigen receptors described herein, it allows the chimeric fusion protein to maintain specific binding to CLEC14A.

In certain embodiments, one or more cysteine residues in a wild type immunoglobulin hinge region may be substituted by one or more other amino acid residues (e.g., one or more serine residues). An altered immunoglobulin hinge region may alternatively or additionally have a proline residue of a wild type immunoglobulin hinge region substituted by another amino acid residue (e.g., a serine residue).

Hinge regions comprising the CH2 and CH3 constant region domains are described in the art for use in CARs (for example the CH2CH3 hinge, referred to as as an "Fc hinge" or "IgG hinge", as shown in SEQ ID NO.72). However, it is preferred that when the hinge domain is based on or derived from an immunoglobulin it does not comprise a CH3 domain, e.g. it may comprise or consist of the CH2 domain or a fragment or part thereof, without including CH3.

In one preferred embodiment the hinge domain has or comprises the amino acid sequence of SEQ ID NO. 66 (which represents the hinge domain of CD8α) or an amino acid sequence having at least 95% sequence identity thereto.

In another preferred embodiment the hinge domain has or comprises the amino acid sequence of SEQ ID NO. 67 (which represents a shortened IgG hinge) or an amino acid sequence having at least 95% sequence identity thereto.

The hinge domain may be attached to the transmembrane domain by a linker sequence, which may be a linker sequence as defined above. An exemplary linker sequence is KDPK (SEQ ID NO.68). A shortened IgG hinge with linker sequence is shown in SEQ ID NO.69. Such a sequence, or a sequence having at least 95% sequence identity thereto, may be included in a CAR of the present invention. More particularly such a sequence may be included between the extracellular domain (e.g. the scFv part) and the transmembrane domain.

The transmembrane domain may be based on or derived from the transmembrane domain of any transmembrane protein. Typically it may be, or may be derived from, a transmembrane domain from CD8α, CD28, CD4, CD3ζ CD45, CD9, CD16, CD22, CD33, CD64, CD80, CD86, CD134, CD137, and CD154, preferably from a human said protein. In one embodiment, the transmembrane domain may be, or may be derived from, a transmembrane domain from CD8α, CD28, CD4, or CD3ζ, preferably from human CD28, CD4, or CD3ζ. In another embodiment the transmembrane domain may be synthetic in which case it would comprise predominantly hydrophobic residues such as leucine and valine.

In a preferred embodiment the transmembrane domain is the CD8α transmembrane domain having the amino acid sequence of SEQ ID NO. 70 or an amino acid sequence having at least 95% sequence identity thereto. This transmembrane sequence may further be attached to a hinge domain from CD8α as shown in SEQ ID NO. 66, or a sequence having at least 95% sequence identity thereto.

In another embodiment the transmembrane domain may be the transmembrane domain of human CD28 having the amino acid sequence of SEQ ID NO. 71 or an amino acid sequence having at least 95% sequence identity thereto.

The "intracellular signalling domain" refers to the part of the CAR protein that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. The term "effector function" refers to a specialized function of the cell. Effector function of the T cell, for example, may be cytolytic activity or help or activity including the secretion of a cytokine. Thus, the term "intracellular signalling domain" refers to the portion of a protein which transduces the effector function signal and that directs the cell to perform a specialized function. While the entire intracellular signalling domain can be employed, in many cases it is not necessary to use the entire domain. To the extent that a truncated portion of an intracellular signalling domain is used, such truncated portion may be used in place of the entire domain as long as it transduces the effector function signal. The term intracellular signalling domain is meant to include any truncated portion of the intracellular signalling domain sufficient to transduce effector function signal. The intracellular signalling domain is also known as the, "signal transduction domain," and is typically derived from portions of the human CD3ζ or FcRy chains.

Additionally to allow or to augment full activation of the immune effector cell the CAR may be provided with a secondary, or co-stimulatory domain. Thus, the intracellular signalling domain may initiate antigen dependent primary activation (i.e. may be a primary cytoplasmic signalling sequence) and the co-stimulatory domain may act in an antigen independent manner to provide a secondary or co-stimulatory signal (secondary cytoplasmic signalling sequence(s)). Primary cytoplasmic signalling sequences may regulate primary activation, including in an inhibitory way. Primary cytoplasmic signalling sequences that act in a co-stimulatory manner may contain signalling motifs which are known as immunoreceptor tyrosine-based activation motif or ITAMs.

Examples of ITAM containing primary cytoplasmic signalling sequences that may be used in the invention include those derived from TCRζ, FcRy, FcRβ, CD3γ, CD3δ, CD3ε, CD5, CD22, CD79a, CD79b and CD66d. In certain particular embodiments, the intracellular signalling domain is derived from CD3ζ or FcRγ, preferably human CD3ζ or FcRγ.

In a preferred representative embodiment the intracellular signalling domain is preferably a human CD3ζ domain, more preferably a human CD3ζ domain having the amino acid sequence of SEQ ID NO.73 or an amino acid sequence having at least 95% sequence identity thereto.

The term "co-stimulatory signalling domain" or "co-stimulatory domain", refers to the portion of the CAR comprising the intracellular domain of a co-stimulatory molecule. Co-stimulatory molecules are cell surface molecules other than antigen receptors or Fc receptors that provide a second signal that is typically required for efficient activation and function of an immune effector cell (e.g. a T-cell) upon binding to antigen. Examples of such co-stimulatory molecules include CD27, CD28, 4-IBB (CD137), OX40 (CD134), CD30, CD40, ICOS (CD278), LFA-1, CD2, CD7, LIGHT, NKD2C, B7-H2 and a ligand that specifically binds CD83, more particularly the intracellular domains of such molecules. However, in some embodiments, the co-stimulatory molecule provides a second signal that prevents stimulation of an immune effector cell (e.g. a T-cell) upon binding to a ligand. For instance, and as discussed below in more detail, it may be useful to provide an immune effector cell comprising more than one CAR, wherein a second CAR is capable of binding to a ligand presented on non-target cells, e.g. non-tumour cells, such that if the second (or further) CAR binds to its ligand, it provides a negative signal preventing stimulation of the immune effector cell. Examples of such co-stimulatory molecules include PD-1 and CTLA4. Preferably the molecules are human. Accordingly, while exemplary or preferred co-stimulatory domains are derived from 4-1BB, CD28 or OX40 (CD134), other co-stimulatory domains are contemplated for use with the CARs described herein. The co-stimulatory domains may be used singly or in combination (i.e. one or more co-stimulatory domains may be included). The inclusion of one or more co-stimulatory signalling domains may enhance the efficacy and expansion of immune effector cells expressing the CARs.

The intracellular signalling and co-stimulatory signalling domains may be linked in any order in tandem to the carboxyl terminus of the transmembrane domain.

In a preferred embodiment the co-stimulatory domain is the intracellular domain of 4-1BB having the amino acid sequence of SEQ ID NO. 74 or an amino acid sequence having at least 95% sequence identity thereto.

In another embodiment the co-stimulatory domain may be, or may include, the intracellular domain of human CD28 having the amino acid sequence of SEQ ID NO. 75 or an amino acid sequence having at least 95% sequence identity thereto and/or an OX40 (CD134) co-stimulatory domain having the amino acid sequence of SEQ ID NO. 76 or an amino acid sequence having at least 95% sequence identity thereto.

In a preferred embodiment of the invention, the CAR (or more particularly the "signalling tail" thereof) comprises an optional hinge domain from CD8α or a truncated IgG hinge domain not including the CH3 domain, a CD8α transmembrane domain, a 4-1BB co-stimulatory domain and a CD3ζ intracellular signalling domain.

In other embodiments the CAR (or the "signalling tail" thereof) comprises an optional hinge domain from CD8α or a truncated IgG hinge domain not including the CH3 domain, a CD28 transmembrane domain, a CD28 intracellular domain and/or OX40 co-stimulatory domain and a CD3ζ intracellular signalling domain.

Further, the polynucleotide of the invention may encode a CAR comprising 1) transmembrane and costimulatory domains from CD28 and an intracellular signalling domain from CD3 zeta; 2) a transmembrane domain from CD8α, a costimulatory domain from 4-1BB and an intracellular signalling domain from CD3 zeta; 3) a transmembrane domain from CD8α, a costimulatory domain from OX40 and an intracellular signalling domain from CD3 zeta; 4) a transmembrane domain from CD28, costimulatory domains from CD28 and 4-1BB and an intracellular signalling domain from CD3 zeta; 5) a transmembrane domain from CD28, costimulatory domains from CD28 and OX40 and an intracellular signalling domain from CD3 zeta; 6) a transmembrane domain from CD8α, costimulatory domains from 4-1BB and OX40 and an intracellular signalling domain from CD3 zeta; 7) a transmembrane domain from CD8α, a costimulatory domain from CD28 and an intracellular signalling domain from CD3 zeta; 8) a transmembrane domain from CD8α, costimulatory domains from CD28 and 4-1BB and an intracellular signalling domain from CD3 zeta or 9) a transmembrane domain from CD8α, costimulatory domain from CD28 and OX40 and an intracellular signalling domain from CD3 zeta. Particularly, any one of the constructs comprising a transmembrane domain from CD8α may further comprise a hinge or spacer domain which is also derived from CD8α.

Such a CAR according to the invention may include a scFv antigen binding domain as defined above and may further comprises a plasma membrane targeting sequence positioned upstream of the scFv.

Thus the CAR of the invention may in certain representative embodiments comprise, in addition to a signalling tail as defined above, an extracellular domain having the sequence of SEQ ID NO. 9, 19, 49, 50 or 51 or a sequence having at least 95% sequence identity thereto.

A representative CAR according to the present invention may thus have or comprise the amino acid sequence of SEQ ID NO. 10 or 30, or an amino acid having at least 95% sequence identity thereto.

A nucleic acid molecule of the invention may comprise the nucleotide sequence of SEQ ID NO.20 or SEQ ID NO.40 or a nucleotide sequence having at least 95% sequence identity thereto.

The present disclosure provides CAR polypeptides, and fragments thereof. Particularly, the invention provides CARs encoded by a nucleic acid molecule of the invention as previously defined. The terms "polypeptide" "protein" and are used interchangeably and mean a polymer of amino acids not limited to any particular length. The term does not exclude modifications such as myristylation, sulfation, glycosylation, phosphorylation and addition or deletion of signal sequences. The terms "polypeptide" or "protein" or "peptide" mean one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass the CARs of the present disclosure, or sequences that have deletions from, additions to, and/or substitutions of one or more amino acid of a CAR as disclosed herein.

As is clear from the above, the various domains of the CAR may comprise one or more amino acid sequence modifications with respect to the native sequences of the molecules from which they are derived. For example, it may be desirable to improve the binding affinity and/or other biological properties of the CAR. For example, amino acid sequence variants of a CAR, or binding domain, or a stimulatory signalling domain thereof, may be prepared by introducing appropriate nucleotide changes into a polynucleotide that encodes the CAR, or a domain thereof. Such modifications include, for example, deletions from, and/or insertions into and/or substitutions of, residues within the amino acid sequences of the CAR. Any combination of deletion, insertion, and substitution may be made to arrive at the final CAR, provided that the final construct possesses the desired characteristics, such as specific binding to CLEC14A by the binding domain, or increased signalling by the intracellular signalling domain and/or co-stimulatory domain. The amino acid changes also may alter post-translational processes of the CAR, such as changing the number or position of glycosylation sites. Any of the variations and modifications described above may be included in the CARs of the present invention.

In particular embodiments, the various domains of a CAR (other than the VL and VH sequences) may have an amino acid sequence that is at least 80% identical, at least 85%, at least 90%, at least 95% identical, or at least 98% or 99% identical, to the native sequence of the domains of the proteins from which they are derived. Thus, in particular embodiments the domains may have an amino acid sequence that has at least 80, 85, 90, 95, 98 or 99% sequence identity to any of SEQ ID NOs. 66-76.

It will be appreciated by those of ordinary skill in the art that, as a result of the degeneracy of the genetic code, there are many nucleotide sequences that may encode a CAR as described herein.

The nucleic acid molecule may be introduced into a host cell, particularly an immune effector cell, as mRNA or as DNA for expression in the cell. Vectors may be used to transfer the nucleic acid molecule into the cell or to produce the nucleic acid for transfer (e.g. to produce mRNA for transfer, or to produce a nucleic acid molecule for preparation of an expression vector for transfer into a cell).

Accordingly, a further aspect of the invention provides a vector comprising the nucleic acid molecule of the invention as defined herein.

The vector may for example be an mRNA expression vector, a cloning vector or an expression vector for transfer into an immune cell e.g. a viral vector.

Thus, another aspect of the invention provides a virus comprising the nucleic acid molecule or vector of the invention as defined herein.

Another aspect of the invention provides a host cell, particularly an immune effector cell, comprising a nucleic acid molecule or vector (or CAR) of the invention as defined herein.

In preferred embodiments the immune effector cell may be a T-cell or an NK cell.

Also provided is a method of generating a host cell, particularly a CLEC14A-specific immune effector cell, said method comprising introducing a nucleic acid molecule or vector of the invention as defined herein into a host cell, particularly an immune effector cell.

Such a method may comprise stimulating the cell and inducing it to proliferate before and/or after introducing the nucleic acid molecule or vector.

The nucleic acid molecules and vectors of the invention may be introduced to a host cell to produce an antibody or CAR of the invention. Thus, a still further aspect of the invention is a method of producing an antibody or CAR of the invention comprising culturing a host cell comprising a nucleic acid molecule or vector of the invention under conditions whereby said antibody is expressed and recovering said molecule thus produced.

Vectors or constructs (nucleic acid molecules) may be introduced into a cell of the invention by a variety of means, including chemical transfection agents (such as calcium phosphate, branched organic compounds, liposomes or cationic polymers), electroporation, cell squeezing, sonoporation, optical transfection, hydrodynamic delivery, or viral transduction. In a preferred embodiment, a vector or construct is introduced by viral transduction. This may allow for more persistent expression of the CAR. However, in some situations, e.g. in clinical trials, or in some clinical situations, it may be desirable to have a more transient period of expression of CAR protein. In such a situation it may be desirable to deliver the nucleic acid molecule to the immune effector cell as mRNA. mRNA expression vectors for production of mRNA may be prepared according to methods known in the art (e.g. using Gateway Technology) and are known in the art (e.g. pCIpA102, Sæbøze-Larssen et al, 2002. J. Immunol. Methods 259, p 191-203 and pCIpA120-G, Wälchli et al, 2011, PLoS ONE 6 (11) e27930).

The mRNA can be produced in vitro by e.g. in vitro transcription. The mRNA may then be introduced into the immune effector cells, e.g. as naked mRNA, e.g. by electroporation (as described for example in Almasbak et al., Cytotherapy 2011, 13, 629-640, Rabinovich et al., Hum. Gene Ther., 2009, 20, 51-60 and Beatty et al., Cancer Immunol. Res. 2014, 2, 112-120). Alternatively, mRNA may be introduced by other means such as by liposomes or cationic molecules etc. Heterologous nucleic acid molecules introduced into a cell may be expressed episomally, or may be integrated into the genome of the cell at a suitable locus.

It is within the scope of the invention to include gene segments that cause the immune effector cells of the invention, e.g., T cells, to be susceptible to negative selection in vivo. By "negative selection" is meant that the infused cell can be eliminated as a result of a change in the in vivo condition of the individual. The negative selectable phenotype may result from the insertion of a gene (e.g. a so-called suicide gene) that confers sensitivity to an administered agent, for example, a compound. Negative selectable genes are known in the art, and include, inter alia the following: the Herpes simplex virus type I thymidine kinase (HSV-I TK) gene (Wigler et al., Cell 11 (1):223-232, 1977) which confers ganciclovir sensitivity; the cellular hypoxanthine-phosphribosyltransferase (HPRT) gene, the cellular adenine phosphoribosyltransferase (APRT) gene, bacterial cytosine deaminase, (Mullen et al., Proc. Natl. Acad. Sci. USA. 89:33-37 (1992)).

In some embodiments it may be useful to include in the genetically modified immune effector cells, such as T cells, a positive marker that enables the selection of cells of the negative selectable phenotype in vitro. The positive selectable marker may be a gene which, upon being introduced into the host cell expresses a dominant phenotype permitting positive selection of cells carrying the gene. Genes of this type are known in the art, and include, inter alia, hygromycin-B phosphotransferase gene (hph) which confers resistance to hygromycin B, the amino glycoside phosphotransferase gene (neo or aph) from Tn5 which codes for resistance to the antibiotic G418, the dihydrofolate reductase (DHFR) gene, the adenosine deaminase gene (ADA), and the multi-drug resistance (MDR) gene. Other positive selectable markers may include genes that encode proteins that are expressed in or on the cell membrane, which permit sorting of the transduced cells, e.g. a gene encoding a fluorescent protein, such as GFP, which would enable transduced cells to be selected using fluorescence activated cell sorting (FACS). Any suitable positive selectable marker may be used in the present invention.

Preferably, the positive selectable marker and the negative selectable element are linked such that loss of the negative selectable element necessarily also is accompanied by loss of the positive selectable marker. Even more preferably, the positive and negative selectable markers are fused so that loss of one obligatorily leads to loss of the other. An example of a fused polynucleotide that yields as an expression product a polypeptide that confers both the desired positive and negative selection features described above is a hygromycin phosphotransferase thymidine kinase fusion gene (HyTK). Expression of this gene yields a polypeptide that confers hygromycin B resistance for positive selection in vitro, and ganciclovir sensitivity for negative selection in vivo. See Lupton S. D., et al, Mol. and Cell. Biology 11:3374-3378, 1991.

In some embodiments, it may be desirable to express a polypeptide from the CAR expressing vector of the invention, to allow detection of the expression of the CAR in the immune effector cell. Thus, it may be possible to identify the successful transduction of an immune effector cell with the vector and the successful expression of a CAR molecule by detecting the expression of a further polypeptide under the control of the same (or a different promoter) to the nucleotide sequence encoding the CAR. Particularly, the CAR molecules of the invention may additionally comprise a CD34 molecule or a modified CD34 molecule, e.g. a truncated CD34 molecule, where such a molecule comprises an extracellular portion which allows its detection by well-known techniques, e.g. immunofluorescence using a suitable antibody and label. In a particular embodiment, the vector of the invention may additionally comprise the nucleotide sequence of SEQ ID NO. 77, or a nucleotide sequence having at least 80% sequence identity thereto. Alternatively viewed, the vector may additionally encode an amino acid sequence of SEQ ID NO. 78 or a sequence having at least 80% sequence identity thereto.

An "immune effector cell" is any cell of the immune system that has one or more effector functions (e.g., cytotoxic cell killing activity, secretion of cytokines, induction of ADCC and/or CDC). Representative immune effector cells thus include T lymphocytes, in particular cytotoxic T cells (CTLs; CD8+ T cells) and helper T cells (HTLs; CD4+ T cells). Other populations of T cells are also useful herein, for example naive T cells and memory T cells. Other immune effector cells include NK cells, NKT cells, neutrophils, and macrophages. As noted above, immune effector cells also include progenitors of effector cells, wherein such progenitor cells can be induced to differentiate into an immune effector cells in vivo or in vitro.

T-cells, particularly CD8+ T-cells, and NK cells represent preferred immune effector cells according to the invention.

The term "NK cell" refers to a large granular lymphocyte, being a cytotoxic lymphocyte derived from the common lymphoid progenitor which does not naturally comprise an antigen-specific receptor (e.g. a T-cell receptor or a B-cell receptor). NK cells may be differentiated by their $CD3^-$, $CD56^+$ phenotype. The term as used herein thus includes any known NK cell or any NK-like cell or any cell having the characteristics of an NK cell. Thus primary NK cells may be used or in an alternative embodiment, a NK cell known in the art that has previously been isolated and cultured may be used. Thus a NK cell-line may be used. A number of different NK cells are known and reported in the literature and any of these could be used, or a cell-line may be prepared from a primary NK cell, for example by viral transformation (Vogel et al. 2014, Leukaemia 28:192-195). Suitable NK cells include (but are by no means limited to), in addition to NK-92, the NK-YS, NK-YT, MOTN-1, NKL, KHYG-1, HANK-1, or NKG cell lines. In a preferred embodiment, the cell is an NK-92 cell (Gong et al. 1994, Leukaemia 8:652-658), or a variant thereof. A number of different variants of the original NK-92 cells have been prepared and are described or available, including NK-92 variants which are non-immunogenic. Any such variants can be used and are included in the term "NK-92". Variants of other cell lines may also be used.

Where the immune effector cell is a non-autologous cell for therapeutic use (i.e. is a donor cell) it is preferred that it is non-immunogenic, such that it does not, when administered to a subject, generate an immune response which affects, interferes with, or prevents the use of the cells in therapy.

NK cells may be naturally non-immunogenic, but NK cells or other immune effector cells may be modified to be non-immunogenic. Naturally non-immunogenic NK cells will not express the MHC molecule or only weakly express the MHC molecule, or may express a non-functional MHC molecule which does not stimulate an immunological response. Immune effector cells which would be immunogenic may be modified to eliminate expression of the MHC molecule, or to only weakly express the MHC molecule at their surface. Alternatively, such cells may be modified to express a non-functional MHC molecule.

Any means by which the expression of a functional MHC molecule is disrupted is encompassed. Hence, this may include knocking out or knocking down a molecule of the MHC complex, and/or it may include a modification which prevents appropriate transport to and/or correct expression of an MHC molecule, or of the whole complex, at the cell surface.

In particular, the expression of one or more functional MHC class-I proteins at the surface of a cell of the invention may be disrupted. In one embodiment the cells may be human cells which are H LA-negative and accordingly cells in which the expression of one or more HLA molecules is disrupted (e.g. knocked out), e.g. molecules of the HLA MHC class I complex.

In a preferred embodiment, disruption of MHC class-I may be performed by knocking out the gene encoding $\beta_2$-microglobulin ($\beta_2$m), a component of the mature MHC class-I complex. Expression of $\beta_2$m may be eliminated through targeted disruption of the $\beta_2$m gene, for instance by site-directed mutagenesis of the $\beta_2$m promoter (to inactivate the promoter), or within the gene encoding the $\beta_2$m protein to introduce an inactivating mutation that prevents expression of the $\beta_2$m protein, e.g. a frame-shift mutation or premature 'Stop' codon within the gene. Alternatively, site-directed mutagenesis may be used to generate non-functional $\beta_2$m protein that is not capable of forming an active MHC protein at the cell surface. In this manner the $\beta_2$m protein or MHC may be retained intracellularly, or may be present but non-functional at the cell surface.

Immune effector cells may alternatively be irradiated prior to being administered to a subject. Without wishing to be bound by theory, it is thought that the irradiation of cells results in the cells only being transiently present in a subject, thus reducing the time available for a subject's immune system to mount an immunological response against the cells. Whilst such cells may express a functional MHC molecule at their cell surface, they may also be considered to be non-immunogenic. Radiation may be from any source of $\alpha$, $\beta$ or $\gamma$ radiation, or may be X-ray radiation or ultraviolet light. A radiation dose of 5-10 Gy may be sufficient to abrogate proliferation, however other suitable radiation doses may be 1-10, 2-10, 3-10, 4-10, 6-10, 7-10, 8-10 or 9-10 Gy, or higher doses such as 11, 12, 13, 14, 15 or 20 Gy. Alternatively, the cells may be modified to express a 'suicide gene', which allows the cells to be inducibly killed or prevented from replicating in response to an external stimulus.

Thus, an immune effector cell according to the invention may be modified to be non-immunogenic by reducing its ability, or capacity, to proliferate, that is by reducing its proliferative capacity.

The modified immune effector cells of the invention may also be subject to modification in other ways, for example to alter or modify other aspects of cell function or behaviour, and/or to express other proteins. For instance, the cells may be modified to express a homing receptor, or localisation receptor, which acts to target or improve the localisation of the cells to a particular tissue or location in the body.

For instance, it may be desirable to make further modifications to immune effector cells transduced with or to be transduced with a vector or nucleic acid of the invention. In particular, modifications to immune cells which prolong or enhance their response to CLEC14A may be desirable. For example, it is known that TGFβ is secreted by tumours and that this may suppress the induction of T cells. In this respect, it may be desirable for the modified immune effector cells e.g. T cells, of the invention (i.e. those transduced with a nucleic acid or a vector of the invention), to be capable of neutralising the effect of TGFβ, e.g. by expressing a dominant-negative TGFβ receptor II. Additionally, or alternatively, an immune effector cell of the invention may be transduced with a nucleic acid encoding a cytokine, e.g. IL-15, or IL-2, IL-7, IL-12 etc., which may enhance the effector function of the cell. Any additional nucleic acid sequences may be expressed from the same or a different vector to the CAR molecule.

It will further be appreciated that an immune effector cell of the invention may comprise more than one nucleic acid or vector of the invention. Particularly, an immune effector cell of the invention may comprise 2, 3, 4 or 5 or more nucleic acids or vectors of the invention which each express a different CAR molecule. Thus, an immune effector cell of the invention may comprise different CAR molecules which are capable of binding to CLEC14A, e.g. at the same or different positions on CLEC14A.

Thus, in some embodiments, the immune effector cell of the invention comprises more than one of the nucleic acid molecules described below, e.g. 2, 3 or 4 of the nucleic acid molecules described below, such as a nucleic acid molecule encoding an antigen binding domain comprising (1) and a nucleic acid molecule encoding an antigen binding domain comprising (2), wherein each said nucleic acid molecule encodes a CAR directed against the antigen CLEC14A, wherein said CAR when expressed on the surface of an immune effector cell is capable of binding to the antigen CLEC14A expressed on a target cell surface and comprises an antigen binding domain comprising:

(1) (a) a VH CDR sequence comprising:

(i) a VH CDR1 that has the amino acid sequence of SEQ ID NO: 2 or 42; and/or (ii) a VH CDR2 that has the amino acid sequence of SEQ ID NO: 3 or 43; and/or (iii) a VH CDR3 that has the amino acid sequence of SEQ ID NO: 4 or 44; and/or (b) a VL CDR sequence comprising:

(i) a VL CDR1 that has the amino acid sequence of SEQ ID NO: 6 or 46; and/or (ii) a VL CDR2 that has the amino acid sequence of SEQ ID NO: 7 or 47; and/or (vi) a VL CDR3 that has the amino acid sequence of SEQ ID NO: 8 or 48; and/or one or more sequences substantially homologous to the SEQ ID NOs set forth in (a) or (b); or (2) (a) a VH CDR sequence comprising:

(i) a VH CDR1 that has the amino acid sequence of SEQ ID NO: 22; and/or (ii) a VH CDR2 that has the amino acid sequence of SEQ ID NO: 23; and/or (iii) a VH CDR3 that has the amino acid sequence of SEQ ID NO: 24; and/or (b) a VL CDR sequence comprising:

(i) a VL CDR1 that has the amino acid sequence of SEQ ID NO: 26; and/or (ii) a VL CDR2 that has the amino acid sequence of SEQ ID NO: 27; and/or (iii) a VL CDR3 that has the amino acid sequence of SEQ ID NO: 28; and/or one or more sequences substantially homologous to the SEQ ID NOs set forth in (a) or (b). In some embodiments, an immune effector cell of invention may comprise at least one other receptor, particularly an exogenous receptor, (e.g. multiple receptors) in addition to the expressed CAR(s) of the invention, which may be used together with the CAR in a combinatorial approach to bind to the target cells (e.g. CLEC14A expressing tumour cells, e.g. tumour vasculature). Thus, in such an approach, binding of both the CAR and the at least one other receptor to the target cell may be required to stimulate an immune response against the target cell (e.g. each CAR/receptor may only provide a partial signal for immune cell stimulation, which alone may not be sufficient for immune cell stimulation but together allows for immune effector cell stimulation). In the case where the immune effector cell of the invention is a T cell, the CAR(s) binding to CLEC14A and the at least one other receptor binding to its ligand on the CLEC14A expressing cell may be necessary to stimulate the T cell. The at least one other receptor may be a further CAR molecule.

In a variation of this embodiment, a CAR within an immune effector cell of the invention may be inducibly expressed. Particularly, in this embodiment, the binding of the at least one other receptor expressed on the immune effector cell to its target may allow or control the expression of the CAR molecule. Thus, in this instance, the binding of the at least one other receptor to its ligand is required before CAR expression occurs, and immune effector cell stimulation thus requires the binding of the at least one other receptor to its ligand and the subsequent binding of the CAR to the target cell. Such a particular system may comprise the additional expression of a SynNotch receptor, which is engineered with an extracellular ligand binding domain directed to an antigen of interest e.g. CD19, and an orthogonal transcription factor (e.g. TetR or Gal4). Upon binding to the antigen of interest, the orthogonal transcription factor is cleaved from the tail of the SynNotch receptor and activates the expression of the CAR. Thus, an immune effector cell of the invention may further comprise a nucleic acid or vector encoding a receptor which binds to an antigen other than CLEC14A, particularly to a tumour associated antigen other than CLEC14A.

Alternatively, a combinatorial approach may also be used where a further receptor in addition to the CAR of the invention is expressed on an immune effector cell of the invention, wherein said further receptor is capable of binding to off target cells or tissue (e.g. to non-tumour cells). In this case, if the further receptor binds to its ligand, a negative signal is produced, preventing immune cell stimulation (e.g. T cell stimulation).

A further combination approach may use a further receptor in combination with a CAR of the invention where both receptors bind to different targets and induce different effects to treat a tumour. Thus, both anti-tumour effects may be completely independent of each other but together may present an effective therapy against a tumour. In this regard, a CAR of the invention may be used in combination with a TCR therapy, where immune cells may be transduced with one or more nucleic acid molecules encoding a CAR of the invention and a TCR which is capable of binding to a particular MHC/peptide combination which may be found on a tumour cell (e.g. on a particular type of tumour cell or on any tumour cell). Alternatively, immune cells transduced with a nucleic acid encoding a CAR and a separate population of immune cells transduced with a nucleic acid encoding a TCR may be provided separately, sequentially or simultaneously. Gene therapy treatments using one or more nucleic acids encoding a CAR of the invention and a TCR which recognises a tumour MHC/peptide combination are also envisaged.

The present invention provides methods for making the immune effector cells which express the CAR as described herein. In one embodiment, the method comprises transfecting or transducing immune effector cells isolated from subject such that the immune effector cells express one or more CAR as described herein. In certain embodiments, the immune effector cells are isolated from a subject and modified by introduction of the nucleic acid molecule without further manipulation in vitro. Such cells can then be directly re-administered into the subject. In further embodiments, the immune effector cells are first activated and stimulated to proliferate in vitro prior to being modified to express a CAR. In this regard, the immune effector cells may be cultured before or after being genetically modified (i.e., transduced or transfected to express a CAR as described herein).

T cells can be obtained from a number of sources, including peripheral blood mononuclear cells, bone marrow, lymph nodes tissue, cord blood, thymus issue, tissue from a site of infection, ascites, pleural effusion, spleen tissue, and tumours. In certain embodiments, T cells can be obtained from a unit of blood collected from the subject using any number of techniques known to the skilled person, such as FICOLL™ separation. In one embodiment, cells from the circulating blood of a subject are obtained by apheresis. The apheresis product typically contains lymphocytes, including T cells, monocytes, granulocyte, B cells, other nucleated white blood cells, red blood cells, and platelets. In one embodiment, the cells collected by apheresis may be washed to remove the plasma fraction and to place the cells in an appropriate buffer or media for subsequent processing. In one embodiment of the invention, the cells are washed with PBS. In an alternative embodiment, the washed solution lacks calcium and/or magnesium or may lack many if not all divalent cations. As would be appreciated by those of ordinary skill in the art, a washing step may be accomplished by methods known to those in the art, such as by using a semi-automated flowthrough centrifuge. For example, the Cobe 2991 cell processor, the Baxter CytoMate, or the like. After washing, the cells may be resuspended in a variety of biocompatible buffers or other saline solution with or without buffer. In certain embodiments, the undesirable components of the apheresis sample may be removed in the cell directly resuspended culture media.

In certain embodiments, T cells are isolated from peripheral blood mononuclear cells (PBMCs) by lysing the red blood cells and depleting the monocytes, for example, by centrifugation through a PERCOLL™ gradient. A specific subpopulation of T cells, such as CD28+, CD4+, CD8+, CD45RA+, and CD45RO+ T cells, can be further isolated by positive or negative selection techniques. For example, enrichment of a T cell population by negative selection can be accomplished with a combination of antibodies directed to surface markers unique to the negatively selected cells. One method for use herein is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD 14, CD20, CDI Ib, CD16, HLA-DR, and CD8. Flow cytometry and cell sorting may also be used to isolate cell populations of interest for use in the present invention.

PBMC may be used directly for genetic modification using methods as described herein. In certain embodiments, after isolation of PBMC, T lymphocytes are further isolated and in certain embodiments, both cytotoxic and helper T lymphocytes can be sorted into naive, memory, and effector T cell subpopulations either before or after genetic modification and/or expansion. CD8+ cells can be obtained by using standard methods. In some embodiments, CD8+ cells are further sorted into naive, central memory, and effector cells by identifying cell surface antigens that are associated with each of those types of CD8+ cells. In embodiments, memory T cells are present in both CD62L+ and CD62L− subsets of CD8+ peripheral blood lymphocytes. PBMC are sorted into CD62L-CD8+ and CD62L+CD8+ fractions after staining with anti-CD8 and anti-CD62L antibodies. In some embodiments, the expression of phenotypic markers of central memory TCM include CD45RO, CD62L, CCR7, CD28, CD3, and CD127 and are negative for granzyme B. In some embodiments, central memory T cells are CD45RO+, CD62L+, CD8+ T cells. In some embodiments, effector T cells are negative for CD62L, CCR7, CD28, and CD 127, and positive for granzyme B and perforin. In some embodiments, naive CD 8+ T lymphocytes are characterized by the expression of phenotypic markers of naive T cells including CD62L, CCR7, CD28, CD3, CD 127, and CD45RA.

The immune effector cells, such as T cells, can be modified following isolation, or the immune effector cells can be activated and expanded (or differentiated in the case of progenitors) in vitro prior to being modified. In another embodiment, the immune effector cells, such as T cells, are modified by introduction of the nucleic acid molecules and then are activated and expanded in vitro. Methods for activating and expanding T cells are known in the art and are described, for example, in U.S. Pat. Nos. 6,905,874; 6,867,041; 6,797,514; WO2012079000. Generally, such methods include contacting PBMC or isolated T cells with a stimulatory agent and co-stimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). In other embodiments, the T cells may be activated and stimulated to proliferate with feeder cells and appropriate antibodies and cytokines using methods such as those described in U.S. Pat. Nos. 6,040,177; 5,827,642; and WO2012129514.

In one embodiment, CD34+ cells are transduced or transfected with a CAR encoding nucleic acid molecule in accordance with the invention. In certain embodiments, the modified (e.g. transfected or transduced) CD34+ cells differentiate into mature immune effector cells in vivo following administration into a subject, generally the subject from whom the cells were originally isolated. In another embodiment, CD34+ cells may be stimulated in vitro prior to or after introduction of the nucleic acid molecule, with one or more of the following cytokines: Flt-3 ligand (FL), stem cell factor (SF), megakaryocyte growth and differentiation factor (TPO), IL-3 and IL-6 according to the methods known in the art.

The invention provides a modified immune effector cell for use in therapy as described in more detail below, the modified immune effector cell expressing a CAR as disclosed herein. For example, the modified immune effector cells may be prepared from peripheral blood mononuclear cells (PBMCs) obtained from a patient diagnosed with cancer, particularly a solid tumour.

Standard procedures may be used for storage, e.g. cryopreservation, of the modified immune effector cells and/or preparation for use in a human or other subject.

The CAR-expressing immune effector cells can be utilized in methods and compositions for adoptive immunotherapy in accordance with known techniques. In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin. A treatment-effective amount of cells in the composition is at least 2 cells (for example, at least 1 CD8+ central memory T cell and at least 1 CD4+ helper T cell subset) or is more typically greater than $10^2$ cells, and up to $10^6$, up to and including $10^8$ or $10^9$ cells and can be more than $10^{10}$ cells. The number of cells will depend upon the ultimate use for which the composition is intended as will the type of cells included therein. For uses provided herein, the cells are generally in a volume of a litre or less, 500 ml or less, even 250 ml or 100 ml or less. Hence the density of the desired cells is typically greater than $10^6$ cells/ml and generally is greater than $10^7$ cells/ml, generally 10 cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. For example, 2, 3, 4, 5, 6 or more separate infusions may be administered to a patient, at intervals of 24 or 48 hours, or every 3, 4, 5, 6 or 7 days. Infusions may also be spaced at weekly, fortnightly or monthly intervals, or intervals of 6 weeks or 2, 3, 4, 5, or 6 months. It is also possible that yearly infusions may be administered. In some aspects of the present invention, since all the infused cells are redirected to a particular target antigen (namely CLEC14A), lower numbers of cells, in the range of $10^6$/kilogram ($10^6$-$10^9$ per patient) may be administered. The cell compositions may be administered multiple times at dosages within these ranges. If desired, the treatment may also include administration of mitogens (e.g., PHA) or lymphokines, cytokines, and/or chemokines (e.g., IFN-γ, IL-2, IL-12, TNF-alpha, IL-18, and TNF-beta, GM-CSF, IL-4, IL-13, Flt3-L, RANTES etc.) to enhance induction of the immune response.

The CAR expressing immune effector cells of the present invention may be administered either alone, or as a pharmaceutical composition in combination with diluents and/or with other components such as IL-2 or other cytokines or cell populations. Briefly, pharmaceutical compositions of the present invention may comprise a CAR-expressing immune effector cell population, such as T cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminium hydroxide); and preservatives. Compositions of the present invention are preferably formulated for intravenous administration and a described further below.

As noted elsewhere with regard to in vivo selectable markers for use in the vectors encoding the CAR, adverse events may be minimized by transducing the immune effector cells containing CAR with a suicide gene, such as inducible caspase 9 or a thymidine kinase, before, after or at the same time, as the cells are modified with nucleic acid molecule of the present invention.

The immune response induced in a subject by administering CAR expressing immune effector cells described herein may include cellular immune responses mediated by cytotoxic T cells capable of killing infected cells, regulatory T cells, and helper T cell responses. Humoral immune responses, mediated primarily by helper T cells capable of activating B cells thus leading to antibody production, may also be induced.

When an "effective amount" is indicated, the precise amount of the compositions to be administered can be determined by a physician with consideration of individual differences in age, weight, extent of malignancy, and general condition of the patient (subject). The optimal dosage and treatment regime for a particular patient can readily be determined by one skilled in the art of medicine by monitoring the subject for signs of disease and adjusting the treatment accordingly.

The term "target cell" refers to any cell which is to be killed or abrogated by the modified immune effector cells of the invention. As noted above, it will be generally be a CLEC14A-expressing endothelial cell (e.g. an endothelial cell within a tumour, preferably a solid tumour, e.g. a cancer cell).

Possible expression vectors include but are not limited to cosmids, plasmids, or modified viruses (e.g., replication defective retroviruses, adenoviruses and adeno-associated viruses), so long as the vector is compatible with the host cell used. The expression vectors are "suitable for transformation of a host cell", which means that the expression vectors contain a nucleic acid molecule of the invention and regulatory sequences selected on the basis of the host cells to be used for expression, which are operatively linked to the nucleic acid molecule. Operatively linked is intended to mean that the nucleic acid is linked to regulatory sequences in a manner that allows expression of the nucleic acid.

The invention therefore contemplates a recombinant expression vector containing a nucleic acid molecule of the invention, or a fragment thereof, and the necessary regulatory sequences for the transcription and translation of the protein sequence encoded by the nucleic acid molecule of the invention.

Suitable regulatory sequences may be derived from a variety of sources, including bacterial, fungal, viral, mammalian, or insect genes. Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors of the invention may also contain a selectable marker gene that facilitates the selection of host cells transformed or transfected with a recombinant molecule of the invention. Examples of selectable marker genes are genes encoding a protein such as neomycin and hygromycin that confer resistance to certain drugs, β-galactosidase, chloramphenicol acetyltransferase, firefly luciferase, or an immunoglobulin or portion thereof such as the Fc portion of an immunoglobulin, preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes that encode a fusion moiety that provides increased expression of the recombinant protein; increased solubility of the recombinant protein; and aid in the purification of the target recombinant protein by acting as a ligand in affinity purification (for example appropriate "tags" to enable purification and/or identification may be present, e.g., His tags or myc tags). For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transduced host cell. The terms "transduced with", "transformed with", "transfected with", "transformation" and "transfection" are intended to encompass introduction of nucleic acid (e.g., a vector) into a cell by one of many possible techniques known in the art. The term "transformed host cell" as used herein is intended to also include cells capable of glycosylation that have been transformed with a recombinant expression vector of the invention. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofection, electroporation or microinjection. Suitable methods for transforming and transfecting host cells can be found in Sambrook et al., 1989 (supra), and other laboratory textbooks.

Suitable host cells include a wide variety of eukaryotic host cells and prokaryotic cells. For example, the proteins (e.g. antibodies) of the invention may be expressed in yeast cells or mammalian cells. In addition, the proteins of the invention may be expressed in prokaryotic cells, such as *Escherichia coli*.

Yeast and fungi host cells suitable for carrying out the present invention include, but are not limited to *Saccharomyces cerevisiae*, the genera *Pichia* or *Kluyveromyces* and various species of the genus *Aspergillus*. Examples of vectors for expression in yeast *S. cerevisiae* include pYepSec1, pMFa, pJRY88, and pYES2 (Invitrogen Corporation, San Diego, Calif.). Protocols for the transformation of yeast and fungi are well known to those of ordinary skill in the art.

Mammalian cells suitable for carrying out the present invention include, among others: COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573), NS-1 cells, NS0 (ATCC CRL-11177), and Per.C6® (Crucell, Leiden, Netherlands). Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 and pMT2PC.

Given the teachings provided herein, promoters, terminators, and methods for introducing expression vectors of an appropriate type into plant, avian, and insect cells may also be readily accomplished. For example, within one embodiment, the proteins of the invention may be expressed from plant cells.

Insect cells suitable for carrying out the present invention include cells and cell lines from *Bombyx, Trichoplusia* or *Spodotera* species. Baculovirus vectors available for expression of proteins in cultured insect cells (SF 9 cells) include the pAc series and the pVL series.

Alternatively, the proteins of the invention may also be expressed in non-human transgenic animals such as, rats, rabbits, sheep and pigs (U.S. Pat. No. 4,736,866).

The proteins of the invention may also be prepared by chemical synthesis using techniques well known in the chemistry of proteins such as solid phase synthesis or synthesis in homogenous solution.

N-terminal or C-terminal fusion proteins comprising the antibodies and proteins of the invention conjugated to other molecules (e.g. immunoconjugates), such as proteins, may be prepared by fusing through recombinant techniques. The resultant fusion proteins contain an antibody or protein of the invention fused to the selected protein or marker protein, or tag protein as described herein. The antibodies and proteins of the invention may also be conjugated to other proteins by known techniques. For example, the proteins may be coupled using heterobifunctional thiol-containing linkers as described in WO 90/10457, N-succinimidyl-3-(2-pyridyldithio-proprionate) or N-succinimidyl-5 thioacetate. Examples of proteins that may be used to prepare fusion proteins or conjugates include cell binding proteins such as immunoglobulins, hormones, growth factors, lectins, insulin, low density lipoprotein, glucagon, endorphins, transferrin, bombesin, asialoglycoprotein glutathione-S-transferase (GST), hemagglutinin (HA), and truncated myc.

As discussed above and in more detail in the Examples below, the inventors have determined that the antibodies of the invention have an effect on angiogenesis. Accordingly, the antibodies (including fusion proteins and conjugates thereof, e.g. immunoconjugates etc.), CARs, nucleic acid molecules (including vectors, particularly expression vectors comprising said nucleic acid molecules) and immune effector cells of the invention have a utility in therapy. Accordingly, further aspects of the invention include:

a composition, particularly a therapeutic or pharmaceutical composition, comprising an antibody, CAR (i.e. a CAR polypeptide), nucleic acid molecule (e.g. encoding a CAR, e.g. an expression vector) or immune effector cell of the invention as defined herein and at least one physiologically acceptable carrier or excipient;

an antibody, CAR (i.e. a CAR polypeptide), nucleic acid molecule (e.g. encoding a CAR, e.g. an expression vector) or immune effector cell or a composition of the invention as defined herein for use in therapy, particularly adoptive cell transfer therapy;

an antibody, CAR (i.e. a CAR polypeptide), nucleic acid molecule (e.g. encoding a CAR, e.g. an expression vector) or immune effector cell or a composition of the invention as defined herein for use in combating a disease or condition associated with expression of CLEC14A, e.g. for inhibiting angiogenesis, particularly tumour angiogenesis, e.g. in the treatment of cancer;

a method of combating a disease or condition associated with expression of CLEC14A, e.g. for inhibiting angiogenesis, particularly tumour angiogenesis, e.g. a method of treating cancer, said method comprising administering to a subject in need thereof an antibody, CAR (i.e. a CAR polypeptide), nucleic acid molecule (e.g. encoding a CAR, e.g. an expression vector), immune effector cell or a composition of the invention as defined herein, particularly an effective amount of said antibody, CAR, nucleic acid molecule, cell or composition; and use of an antibody, CAR (i.e. a CAR polypeptide), nucleic acid molecule (e.g. encoding a CAR, e.g. an expression vector) or immune effector cell of the invention as defined herein for the manufacture of a medicament (or composition) for combating a disease or condition associated with expression of CLEC14A, e.g. for inhibiting angiogenesis, particularly tumour angiogenesis, e.g. for treating cancer.

For the avoidance of doubt, it will also be appreciated that the invention also includes an in vitro or ex vivo method of inhibiting angiogenesis (e.g. tumour angiogenesis) comprising administering an antibody, CAR (i.e. a CAR polypeptide), nucleic acid molecule (e.g. encoding a CAR, e.g. an expression vector), immune effector cell or composition as defined herein to tissue or cells in vitro or ex vivo. The cells may be established cell lines, or cells that have been removed from an individual. The tissue or cells are preferably mammalian tissue or cells (e.g. endothelial tissue or cells), and most preferably are human tissue or cells. When the method is an ex vivo method, the agent may be administered to an angiogenesis model ex vivo. Suitable angiogenesis assays include assays for endothelial cell proliferation, migration and invasion, sponge assays and aortic ring assays. Further angiogenesis assays are described below and in the Examples.

By "combating" we include the meaning that the method can be used to alleviate symptoms of the disorder (i.e. the method is used palliatively), or to treat the disorder, or to prevent the disorder (i.e. the method is used prophylactically).

By a disease or condition associated with expression of CLEC14A, we include, any disease or condition associated with cells which express CLEC14A. For example, the cells may be unwanted cells. The unwanted cells may be any cell whose presence in a host is undesired. Accordingly, the disease or condition associated with expression of CLEC14A may be any condition characterised by the presence of cells that express CLEC14A and which are unwanted, for example, any biological or medical condition or disorder in which at least part of the pathology is mediated by the presence of such unwanted cells expressing CLEC14A. The condition may be caused by the presence of the unwanted cells or else the presence of the unwanted cells may be an effect of the condition.

By expression of CLEC14A we include the meaning that CLEC14A protein is able to be detected on or in a cell or in extracts prepared from cells, or expression of the polypeptide may be inferred by detection of CLEC14A mRNA. In order to confirm the expression of CLEC14A in a cell, a variety of assays may be performed. Such assays include, for example, biochemical assays well known to those skilled in the art, such as detecting the presence of a particular protein (i.e. CLEC14A) by immunological means (ELISAs and Western blots), or molecular biological assays well known to those of skill in the art, such as Northern blotting, RT-PCR and PCR for detecting the presence CLEC14A mRNA.

As mentioned above, the inventors have found that CLEC14A is an endothelial cell marker, and so it will be appreciated that the antibodies, CARs, nucleic acid molecules, expression vectors, immune effector cells and compositions of the invention will be particularly useful in combating any disease or condition involving unwanted, undesirable or inappropriate angiogenesis. Such conditions include tumours/cancer, psoriasis, menorrhagia, endometriosis, arthritis (both inflammatory and rheumatoid), macular degeneration, Paget's disease, retinopathy and its vascular complications (including proliferative and of prematurity, and diabetic retinopathy), benign vascular proliferations, fibroses, obesity and inflammation.

The term "inhibiting angiogenesis" is intended to mean reducing the rate or level of angiogenesis. The reduction can be a low level reduction of about 10%, or about 20%, or about 30%, or about 40% of the rate or level of angiogenesis. Preferably, the reduction is a medium level reduction of about 50%, or about 60%, or about 70%, or about 80% reduction of the rate or level of angiogenesis. More preferably, the reduction is a high level reduction of about 90%, or about 95%, or about 99%, or about 99.9% of the rate or level of angiogenesis. Most preferably, inhibition can also include the elimination of angiogenesis or its reduction to an undetectable level. Methods and assays for determining the rate or level of angiogenesis, and hence for determining whether and to what extent an antibody, CAR, nucleic acid molecule, expression vector, immune effector cell or composition inhibits angiogenesis, are known in the art and are described in further detail herein, including in the Examples.

Typically, the angiogenesis that is inhibited is tumour angiogenesis. Thus, the individual may have a solid tumour, which can be treated by inhibiting tumour angiogenesis, i.e. the solid tumour is associated with new blood vessel production. The term "tumour" is to be understood as referring to all forms of neoplastic cell growth including, but not limited to, tumours of the breast, ovary, liver, bladder, prostate, kidney, pancreas, stomach, oesophagus, lung and thyroid.

Typically, the tumour is associated with undesirable neovasculature formation. The reduction of undesirable neovasculature formation may halt the progression of the tumour and can lead to a clinically useful reduction of tumour size and growth. Thus, the inhibition of tumour angiogenesis can be used to treat the tumour, for example, to prevent the (further) growth of the tumour, to prevent the spread of the tumour (metastasis), or to reduce the size of the tumour.

Preferably, the antibody, CAR, nucleic acid molecule, expression vector, immune effector cell, method and composition of the invention is used to treat humans, in which case the antibody, CAR, or immune effector cell is capable of binding to human CLEC14A or the nucleic acid molecule or expression vector that encodes an antibody or CAR capable of binding to human CLEC14A. It is appreciated, however, that when the antibody, CAR, nucleic acid molecule, expression vector, immune effector cell, method and composition of the invention is for use in the treatment of non-human mammals, it is preferred if the antibody, CAR or immune effector cell is capable of binding CLEC14A from the other species or the nucleic acid molecule or expression vector encodes an antibody or CAR capable of binding CLEC14A from the other species.

As discussed above, CLEC14A is expressed on certain tumour cells (e.g. endothelial cells) and the antibodies of the invention localize to CLEC14A+ cells. Consequently, the antibodies of the invention can target body sites (e.g. tumours) at which CLEC14A+ cells are present, whereupon the antibody can act at the target site. In particular, the ability of the antibodies to localize to CLEC14A+ endothelial cells in tumour blood vessels means that the antibodies of the invention can target body sites at which CLEC14A+ tumour cells are present, whereupon the antibody can act at the target site.

As shown in the Examples, the antibody of the invention may have an anti-CLEC14A+ cell effect (e.g. an inhibitory effect on angiogenesis or an anti-cancer effect) itself, i.e. as a naked antibody, e.g. by inhibiting, reducing or blocking the function or activity of CLEC14A. This ability to act as a naked antibody is advantageous and thus in some embodiments the compositions, uses and methods of the invention utilise an antibody of the invention, which is not conjugated to any other active agent, e.g. therapeutically active agent.

It is known that the angiogenesis inhibitor anti-VEGF monoclonal antibody bevacizumab improves the clinical outcome for a number of solid tumours when administered in combination with standard chemotherapy. Combinations that have been used include bevacizumab in combination with irinotecan, fluorouracil, and leucovorin; bevacizumab in combination with FOLFOX4 (a regimen of oxaliplatin, 5-fluorouracil and leucovorin); bevacizumab in combination with paclitaxel; and bevacizumab in combination with paclitaxel and carboplatin.

Thus, the skilled person would appreciate that although the antibodies, CARs, nucleic acid molecules, expression vectors, compositions and immune effector cells of the invention may be clinically effective in the absence of any other therapeutic agent (e.g. anti-cancer and/or anti-angiogenesis compound/agent), it may be advantageous to administer antibodies, CARs, nucleic acid molecules, expression vectors, compositions and immune effector cells of the invention in conjunction with a further therapeutic agent (e.g. an anti-cancer and/or anti-angiogenesis compound/agent).

Accordingly, in a further embodiment of the invention, the method may also comprise administering to the individual at least one further or additional therapeutic agent (e.g. an anti-cancer and/or anti-angiogenesis compound/agent). The method may comprise administering to the individual a pharmaceutical composition containing the antibody, CAR, nucleic acid molecule, expression vector, or immune effector cell and the further therapeutic agent (e.g. anti-cancer and/or anti-angiogenesis compound/agent). However, it is appreciated that the antibody, CAR, nucleic acid molecule, expression vector, composition or immune effector cell of the invention and further therapeutic agent (e.g. anti-cancer and/or anti-angiogenesis compound/agent) may be administered separately, for instance by separate routes of administration. Additionally, the antibody, CAR, nucleic acid molecule, expression vector, composition or immune effector cell of the invention and the at least one further therapeutic agent (e.g. anti-cancer and/or anti-angiogenesis compound/agent) can be administered sequentially or (substantially) simultaneously. They may be administered within the same pharmaceutical formulation or medicament or they may be formulated and administered separately.

In a particular embodiment, the invention provides a method of combating a disease or condition associated with expression of CLEC14A, e.g. for inhibiting angiogenesis, particularly tumour angiogenesis, e.g. a method of treating cancer, said method comprising administering an antibody, CAR, nucleic acid molecule, expression vector, immune effector cell or a composition of the invention as defined herein, particularly an effective amount of said antibody, cell or composition, and separately, simultaneously or sequentially administering of one or more additional active (e.g. therapeutic) agents (e.g. anti-cancer and/or anti-angiogenesis compound/agent) to a subject in need thereof.

Alternatively viewed, there is provided an antibody, CAR, nucleic acid molecule, expression vector, immune effector cell or a composition of the invention as defined herein for use in combination with one or more additional active (e.g. therapeutic) agents (e.g. anti-cancer and/or anti-angiogenesis compound/agent) for use in combating a disease or condition associated with expression of CLEC14A, e.g. for use in inhibiting angiogenesis, particularly tumour angiogenesis, e.g. for use in treating cancer.

Thus, there is provided the use of an antibody, CAR, nucleic acid molecule, expression vector or immune effector cell of the invention as defined herein in the manufacture of a medicament for use in combination with one or more additional active agents (e.g. therapeutic) agents (e.g. anti-cancer and/or anti-angiogenesis compound/agent) for combating a disease or condition associated with expression of CLEC14A, e.g. for inhibiting angiogenesis, particularly tumour angiogenesis, e.g. for treating cancer.

Thus, in one embodiment the medicament may further comprise one or more additional active (e.g. therapeutic) agents (e.g. anti-cancer and/or anti-angiogenesis compound/agent).

The medicament may be in the form of a single composition comprising both the antibody, CAR, nucleic acid molecule, expression vector or immune effector cell of the invention as defined herein and the one or more additional active (e.g. therapeutic) agents (e.g. anti-cancer and/or anti-angiogenesis compound/agent), or it may be in the form of a kit or product containing them for separate (e.g. simultaneous or sequential) administration.

In some embodiments, the further therapeutic agent is an anti-cancer agent. The further anti-cancer agent may be selected from alkylating agents including nitrogen mustards such as mechlorethamine ($HN_2$), cyclophosphamide, ifosfamide, melphalan (L-sarcolysin) and chlorambucil; ethylenimines and methylmelamines such as hexamethylmelamine, thiotepa; alkyl sulphonates such as busulphan; nitrosoureas such as carmustine (BCNU), lomustine (CCNU), semustine (methyl-CCNU) and streptozocin (streptozotocin); and triazenes such as decarbazine (DTIC; dimethyltriazenoimidazole-carboxamide); antimetabolites including folic acid analogues such as methotrexate (amethopterin); pyrimidine analogues such as fluorouracil (5-fluorouracil; 5-FU), floxuridine (fluorodeoxyuridine; FUdR) and cytarabine (cytosine arabinoside); and purine analogues and related inhibitors such as mercaptopurine (6-mercaptopurine; 6-MP), thioguanine (6-thioguanine; TG) and pentostatin (2'-deoxycoformycin); natural products including vinca alkaloids such as vinblastine (VLB) and vincristine; epipodophyllotoxins such as etoposide and teniposide; antibiotics such as dactinomycin (actinomycin D), daunorubicin (daunomycin; rubidomycin), doxorubicin, bleomycin, plicamycin (mithramycin) and mitomycin (mitomycin C); enzymes such as L-asparaginase; and biological response modifiers such as interferon alphenomes; miscellaneous agents including platinum coordination complexes such as cisplatin (cis-DDP) and carboplatin; anthracenedione such as mitoxantrone and anthracycline; substituted urea such as hydroxyurea; methyl hydrazine derivative such as procarbazine (N-methylhydrazine, MIH); and adrenocortical suppressant such as mitotane (o,p'-DDD) and aminoglutethimide; taxol and analogues/derivatives; cell cycle inhibitors; proteosome inhibitors such as Bortezomib (Velcade®); signal transductase (e.g. tyrosine kinase) inhibitors such as Imatinib (Glivec®), COX-2 inhibitors, and hormone agonists/antagonists such as flutamide and tamoxifen.

The clinically used anti-cancer agents are typically grouped by mechanism of action: Alkylating agents, Topoisomerase I inhibitors, Topoisomerase II inhibitors, RNA/DNA antimetabolites, DNA antimetabolites and Antimitotic agents. The US NIH/National Cancer Institute website lists 122 compounds (http://dtp.nci.nih.gov/docs/cancer/searches/standard_mechanism.html), all of which may be used in conjunction with the antibody, composition or immune effector cell of the invention. They include Alkylating agents including Asaley, AZQ, BCNU, Busulfan, carboxyphthalatoplatinum, CBDCA, CCNU, CHIP, chlorambucil, chlorozotocin, cis-platinum, clomesone, cyanomorpholino-doxorubicin, cyclodisone, dianhydrogalactitol, fluorodopan, hepsulfam, hycanthone, melphalan, methyl CCNU, mitomycin C, mitozolamide, nitrogen mustard, PCNU, piperazine, piperazinedione, pipobroman, porfiromycin, spirohydantoin mustard, teroxirone, tetraplatin, picoplatin (SP-4-3) (cis-aminedichloro(2-methylpyridine)Pt (II)), thio-tepa, triethylenemelamine, uracil nitrogen mustard, Yoshi-864; anitmitotic agents including allocolchicine, Halichondrin B, colchicine, colchicine derivative, dolastatin 10, maytansine, rhizoxin, taxol, taxol derivative, thiocolchicine, trityl cysteine, vinblastine sulphate, vincristine sulphate; Topoisomerase I Inhibitors including camptothecin, camptothecin, Na salt, aminocamptothecin, 20 camptothecin derivatives, morpholinodoxorubicin; Topoisomerase II Inhibitors including doxorubicin, amonafide, m-AMSA, anthrapyrazole derivative, pyrazoloacridine, bisantrene HCL, daunorubicin, deoxydoxorubicin, mitoxantrone, menogaril, N,N-dibenzyl daunomycin, oxanthrazole, rubidazone, VM-26, VP-16; RNA/DNA antimetabolites including L-alanosine, 5-azacytidine, 5-fluorouracil, acivicin, 3 aminopterin derivatives, an antifol, Baker's soluble antifol, dichlorallyl lawsone, brequinar, ftorafur (pro-drug), 5,6-dihydro-5-azacytidine, methotrexate, methotrexate derivative, N-(phosphonoacetyl)-L-aspartate (PALA), pyrazofurin, trimetrexate; DNA antimetabolites including, 3-HP, 2'-deoxy-5-fluorouridine, 5-HP, alpha-TGDR, aphidicolin glycinate, ara-C, 5-aza-2'-deoxycytidine, beta-TGDR, cyclocytidine, guanazole, hydroxyurea, inosine glycodialdehyde, macbecin II, pyrazoloimidazole, thioguanine and thiopurine.

In some preferred embodiments, the at least one further anti-cancer agent is selected from cisplatin; carboplatin; picoplatin; 5-flurouracil; paclitaxel; mitomycin C; doxorubicin; gemcitabine; tomudex; pemetrexed; methotrexate; irinotecan, fluorouracil and leucovorin; oxaliplatin, 5-fluorouracil and leucovorin; and paclitaxel and carboplatin.

When the further anti-cancer agent has been shown to be particularly effective for a specific tumour type, it may be preferred that the antibody, CAR, nucleic acid molecule, expression vector, composition or immune effector cell of the invention is used in combination with that further anti-cancer agent to treat that specific tumour type.

In some embodiments, the anti-angiogenesis compound may be selected from any one of the following: bevacizumab (Avastin®); itraconazole; carboxyamidotriazole; TNP-470 (an analog of fumagillin); CM101; IFN-α; IL-12; platelet factor-4; suramin; SU5416; thrombospondin; VEGFR antagonists; angiostatic steroids+heparin; Cartilage-Derived Angiogenesis Inhibitory Factor; matrix metalloproteinase inhibitors; angiostatin; endostatin; 2-methoxyestradiol; tecogalan; tetrathiomolybdate; thalidomide; prolactin; αVβ3 inhibitors; linomide; tasquinimod; ranibizumab; sorafenib; (Nexavar®); sunitinib (Sutent®); pazopanib (Votrient®); and everolimus (Afinitor®).

In some embodiments, the further therapeutic agent may be an immune checkpoint inhibitor, particularly for use in combination with an immune effector cell of the invention. Such inhibitors generally function by blocking the interaction between an immune cell and a target cell (e.g. tumour cell) which interaction prevents or downregulates the stimulation of the immune cell. Particularly, checkpoint inhibitors prevent or reduce the interaction between a protein expressed on a T cell and a protein expressed on a tumour cell, which interaction would prevent or reduce stimulation of the T cell. A checkpoint inhibitor may for example prevent the interaction between PD1 and PDL1 and particularly may constitute an agent which binds to PD1. Alternatively, a checkpoint inhibitor may bind to CTLA-4. Such checkpoint inhibitors are well known in the art and include monoclonal antibodies such as Penbrolizumab, Nivolumab or Ipilimumab.

The further active agent may also be a sphingosine-1-phosphate agonist, e.g. FTY720, which is capable of sequestering lymphocytes in the lymphoid organs by blocking signals from the sphingosine-1 phosphate receptor. In this way, such compounds may limit the competition for cytokines such as IL-7 and IL-15 and may thus allow an increased proliferation of the administered immune effector cell. Particularly, such compounds may be administered before the nucleic acid, expression vector, CAR or immune effector cell of the invention, e.g. at least 12 hours, 24 hours, 36 hours or 48 hours before.

Alternatively, or in addition, the antibody of the invention may have anti-CLEC14A+ cell effect (e.g. an inhibitory effect on angiogenesis or an anti-cancer effect) by virtue of being conjugated to an additional therapeutic molecule, e.g. a toxin or other anti-cancer molecule or an anti-angiogenesis agent as described herein.

In this respect, as shown in the Examples, some antibodies of the invention are capable of being internalized into the cells to which they become bound. Thus, in some embodiments of the invention the antibodies are capable of being internalized. This property may be particularly advantageous for use in immunoconjugates as any other agent attached to the antibody molecule should be internalized with the antibody molecule. In other embodiments no significant internalization is seen.

Thus, in a further embodiment, the invention provides a range of conjugated antibodies and fragments thereof (as defined herein) in which the antibody or fragment is operatively attached to at least one other therapeutic or diagnostic agent. The term "immunoconjugate" is broadly used to define the operative association of the antibody (including fragments thereof) with another effective agent and is not intended to be limited to any specific type of operative association, and is particularly not limited to chemical "conjugation". Recombinant fusion proteins are particularly contemplated. So long as the delivery or targeting agent is able to bind to the target and the therapeutic or diagnostic agent is sufficiently functional upon delivery, the mode of attachment will be suitable.

Thus, in some embodiments, the antibody of the invention may be an immunoconjugate and/or the antibody of the invention for use in the methods, compositions and uses defined herein is an immunoconjugate, i.e. an antibody conjugated (i.e. coupled, attached or linked) to an additional therapeutic molecule, e.g. a toxin or other anti-cancer molecule or an anti-angiogenesis agent, or a diagnostic molecule.

Antibody-drug conjugates (ADCs), such as for cancer therapy are reviewed by Carter & Senter (2008), Cancer J. 14(3): 154-69, and Chari et al (2014) Angewandte Chemie International Edition 53: 3751, incorporated herein by reference, and it will be appreciated that the immunoconjugates of the invention may considered to include such antibody-drug conjugates (see also U.S. Pat. Nos. 5,773,001; 5,767,285; 5,739,116; 5,693,762; 5,585,089; US 2006/0088522; US 2011/0008840; U.S. Pat. No. 7,659,241; Hughes (2010) Nat Drug Discov 9: 665, Lash (2010); In vivo: The Business & Medicine Report 32-38; Mahato et al (2011) Adv Drug Deliv Rev 63: 659; Jeffrey et al (2006) BMCL 16: 358; Drugs R D 11(1): 85-95). ADCs generally comprise a monoclonal antibody against a target present on a tumour cell, a cytotoxic drug, and a linker that attaches the antibody to the drug.

Thus, in a further aspect the invention provides an immunoconjugate (e.g. an antibody-drug conjugate) comprising an antibody of the invention and a cytotoxic moiety.

The cytotoxic moiety may be directly or indirectly toxic to cells in neovasculature or cells which are in close proximity to and associated with neovasculature. By "directly cytotoxic" we include the meaning that the moiety is one which on its own is cytotoxic. By "indirectly cytotoxic" we include the meaning that the moiety is one which, although is not itself cytotoxic, can induce cytotoxicity, for example by its action on a further molecule or by further action on it. For example, an indirect cytotoxic moiety may act to recruit an immune cell (e.g. a cytotoxic immune cell such as a cytotoxic T cell), and thereby indirectly induce a cytotoxic effect.

Typically, the cytotoxic moiety is selected from a directly cytotoxic chemotherapeutic agent, a directly cytotoxic polypeptide, a moiety which is able to convert a prodrug into a cytotoxic drug, a radiosensitizer, a directly cytotoxic nucleic acid, a nucleic acid molecule that encodes a directly or indirectly cytotoxic polypeptide or a radioactive atom. Examples of such cytotoxic moieties, as well as methods of making the conjugates comprising the antibody and the cytotoxic moiety, are provided in WO 02/36771, WO 2004/046191 and WO 2011/027132 incorporated herein by reference.

In some embodiments the cytotoxic moiety is a cytotoxic chemotherapeutic agent. Cytotoxic chemotherapeutic agents, such as anti-cancer agents, are well known in the art, and include those described above.

Various of the cytotoxic moieties mentioned above, such as cytotoxic chemotherapeutic agents, have previously been attached to antibodies and other targeting agents, and so immunoconjugates of the invention comprising these agents may readily be made by the person skilled in the art. For example, carbodiimide conjugation (Bauminger & Wilchek (1980) Methods Enzymol. 70, 151-159) may be used to conjugate a variety of agents, including doxorubicin, to antibodies. Other methods for conjugating a cytotoxic moiety to an antibody can also be used. For example, sodium periodate oxidation followed by reductive alkylation of appropriate reactants can be used, as can glutaraldehyde cross-linking. Methods of cross-linking polypeptides are known in the art and described in WO 2004/046191. However, it is recognised that, regardless of which method of producing a compound of the invention is selected, a determination must be made that the antibody maintains its targeting ability and that the attached moiety maintains its relevant function.

In some embodiments of the invention, the cytotoxic moiety may be a cytotoxic peptide or polypeptide moiety by which we include any moiety which leads to cell death. Cytotoxic peptide and polypeptide moieties are well known in the art and include, for example, ricin, abrin, Pseudomonas exotoxin, tissue factor and the like. Methods for linking them to targeting moieties such as antibodies are also known in the art, and include, for example, conventional ways of crosslinking polypeptides and production of the compound as a fusion polypeptide using recombinant DNA techniques. The use of ricin as a cytotoxic agent is described in Burrows & Thorpe (1993) Proc. Natl. Acad. Sci. USA 90, 8996-9000, and the use of tissue factor, which leads to localised blood clotting and infarction of a tumour, has been described by Ran et al (1998) Cancer Res. 58, 4646-4653 and Huang et al (1997) Science 275, 547-550. Tsai et al (1995) Dis. Colon Rectum 38, 1067-1074 describes the abrin A chain conjugated to a monoclonal antibody. Other ribosome inactivating proteins are described as cytotoxic agents in WO 96/06641. Pseudomonas exotoxin may also be used as the cytotoxic polypeptide moiety (Aiello et al (1995) Proc. Natl. Acad. Sci. USA 92, 10457-10461).

Certain cytokines, such as TNFα, INFγ and IL-2, may also be useful as cytotoxic agents.

Certain radioactive atoms may also be cytotoxic if delivered in sufficient doses. Thus, in some embodiments the cytotoxic moiety may comprise a radioactive atom which, in use, delivers a sufficient quantity of radioactivity to the target site so as to be cytotoxic. Suitable radioactive atoms include phosphorus-32, iodine-125, iodine-131, indium-111, rhenium-186, rhenium-188 or yttrium-90, or any other isotope which emits enough energy to destroy neighbouring cells, organelles or nucleic acid. Preferably, the isotopes and density of radioactive atoms in the compound of the invention are such that a dose of more than 4000 cGy (preferably at least 6000, 8000 or 10000 cGy) is delivered to the target site and, preferably, to the cells at the target site and their organelles, particularly the nucleus.

The radioactive atom may be attached to the antibody in known ways. For example EDTA or another chelating agent may be attached to the antibody and used to attach $^{111}$In or $^{90}$Y. Tyrosine residues may be labelled with $^{125}$I or $^{131}$I.

In some embodiments the cytotoxic moiety may be a radiosensitizer. Radiosensitizers include fluoropyrimidines, thymidine analogues, hydroxyurea, gemcitabine, fludarabine, nicotinamide, halogenated pyrimidines, 3-aminobenzamide, 3-aminobenzodiamide, etanixadole, pimonidazole and misonidazole (see, for example, McGinn et al (1996) J. Natl. Cancer Inst. 88, 1193-11203; Shewach & Lawrence (1996) Invest. New Drugs 14, 257-263; Horsman (1995) Acta Oncol. 34, 571-587; Shenoy & Singh (1992) Clin. Invest. 10, 533-551; Mitchell et al (1989) Int. J. Radiat. Biol. 56, 827-836; Iliakis & Kurtzman (1989) Int. J. Radiat. Oncol. Biol. Phys. 16, 1235-1241; Brown (1989) Int. J. Radiat. Oncol. Biol. Phys. 16, 987-993; Brown (1985) Cancer 55, 2222-2228).

In some embodiments the cytotoxic moiety may be a procoagulant factor, such as the extracellular domain of tissue factor (Rippmann et al (2000) "Fusion of the tissue factor extracellular domain to a tumour stroma specific single-chain fragment variable antibody results in an antigen-specific coagulation-promoting molecule." Biochem J. 349: 805-12; Huang et al (1997) "Tumor infarction in mice by antibody-directed targeting of tissue factor to tumor vasculature." Science. 275(5299): 547-550.

In some embodiments the cytotoxic moiety may be an indirectly cytotoxic polypeptide. In a particularly preferred embodiment, the indirectly cytotoxic polypeptide is a polypeptide which has enzymatic activity and can convert a relatively non-toxic prodrug into a cytotoxic drug. When the targeting moiety is an antibody, this type of system is often referred to as ADEPT (Antibody-Directed Enzyme Prodrug Therapy). The system requires that the targeting moiety locates the enzymatic portion to the desired site in the body of the patient (e.g. the site of new vascular tissue associated with a tumour) and after allowing time for the enzyme to localise at the site, administering a prodrug which is a substrate for the enzyme, the end product of the catalysis being a cytotoxic compound. The object of the approach is to maximise the concentration of drug at the desired site and to minimise the concentration of drug in normal tissues (Senter et al (1988) "Anti-tumor effects of antibody-alkaline phosphatase conjugates in combination with etoposide phosphate" Proc. Natl. Acad. Sci. USA 85, 4842-4846; Bagshawe (1987) Br. J. Cancer 56, 531-2; and Bagshawe, et al (1988) "A cytotoxic agent can be generated selectively at cancer sites" Br. J. Cancer. 58, 700-703); Bagshawe (1995) Drug Dev. Res. 34, 220-230 and WO 2004/046191, describe various enzyme/prodrug combinations which may be suitable in the context of this invention.

Typically, the prodrug is relatively non-toxic compared to the cytotoxic drug. Typically, it has less than 10% of the toxicity, preferably less than 1% of the toxicity as measured in a suitable in vitro cytotoxicity test.

The term "prodrug" as used in this application refers to a precursor or derivative form of a pharmaceutically active substance that is less active compared to the parent drug and is capable of being enzymatically activated or converted into the more active parent form (see, for example, D. E. V. Wilman "Prodrugs in Cancer Chemotherapy" Biochemical Society Transactions 14, 375-382 (615th Meeting, Belfast 1986) and V. J. Stella et al. "Prodrugs: A Chemical Approach to Targeted Drug Delivery" Directed Drug Delivery R. Borchardt et al (ed.) pages 247-267 (Humana Press 1985)).

It is likely that the moiety which is able to convert a prodrug to a cytotoxic drug will be active in isolation from the rest of the compound but it is necessary only for it to be active when (a) it is in combination with the rest of the compound and (b) the compound is attached to, adjacent to or internalised in target cells.

The cytotoxic moiety may be one which becomes cytotoxic, or releases a cytotoxic moiety, upon irradiation. For example, the boron-10 isotope, when appropriately irradiated, releases a particles which are cytotoxic (U.S. Pat. No. 4,348,376; Primus et al (1996) Bioconjug. Chem. 7: 532-535).

Similarly, the cytotoxic moiety may be one which is useful in photodynamic therapy such as photofrin (see, for example, Dougherty et al (1998) J. Natl. Cancer Inst. 90, 889-905).

In some embodiments the cytotoxic moiety is an antibody, such as one that specifically binds to an immune cell, such as a cytotoxic immune cell (e.g. T cell). Thus, in this case, the compound of the invention may be an asymmetric IgG-like antibody (e.g. triomab/quadroma, Trion Pharma/

Fresenius Biotech; knobs-into-holes, Genentech; Cross MAbs, Roche; electrostatically matched antibodies, AMGEN; LUZ-Y, Genentech; strand exchange engineered domain (SEED) body, EMD Serono; biolonic, erus; and Fab-exchanged antibodies, Genmab), symmetric IgG-like antibodies (eg dual targeting (DT)-Ig, GSK/Domantis; two-in-one antibody, Genentech; crosslinked MAbs, karmanos cancer center; mAb <2>, F-star; and Coy X-body, Coy X/Pfizer), IgG fusions (eg dual variable domain (DVD)-Ig, Abbott; IgG-like bispecific antibodies, Eli Lilly; Ts2Ab, Medimmune/AZ; BsAb, ZymoGenetics; HERCULES, Biogen Idee; TvAb, Roche) Fc fusions (e.g. ScFv/Fc fusions, Academic Institution; SCORPION, Emergent BioSolutions/Trubion, ZymoGenetics/BMS; dual affinity retargeting technology (Fc-DART), MacroGenics; dual (ScFv) 2-Fab, National Research Center for Antibody Medicine) Fab fusions (eg F(ab) 2, Medarex/AMGEN; dual-action or Bis-Fab, Genentech; Dock-and-Lock (DNL), ImmunoMedics; bivalent bispecific, Biotechnol; and Fab-Fv, UCB-Celltech), ScFv- and diabody-based antibodies (eg bispecific T cell engagers (BiTEs), Micromet; tandem diabodies (Tandab), Affimed; DARTs, MacroGenics; Single-chain diabody, Academic; TCR-like antibodies, AIT, Receptor Logics; human serum albumin ScFv fusion, Merrimack; and COMBODIES, Epigen Biotech), IgG/non-IgG fusions (e.g. immunocytokins, EMDSerono, Philogen, ImmunGene, ImmunoMedics; superantigen fusion protein, Active Biotech; and immune mobilising mTCR Against Cancer, ImmTAC) and oligoclonal antibodies (e.g. Symphogen and Merus).

In some embodiments the cytotoxic moiety is a pyrrolobenzodiazepine dimer (PBD). PBDs are potent anticancer agents which have been shown to have broad spectrum anti-tumour activity in vivo. These drugs exert their activity by binding the minor groove of DNA and linking the two DNA strands together in a way that cells find difficult to recognise and repair. Thus, in some embodiments the immunoconjugate of the invention may be an antibody of the invention comprising a PBD. Further information on PBDs can be found in Hartley et al, 2012 (Invest New Drugs 30: 950-958).

As discussed above, in some embodiments, the immunoconjugate of the invention may be a fusion protein/polypeptide comprising an antibody of the invention and a cytotoxic polypeptide. Thus, in a further embodiment the invention provides a nucleic acid molecule encoding an immunoconjugate of the invention, e.g. a fusion protein/polypeptide comprising an antibody of the invention and a cytotoxic polypeptide.

Thus, alternatively viewed, the invention may also be seen to provide a method of targeting a cytotoxic agent to neovasculature in the body of a subject, the method comprising administering to the subject an immunoconjugate of the invention (e.g. an antibody of the invention conjugated to a cytotoxic agent). Preferably, the neovasculature is tumour neovasculature.

Accordingly, a further aspect of the invention includes an immunoconjugate of the invention (e.g. an antibody of the invention conjugated to a cytotoxic agent) for use in targeting a cytotoxic agent to neovasculature (e.g. tumour neovasculature) in the body of a subject.

Thus, a further aspect of the invention includes the use of an immunoconjugate of the invention (e.g. an antibody of the invention conjugated to a cytotoxic agent) in the preparation or manufacture of a medicament for targeting a cytotoxic agent to neovasculature (e.g. tumour neovasculature) in the body of a subject.

The skilled person would appreciate that targeting a cytotoxic agent to neovasculature will act to inhibit angiogenesis. Hence, it is evident that the immunoconjugate of the invention may be used in the therapeutic methods and uses described above. It will also be appreciated that whilst the immunoconjugate of the invention may be clinically effective in the absence of any other therapeutic agent (e.g. anti-cancer and/or anti-angiogenesis compound/agent), it may nevertheless be advantageous to administer the immunoconjugate in conjunction (separately, sequentially or subsequently) with a further anti-cancer and/or anti-angiogenesis compound/agent, as described above.

The antibodies of the invention bind to CLEC14A. Thus the antibodies of the invention can be used to detect CLEC14A in vivo or in vitro, in particular to detect CLEC14A+ cells. For example, as CLEC14A is expressed on certain tumour cells, the antibodies of the invention can be used to detect tumour cells in vivo or in vitro, particularly when conjugated (coupled, attached or linked) to a detectable moiety.

Thus, in a further embodiment the invention provides an immunoconjugate comprising an antibody of the invention and a detectable moiety. Such a compound can be used, in combination with an appropriate detection method, to detect the location of the CLEC14A, particularly CLEC14A+ cells in a subject, and hence to identify the sites and extent of angiogenesis (e.g. tumour angiogenesis) in the subject, as well as inhibition of angiogenesis (e.g. tumour angiogenesis) in the subject.

Alternatively viewed, the invention provides diagnostic or imaging agents comprising the antibodies of the invention attached to a label (a detectable moiety) that produces a detectable signal, directly or indirectly.

In some embodiments, the immunoconjugate of the invention may be a fusion protein/polypeptide comprising an antibody of the invention and a detectable moiety comprising a polypeptide (e.g. a polypeptide that is directly signal giving or may be used to produce or generate a detectable signal). Thus, in a further embodiment the invention provides a nucleic acid molecule encoding an immunoconjugate of the invention, e.g. a fusion protein/polypeptide comprising an antibody of the invention and a detectable moiety comprising a polypeptide polypeptide.

By a "detectable moiety" we include the meaning that the moiety is one which, when located at the target site following administration of the compound of the invention into a patient, may be detected, typically non-invasively from outside the body, and the site of the target located. Thus, the immunoconjugates of the invention may also be useful in imaging and diagnosis, especially in the imaging and diagnosis of neovasculature of solid tumours, as is described further below.

In some embodiments the detectable moiety is or comprises a magnetic nano-particle, a radionuclide or a fluorophore.

Thus, in some embodiments the detectable moiety may be a radioactive atom which is useful in imaging. Suitable radioactive atoms include technetium$^{99}$m or iodine$^{123}$ for scintigraphic studies. Others may be selected from the group consisting of: iodine$^{124}$; iodine$^{125}$; iodine$^{126}$; iodine$^{131}$; iodine$^{133}$; indium-$^{111}$; indium-$^{113}$m fluorine$^{18}$; fluorine$^{19}$; carbon$^{11}$; carbon$^{13}$; copper$^{64}$; copper$^{67}$; nitrogen$^{13}$; nitrogen$^{15}$; oxygen$^{15}$; oxygen$^{17}$; arsenic$^{72}$; gadolinium; manganese; iron; deuterium; tritium; yttrium$^{86}$; zirconium$^{89}$; bromine$^{77}$, gallium$^{67}$; gallium$^{68}$, ruthenium$^{95}$, ruthenium$^{97}$, ruthenium$^{103}$, ruthenium$^{105}$, mercury$^{107}$, rhenium$^{99m}$, rhenium$^{101}$, rhenium$^{105}$, scandium$^{47}$. Suitable methods for coupling such radioisotopes to the antibodies—either directly or via a chelating agent such as EDTA or DTPA—can be employed, as is known in the art.

In some embodiments, the detectable moiety includes an X-ray detectable compound, such as bismuth (III), gold (III), lanthanum (III) or lead (II); a radioactive ion, such as gallium$^{67}$, gallium$^{68}$, mercury$^{197}$, mercury$^{203}$, rhenium$^{186}$, rhenium$^{188}$, rubidium$^{97}$, rubidium$^{103}$, or yttrium$^{90}$; a nuclear magnetic spin-resonance isotope, such as cobalt (II), copper (II), chromium (III), dysprosium (III), erbium (III), gadolinium (III), holmium (III), iron (II), iron (III), manganese (II), neodymium (III), nickel (II), samarium (III), terbium (III), vanadium (II) or ytterbium (III); or rhodamine or fluorescein.

Other readily detectable moieties that may be used include, for example, spin labels for magnetic resonance imaging (MRI) such as iodine$^{123}$, iodine$^{131}$, indium$^{111}$, fluorine$^{19}$, carbon$^{13}$, nitrogen$^{15}$, oxygen$^{17}$, gadolinium, manganese or iron.

The radio- or other label may be incorporated in the compound in known ways. For example, if the antibody may be biosynthesised or synthesised by chemical amino acid synthesis using suitable amino acid precursors involving, for example, fluorine$^{19}$ in place of hydrogen. Labels such as 99mTc, 123I, 186Rh, 188Rh and 111In can, for example, be attached via cysteine residues in the antibody. Yttrium$^{90}$ can be attached via a lysine residue. The IODOGEN method (Fraker et al (1978) Biochem. Biophys. Res. Comm. 80, 49-57) can be used to incorporate iodine$^{123}$. The reference ("Monoclonal Antibodies in Immunoscintigraphy", J. F. Chatal, CRC Press, 1989) describes other methods in detail.

Many suitable fluorophores and detection methods are well known in the art and are described, for example by Stefan Andersson-Engels et al (1997) "In vivo fluorescence imaging for tissue diagnostics. Phys. Med. Biol. 42: 815-824; Altinoğlu et al (2008) "Near-Infrared Emitting Fluorophore-Doped Calcium Phosphate Nanoparticles for In Vivo Imaging of Human Breast Cancer" ACS Nano 2(10): 2075-84; and Chin et al (2009) "In-vivo optical detection of cancer using chlorin e6-polyvinylpyrrolidone induced fluorescence imaging and spectroscopy" BMC Medical Imaging 9:1 (doi:10.1186/1471-2342-9-1). Examples include fluorescein and its derivatives, fluorochrome, rhodamine and its derivatives, Green Fluorescent Protein (GFP), dansyl, umbelliferone etc. In such conjugates, the antibodies of the invention or their functional fragments can be prepared by methods known to the person skilled in the art.

The detectable moiety may comprise a detectable enzyme such as peroxidase, alkaline phosphatase, beta-D-galactosidase, glucose oxidase, glucose amylase, carbonic anhydrase, acetylcholinesterase, lysozyme, malate dehydrogenase or glucose 6-phosphate dehydrogenase.

The detectable moiety may comprise a molecule such as biotin, digoxygenin or 5-bromodeoxyuridine.

The detectable moiety may comprise a chemiluminescent label such as luminol and the dioxetanes, or a bioluminescent label such as luciferase and luciferin.

Thus, in a further embodiment the invention provides a method of imaging neovasculature in the body of a subject the method comprising:

administering to the subject an imaging agent of the invention (e.g. an immunoconjugate comprising an antibody of the invention and a detectable moiety), and imaging the detectable moiety in the body. Preferably, the neovasculature is tumour neovasculature.

In some embodiments, the subject may have a solid tumour, preferably such as those described above, and the neovasculature of the tumour is imaged. Thus, the localisation of the imaging agent (e.g. immunoconjugate) at a particular organ in the body indicates that the individual may have or may be developing a solid tumour at that organ. This method may be useful, for example, in determining the size of a previously diagnosed solid tumour, determining the effectiveness of a therapy against the solid tumour, or determining the extent of metastasis of the tumour. Methods for imaging the detectable moiety in the body are well known in the art, and include PET (positron emission tomography).

Accordingly, the invention may also be seen to provide a method of detecting, diagnosing and prognosing a solid tumour in a subject, the method comprising: administering to the subject an imaging agent (e.g. immunoconjugate) of the invention, and detecting the presence and/or location of the detectable moiety in the body.

It will be evident from the discussion above that the invention provides a various compositions, e.g. pharmaceutical, therapeutic, diagnostic, imaging, comprising an antibody of the invention (including immunoconjugates described above) and/or immune effector cell of the invention, and a pharmaceutically acceptable diluent, carrier or excipient. In this respect, it is appreciated that the agents of the invention (i.e. antibody, immune effector cell, vector, virus etc.) will typically be formulated for administration to an individual (i.e. subject) as a pharmaceutical composition, i.e. together with a pharmaceutically acceptable carrier, diluent or excipient.

By "pharmaceutically acceptable" is included that the formulation is sterile and pyrogen free. Suitable pharmaceutical carriers, diluents and excipients are well known in the art of pharmacy. The carrier(s) must be "acceptable" in the sense of being compatible with the inhibitor and not deleterious to the recipients thereof. Typically, the carriers will be water or saline which will be sterile and pyrogen free; however, other acceptable carriers may be used.

In some embodiments the pharmaceutical compositions or formulations of the invention are for parenteral administration, more particularly for intravenous administration. In a preferred embodiment, the pharmaceutical composition is suitable for intravenous administration to a patient, for example by injection.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The liquid pharmaceutical compositions, whether they be solutions, suspensions or other like form, may include one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulphite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

Preferably, the formulation is a unit dosage containing a daily dose or unit, daily sub-dose or an appropriate fraction thereof, of the active ingredient.

The agents or compositions of the invention may be administered orally or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the agent or composition of the invention will generally be administered in admixture with a suitable pharmaceutical excipient, diluent or carrier selected with regard to the intended route of administration and standard pharmaceutical practice.

For example, the agent or composition of the invention may be administered orally, buccally or sublingually in the form of tablets, capsules, ovules, elixirs, solutions or suspensions, which may contain flavouring or colouring agents, for immediate-, delayed- or controlled-release applications. The agent or composition of the invention may also be administered via intracavernosal injection.

Suitable tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxy-propylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The agent or composition of the invention can also be administered parenterally, for example, intravenously, intra-arterially, intraperitoneally, intrathecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of an agent or composition of the invention will usually be from 1 to 1,000 mg per adult (i.e. from about 0.015 to 15 mg/kg), administered in single or divided doses.

Thus, for example, the tablets or capsules of the agent or composition of the invention may contain from 1 mg to 1,000 mg of active agent for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The agent or composition of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of an antibody and a suitable powder base such as lactose or starch. Such formulations may be particularly useful for treating solid tumours of the lung, such as, for example, small cell lung carcinoma, non-small cell lung carcinoma, pleuropulmonary blastoma or carcinoid tumour.

Aerosol or dry powder formulations are preferably arranged so that each metered dose or "puff" contains at least 1 mg of the inhibitor for delivery to the patient. It will be appreciated that the overall daily dose with an aerosol will vary from patient to patient, and may be administered in a single dose or, more usually, in divided doses throughout the day.

In some embodiments the agent or composition of the invention can be administered in the form of a suppository or pessary, particularly for treating or targeting colon, rectal or prostate tumours.

In some embodiments the agent or composition of the invention may be administered by the ocular route. For ophthalmic use, the agent or composition of the invention can be formulated as, e.g., micronised suspensions in isotonic, pH adjusted, sterile saline, or, preferably, as solutions in isotonic, pH adjusted, sterile saline, optionally in combination with a preservative such as a benzylalkonium chloride. Alternatively, the agent or composition of the invention may be formulated in an ointment such as petrolatum. Such formulations may be particularly useful for treating solid tumours of the eye, such as retinoblastoma, medulloepithelioma, uveal melanoma, rhabdomyosarcoma, intraocular lymphoma, or orbital lymphoma.

In some embodiments the agent or composition of the invention may be suitable for topical administration to a patient. The agent or composition of the invention may be applied topically in the form of a lotion, solution, cream, ointment or dusting powder, or may be transdermally administered, for example, by the use of a skin patch. For application topically to the skin, the agent or composition of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water. Such formulations may be particularly useful for treating solid tumours of the skin, such as, for example, basal cell cancer, squamous cell cancer or melanoma.

For skin cancers, the agent or composition of the invention can also be delivered by electroincorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with inhibitor or can simply act as "bullets" that generate pores in the skin through which the agent or composition of the invention can enter.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier. Such formulations may be particularly useful for treating solid tumours of the mouth and throat.

In some embodiments, the agent or composition of the invention may be delivered using an injectable sustained-release drug delivery system. These are designed specifically to reduce the frequency of injections. An example of such a system is Nutropin Depot which encapsulates recombinant human growth hormone (rhGH) in biodegradable microspheres that, once injected, release rhGH slowly over a sustained period.

The agent or composition of the invention can be administered by a surgically implanted device that releases the drug directly to the required site, for example, into the eye to treat ocular tumours. Such direct application to the site of disease achieves effective therapy without significant systemic side-effects.

An alternative method for delivery of agent or composition of the invention, is the ReGel injectable system that is thermo-sensitive. Below body temperature, ReGel is an injectable liquid while at body temperature it immediately forms a gel reservoir that slowly erodes and dissolves into known, safe, biodegradable polymers. The active drug is delivered over time as the biopolymers dissolve.

The agent or composition of the invention can also be delivered orally. The process employs a natural process for oral uptake of vitamin B12 in the body to co-deliver proteins and peptides. By riding the vitamin B12 uptake system, the protein or peptide can move through the intestinal wall. Complexes are synthesised between vitamin B12 analogues and the drug that retain both significant affinity for intrinsic factor (IF) in the vitamin B12 portion of the complex and significant bioactivity of the drug portion of the complex.

The nucleic acid molecule agents of the invention (e.g. nucleic acid molecules, vectors etc.) may be administered as a suitable genetic construct as described below and delivered to the patient where it is expressed. Typically, the nucleic acid in the genetic construct is operatively linked to a promoter which can express the compound in the cell. The genetic constructs of the invention can be prepared using methods well known in the art, for example in Sambrook et al (2001).

Although genetic constructs for delivery of polynucleotides can be DNA or RNA, it is preferred if they are DNA.

Preferably, the genetic construct is adapted for delivery to a human cell, e.g. transposon systems (e.g. sleeping beauty, piggyBac) may be used to integrate the target DNA into the host cell genome. Means and methods of introducing a genetic construct into a cell are known in the art, and include the use of immunoliposomes, liposomes, viral vectors (including vaccinia, modified vaccinia, lentivirus, parvovirus, retroviruses, adenovirus and adeno-associated viral (AAV) vectors), and by direct delivery of DNA, e.g. using a gene-gun and electroporation. Furthermore, methods of delivering polynucleotides to a target tissue of a patient for treatment are also well known in the art. In an alternative method, a high-efficiency nucleic acid delivery system that uses receptor-mediated endocytosis to carry DNA macromolecules into cells is employed. This is accomplished by conjugating the iron-transport protein transferrin to polycations that bind nucleic acids. High-efficiency receptor-mediated delivery of the DNA constructs or other genetic constructs of the invention using the endosome-disruption activity of defective or chemically inactivated adenovirus particles produced by the methods of Cotten et al (1992) Proc. Natl. Acad. Sci. USA 89, 6094-6098 may also be used. It will be appreciated that "naked DNA" and DNA complexed with cationic and neutral lipids may also be useful in introducing the DNA of the invention into cells of the individual to be treated. Non-viral approaches to gene therapy are described in Ledley (1995, Human Gene Therapy 6, 1129-1144).

Although for cancer/tumours of specific tissues it may be useful to use tissue-specific promoters in the vectors encoding a polynucleotide inhibitor, this is not essential, as the risk of expression of the nucleic acid molecule agent in the body at locations other than the cancer/tumour would be expected to be tolerable in compared to the therapeutic benefit to a patient suffering from a cancer/tumour. It may be desirable to be able to temporally regulate expression of the polynucleotide inhibitor in the cell, although this is also not essential.

The agents and compositions of the invention may be lyophilised for storage and reconstituted in a suitable carrier prior to use. Any suitable lyophilisation method (e.g. spray drying, cake drying) and/or reconstitution techniques can be employed. It will be appreciated by those skilled in the art that lyophilisation and reconstitution can lead to varying degrees of antibody activity loss (e.g. with conventional immunoglobulins, IgM antibodies tend to have greater activity loss than IgG antibodies) and that use levels may have to be adjusted upward to compensate. In one embodiment, the lyophilised (freeze dried) antibody loses no more than about 20%, or no more than about 25%, or no more than about 30%, or no more than about 35%, or no more than about 40%, or no more than about 45%, or no more than about 50% of its activity (prior to lyophilisation) when re-hydrated.

The agents of the invention (e.g. antibodies, immune effector cell, nucleic acid molecule, vector etc.) for administration may be appropriately modified for use in a pharmaceutical composition. For example agent may be stabilized in the compositions of the invention against degradation for example by the use of appropriate additives such as salts or non-electrolytes, acetate, EDTA, citrate, Tris, phosphate or acetate buffers, mannitol, glycine, HSA (human serum albumin) or polysorbate. Numerous stabilizing agents are known in the art.

The antibodies of the invention as defined herein may also be used as molecular tools for in vitro or in vivo applications and assays. As the antibodies have an antigen binding site, these can function as members of specific binding pairs and these molecules can be used in any assay where the particular binding pair member is required.

Thus, yet further aspects of the invention provide a reagent that comprises an antibody of the invention as defined herein and the use of such antibodies as molecular tools, for example in in vitro or in vivo assays.

The invention further includes kits comprising one or more of the antibodies, CARs, immunoconjugates or compositions of the invention or one or more of the nucleic acid molecules encoding the antibodies or CARs of the invention, or one or more recombinant expression vectors comprising the nucleic acid sequences of the invention, or one or more host cells (including immune effector cells) or viruses comprising the recombinant expression vectors or nucleic acid sequences of the invention. Preferably said kits are for use in the methods and uses as described herein, e.g., the therapeutic, diagnostic or imaging methods as described herein, or are for use in the in vitro assays or methods as described herein. The antibody in such kits may preferably be an antibody conjugate (an immunoconjugate) as described elsewhere herein, e.g., may be conjugated to a detectable moiety or therapeutic or cytotoxic agent. Preferably said kits comprise instructions for use of the kit components, for example in diagnosis. Preferably said kits are for diagnosing or treating diseases as described elsewhere herein and optionally comprise instructions for use of the kit components to diagnose or treat such diseases.

Cancer treatment may also be carried out by:

(a) forming an image of a tumour by administering to an animal or patient (i.e. a subject) having a tumour a diagnostic amount of at least a first detectably-labelled anti-CLEC14A antibody of the invention (e.g. an imaging agent of the invention), thereby forming a detectable image of the tumour; and (b) subsequently administering to the same animal or patient a therapeutically optimized amount of at least a first therapeutic agent of the invention (e.g. an antibody, immune effector cell or composition), thereby causing an anti-tumour effect.

Any reference to “tumour(s)” herein also refers to “cancer(s)” or “carcinoma(s)”. Metastatic cancers can also be treated, as can the reduction of metastases from a primary tumour. So-called minimal residual disease (MRD), which is left in post-surgery patients, may be amenable for immunotherapy with anti-CLEC14A antibodies and other agents of the invention, e.g. immune effector cell or composition.

The subject to be treated using the methods and cells of the present invention may be any species of mammal. For instance, the subject may be any species of domestic pet, such as a mouse, rat, gerbil, rabbit, guinea pig, hamster, cat or dog, or livestock, such as a goat, sheep, pig, cow or horse. In a further preferred embodiment of the invention the subject may be a primate, such as a monkey, gibbon, gorilla, orang-utang, chimpanzee or bonobo. However, in a preferred embodiment of the invention the subject is a human.

As used throughout the entire application, the terms “a” and “an” are used in the sense that they mean “at least one”, “at least a first”, “one or more” or “a plurality” of the referenced components or steps, except in instances wherein an upper limit is thereafter specifically stated. Therefore, an “antibody”, as used herein, means “at least a first antibody”. The operable limits and parameters of combinations, as with the amounts of any single agent, will be known to those of ordinary skill in the art in light of the present disclosure.

The invention will now be described in more detail in the following non-limited examples with reference to the Figures in which:

FIG. 1 shows a graph showing the relative expression of CLEC14A in HUVECs and other primary cells. CLEC14A was expressed specifically in endothelial cells (HUVEC), and not in human aortic smooth muscle cells (HASMC), human lung fibroblasts (MRC5), human bronchial epithelial cells (HBE), hepatocytes, or peripheral blood mononuclear-cells (PBMC).

FIG. 2 shows [A] siRNA duplex targeting CLEC14A can efficiently knockdown CLEC14A mRNA expression in HUVEC, as determined by qPCR. Relative expression was determined by normalising expression to flotilin2. [B] Knockdown of CLEC14A at the protein level was determined by Western blot analysis. Tubulin was used as a loading control. [C] Representative images of sprout outgrowth after 16 hours for control or clec14a targeted siRNA treated HUVEC. [D] Quantitation of sprouts for 27 spheroids (9 spheroids from 3 cords) for control and CLEC14A knockdown HUVEC; Mann-Whitney statistical test $p<0.001$. [E] Representative images of sprout outgrowth after 24 hours for mixed control (green) and clec14a targeted siRNA treated HUVEC (red). [F] Quantitation of the percentage of tip and stalk cells derived from control (CON) and CLEC14A knockdown (KD) HUVEC; two-way ANOVA statistical test with Bonferroni post-tests ***=$p<0.001$, ns=not significant.

FIG. 3 shows [A] a schematic diagram of clec14a gene in C57BL/6 (clec14a +/+) or C57BL/6(Clec14atm1(KOMP) Vlcg) (clec14a −/−) mice. [B] Quantitative PCR analysis of cDNA generated from three clec14a +/+ mice (white bars) and three clec14a −/− mice (black bars) for the 5' untranslated region (UTR), coding sequence (CDS) and 3' UTR of clec14a. Relative expression was determined by normalising expression to flotilin2. [C] Western blot analysis of CLEC14A protein expression in lung lysates from clec14a +/+ and clec14a −/− mice using polyclonal antisera against murine CLEC14A. Tubulin was used as a loading control. [D] Representative images of the aortic ring sprouting assay from clec14a +/+ and clec14a −/− mice. Quantitation of tubes formed per ring [E], and quantitation of the maximal distance migrated by an endothelial tube from the aortic ring [F], data from 48 rings per genotype, 6 mice for each genotype; Mann-Whitney statistical test $p<0.001$. [G] Representative images of haematoxylin and eosin stained sections of sponge implant from clec14a +/+ and clec14a −/− mice, sections at the centre of the sponge were analysed. [H] Quantitation of cellular invasion into the sponge implants shown in G; Mann-Whitney statistical test $p<0.05$. [I] Quantitation of vessel density; Mann-Whitney statistical test $p<0.001$. [J] Sections of liver and sponge tissue stained with x-gal from clec14a −/− mice, counterstained with haematoxylin and eosin.

FIG. 4 shows [A] Lewis lung carcinoma (LLC) tumour growth in clec14a +/+ (black line with dots) and clec14a −/−

(black line with squares) mice; two-way ANOVA statistical analysis, *=$p<0.05$, =$p<0.01$, *=$p<0.001$. [B] Representative images of LLC tumours. [C] Endpoint tumour weight for 7 clec14a +/+ (dots) and 7 clec14a −/− (squares) mice; Mann-Whitney statistical test $p<0.001$. [D] Representative images of immunofluorescent staining of LLC tumour sections stained for murine CD31. Quantitation of vessel density [E] and percentage endothelial coverage [F] from clec14a +/+ and clec14a −/− mice; Mann-Whitney statistical test $p<0.0001$. [G] Sections of liver and LLC tumour tissue from clec14a −/− mice stained with x-gal, counterstained with haematoxylin and eosin.

FIG. 5 shows (A) a light microscopy image of the results of a HUVEC scratch wound healing assay with anti-CLEC14A monoclonal antibody CRT-3 showing a retardation of wound closure. (B) Graphical representation of the results from (A).

FIG. 6 shows analysis of tubule formation assays with CLEC14A antibody treated HUVECS. HUVECS were treated with 20 μg/ml CRT2, 3 or 4 or mouse IgG isotype control. Images of tubules were taken at 16 hours and analysed for total tubule length, number of junctions, number of branches, branch length, number of meshes and total mesh area. Data shown represents three experiments with five data points analysed for each. Error bars show SEM. *p, 0.05. **$p<0.01$.

FIG. 7 shows graphs of flow cytometry analysis of CRT-2 and CRT-3 binding to (A) HEK293T transfected with CLEC14A and (B) HEK293T transfected with thrombomodulin.

FIG. 8 shows graphs of flow cytometry analysis of CRT-2 and CRT-3 binding to (A) HEK293T transfected with a chimera containing CTLD of thrombomodulin and the remainder of CLEC14A, (B) HEK293T transfected with the a chimera containing the sushi-like domain of thrombomodulin and the remainder of CLEC14A and (C) HEK293T transfected with a chimera containing loop residues 97-108 of thrombomodulin and the remainder of CLEC14A.

FIG. 9 shows the alignment of CLEC14A regions 1-42 of CD141; CLEC14A regions 97-108 of CD141; and CLEC14A regions 122-142 of CD141.

FIG. 10 shows CAR expression vector design and expression of the CAR in transduced human T cells wherein (A) shows a retroviral CAR vector (based on pMP71) that co-expresses a truncated CD34 marker gene and an scFv fragment/CD3 zeta chain chimeric receptor. Expression is driven from the LTR promoter and the 2A peptide linker ensures equimolar expression of both the CD34 and the CAR. Second generation CAR constructs included the CD28 co-stimulatory domain. (B) shows CD34 staining analysed by flow cytometry demonstrating successful transduction of T cells using retroviral constructs that co-express a CLEC14A-specific CAR. First generation CARs based on the antibody CRT-3 is referred to as CRT3.z. Second generation CARs based on the antibody CRT-3 is referred to as CRT3.28z. (C). shows cells analysed by flow cytometry stained directly for expression of CAR using CLEC14A-Fc (% values show specific binding of CLEC14A-Fc having subtracted background staining with Fc alone).

FIG. 11 shows CAR-transduced T cells respond to CLEC14A in vitro. T cells transduced to express 1st or 2nd generation CARs based on antibody CRT-3 or mock-transduced (control) T cells were tested for their ability to respond to CLEC14A expressed either as (A) plate-bound recombinant Fc fusion protein, (B) expressed on engineered CHO cells, or (C) expressed on human umbilical vein endothelial cells (HUVECs) which naturally express CLEC14A when grown in static culture. T cell response was measured using an ELISA for interferon gamma production. Data shown are representative of that obtained from 3-7 repeat experiments. T cells were adjusted to equalise the frequency of transgene expressing cells. All histograms show mean response+SD.

FIG. 12 shows further in vitro functional testing of CLEC14A-specific CAR-transduced T cells. T cells transduced to express 1st or 2nd generation CARs based on antibody CRT-3, or mock-transduced (control) T cells, were tested for their ability to respond to CLEC14A in the following functional assays: (A) Cytotoxicity, using CHO cells engineered to express human CLEC14A (having subtracted background levels of lysis of CHO alone (control cells)). Data shown are representative of 5 repeat experiments. (B) Proliferation, using CFSE-labelled CAR-transduced T cells we measured the proliferation of CAR+ (CD34+) and CAR− (CD34−) cell subsets when co-cultured for 4 days with HUVECs. Data shown are representative of 2 repeat experiments. (C) The response of (CLEC14A-specific CAR-transduced T cells to both human and mouse CLEC14A was assessed using interferon gamma release. T cells were adjusted to equalise the frequency of transgene expressing cells. Data shown are representative of 6 repeat experiments. All histograms show mean response+SD.

FIG. 13 shows histological pictures of tissue samples following toxicity testing in vivo using healthy C57/BL6 mice injected with CLEC14A-specific CAR-transduced mouse T cells.

FIG. 14 shows graphs of Lewis Lung carcinoma tumour volume from mice treated with T cells transduced to express 2nd generation CARs based on antibody CRT-3 or mock-transduced (control) T cells. Mice received a total of 20 million T cells (CD8:CD4=5:2) with CRT3.28z expressed on 2.2 million of these cells. Tumour growth was then monitored using (A) Bioluminescence or (B) Calipers.

Figure 19:

FIG. 19 shows the design of CARs with different costimulatory domains 1) tCD34-F2A-scFv-CD28 TM-CD28 signal-CD3zeta, 2) tCD34-F2A-scFv-CD8 TM-4-1BB signal-CD3 zeta, 3) tCD34-F2A-scFv-CD8 TM-OX40 signal-CD3 zeta, 4) tCD34-F2A-scFv-CD28 TM-CD28 signal-4-1BB signal-CD3zeta, 5) tCD34-F2A-scFv-CD28 TM-CD28 signal-OX40 signal-CD3 zeta, 6) tCD34-F2A-scFv-CD8 TM-4-1BB signal-OX40signal-CD3zeta. The tCD34 is included to identify successfully transduced cells and thus constructs may exclude this and F2A. A hinge or spacer region may additionally be included e.g. one from CD8α.

Figure 20:
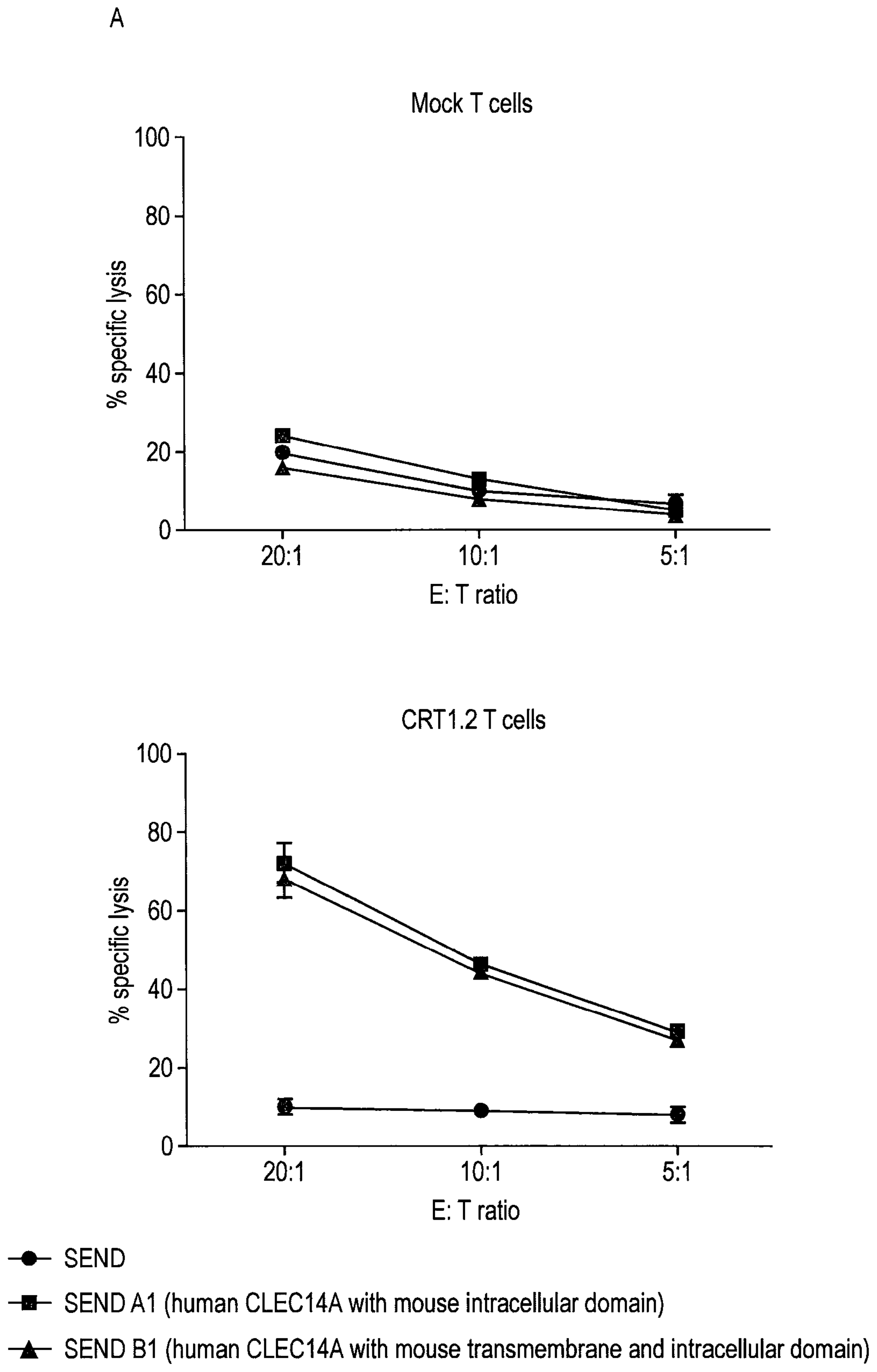
Figure 20:
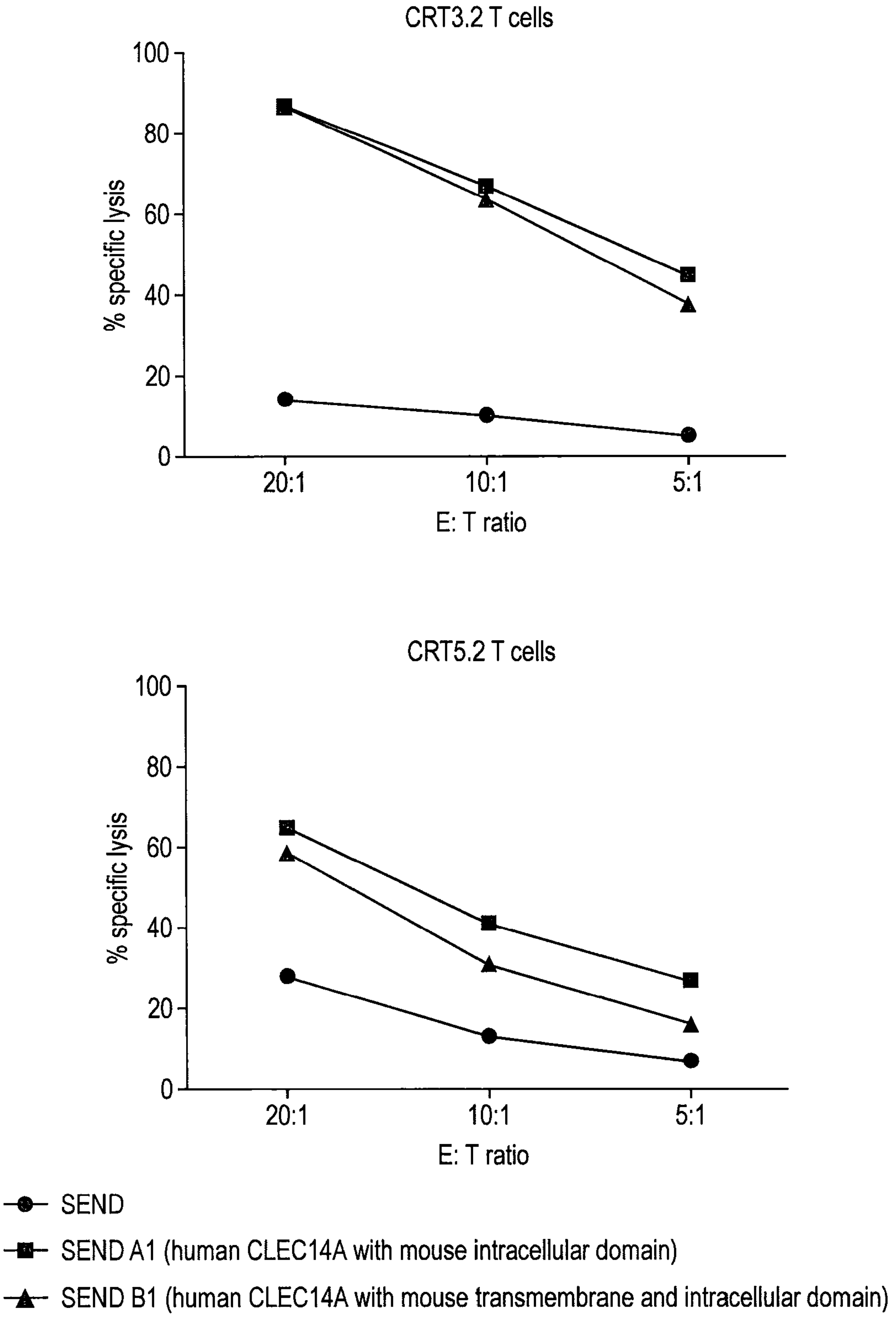
Figure 20:
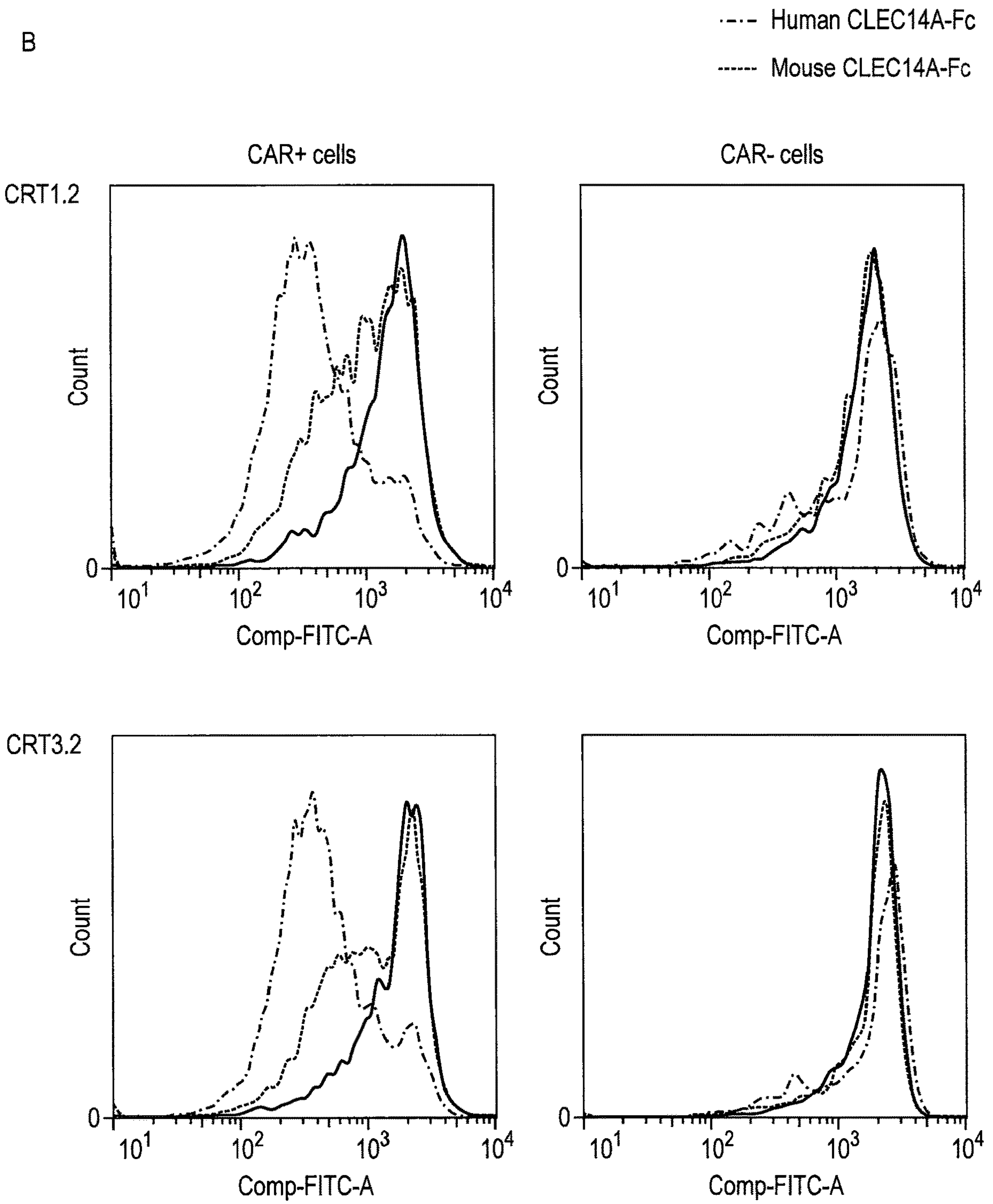
Figure 20:
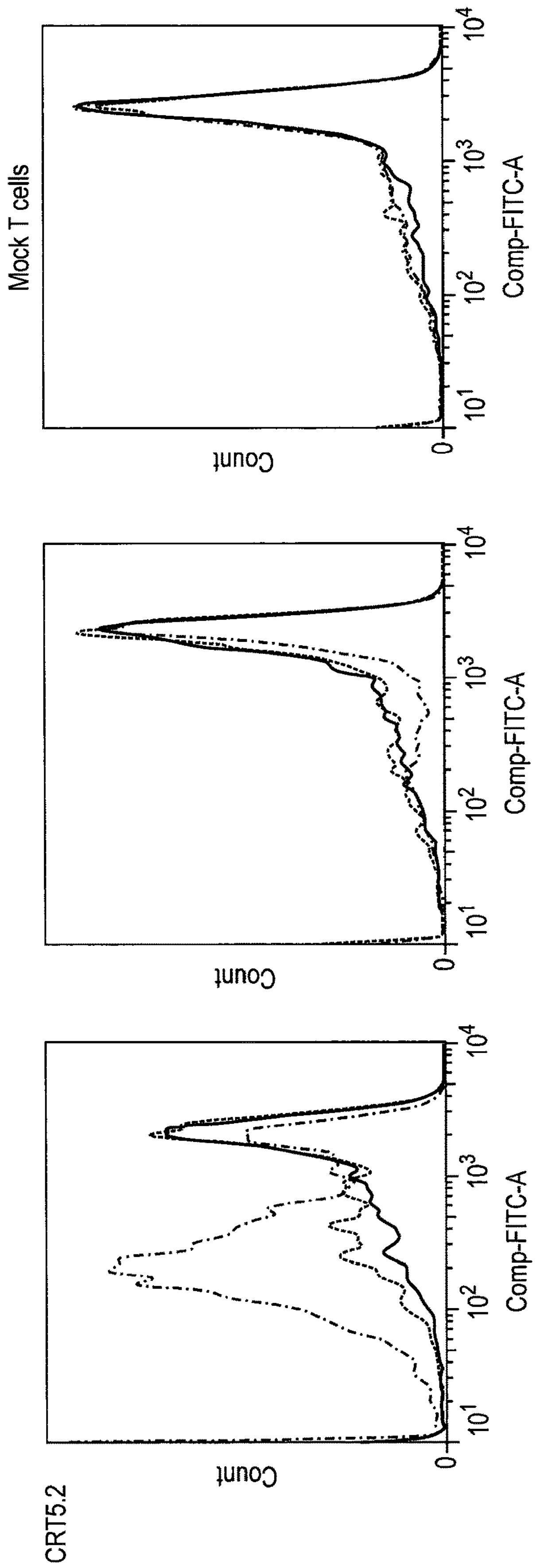

FIG. 20 shows the results of a cytotoxicity assay with CRT1, 3 and 5 CARs vs mouse endothelial cells expressing CLEC14A (FIG. 20A). The results of a proliferative assay for CRT 1, 3 and 5 CARs are shown in FIG. 20B.

Figure 21:
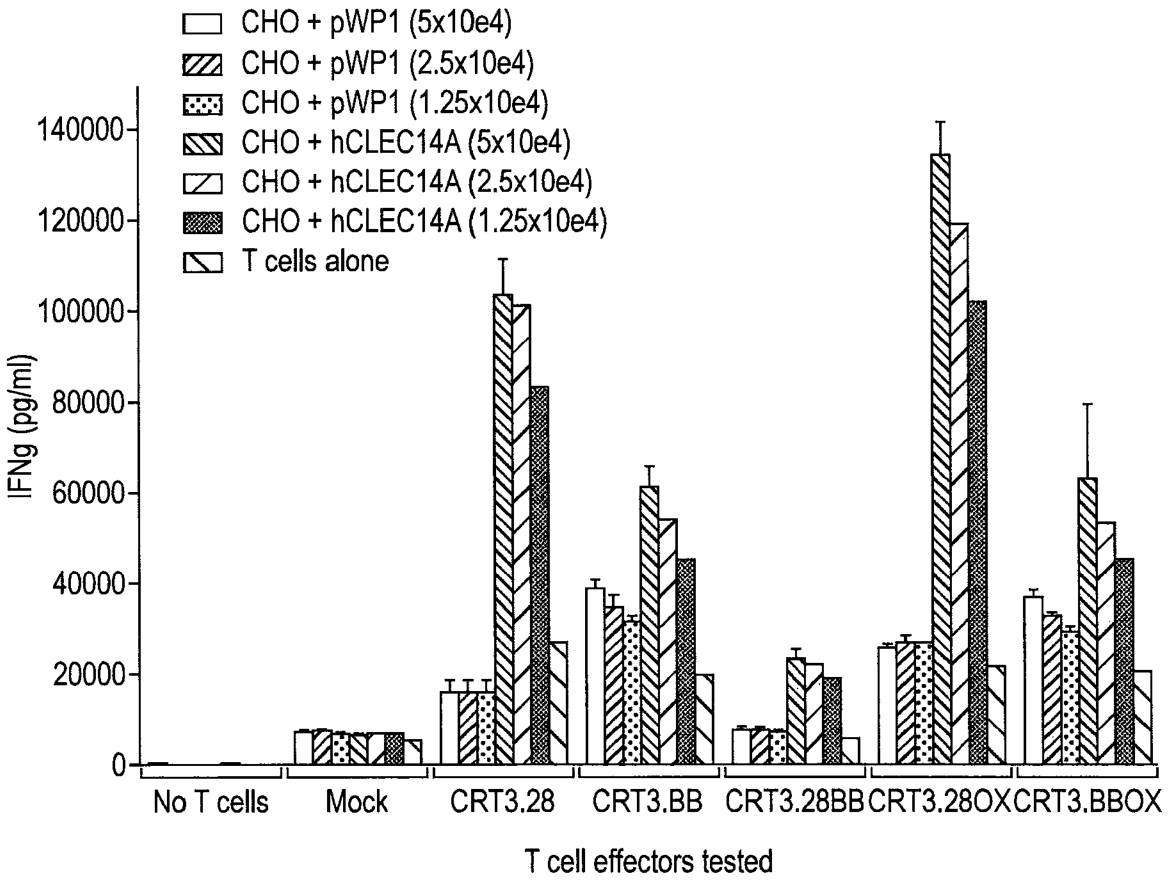

FIG. 21 shows the functional testing of CRT3 CAR T cells comprising different costimulatory domains and shows the IFNgamma production in response to titrated numbers of CHO cells expressing human CLEC14A.

Figure 22:
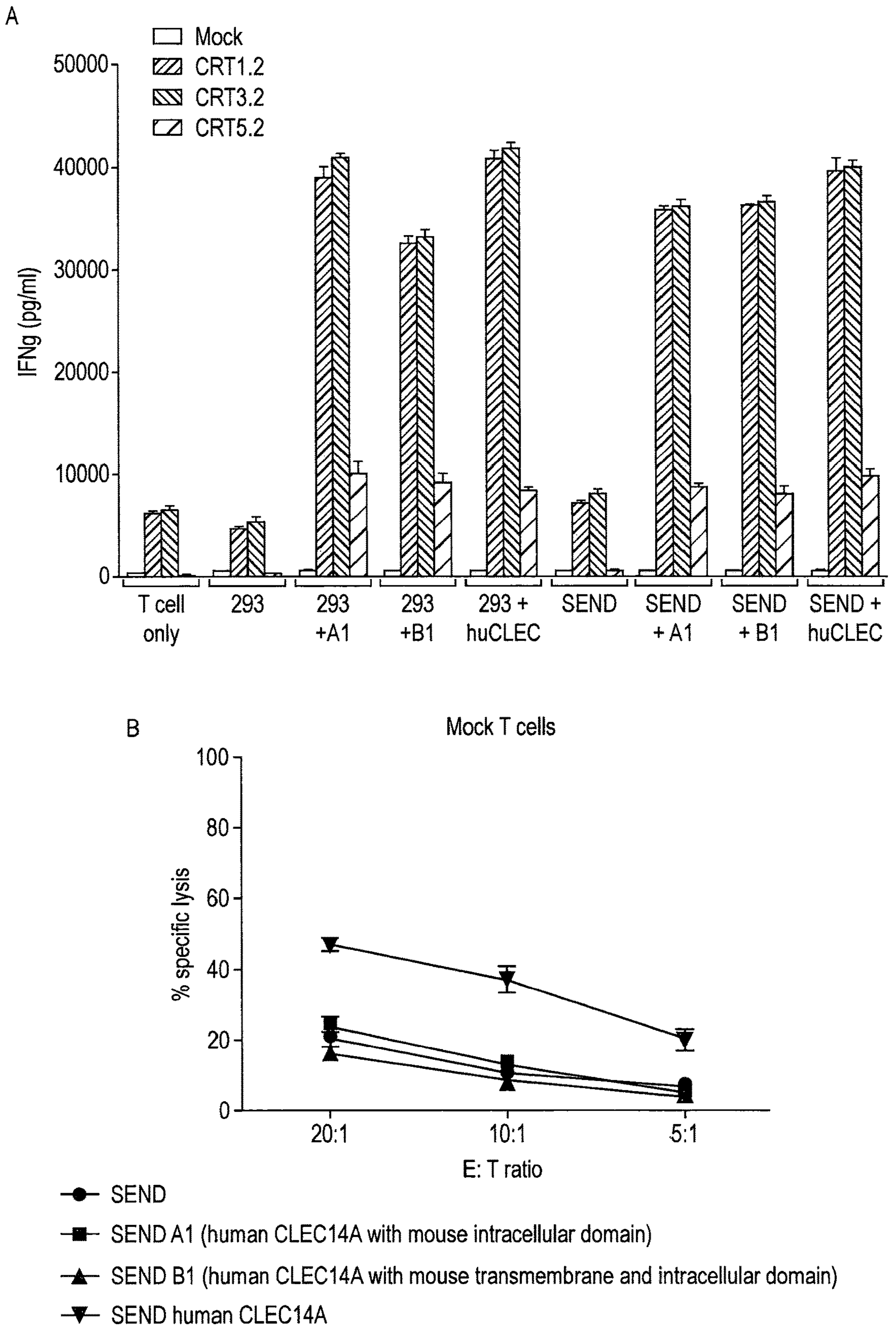
Figure 22:
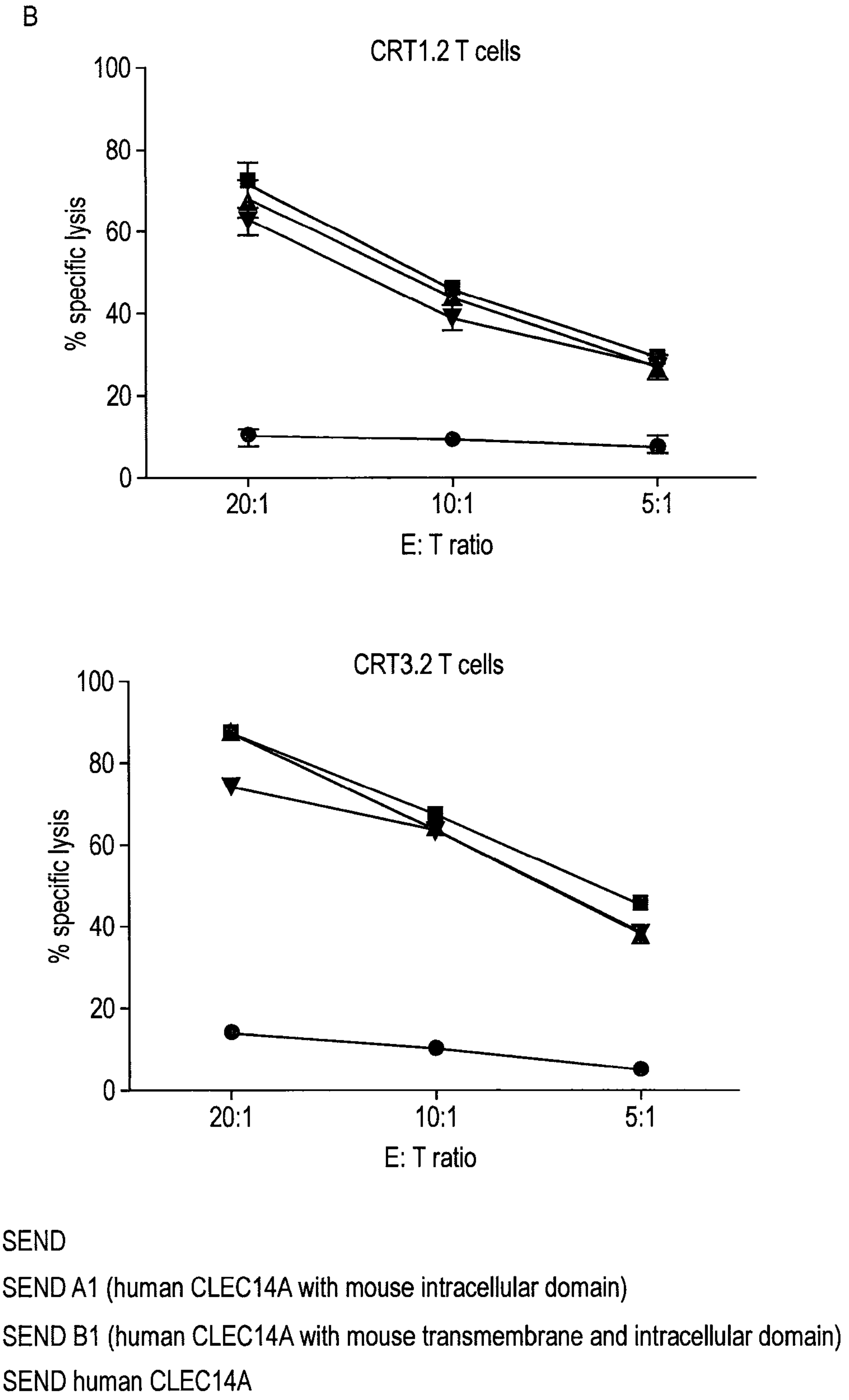
Figure 22:
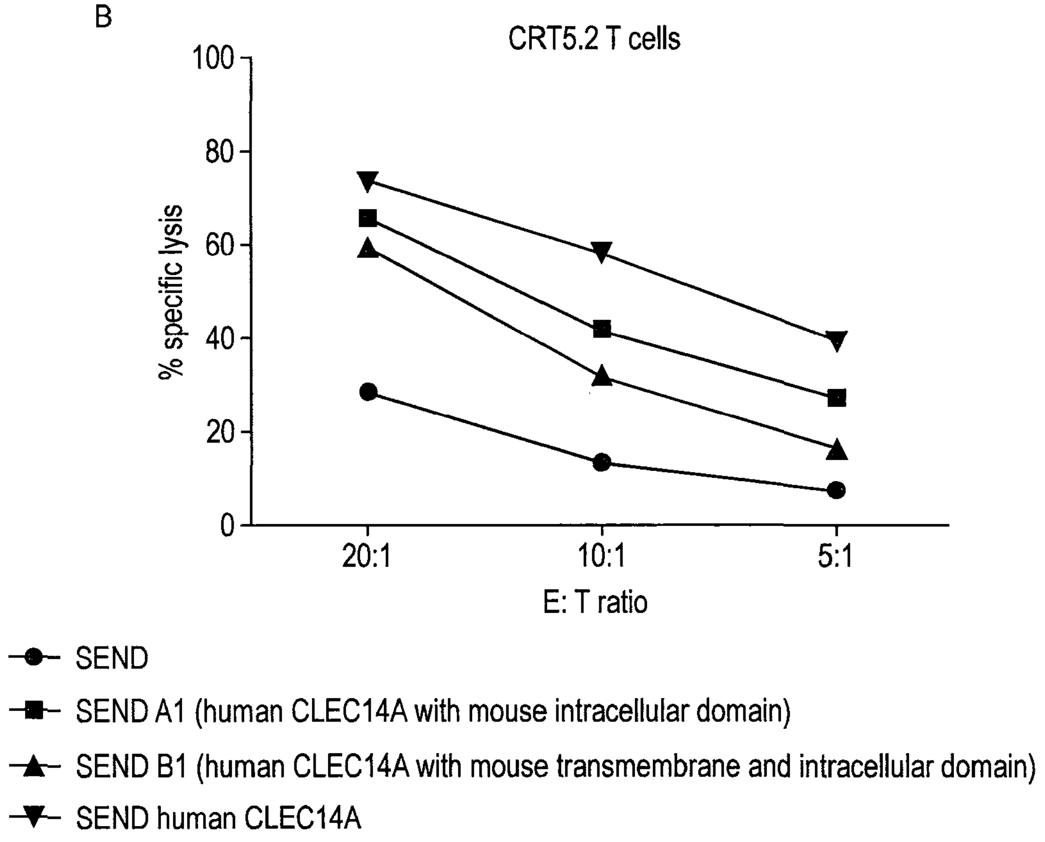

FIG. 22 shows the IFN gamma release by CRT1, 3 and 5 CAR (CD28 costimulatory domain) T cells after incubated with 293 or SEND cells engineered to express CLEC14A chimera (A1-human CLEC14A with mouse intracellular domain, B1-human CLEC14A with mouse transmembrane and intracellular domains, huCLEC-human CLEC14A). Cytotoxicity data are shown in FIG. 22B for the CAR T cells after incubation with SEND cells.

Figure 23:
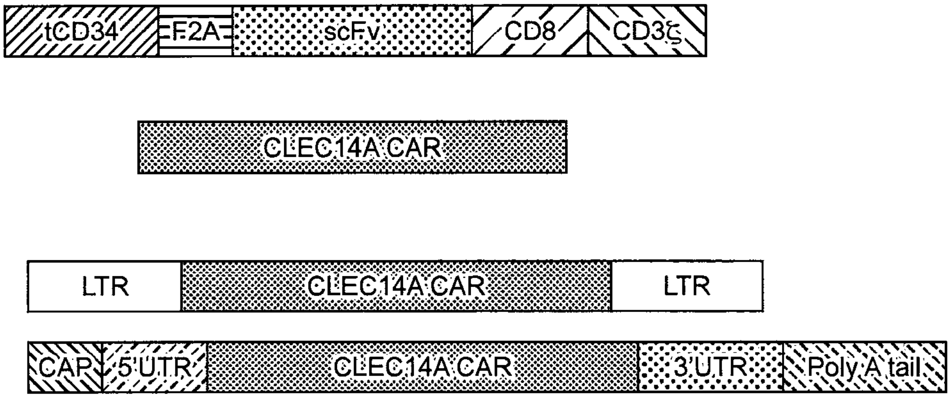

FIG. 23 shows a schematic of a suitable vector to generate RNA for electroporation by in vitro transcription.

Figure 24:
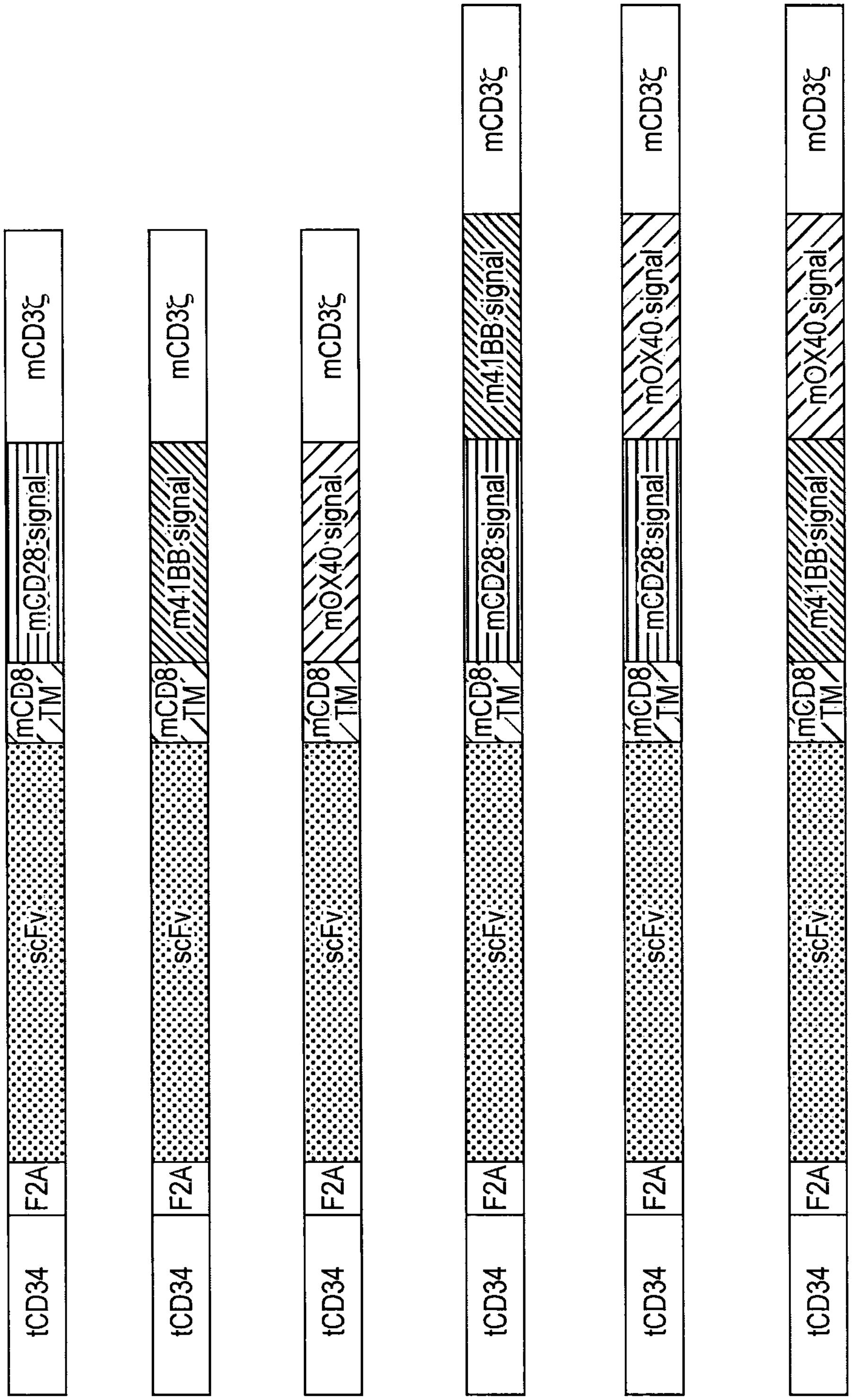

FIG. 24 shows constructs which encode CARs which can be used to transduce murine T cells. The constructs comprise transmembrane, costimulatory and intracellular signalling sequences from murine proteins (see SEQ ID NOs 116-121). The constructs may further comprise a hinge or spacer domain from murine CD8α.

| Sequence name (sequence type) | SEQ ID NO: | Sequence |
|---|---|---|
| VH (aa) | 1 | M A E V Q L Q Q S G T V L A R P G A S V K M<br>S C K A S G Y T F T S Y W M H W V K Q R P<br>G Q G L E W I G A I Y P G N S D T S Y N Q K<br>F K G K A K L T A V T S T S T A Y M E L S S L<br>T N E D S A V F Y C T H Y Y G S D Y A M D Y<br>W G Q G T S V T V |
| VH CDR1 (aa) | 2 | GYTFTSYW |
| VH CDR2 (aa) | 3 | IYPGNSDT |
| VH CDR3 (aa) | 4 | THYYGSDYAMDY |
| VL (aa) | 5 | Q I V L T Q S P A I M S A S L G E R V T M T C<br>T A S S S V S S S Y L H W Y Q Q K P G S S P<br>K L W I Y S T S N L A S G V P A R F S G S G<br>S G T S Y S L T I S S M E A E D A A T Y Y C H<br>Q Y H R S P R T F G G G T K L E I K R A A A |
| VL CDR1 (aa) | 6 | SSVSSSY |
| VL CDR2 (aa) | 7 | STS |
| VL CDR3 (aa) | 8 | HQYHRSPRT |
| ScFv (aa) | 9 | M A E V Q L Q Q S G T V L A R P G A S V K M<br>S C K A S G Y T F T S Y W M H W V K Q R P<br>G Q G L E W I G A I Y P G N S D T S Y N Q K<br>F K G K A K L T A V T S T S T A Y M E L S S L<br>T N E D S A V F Y C T H Y Y G S D Y A M D Y<br>W G Q G T S V T V S S G G G G S G G G G S<br>G G G G S Q I V L T Q S P A I M S A S L G E<br>R V T M T C T A S S S V S S S Y L H W Y Q Q<br>K P G S S P K L W I Y S T S N L A S G V P A<br>R F S G S G S G T S Y S L T I S S M E A E D<br>A A T Y Y C H Q Y H R S P R T F G G G T K L<br>E I K R A A A |
| CAR3 full-aa | 10 | M G V L L T Q R T L L S L V L A L L F P S M A<br>S M A E V Q L Q Q S G T V L A R P G A S V K<br>M S C K A S G Y T F T S Y W M H W V K Q R<br>P G Q G L E W I G A I Y P G N S D T S Y N Q<br>K F K G K A K L T A V T S T S T A Y M E L S S<br>L T N E D S A V F Y C T H Y Y G S D Y A M D<br>Y W G Q G T S V T V S S G G G G S G G G G<br>S G G G G S Q I V L T Q S P A I M S A S L G<br>E R V T M T C T A S S S V S S S Y L H W Y Q<br>Q K P G S S P K L W I Y S T S N L A S G V P<br>A R F S G S G S G T S Y S L T I S S M E A E<br>D A A T Y Y C H Q Y H R S P R T F G G G T K<br>L E I K R A A A I E V M Y P P P Y L D N E K S<br>N G T I I H V K G K H L C P S P L F P G P S K<br>P F W V L V V V G G V L A C Y S L L V T V A<br>F I I F W V R S K R S R L L H S D Y M N M T P<br>R R P G P T R K H Y Q P Y A P P R D F A A Y<br>R S R V K F S R S A D A P A Y Q Q G Q N Q L<br>Y N E L N L G R R E E Y D V L D K R R G R D<br>P E M G G K P Q R R K N P Q E G L Y N E L Q<br>K D K M A E A Y S E I G M K G E R R R G K G<br>H D G L Y Q G L S T A T K D T Y D A L H M Q<br>A L P P R |

-continued

| Sequence name (sequence type) | SEQ ID NO: | Sequence |
|---|---|---|
| VH (nt) | 11 | atggccgaggtccagctgcagcagtctgggactgtgctggcaaggcctgg ggcttcagtgaagatgtcctgcaaggcttctggctacacctttaccagct actggatgcactgggtaaaacagaggcctggacagggtctggaatggatt ggcgctatttatcctggaaatagtgatactagctacaaccagaagttcaa gggcaaggccaaactgactgcagtcacatccaccagcactgcctacatgg agctcagcagcctgacaaatgaggactctgcggtcttttactgtacacat tactacggtagtgactatgctatggactactggggtcaaggaacctcagt cactgtc |
| VH CDR1 (nt) | 12 | ggctacacctttaccagctactgg |
| VH CDR2 (nt) | 13 | atttatcctggaaatagtgatact |
| VH CDR3 (nt) | 14 | acacattactacggtagtgactatgctatggactac |
| VL (nt) | 15 | caaattgttctcacccagtctccagcaatcatgtctgcatctctagggga acgggtcaccatgacctgcactgccagctcaagtgtaagttccagttact tgcactggtaccagcagaagccaggatcctcccccaaactctggatttat agcacatccaacctggcttctggagtcccagctcgcttcagtggcagtgg gtctgggacctcttactctctcacaatcagcagcatggaggctgaagatg ctgccacttattactgccaccagtatcatcgttccccacggacgttcggt ggaggcaccaagctggaaatcaaacgt |
| VL CDR1 (nt) | 16 | tcaagtgtaagttccagttac |
| VL CDR2 (nt) | 17 | agcacatcc |
| VL CDR3 (nt) | 18 | caccagtatcatcgttccccacggacg |
| ScFv (nt) | 19 | atggccgaggtccagctgcagcagtctgggactgtgctggcaaggcctgg ggcttcagtgaagatgtcctgcaaggcttctggctacacctttaccagct actggatgcactgggtaaaacagaggcctggacagggtctggaatggatt ggcgctatttatcctggaaatagtgatactagctacaaccagaagttcaa gggcaaggccaaactgactgcagtcacatccaccagcactgcctacatgg agctcagcagcctgacaaatgaggactctgcggtcttttactgtacacat tactacggtagtgactatgctatggactactggggtcaaggaacctcagt cactgtctcctcaggtggaggcggttcaggcggaggtggctctggcggtg gcggatcgcaaattgttctcacccagtctccagcaatcatgtctgcatct ctaggggaacgggtcaccatgacctgcactgccagctcaagtgtaagttc cagttacttgcactggtaccagcagaagccaggatcctcccccaaactct ggatttatagcacatccaacctggcttctggagtcccagctcgcttcagt ggcagtgggtctgggacctcttactctctcacaatcagcagcatggaggc tgaagatgctgccacttattactgccaccagtatcatcgttccccacgga cgttcggtggaggcaccaagctggaaatcaaacgtgcggccgca |
| CAR3 full-nt | 20 | atgggcgtgctgctgacccagaggaccctgctgagcctggtgctggccct gctgtttccatctatggcatcgatggccgaggtccagctgcagcagtctg ggactgtgctggcaaggcctggggcttcagtgaagatgtcctgcaaggct tctggctacacctttaccagctactggatgcactgggtaaaacagaggcc tggacagggtctggaatggattggcgctatttatcctggaaatagtgata ctagctacaaccagaagttcaagggcaaggccaaactgactgcagtcaca tccaccagcactgcctacatggagctcagcagcctgacaaatgaggactc tgcggtcttttactgtacacattactacggtagtgactatgctatggact actggggtcaaggaacctcagtcactgtctcctcaggtggaggcggttca ggcggaggtggctctggcggtggcggatcgcaaattgttctcacccagtc tccagcaatcatgtctgcatctctaggggaacgggtcaccatgacctgca ctgccagctcaagtgtaagttccagttacttgcactggtaccagcagaag ccaggatcctcccccaaactctggatttatagcacatccaacctggcttc tggagtcccagctcgcttcagtggcagtgggtctgggacctcttactctc tcacaatcagcagcatggaggctgaagatgctgccacttattactgccac cagtatcatcgttccccacggacgttcggtggaggcaccaagctggaaat caaacgtgcggccgcaattgaagttatgtatcctcctccttacctagaca atgagaagagcaatggaaccattatccatgtgaaagggaaacacctttgt ccaagtcccctatttcccggaccttctaagcccttttgggtgctggtggt ggttggtggagtcctggcttgctatagcttgctagtaacagtggccttta ttattttctgggtgaggagtaagaggagcaggctcctgcacagtgactac atgaacatgactccccgccgccccgggcccacccgcaagcattaccagcc ctatgccccaccacgcgacttcgcagcctatcgctccagagtgaagttca gcaggagcgcagacgcccccgcgtaccagcagggccagaaccagctctat aacgagctcaatctaggacgaagagaggagtacgatgttttggacaagag acgtggccgggaccctgagatggggggaaagccgcagagaaggaagaacc ctcaggaaggcctgtacaatgaactgcagaaagataagatggcggaggcc tacagtgagattgggatgaaaggcgagcgccggaggggcaaggggcacga tggcctttaccagggtctcagtacagccaccaaggacacctacgacgccc ttcacatgcaggccctgccccctcgctaataaaagcttaacacgagcca |

-continued

| Sequence name (sequence type) | SEQ ID NO: | Sequence |
|---|---|---|
| VH (aa) | 21 | M A E V Q G V E S G G G L V Q P K G S L K L<br>S C A A S G F T F N T Y A M H W V C Q A P G<br>K G L E W V A R I R S K S N N Y A T Y Y A D<br>S V K D R F T I S R D D S Q S M L Y L Q M N<br>N L K T E D T A M Y Y C V R E G V Y Y Y G S<br>S G Y Y A M D Y W G Q G T S V T V S S G |
| VH CDR1 (aa) | 22 | GFTFNTYA |
| VH CDR2 (aa) | 23 | IRSKSNNYAT |
| VH CDR3 (aa) | 24 | VREGVYYYGSSGYYAMDY |
| VL (aa) | 25 | EIVLTQSPAIMSASPGEKVTITCSASSSVSYMHWFQQKPGT<br>SPKLWIYSTSNLASGVPARFSGSGSGTSYSLTISRMEAEDA<br>ATYYCQQRSSYPLTFGAPGKLELKRAA |
| VL CDR1 (aa) | 26 | SYMHWF |
| VL CDR2 (aa) | 27 | LWIYSTSNLA |
| VL CDR3 (aa) | 28 | QQRSSYPL |
| ScFv (aa) | 29 | M A E V Q G V E S G G G L V Q P K G S L K L<br>S C A A S G F T F N T Y A M H W V C Q A P G<br>K G L E W V A R I R S K S N N Y A T Y Y A D<br>S V K D R F T I S R D D S Q S M L Y L Q M N<br>N L K T E D T A M Y Y C V R E G V Y Y Y G S<br>S G Y Y A M D Y W G Q G T S V T V S S GGGG<br>GSGGGGSGGGGSEIVLTQSPAIMSASPGEKVTITCSASSSV<br>SYMHWFQQKPGTSPKLWIYSTSNLASGVPARFSGSGSGT<br>SYSLTISRMEAEDAATYYCQQRSSYPLTFGAPGKLELKRAA |
| CAR2 full-aa | 30 | M P R G W T A L C L L S L L P S G F M S<br>L D N N G T A T P E L P T Q G T F S N V<br>S T N V S Y Q E T T T P S T L G S T S L H<br>P V S Q H G N E A T T N I T E T T V K F T<br>S T S V I T S V Y G N T N S S V Q S Q T S<br>V I S T V F T T P A N V S T P E T T L K P<br>S L S P G N V S D L S T T S T S L A T S P<br>T K P Y T S S S P I L S D I K A E I K C S<br>G I R E V K L T Q G I C L E Q N K T S S C<br>A E F K K D R G E G L A R V L C G E E Q<br>A D A D A G A Q V C S L L L A Q S E V R<br>P Q C L L L V L A N R T E I S S K L Q L M<br>K K H Q S D L K K L G I L D F T E Q D V<br>A S H Q S Y S Q K T L I A L V T S G A L L<br>A V L G I T G Y F L M N R R S W S P T G<br>E R L E L E P V D R V K Q T L N F D L L<br>K L A G D V E S N P G P G N M G V L L T<br>Q R T L L S L V L A L L F P S M A SM A E<br>V Q G V E S G G G L V Q P K G S L K L S<br>C A A S G F T F N T Y A M H W V C Q A P<br>G K G L E W V A R I R S K S N N Y A T Y<br>Y A D S V K D R F T I S R D D S Q S M L<br>Y L Q M N N L K T E D T A M Y Y C V R E<br>G V Y Y Y G S S G Y Y A M D Y W G Q G T<br>S V T V S S<br>GGGGGSGGGGSGGGGSEIVLTQSPAIMSASPGEKVT<br>ITCSASSSVSYMHWFQQKPGTSPKLWIYSTSNLASG<br>VPARFSGSGSGTSYSLTISRMEAEDAATYYCQQRSS<br>YPLTFGAPGKLELKRAA I E V M Y P P P Y L D<br>N E K S N G T I I H V K G K H L C P S P L<br>F P G P S K P F W V L V V V G G V L A C<br>Y S L L V T V A F I I F W V R S K R S R L<br>L H S D Y M N M T P R R P G P T R K H Y<br>Q P Y A P P R D F A A Y R S R V K F S R<br>S A D A P A Y Q Q G Q N Q L Y N E L N L<br>G R R E E Y D V L D K R R G R D P E M G<br>G K P Q R R K N P Q E G L Y N E L Q K D<br>K M A E A Y S E I G M K G E R R R G K G<br>H D G L Y Q G L S T A T K D T Y D A L H<br>M Q A L P P R |

-continued

| Sequence name (sequence type) | SEQ ID NO: | Sequence |
|---|---|---|
| VH (nt) | 31 | GACGCTTATCGATGGCCGAGGTGCAGGGGGTGGAGTCT<br>GGTGGAGGATTGGTGCAGCCTAAAGGATCATTGAAACTC<br>TCATGTGCCGCCTCTGGTTTCACCTTCAATACCTATGCC<br>A<br>TGCACTGGGTCTGCCAGGCTCCAGGAAAGGGTTTGGAA<br>TGGGTTGCTCGCATAAGAAGTAAAAGTAATAATTATGCAA<br>CATATTATGCCGATTCAGTGAAAGACAGATTCACCATCTC<br>CAGAGATGATTCACAAAGCATGCTCTATCTGCAAATGAA<br>CAACCTGAAAACTGAGGACACAGCCATGTATTACTGTGT<br>GAGAGAAGGGGTTTATTACTACGGTAGTAGTGGGTACTA<br>TGCTATGGACTACTGGGGTCAAGGAACCTCAGTCACCGT<br>CTCCTCAGGT |
| VH CDR1 (nt) | 32 | GGTTTCACCTTCAATACCTATGCC |
| VH CDR2 (nt) | 33 | ATAAGAAGTAAAAGTAATAATTATGCAACA |
| VH CDR3 (nt) | 34 | GTGAGAGAAGGGGTTTATTACTACGGTAGTAGTGGGTAC<br>TATGCTATGGACTAC |
| VL (nt) | 35 | GAAATTGTTCTCACCCAGTCTCCAGCAATCATGTCTGCAT<br>CTCCAGGGGAGAAGGTCACC<br>ATAACCTGCAGTGCCAGCTCAAGTGTAAGTTACATGCAC<br>TGGTTCCAGCAGAAG<br>CCAGGCACTTCTCCCAAACTCTGGATTTATAGCACATCC<br>AACCTGGCTTCTGGAGTCCCT<br>GCTCGCTTCAGTGGCAGTGGATCTGGGACCTCTTACTCT<br>CTCACAATCAGCCGAATGGAG<br>GCTGAAGATGCTGCCACTTATTACTGCCAGCAAAGGAGT<br>AGTTACCCCCTCACGTTCGGT<br>GCTGGGACCAAGCTGGAGCTGAAACGTGCGGCCGC |
| VL CDR1 (nt) | 36 | AGTTACATGCACTGGTTC |
| VL CDR2 (nt) | 37 | CTCTGGATTTATAGCACATCCAACCTGGCT |
| VL CDR3 (nt) | 38 | CAGCAAAGGAGTAGTTACCCCCTC |
| ScFv (nt) | 39 | GACGCTTATCGATGGCCGAGGTGCAGGGGGTGGAGTCT<br>GGTGGAGGATTGGTGCAGCCTAAAGGATCATTGAAACTC<br>TCATGTGCCGCCTCTGGTTTCACCTTCAATACCTATGCC<br>ATGCACTGGGTCTGCCAGGCTCCAGGAAAGGGTTTGGA<br>ATGGGTTGCTCGCATAAGAAGTAAAAGTAATAATTATGCA<br>ACATATTATGCCGATTCAGTGAAAGACAGATTCACCATCT<br>CCAGAGATGATTCACAAAGCATGCTCTATCTGCAAATGA<br>ACAACCTGAAAACTGAGGACACAGCCATGTATTACTGTG<br>TGAGAGAAGGGGTTTATTACTACGGTAGTAGTGGGTACT<br>ATGCTATGGACTACTGGGGTCAAGGAACCTCAGTCACCG<br>TCTCCTCAGGTtcctcaggtggaggcggttcaggcggaggtggctctggc<br>ggtggcggatcgGAAATTGTTCTCACCCAGTCTCCAGCAATCAT<br>GTCTGCATCTCCAGGGGAGAAGGTCACC<br>ATAACCTGCAGTGCCAGCTCAAGTGTAAGTTACATGCAC<br>TGGTTCCAGCAGAAG<br>CCAGGCACTTCTCCCAAACTCTGGATTTATAGCACATCC<br>AACCTGGCTTCTGGAGTCCCT<br>GCTCGCTTCAGTGGCAGTGGATCTGGGACCTCTTACTCT<br>CTCACAATCAGCCGAATGGAG<br>GCTGAAGATGCTGCCACTTATTACTGCCAGCAAAGGAGT<br>AGTTACCCCCTCACGTTCGGT<br>GCTGGGACCAAGCTGGAGCTGAAACGTGCGGCCGC |
| CAR2 full-nt | 40 | atgcctcgcggctggacagccctgtgcctgctgtctctgctgccatcc<br>ggcttcatgagcctggataataacggcacagccaccccagagctgc<br>ctacacagggcaccttcagcaatgtgtccacaaacgtgagctatcag<br>gagaccacaaccccttctaccctgggatccacaagcctgcaccccgt<br>gtctcagcacggcaacgaagccaccaccaacatcaccgagaccac<br>agtgaagtttacctccacctctgtgattacctctgtgtacggaaatacaa<br>actccagcgtgcagtctcagacatctgtgatctccacagtgtttacaac<br>acctgccaatgtgtccaccccagagacaaccctgaagcccagcctg<br>tctcctggaaatgtgtccgatctgtctaccacctccaccagcctggcca<br>cctctcccaccaagccctatacctcctcttctcccatcctgagcgatat<br>caaagccgagatcaaatgcagcgggattcgggaagtgaaactgaca<br>cagggcatctgcctggaacagaataagacatccagctgcgccgagtt<br>taagaaagatagaggagagggactggccagggtgctgtgtggcga<br>agagcaggccgacgccgatgccggcgcccaggtgtgttccctgctg<br>ctggcccagtctgaggtgcgcccccagtgcctgctgctggtgctggc<br>caatcggacagaaattagcagcaagctgcagctgatgaaaaaacac |

-continued

| Sequence name (sequence type) | SEQ ID NO: | Sequence |
|---|---|---|
| | | cagagcgatctgaaaaagctgggcatcctggactttaccgagcagg<br>acgtggcctctcaccagagctacagccagaaaacactgatcgccct<br>ggtgaccagcggagccctgctggccgtgctgggcatcaccggatatt<br>tcctgatgaataggcgcagctggagccccaccggcgagcggctgg<br>agctggagcctgtcgaccgagtgaagcagaccctgaactttgatctg<br>ctgaagctggccggcgacgtggagtccaaccccgggccagggaat<br>atgggcgtgctgctgacccagaggaccctgctgagcctggtgctgg<br>ccctgctgtttccatctatggcatcgGACGCTTATCGATGGCC<br>GAGGTGCAGGGGGTGGAGTCTGGTGGAGGATTGG<br>TGCAGCCTAAAGGATCATTGAAACTCTCATGTGCC<br>GCCTCTGGTTTCACCTTCAATACCTATGCCATGCAC<br>TGGGTCTGCCAGGCTCCAGGAAAGGGTTTGGAAT<br>GGGTTGCTCGCATAAGAAGTAAAAGTAATAATTAT<br>GCAACATATTATGCCGATTCAGTGAAAGACAGATT<br>CACCATCTCCAGAGATGATTCACAAAGCATGCTCT<br>ATCTGCAAATGAACAACCTGAAAACTGAGGACACA<br>GCCATGTATTACTGTGTGAGAGAAGGGGTTTATTA<br>CTACGGTAGTAGTGGGTACTATGCTATGGACTACT<br>GGGGTCAAGGAACCTCAGTCACCGTCTCCTCAGGT<br>tcctcaggtggaggcggttcaggcggaggtggctctggcggtggcg<br>gatcgGAAATTGTTCTCACCCAGTCTCCAGCAATCAT<br>GTCTGCATCTCCAGGGGAGAAGGTCACC<br>ATAACCTGCAGTGCCAGCTCAAGTGTAAGTTACAT<br>GCACTGGTTCCAGCAGAAG<br>CCAGGCACTTCTCCCAAACTCTGGATTTATAGCAC<br>ATCCAACCTGGCTTCTGGAGTCCCT<br>GCTCGCTTCAGTGGCAGTGGATCTGGGACCTCTTA<br>CTCTCTCACAATCAGCCGAATGGAG<br>GCTGAAGATGCTGCCACTTATTACTGCCAGCAAAG<br>GAGTAGTTACCCCCTCACGTTCGGT<br>GCTGGGACCAAGCTGGAGCTGAAACGTGCGGCCG<br>Caattgaagttatgtatcctcctccttacctagacaatgagaagagcaa<br>tggaaccattatccatgtgaaagggaaacacctttgtccaagtcccta<br>tttcccggaccttctaagcccttttgggtgctggtggtggttggtggagt<br>cctggcttgctatagcttgctagtaacagtggcctttattattttctggg<br>tgaggagtaagaggagcaggctcctgcacagtgactacatgaacatga<br>ctccccgccgccccgggcccacccgcaagcattaccagccctatgc<br>cccaccacgcgacttcgcagcctatcgctccagagtgaagttcagca<br>ggagcgcagacgcccccgcgtaccagcagggccagaaccagctc<br>tataacgagctcaatctaggacgaagagaggagtacgatgttttggac<br>aagagacgtggccgggaccctgagatggggggaaagccgcagag<br>aaggaagaaccctcaggaaggcctgtacaatgaactgcagaaagat<br>aagatggcggaggcctacagtgagattgggatgaaaggcgagcgc<br>cggaggggcaaggggcacgatggcctttaccagggtctcagtacag<br>ccaccaaggacacctacgacgcccttcacatgcaggccctgccccc<br>tcgctaataa |
| VH* (aa) | 41 | MAEVQLQQSGTVLARPGASVKMSCKASGYTFTSYWMHW<br>VKQRPGQGLEWIGAIYPGNSDTSYNQKFKGKAKLTAVTST<br>STAYMELSSLTNEDSAVFYCTHYGSDYAMDYWGQGTSVTI<br>SSG |
| VH CDR1* (aa) | 42 | TSYWMH |
| VH CDR2* (aa) | 43 | WIGAIYPGNSDTS |
| VH CDR3* (aa) | 44 | THYYGSDYAMD |
| VL* (aa) | 45 | QIVLTQSPAIMSASLGERVTMTCTASSSVSSSYLHWYQQKP<br>GSSPKLWIYSTSNLASGVPARFSGSGSGTSYSLTISSMEAE<br>DAATYYCHQYHRSPRTFGGGTKLEIKRAA |
| VL CDR1* (aa) | 46 | SSSYLHWY |
| VL CDR2* (aa) | 47 | LWIYSTSNLA |
| VL CDR3* (aa) | 48 | HQYHRSPR |
| ScFv* (aa) | 49<br>(VH*) | MAEVQLQQSGTVLARPGASVKMSCKASGYTFTSYWMHW<br>VKQRPGQGLEWIGAIYPGNSDTSYNQKFKGKAKLTAVTST<br>STAYMELSSLTNEDSAVFYCTHYGSDYAMDYWGQGTSVTI<br>SSG S S G G G G S G G G G S G G G G S Q I<br>V L T Q S P A I M S A S L G E R V T M T C T<br>A S S S V S S S Y L H W Y Q Q K P G S S P K |

-continued

| Sequence name (sequence type) | SEQ ID NO: | Sequence |
|---|---|---|
| | | L W I Y S T S N L A S G V P A R F S G S G S<br>G T S Y S L T I S S M E A E D A A T Y Y C H<br>Q Y H R S P R T F G G G T K L E I K R A A A |
| ScFv* (aa) | 50<br>(VL*) | M A E V Q L Q Q S G T V L A R P G A S V K M<br>S C K A S G Y T F T S Y W M H W V K Q R P<br>G Q G L E W I G A I Y P G N S D T S Y N Q K<br>F K G K A K L T A V T S T S T A Y M E L S S L<br>T N E D S A V F Y C T H Y Y G S D Y A M D Y<br>W G Q G T S V T V S S G G G G S G G G G S<br>G G G G<br>SQIVLTQSPAIMSASLGERVTMTCTASSSVSSSYLHWYQQK<br>PGSSPKLWIYSTSNLASGVPARFSGSGSGTSYSLTISSMEA<br>EDAATYYCHQYHRSPRTFGGGTKLEIKRAA |
| ScFv* (aa) | 51<br>(VH*VL*) | MAEVQLQQSGTVLARPGASVKMSCKASGYTFTSYWMHW<br>VKQRPGQGLEWIGAIYPGNSDTSYNQKFKGKAKLTAVTST<br>STAYMELSSLTNEDSAVFYCTHYGSDYAMDYWGQGTSVTI<br>SSG S S G G G G S G G G G S G G G G S<br>QIVLTQSPAIMSASLGERVTMTCTASSSVSSSYLHWYQQKP<br>GSSPKLWIYSTSNLASGVPARFSGSGSGTSYSLTISSMEAE<br>DAATYYCHQYHRSPRTFGGGTKLEIKRAA |
| CLEC14A (aa) | 52 | MRPAFALCLL WQALWPGPGG GEHPTADRAG<br>CSASGACYSL HHATMKRQAA EEACILRGGA<br>LSTVRAGAEL RAVLALLRAG PGPGGGSKDL<br>LFWVALERRR SHCTLENEPL RGFSWLSSDP<br>GGLESDTLQW VEEPQRSCTA RRCAVLQATG<br>GVEPAGWKEM RCHLRANGYL CKYQFEVLCP<br>APRPGAASNL SYRAPFQLHS AALDFSPPGT<br>EVSALCRGQL PISVTCIADE IGARWDKLSG<br>DVLCPCPGRY LRAGKCAELP NCLDDLGGFA<br>CECATGFELG KDGRSCVTSG EGQPTLGGTG<br>VPTRRPPATA TSPVPQRTWP IRVDEKLGET<br>PLVPEQDNSV TSIPEIPRWG SQSTMSTLQM<br>SLQAESKATI TPSGSVISKF NSTTSSATPQ AFDSSSAVVF<br>IFVSTAVVVL VILTMTVLGL VKLCFHESPS SQPRKESMGP<br>PGLESDPEPA ALGSSSAHCT NNGVKVGDCD<br>LRDRAEGALL AESPLGSSDA |
| CLEC14A (nt) | 53 | CTCCTCTTGC TCTAAGCAGG GTGTTTGACC<br>TTCTAGTCGA CTGCGTCCCC TGTACCCGGC<br>GCCAGCTGTG TTCCTGACCC CAGAATAACT<br>CAGGGCTGCA CCGGGCCTGG CAGCGCTCCG<br>CACACATTTC CTGTCGCGGC CTAAGGGAAA<br>CTGTTGGCCG CTGGGCCCGC GGGGGGATTC<br>TTGGCAGTTG GGGGGTCCGT CGGGAGCGAG<br>GGCGGAGGGG AAGGGAGGGG GAACCGGGTT<br>GGGGAAGCCA GCTGTAGAGG GCGGTGACCG<br>CGCTCCAGAC ACAGCTCTGC GTCCTCGAGC<br>GGGACAGATC CAAGTTGGGA GCAGCTCTGC<br>GTGCGGGGCC TCAGAGAATG AGGCCGGCGT<br>TCGCCCTGTG CCTCCTCTGG CAGGCGCTCT<br>GGCCCGGGCC GGGCGGCGGC GAACACCCCA<br>CTGCCGACCG TGCTGGCTGC TCGGCCTCGG<br>GGGCCTGCTA CAGCCTGCAC CACGCTACCA<br>TGAAGCGGCA GGCGGCCGAG GAGGCCTGCA<br>TCCTGCGAGG TGGGGCGCTC AGCACCGTGC<br>GTGCGGGCGC CGAGCTGCGC GCTGTGCTCG<br>CGCTCCTGCG GGCAGGCCCA GGGCCCGGAG<br>GGGGCTCCAA AGACCTGCTG TTCTGGGTCG<br>CACTGGAGCG CAGGCGTTCC CACTGCACCC<br>TGGAGAACGA GCCTTTGCGG GGTTTCTCCT<br>GGCTGTCCTC CGACCCCGGC GGTCTCGAAA<br>GCGACACGCT GCAGTGGGTG GAGGAGCCCC<br>AACGCTCCTG CACCGCGCGG AGATGCGCGG<br>TACTCCAGGC CACCGGTGGG GTCGAGCCCG<br>CAGGCTGGAA GGAGATGCGA TGCCACCTGC<br>GCGCCAACGG CTACCTGTGC AAGTACCAGT<br>TTGAGGTCTT GTGTCCTGCG CCGCGCCCCG<br>GGGCCGCCTC TAACTTGAGC TATCGCGCGC<br>CCTTCCAGCT GCACAGCGCC GCTCTGGACT<br>TCAGTCCACC TGGGACCGAG GTGAGTGCGC<br>TCTGCCGGGG ACAGCTCCCG ATCTCAGTTA 1021<br>CTTGCATCGC GGACGAAATC GGCGCTCGCT<br>GGGACAAACT CTCGGGCGAT GTGTTGTGTC |

-continued

| Sequence name (sequence type) | SEQ ID NO: | Sequence |
|---|---|---|
| | | CCTGCCCCGG GAGGTACCTC CGTGCTGGCA<br>AATGCGCAGA GCTCCCTAAC TGCCTAGACG<br>ACTTGGGAGG CTTTGCCTGC GAATGTGCTA<br>CGGGCTTCGA GCTGGGGAAG GACGGCCGCT 1201<br>CTTGTGTGAC CAGTGGGGAA GGACAGCCGA<br>CCCTTGGGGG GACCGGGGTG CCCACCAGGC<br>GCCCGCCGGC CACTGCAACC AGCCCCGTGC<br>CGCAGAGAAC ATGGCCAATC AGGGTCGACG<br>AGAAGCTGGG AGAGACACCA CTTGTCCCTG<br>AACAAGACAA TTCAGTAACA TCTATTCCTG |
| VH* (nt) | 54 | ATGGCCGAGGTCCAGCTGCAGCAGTCTGGGACTGTGCT<br>GGCAAGGCCTGGGGCTTCAGTGAAGATGTCCTGC<br>AAGGCTTCTGGCTACACCTTTACCAGCTACTGGATGCAC<br>TGGGTAAAACAGAGGCCTGGACAGGGTCTGGAATGGAT<br>TGGCGCTATTTATCCTGGAAATAGTGATACTAGCTACAAC<br>CAGAAGTTCAAGGGCAAGGCCAAACTG<br>ACTGCAGTCACATCCACCAGCACTGCCTACATGGAGCTC<br>AGCAGCCTGACAAATGAGGACTCTGCGGTCTTT<br>TACTGTACACATTACTACGGTAGTGACTATGCTATGGACT<br>ACTGGGGTCAAGGAACCTCAGTCACTGTCTCC<br>TCA |
| VH CDR1* (nt) | 55 | ACCAGCTACTGGATGCAC |
| VH CDR2* (nt) | 56 | TGGATTGGCGCTATTTATCCTGGAAATAGTGATACTAGC |
| VH CDR3* (nt) | 57 | ACACATTACTACGGTAGTGACTATGCTATGGAC |
| VL* (nt) | 58 | CAAATTGTTCTCACCCAGTCTCCAGCAATCATGTCTGCAT<br>CTCTAGGGGAACGGGTCACCATGACCTGCACTGCCAGC<br>TCAAGTGTAAGTTCCAGTTACTTGCACTGGTACCAGCAG<br>AAGCCAGGATCCTCCCCCAAACTCTGGATTTATAGCACA<br>TCCAACCTGGCTTCTGGAGTCCCAGCTCGCTTCAGTGGC<br>AGTGGGTCTGGGACCTCTTACTCTCTCACAATCAGCAGC<br>ATGGAGGCTGAAGATGCTGCCACTTATTACTGCCACCAG<br>TATCATCGTTCCCCACGGACGTTCGGTGGAGGCACCAA<br>GCTGGAAATCAAACGTGCGGCCGC |
| VL CDR1* (nt) | 59 | AGTTCCAGTTACTTGCACTGGTAC |
| VL CDR2* (nt) | 60 | CTCTGGATTTATAGCACATCCAACCTGGCT |
| VL CDR3* (nt) | 61 | CCACCAGTATCATCGTTCCCCACGG |
| ScFv* (nt) | 62<br>(VH*) | ATGGCCGAGGTCCAGCTGCAGCAGTCTGGGACTGTGCT<br>GGCAAGGCCTGGGGCTTCAGTGAAGATGTCCTGC<br>AAGGCTTCTGGCTACACCTTTACCAGCTACTGGATGCAC<br>TGGGTAAAACAGAGGCCTGGACAGGGTCTGGAATGGAT<br>TGGCGCTATTTATCCTGGAAATAGTGATACTAGCTACAAC<br>CAGAAGTTCAAGGGCAAGGCCAAACTG<br>ACTGCAGTCACATCCACCAGCACTGCCTACATGGAGCTC<br>AGCAGCCTGACAAATGAGGACTCTGCGGTCTTT<br>TACTGTACACATTACTACGGTAGTGACTATGCTATGGACT<br>ACTGGGGTCAAGGAACCTCAGTCACTGTCTCC<br>TCATCCTCAGGTGGAGGCGGTTCAGGCGGAGGTGGCTC<br>TGGCGGTGGCGGATCGcaaattgttctcacccagtctccagcaatcatgt<br>ctgcatctctaggggaacgggtcaccatgacctgcactgccagctcaagt<br>gtaagttccagttacttgcactggtaccagcagaagccaggatcctcccc<br>caaactctggatttatagcacatccaacctggcttctggagtcccagctc<br>gcttcagtggcagtgggtctgggacctcttactctctcacaatcagcagc<br>atggaggctgaagatgctgccacttattactgccaccagtatcatcgttc<br>cccacggacgttcggtggaggcaccaagctggaaatcaaacgt |

-continued

| Sequence name (sequence type) | SEQ ID NO: | Sequence |
|---|---|---|
| ScFv* (nt) | 63 (VL*) | atggccgaggtccagctgcagcagtctgggactgtgctggcaaggcctgg<br>ggcttcagtgaagatgtcctgcaaggcttctggctacacctttaccagct<br>actggatgcactgggtaaaacagaggcctggacagggtctggaatggatt<br>ggcgctatttatcctggaaatagtgatactagctacaaccagaagttcaa<br>gggcaaggccaaactgactgcagtcacatccaccagcactgcctacatgg<br>agctcagcagcctgacaaatgaggactctgcggtcttttactgtacacat<br>tactacggtagtgactatgctatggactactggggtcaaggaacctcagt<br>cactgtcTCCTCAGGTGGAGGCGGTTCAGGCGGAGGTGGCTCTGGCGGTG<br>GCGGATCGCAAATTGTTCTCACCCAGTCTCCAGCAATCATGTCTGCATCT<br>CTAGGGGAACGGGTCACCATGACCTGCACTGCCAGCTCAAGTGTAAGTT<br>CCAGTTACTTGCACTGGTACCAGCAGAAGCCAGGATCCT<br>CCCCCAAACTCTGGATTTATAGCACATCCAACCTGGCTT<br>CTGGAGTCCCAGCTCGCTTCAGTGGCAGTGGGTCTGGG<br>ACCTCTTACTCTCTCACAATCAGCAGCATGGAGGCTGAA<br>GATGCTGCCACTTATTACTGCCACCAGTATCATCGTTCC<br>CCACGGACGTTCGGTGGAGGCACCAAGCTGGAAATCAA<br>ACGTGCGGCCGC |
| ScFv* (nt) | 64 (VH*VL*) | ATGGCCGAGGTCCAGCTGCAGCAGTCTGGGACTGTGCT<br>GGCAAGGCCTGGGGCTTCAGTGAAGATGTCCTGC<br>AAGGCTTCTGGCTACACCTTTACCAGCTACTGGATGCAC<br>TGGGTAAAACAGAGGCCTGGACAGGGTCTGGAATGGAT<br>TGGCGCTATTTATCCTGGAAATAGTGATACTAGCTACAAC<br>CAGAAGTTCAAGGGCAAGGCCAAACTG<br>ACTGCAGTCACATCCACCAGCACTGCCTACATGGAGCTC<br>AGCAGCCTGACAAATGAGGACTCTGCGGTCTTT<br>TACTGTACACATTACTACGGTAGTGACTATGCTATGGACT<br>ACTGGGGTCAAGGAACCTCAGTCACTGTCTCC<br>TCATCCTCAGGTGGAGGCGGTTCAGGCGGAGGTGGCTC<br>TGGCGGTGGCGGATCGCAAATTGTTCTCACCCAGTCTCC<br>AGCAATCATGTCTGCATCTCTAGGGGAACGGGTCACCAT<br>GACCTGCACTGCCAGCTCAAGTGTAAGTTCCAGTTACTT<br>GCACTGGTACCAGCAGAAGCCAGGATCCTCCCCCAAAC<br>TCTGGATTTATAGCACATCCAACCTGGCTTCTGGAGTCC<br>CAGCTCGCTTCAGTGGCAGTGGGTCTGGGACCTCTTACT<br>CTCTCACAATCAGCAGCATGGAGGCTGAAGATGCTGCCA<br>CTTATTACTGCCACCAGTATCATCGTTCCCCACGGACGT<br>TCGGTGGAGGCACCAAGCTGGAAATCAAACGTGCGGCC<br>GC |
| $(G_4S)_3$ linker | 65 | GGGGSGGGGSGGGGS |
| Hinge domain of CD8α | 66 | FVPVFLPAKP TTTPAPRPPT PAPTIASQPL SLRPEACRPA<br>AGGAVHTRGL DFACD |
| shortened IgG hinge | 67 | AEPKSPDKTH TCP |
| Linker sequence | 68 | KDPK |
| shortened IgG hinge + linker | 69 | AEPKSPDKTH TCPKDPK |
| CD8α transmembrane domain | 70 | IYIWAPLAGT CGVLLLSLVI TLYCNHRN |
| CD28 transmembrane domain | 71 | FWVLVVVGGV LACYSLLVTV AFIIFWV |
| CH2CH3 hinge | 72 | DPAEPKSPDK THTCPPCPAP ELLGGPSVFL<br>FPPKPKDTLM ISRTPEVTCV<br>VVDVSHEDPEVKFNWYVDGV EVHNAKTKPR<br>EEQYNSTYRV VSVLTVLHQD WLNGKEYKCK<br>VSNKALPAPI EKTISKAKGQ PREPQVYTLP<br>PSRDELTKNQ VSLTCLVKGF YPSDIAVEWE<br>SNGQPENNYKTTPPVLDSDG SFFLYSKLTV<br>DKSRWQQGNV FSCSVMHEAL HNHYTQKSLS<br>LSPGKKDPK |
| CD3ζ domain | 73 | RVKFSRSADA PAYQQGQNQL YNELNLGRRE<br>EYDVLDKRRG RDPEMGGKPR<br>RKNPQEGLYNELQKDKMAEA YSEIGMKGER<br>RRGKGHDGLY QGLSTATKDT YDALHMQALP PR |

-continued

| Sequence name (sequence type) | SEQ ID NO: | Sequence |
|---|---|---|
| intracellular domain of 4-1BB | 74 | RFSVVKRGRK KLLYIFKQPF MRPVQTTQEE DGCSCRFPEE EEGGCEL |
| intracellular domain of human CD28 | 75 | RSKRSRLLHS DYMNMTPRRP GPTRKHYQPY APPRDFAAYR S |
| OX40 (CD134) co-stimulatory domain | 76 | RDQRLPPDAH KPPGGGSFRT PIQEEQADAH STLAKI |
| Truncated CD34 molecule (nt) | 77 | atgcctcgcggctggacagccctgtgcctgctgtctctgctgccatccgg cttcatgagcctggataataacggcacagccaccccagagctgcctacac agggcaccttcagcaatgtgtccacaaacgtgagctatcaggagaccaca acccccttctaccctgggatccacaagcctgcaccccgtgtctcagcacgg caacgaagccaccaccaacatcaccgagaccacagtgaagtttacctcca cctctgtgattacctctgtgtacggaaatacaaactccagcgtgcagtct cagacatctgtgatctccacagtgtttacaacacctgccaatgtgtccac cccagagacaaccctgaagcccagcctgtctcctggaaatgtgtccgatc tgtctaccacctccaccagcctggccacctctcccaccaagccctatacc tcctcttctcccatcctgagcgatatcaaagccgagatcaaatgcagcgg gattcgggaagtgaaactgacacagggcatctgcctggaacagaataaga catccagctgcgccgagtttaagaaagatagaggagagggactggccagg gtgctgtgtggcgaagagcaggccgacgccgatgccggcgcccaggtgtg ttccctgctgctggcccagtctgaggtgcgcccccagtgcctgctgctgg tgctggccaatcggacagaaattagcagcaagctgcagctgatgaaaaaa caccagagcgatctgaaaaagctgggcatcctggactttaccgagcagga cgtggcctctcaccagagctacagccagaaaacactgatcgccctggtga ccagcggagccctgctggccgtgctgggcatcaccggatatttcctgatg aataggcgcagctggagccccaccggcgagcggctggagctggagcctgt cgaccgagtgaagcagaccctgaactttgatctgctgaagctggccggcg acgtggagtccaaccccgggccagggaatatgggcgtgctgctgacccag aggaccctgctgagcctggtgctggccctgctgtttccatctatggcatc g |
| Truncated CD34 molecule (aa) | 78 | M P R G W T A L C L L S L L P S G F M S L D N N G T A T P E L P T Q G T F S N V S T N V S Y Q E T T T P S T L G S T S L H P V S Q H G N E A T T N I T E T T V K F T S T S V I T S V Y G N T N S S V Q S Q T S V I S T V F T T P A N V S T P E T T L K P S L S P G N V S D L S T T S T S L A T S P T K P Y T S S S P I L S D I K A E I K C S G I R E V K L T Q G I C L E Q N K T S S C A E F K K D R G E G L A R V L C G E E Q A D A D A G A Q V C S L L L A Q S E V R P Q C L L L V L A N R T E I S S K L Q L M K K H Q S D L K K L G I L D F T E Q D V A S H Q S Y S Q K T L I A L V T S G A L L A V L G I T G Y F L M N R R S W S P T G E R L E L E P V D R V K Q T L N F D L L K L A G D V E S N P G P G N M G V L L T Q R T L L S L V L A L L F P S M A S |
| CLEC14A primer | 79 | CTGGGACCGAGGTGAGTG |
| CLEC14A probe | 80 | CGCGATGCAAGTAACTGAGA |
| Flotillin 2 primer | 81 | TGTTGTGGTTCCGACTATAAACAG |
| Flotillin 2 probe | 82 | GGGCTGCAACGTCATAATCT |
| CLEC14A fwd primer | 83 | TAGTAGGAATTCGAGAGAATGAGGCCGGCGTTCGCCCT G |
| CLEC14A rev primer | 84 | AGAACCGCGGCCGCTGGAGGAGTCGAAAGCCTGAGGA GT |
| Murine CLEC14A fwd primer | 85 | TAGTAGGAATTCGAGAGAATGAGGCCAGCGCTTGCCCT G |
| Murine CLEC14A rev primer | 86 | CTACTAGCGGCCGCTCGTGGAAGAGGTGTCGAAAGT |
| Human CLEC14A fwd primer | 87 | TAGTAGTTAATTAAGAGAGAATGAGGCCGGCGTTC |

-continued

| Sequence name (sequence type) | SEQ ID NO: | Sequence |
|---|---|---|
| Murine CLEC14A fwd primer | 88 | TAGTAGTTAATTAAGAGAGAATGAGGCCAGCGCTT |
| Human fc rev primer | 89 | CTACTAGTTTAAACTCATTTACCCGGAGACAGGGA |
| 5' UTR Fwd | 90 | TTCCTTTTCCAGGGTTTGTG |
| 5' UTR rev | 91 | GCCTACAAGGTGGCTTGAAT |
| CDS fwd | 92 | AAGCTGTGCTCCTGCTCTTG |
| CDS rev | 93 | TCCTGAGTGCACTGTGAGATG |
| 3' UTR fwd | 94 | CTGTAGAGGGCGGTGACTTT |
| 3' UTR rev | 95 | AGCTGCTCCCAAGTCCTCT |
| mACTB fwd | 96 | CTAAGGCCAACCGTGAAAAG |
| mACTB rev | 97 | ACCAGAGGCATACAGGGACA |
| CD141 1-42 aa | 98 | MLGVLVLGALALAGLGFPAPAEPQPGGSQCVEHDCFALYP GP |
| CD141 97-108 | 99 | QLPPGCGDPKRL |
| CD141 122-142 | 100 | TSYSRWARLDLNGAPLCGPL |
| | | Codon optimised sequences |
| Human codon optimised scFv nucleotide sequence of CRT3 | 101 | ATGGCCGAGGTGCAGCTGCAGCAGTCTGGCACCGTGCT GGCCAGGCCCGGAGCAAGCGTGAAGATGTCCTGCAAGG CCTCTGGCTACACCTTCACAAGCTATTGGATGCACTGGG TGAAGCAGCGCCCAGGACAGGGCCTGGAGTGGATCGG AGCAATCTACCCCGGCAACTCCGACACCTCTTATAATCA GAAGTTCAAGGGCAAGGCCAAGCTGACAGCCGTGACCT CTACAAGCACCGCCTACATGGAGCTGAGCAGCCTGACC AACGAGGATAGCGCCGTGTTTTATTGCACACACTACTAT GGCTCCGACTACGCTATGGACTATTGGGGCCAGGGCAC CTCCGTGACAGTGTCTAGCGGAGGAGGAGGCAGCGGA GGAGGAGGCTCCGGCGGCGGCGGCTCTCAGATCGTGC TGACCCAGAGCCCTGCCATCATGTCCGCCTCTCTGGGC GAGCGGGTGACAATGACCTGTACAGCCTCCTCTAGCGT GTCCTCTAGCTACCTGCACTGGTATCAGCAGAAGCCCG GCTCCTCTCCTAAGCTGTGGATCTACAGCACCTCCAATC TGGCATCCGGCGTGCCTGCAAGGTTCTCTGGCAGCGGC TCCGGCACCTCTTACAGCCTGACAATCAGCAGCATGGAG GCAGAGGACGCAGCAACATACTATTGTCACCAGTATCAC CGGAGCCCAAGAACCTTTGGCGGCGGCACAAAGCTGGA GATCAAGCGGGCGGCCGCA |
| Murine codon optimised scFv nucleotide sequence of CRT3 | 102 | ATGGCCGAGGTGCAGCTGCAGCAGTCTGGCACCGTGCT GGCTCGGCCCGGAGCTAGCGTGAAGATGTCCTGCAAGG CTTCTGGCTACACCTTCACAAGCTACTGGATGCACTGGG TGAAGCAGCGCCCAGGACAGGGCCTGGAGTGGATCGG CGCCATCTACCCCGGAAACTCCGACACCTCTTACAACCA GAAGTTCAAGGGCAAGGCTAAGCTGACAGCCGTGACCT CTACAAGCACCGCTTACATGGAGCTGAGCAGCCTGACC AACGAGGATAGCGCCGTGTTTTACTGCACACACTACTAC GGCTCCGACTACGCTATGGATTACTGGGGACAGGGCAC CTCCGTGACAGTGTCTAGCGGAGGAGGAGGAAGCGGC GGAGGcGGCAGCGGAGGAGGAGGATCTCAGATCGTGCT GACCCAGTCTCCTGCTATCATGTCCGCCTCTCTGGGCGA GAGGGTGACAATGACCTGTACAGCCTCCTCTAGCGTGTC CTCTAGCTACCTGCACTGGTATCAGCAGAAGCCCGGCTC CTCTCCTAAGCTGTGGATCTACAGCACCTCCAACCTGGC TTCCGGAGTGCCTGCTCGGTTCTCTGGAAGCGGCTCCG GAACCTCTTACAGCCTGACAATCAGCAGCATGGAGGCTG AGGACGCCGCTACATACTACTGTCACCAGTACCACAGGA GCCCAAGAACCTTTGGCGGAGGCACAAAGCTGGAGATC AAGAGGGCGGCCGCA |

-continued

| Sequence name (sequence type) | SEQ ID NO: | Sequence |
|---|---|---|
| Human codon optimised scFv nucleotide sequence of CRT2 | 103 | ATGGCAGAGGTGCAGGGAGTGGAGAGCGGAGGCGGCC TGGTGCAGCCTAAGGGCTCCCTGAAGCTGTCTTGCGCC GCCAGCGGCTTCACCTTTAACACATATGCAATGCACTGG GTGTGCCAGGCACCAGGCAAGGGCCTGGAGTGGGTGG CACGGATCAGAAGCAAGTCCAACAATTATGCCACCTACT ATGCCGACAGCGTGAAGGATAGGTTCACAATCTCCCGC GACGATTCTCAGAGCATGCTGTACCTGCAGATGAACAAT CTGAAGACCGAGGACACAGCCATGTACTATTGCGTGCG GGAGGGCGTGTACTATTACGGCAGCTCCGGCTATTACG CTATGGACTACTGGGGCCAGGGCACCAGCGTGACAGTG TCTAGCGGAGGAGGAGGCTCCGGAGGAGGAGGCTCTG GCGGCGGCGGCAGCGAGATCGTGCTGACCCAGTCCCC AGCAATCATGTCCGCCTCTCCAGGAGAGAAGGTGACCAT CACATGCTCCGCCTCCTCTAGCGTGTCTTATATGCACTG GTTCCAGCAGAAGCCCGGCACCTCTCCTAAGCTGTGGA TCTACAGCACATCCAATCTGGCATCCGGCGTGCCCGCAA GGTTTTCTGGCAGCGGCTCCGGCACCTCTTATAGCCTGA CAATCAGCCGGATGGAGGCAGAGGACGCAGCAACCTAT TACTGTCAGCAGAGATCCTCTTACCCTCTGACCTTTGGC GCCGGCACAAAGCTGGAGCTGAAGCGCGCGGCCGCA |
| Murine codon optimised scFv nucleotide sequence of CRT2 | 104 | ATGGCTGAGGTGCAGGGAGTGGAGAGCGGAGGAGGCC TGGTGCAGCCTAAGGGCTCCCTGAAGCTGTCTTGCGCC GCTAGCGGATTCACCTTTAACACATACGCTATGCACTGG GTGTGCCAGGCTCCAGGAAAGGGCCTGGAGTGGGTGG CCAGGATCAGAAGCAAGTCCAACAACTACGCTACCTACT ACGCCGACAGCGTGAAGGATCGGTTCACAATCTCCCGC GACGATTCTCAGAGCATGCTGTACCTGCAGATGAACAAC CTGAAGACCGAGGACACAGCTATGTACTACTGCGTGCG GGAGGGCGTGTACTACTACGGCAGCTCCGGATACTACG CTATGGACTACTGGGGACAGGGCACCTCCGTGACAGTG TCTAGCGGAGGAGGAGGCTCCGGAGGAGGAGGCTCTG GAGGCGGAGGCAGCGAGATCGTGCTGACCCAGTCTCCA GCTATCATGTCCGCCTCTCCCGGCGAGAAGGTGACCAT CACATGCTCCGCCTCCTCTAGCGTGTCTTACATGCACTG GTTCCAGCAGAAGCCCGGCACCTCTCCTAAGCTGTGGA TCTACAGCACATCCAACCTGGCTAGCGGAGTGCCCGCT CGGTTTTCTGGAAGCGGCTCCGGAACCTCTTACAGCCTG ACAATCTCCAGGATGGAGGCTGAGGACGCCGCTACATA CTACTGTCAGCAGAGATCCTCTTACCCTCTGACCTTTGG CGCCGGAACAAAGCTGGAGCTGAAGCGCGCGGCCGCA |
| Consensus of CRT3 Variants (1 and 2) heavy chain CDR1 (SEQ ID NOs 2 and 42) | 105 | ((GYTF)/X) TSYW ((MH)/X) |
| Consensus of CRT3 Variants (1 and 2) heavy chain CDR2 (SEQ ID NOs 3 and 43) | 106 | ((WIGA)/X)IYPGNSDT(S/X) |
| Consensus of CRT3 Variants (1 and 2) heavy chain CDR3 (SEQ ID NOs 4 and 44) | 107 | THYYGSDYAMD(Y/X) |
| Consensus of CRT3 Variants (1 and 2) light chain CDR1 (SEQ ID NO. 6 and 46) | 108 | ((SSV)/X) SSSY ((LHWY)/X) |

-continued

| Sequence name (sequence type) | SEQ ID NO: | Sequence |
|---|---|---|
| Consensus of CRT3 Variants (1 and 2) light chain CDR2 (SEQ ID NO. 7 and 47) | 109 | ((LWIY)/X) STS ((NLA)/X) |
| Consensus of CRT3 Variants (1 and 2) light chain CDR3 (SEQ ID NO. 8 and 48) | 110 | HQYHRSPR(T/X) |
| Nucleotide sequence encoding Hinge and transmembrane regions of mouse CD8α | 111 | actactaccaagccagtgctgcgaactccctcacctgtgcaccctaccgg gacatctcagccccagagaccagaagattgtcggccccgtggctcagtga aggggaccggattggacttcgcctgtgatatttacatctgggcacccttg gccggaatctgcgtggcccttctgctgtccttgatcatcactctcatctg ctaccacaggagccga |
| Nucleotide sequence encoding mouse intracellular signalling sequences from mouse CD28 | 112 | aatagtagaaggaacagactccttcaaagtgactacatgaacatgactcc ccggaggcctgggctcactcgaaagccttaccagccctacgcccctgcca gagactttgcagcgtaccgcccc |
| Nucleotide sequence encoding mouse 4-1BB domain | 113 | aaatggatcaggaaaaaattcccccacatattcaagcaaccatttaagaa gaccactggagcagctcaagaggaagatgcttgtagctgccgatgtccac aggaagaagaaggaggaggaggaggctatgag ctg |
| Nucleotide sequence encoding mouse CD3 zeta chain | 114 | agagcaaaattcagcaggagtgcagagactgctgccaacctgcaggaccc caaccagctctacaatgagctcaatctagggcgaagagaggaatatgacg tcttggagaagaagcgggctcgggatccagagatgggaggcaaacagcag aggaggaggaacccccaggaaggcgtatacaatgcactgcagaaagacaa gatggcagaagcctacagtgagatcggcacaaaaggcgagaggcggagag gcaaggggcacgatggcctttaccagggtctcagcactgccaccaaggac acctatgatgccctgcatatgcagaccctggccc |
| Nucleotide sequence encoding mouse OX40 domain | 115 | cggaaggcttggagattgcctaacactcccaaaccttgttggggaaacag cttcaggaccccgatccaggaggaacacacagacgcacactttactctgg ccaagatc |
| Nucleotide sequence encoding murine CD8α hinge and transmembrane regions, CD28 intracellular signalling domain and CD3ζ intracellular signalling domain | 116 | ggaggcaccaagctggaaatcaaacgtgcggccgcaactactaccaagcc agtgctgcgaactccctcacctgtgcaccctaccgggacatctcagcccc agagaccagaagattgtcggccccgtggctcagtgaaggggaccggattg tgacttcgcctgtgaatttacatctgggcacccttggccggaatctgcgt ggcccttctgctgtccttgatcatcactctcatctgctaccacaggagcc gaaatagtagaaggaacagactccttcaaagtgactacatgaacatgact ccccggaggcctgggctcactcgaaagccttaccagccctacgcccctgc cagagactttgcagcgtaccgccccagagcaaaattcagcaggagtgcag agactgctgccaacctgcaggaccccaaccagctctacaatgagctcaat ctagggcgaagagaggaatatgacgtcttggagaagaagcgggctcggga tccagagatgggaggcaaacagcagaggaggaggaacccccaggaaggcg tatacaatgcactgcagaaagacaagatggcagaagcctacagtgagatc ggcacaaaaggcgagaggcggagaggcaaggggcacgatggcctttacca gggtctcagcactgccaccaaggacacctatgatgccctgcatatgcaga ccctggcccctcgctaataaaagcttaacacgagccatagatagaataaa ag |

-continued

| Sequence name (sequence type) | SEQ ID NO: | Sequence |
|---|---|---|
| Nucleotide sequence encoding murine CD8α hinge and transmembrane domains, 4-1BB intracellular signalling domain and CD3ζ intracellular signalling domain | 117 | ggaggcaccaagctggaaatcaaacgtgcggccgcaactactaccaagcc<br>agtgctgcgaactccctcacctgtgcaccctaccgggacatctcagcccc<br>agagaccagaagattgtcggccccgtggctcagtgaaggggaccggattg<br>gacttcgcctgtgatatttacatctgggcacccttggccggaatctgcgt<br>ggcccttctgctgtccttgatcatcactctcatctgctaccacaggagcc<br>gaaaatggatcaggaaaaaattcccccacatattcaagcaaccatttaag<br>aagaccactggagcagctcaagaggaagatgcttgtagctgccgatgtcc<br>acaggaagaagaaggaggaggaggaggctatgagctgagagcaaaattca<br>gcaggagtgcagagactgctgccaacctgcaggaccccaaccagctctac<br>aatgagctcaatctagggcgaagagaggaatatgacgtcttggagaagaa<br>gcgggctcgggatccagagatgggaggcaaacagcagaggaggaggaacc<br>cccaggaaggcgtatacaatgcactgcagaaagacaagatggcagaagcc<br>tacagtgagatcggcacaaaaggcgagaggcggagaggcaaggggcacga<br>tggcctttaccagggtctcagcactgccaccaaggacacctatgatgccc<br>tgcatatgcagaccctggcccctcgctaataaaagcttaacacgagccat<br>agatagaataaaag |
| Nucleotide sequence encoding murine CD8α hinge and transmembrane domains, OX40 intracellular signalling domain and CD3ζ intracellular signalling domain | 118 | ggaggcaccaagctggaaatcaaacgtgcggccgcaactactaccaagcc<br>agtgctgcgaactccctcacctgtgcaccctaccgggacatctcagcccc<br>agagaccagaagattgtcggccccgtggctcagtgaaggggaccggattg<br>gacttcgcctgtgatatttacatctgggcacccttggccggaatctgcgt<br>ggcccttctgctgtccttgatcatcactctcatctgctaccacaggagcc<br>gacggaaggcttggagattgcctaacactcccaaaccttgttggggaaac<br>agcttcaggaccccgatccaggaggaacacacagacgcacactttactct<br>ggccaagatcagagcaaaattcagcaggagtgcagagactgctgccaacc<br>tgcaggaccccaaccagctctacaatgagctcaatctagggcgaagagag<br>gaatatgacgtcttggagaagaagcgggctcgggatccagagatgggagg<br>caaacagcagaggaggaggaacccccaggaaggcgtatacaatgcactgc<br>agaaagacaagatggcagaagcctacagtgagatcggcacaaaaggcgag<br>aggcggagaggcaaggggcacgatggcctttaccagggtctcagcactgc<br>caccaaggacacctatgatgccctgcatatgcagaccctggcccctcgct<br>aataaaagcttaacacgagccatagatagaataaaag |
| Nucleotide sequence encoding murine CD8α hinge and transmembrane domains, CD28 and 4-1BB intracellular signalling domains and CD3ζ intracellular signalling domain | 119 | ggaggcaccaagctggaaatcaaacgtgcggccgcaactactaccaagcc<br>agtgctgcgaactccctcacctgtgcaccctaccgggacatctcagcccc<br>agagaccagaagattgtcggccccgtggctcagtgaaggggaccggattg<br>gacttcgcctgtgatatttacatctgggcacccttggccggaatctgcgt<br>ggcccttctgctgtccttgatcatcactctcatctgctaccacaggagcc<br>gaaatagtagaaggaacagactccttcaaagtgactacatgaacatgact<br>ccccggaggcctgggctcactcgaaagccttaccagccctacgcccctgc<br>cagagactttgcagcgtaccgccccaaatggatcaggaaaaaattccccc<br>acatattcaagcaaccatttaagaagaccactggagcagctcaagaggaa<br>gatgcttgtagctgccgatgtccacaggaagaagaaggaggaggaggagg<br>ctatgagctgagagcaaaattcagcaggagtgcagagactgctgccaacc<br>tgcaggaccccaaccagctctacaatgagctcaatctagggcgaagagag<br>gaatatgacgtcttggagaagaagcgggctcgggatccagagatgggagg<br>caaacagcagaggaggaggaacccccaggaaggcgtatacaatgcactgc<br>agaaagacaagatggcagaagcctacagtgagatcggcacaaaaggcgag<br>aggcggagaggcaaggggcacgatggcctttaccagggtctcagcactgc<br>caccaaggacacctatgatgccctgcatatgcagaccctggcccctcgct<br>aataaaagcttaacacgagccatagatagaataaaag |
| Nucleotide sequence encoding murine CD8α hinge and transmembrane domains, CD28 and OX40 intracellular signalling domains and CD3ζ intracellular signalling domain | 120 | ggaggcaccaagctggaaatcaaacgtgcggccgcaactactaccaagcc<br>agtgctgcgaactccctcacctgtgcaccctaccgggacatctcagcccc<br>gagagaccaaagattgtcggccccgtggctcagtgaaggggaccggattg<br>gacttcgcctgtgatatttacatctgggcacccttggccggaatctgcgt<br>ggcccttctgctgtccttgatcatcactctcatctgctaccacaggagcc<br>gaaatagtagaaggaacagactccttcaaagtgactacatgaacatgact<br>ccccggaggcctgggctcactcgaaagccttaccagccctacgcccctgc<br>cagagactttgcagcgtaccgcccccggaaggcttggagattgcctaaca<br>ctcccaaaccttgttggggaaacagcttcaggaccccgatccaggaggaa<br>cacacagacgcacactttactctggccaagatcagagcaaaattcagcag<br>gagtgcagagactgctgccaacctgcaggaccccaaccagctctacaatg<br>agctcaatctagggcgaagagaggaatatgacgtcttggagaagaagcgg<br>gctcgggatccagagatgggaggcaaacagcagaggaggaggaaccccca<br>ggaaggcgtatacaatgcactgcagaaagacaagatggcagaagcctaca<br>gtgagatcggcacaaaaggcgagaggcggagaggcaaggggcacgatggc<br>ctttaccagggtctcagcactgccaccaaggacacctatgatgccctgca<br>tatgcagaccctggcccctcgctaataaaagcttaacacgagccatagat<br>agaataaaag |

-continued

| Sequence name (sequence type) | SEQ ID NO: | Sequence |
|---|---|---|
| Nucleotide sequence encoding murine CD8α hinge and transmembrane domains, 4-1BB and OX40 intracellular signalling domains and CD3ζ intracellular signalling domain | 121 | Ggaggcaccaagctggaaatcaaacgtgcggccgcaactactaccaagcc agtgctgcgaactccctcacctgtgcaccctaccgggacatctcagcccc agagaccagaagattgtcggccccgtggctcagtgaaggggaccggattg gacttcgcctgtgatatttacatctgggcacccttggccggaatctgcgt ggcccttctgctgtccttgaatcatcctctcatctgctaccacaggagcc gaaaatggatcaggaaaaattcccccacatattcaagcaaccatttaag aagaccactggagcagctcaagaggaagatgcttgtagctgccgatgtcc acaggaagaagaaggaggaggaggaggctatgagctgcggaaggcttgga gattgcctaacactcccaaaccttgttggggaaacagcttcaggaccccg atccaggaggaacacacagacgcacactttactctggccaagatcagagc aaaattcagcaggagtgcagagactgctgccaacctgcaggaccccaacc agctctacaatgagctcaatctagggcgaagagaggaatatgacgtcttg gagaagaagcgggctcgggatccagagatgggaggcaaacagcagaggag gaggaacccccaggaaggcgtatacaatgcactgcagaaagacaagatgg cagaagcctacagtgagatcggcacaaaaggcgagaggcggagaggcaag gggcacgatggcctttaccagggtctcagcactgccaccaaggacaccta tgatgccctgcatatgcagaccctggcccctcgctaataaaagcttcaac acgagccatagatagaataaaag |

*refers to variant sequence
X refers to no amino acid being present

EXAMPLES

Example 1

Analysis of CLEC14A Expression

HUVEC Preparation and Culture

Human umbilical vein endothelial cells (HUVECs) were isolated from umbilical cords donated by the UK National Health Service after informed consent of the donors. Cords were dissected from placentas and the vein was washed in sterile PBS to remove blood. 1 mg/ml of collagenase diluted in M199 medium (Sigma) was injected into the vein and then incubated at 37° C. for 20 minutes to detach the endothelial cells. HUVECs were collected by washing in M199 complete medium containing 10% FCS, 10% large vessel endothelial cell growth supplement (TCS Cell Works), and 4 mM L-glutamine, and plated on 0.1% Type 1 gelatin from porcine skin (Sigma) coated dishes.

Primary Cells Source

Human aortic smooth muscle cells (HASMC) and human bronchial epithelial cells (HBE) were purchased from TCS Cell Works. Human lung fibroblasts (MRC5) were obtained from Cancer Research UK Central Services. Human peripheral blood mononuclear cells (PBMCs) were obtained from the Institute of Cancer Studies at the University of Birmingham. Hepatocytes were a gift from Professor David Adams, School of Immunity and Infection, University of Birmingham.

RNA Extraction and Real Time PCR

Total RNA was isolated from primary cells in culture using TRI reagent (Sigma) followed by cDNA synthesis using a High-Capacity cDNA Archive kit (Applied Biosystems) with supplied random primers. ProbeLibrary Real-time PCR Assay System (Exiqon) was employed in the primary cell screening of CLEC14A expression. Flotillin 2 was chosen as the housekeeping gene to which the expression of CLEC14A was normalized. Primer and probe sets for CLEC14A and Flotillin 2 were designed by ProbeFinder software (Roche). For CLEC14A, primer and probe set was:

(SEQ ID NO: 79)
5'-CTGGGACCGAGGTGAGTG-3',
and (SEQ ID NO: 80)
5'-CGCGATGCAAGTAACTGAGA-3', with probe number 24.

For Flotillin 2, primer and probe set was:

(SEQ ID NO: 81)
5'-TGTTGTGGTTCCGACTATAAACAG-3',
and (SEQ ID NO: 82)
5'-GGGCTGCAACGTCATAATCT-3', with probe number 28. Quantitative PCR reactions were performed on the Rotor-Gene RG3000 thermal cycler (Corbett Research). A reaction mix was prepared in triplicate for each primary cell type and 5 ng of cDNA was applied in each reaction. The fold change was calculated using the ΔΔCt method.

HUVEC Immunofluorescence

HUVECs were grown in glass micro-well chambers (Nunc) fixed in ice-cold methanol, washed with PBST blocked in 10% FCS 3% BSA in PBST. Cells were then stained with CLEC14A antibody following the same protocol used for paraffin embedded sections or co-stained with 5 g/m mouse monoclonal IgG antibody against human VE-cadherin, kindly donated by Professor Maria Grazia Lampugnani, Fire Institute for Molecular Oncology, Milan. Sections staining were analyzed with a 510 laser scanning confocal microscope (Carl Zeiss).

Results

Figure 1:
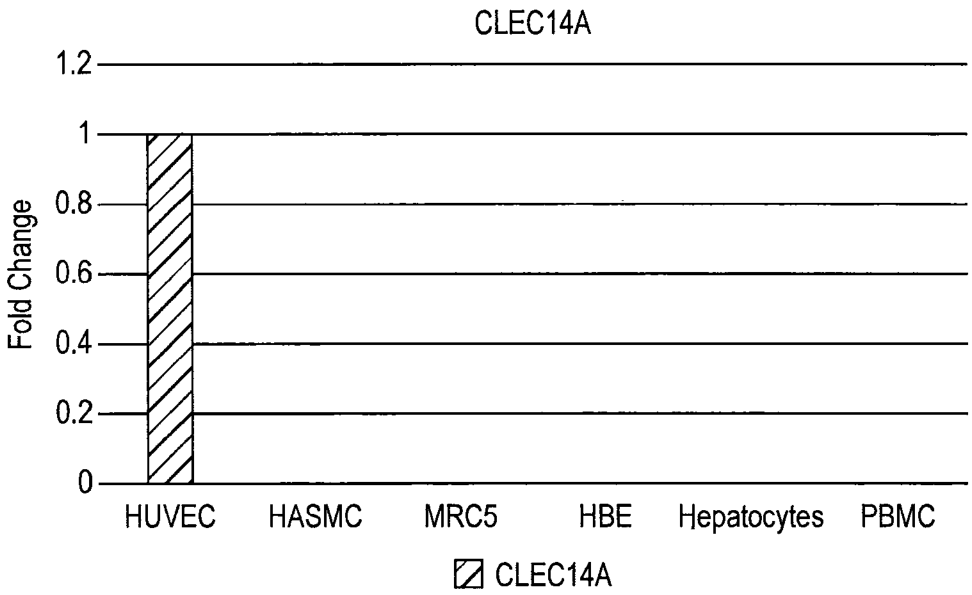

FIG. 1 is a graph showing the relative expression of CLEC14A in HUVECs and other primary cells. CLEC14A was expressed specifically in endothelial cells. This confirms previous findings that CLEC14A is endothelial-specific.

The expression of CLEC14A in sections of solid tumours and normal tissue was examined using CLEC14A-specific probes. CLEC14A expression was measured by immunofluorescence in human ovarian, bladder, liver, breast, colon, rectal, oesophagus, kidney, lung, prostate, stomach, pancreatic and thyroid tumour tissues. Endothelial specificity of CLEC14A expression was confirmed by co-localisation with Ulex europeaus agglutinin I (UEAI) which binds specific fucose residues on endothelial cells. CLEC14A expression was seen in the blood vessels in all tumour tissues analysed. Ovarian, bladder, liver, breast, kidney and prostate tumours were strongly positive for CLEC14A expression, whereas stomach, oesophagus, lung, colon, rectal, pancreatic and thyroid tumour tissues showed a lower level of specific CLEC14A expression. CLEC14A expression was not detected in any of the corresponding normal control (non-tumour) tissues.

Taken together, these results demonstrate that the transmembrane protein CLEC14A is specifically expressed in tumour vasculature and may therefore be used as tumour endothelial marker.

Example 2

Analysis of CLEC14A Function In Vitro and In Vivo

Materials and Methods

For Western blotting and immunoprecipitation; primary antibodies: sheep polyclonal anti-human CLEC14A (R&D systems), mouse monoclonal anti-human Tubulin (Sigma); secondary antibodies: goat polyclonal anti-mouse IgG conjugated to horseradish peroxidase (HRP) (Dako), donkey polyclonal anti-sheep IgG conjugated to HRP (R&D systems). For immunofluorescence; primary antibodies: rabbit polyclonal anti-murine PECAM (Santa Cruz); secondary antibodies: donkey polyclonal anti-rabbit conjugated to Alexa Fluor488 (Invitrogen). For flow cytometry; primary antibodies: mouse monoclonal anti-HA tag (CRUK), mouse monoclonal anti-CLEC14A (C2, C4 described below); secondary antibodies: goat polyclonal anti-mouse IgG conjugated to Alexa Fluor488 (Invitrogen).

For protein production; lentiviral plasmids psPAX2 (lentiviral packaging; Addgene), pMD2G (Envelope plasmid; Addgene) and pWPI hCLEC14A-ECD-Fc (lentiviral mammalian expression plasmid containing IRES-EGFP; Addgene) were used. pWPI hCLEC14A-Fc and mCLEC14A-Fc was generated by initial PCR subcloning from clec14a IMAGE clone (Origene) into pcDNA3-Fc plasmid. The primers used were as follows:

```
human CLEC14A fwd
                                        (SEQ ID NO: 83)
5'TAGTAGGAATTCGAGAGAATGAGGCCGGCGTTCGCCCTG3';

human CLEC14A rev
                                        (SEQ ID NO: 84)
5'AGAACCGCGGCCGCTGGAGGAGTCGAAAGCCTGAGGAGT3';

murine CLEC14A fwd
                                        (SEQ ID NO: 85)
5'TAGTAGGAATTCGAGAGAATGAGGCCAGCGCTTGCCCTG3';

murine CLEC14A rev
                                        (SEQ ID NO: 86)
5'CTACTAGCGGCCGCTCGTGGAAGAGGTGTCGAAAGT3'.
```

EcoR1 and Not1 restriction sites were used to insert CLEC14A. A further round of PCR subcloning was performed to transfer the CLEC14A-Fc fusion into pWPI. The primers used were as follows:

```
human CLEC14A fwd
                                        (SEQ ID NO: 87)
5'TAGTAGTTAATTAAGAGAGAATGAGGCCGGCGTTC3';

murine CLEC14A fwd
                                        (SEQ ID NO: 88)
5'TAGTAGTTAATTAAGAGAGAATGAGGCCAGCGCTT3';

human Fc rev
                                        (SEQ ID NO: 89)
5'CTACTAGTTTAAACTCATTTACCCGGAGACAGGGA3'.
```

For this step, Pac1 and Pme1 restriction sites were used.

Human Umbilical Vein Endothelial Cells were isolated as described previously. Umbilical cords were obtained from Birmingham Women's Health Care NHS Trust with informed consent. HUVECs were used between passages 1-6 and were cultured in M199 complete medium (cM199) containing 10% fetal calf serum (PAA), 1% bovine brain extract, 90 μg/ml heparin, and 4 mM L-glutamine, 100 U/ml penicillin and 100 μg/ml streptomycin (Invitrogen) and were seeded on plates coated in 0.1% type 1 gelatin from porcine skin. HEK293T cells were cultured in DMEM (Sigma) complete medium (cDMEM) containing 10% fetal calf serum (PAA), 4 mM L-glutamine, 100 U/ml penicillin and 100 μg/ml streptomycin (Invitrogen).

SiRNA transfections in HUVEC were performed as previously described. Lentivirus was produced in HEK293T cells by transient transfection with the lentiviral packaging, envelope and expression plasmids above. Plasmids were incubated in OptiMEM (Invitrogen) with polyethylenimine (36 μg/ml) at a 1:4 ratio for 10 minutes at room temperature prior to adding to HEK293T cells in cDMEM. Media supernatant was used to transduce fresh HEK293T cells. GFP positive HEK293T cells were sorted and used for protein production. Expression of MMRN2 in HEK293T cells was achieved by polyethylenimine transient transfection as above using pHL-Avitag3 hMMRN2.

Quantitative PCR cDNA was prepared using the High-Capacity cDNA Archive kit (Applied Biosystems), from 1 μg of extracted total RNA. qPCR reactions were performed with Express qPCR supermix (Invitrogen) on a RG-3000 (Corbett/Qiagen, Manchester, UK) thermocycler. Primers for human clec14a and flotillin-2 were as previously described. Primers for murine clec14a 5' UTR, CDS and 3' UTR and murine beta-actin, are as follows:

```
5'UTR fwd-
                                        (SEQ ID NO: 90)
TTCCTTTTCCAGGGTTTGTG;

5' UTR rev-
                                        (SEQ ID NO: 91)
GCCTACAAGGTGGCTTGAAT;

CDS fwd-
                                        (SEQ ID NO: 92)
AAGCTGTGCTCCTGCTCTTG;

CDS rev-
                                        (SEQ ID NO: 93)
TCCTGAGTGCACTGTGAGATG;

3' UTR fwd-
                                        (SEQ ID NO: 94)
CTGTAGAGGGCGGTGACTTT;

3' UTR rev-
                                        (SEQ ID NO: 95)
AGCTGCTCCCAAGTCCTCT;
```

-continued mACTB fwd-
(SEQ ID NO: 96)
CTAAGGCCAACCGTGAAAAG;

mACTB rev-
(SEQ ID NO: 97)
ACCAGAGGCATACAGGGACA.

Relative expression ratios were calculated according to the efficiency adjusted mathematical model.

Western Blotting and Immunoprecipitation

Whole cell protein lysates were made and co-immunoprecipitation experiments were performed in which protein was extracted from $2\times10^7$ HUVECs. For initial isolation of CLEC14A interacting proteins 5 μg CLEC14A-Fc or an equimolar amount of hFc was used. For endogenous immunoprecipitation experiments 0.4 μg anti-CLEC14A antibody or sheep IgG was used. For blocking experiments 5 μg CLEC14A-Fc or hFc were bound to protein G beads overnight in PBS. Beads were blocked for 5-6 hours in PBS containing 20% FCS (PAA). Bound CLEC14A-Fc or hFc protein was blocked with increasing concentrations of mIgG or anti-CLEC14A antibody (CRT-2, described below) in binding buffer overnight. Standard protocols were used for western blotting and SDS-PAGE. Primary antibodies were used as indicated in the text with corresponding HRP conjugated secondary antibodies.

Flow Cytometry

Cells were detached with cell dissociation buffer (Invitrogen), rinsed in PBS before incubation in blocking buffer (PBS, 3% BSA, 1% NaN3) for 15 minutes. Subsequent staining using 10 μg/ml anti-HA tag (CRUK), 10 μg/ml anti-CLEC14A (CRT-2, described below), as primary antibodies, in blocking buffer for 30 minutes. Cells were rinsed in PBS and stained with goat polyclonal anti-mouse IgG conjugated to Alexa Fluor488 (Invitrogen) in blocking buffer. Data (15,000 events/sample) were collected using a FACSCalibur apparatus (Becton Dickinson, Oxford, UK), and results were analysed with Becton Dickinson Cell Quest software.

Huvec Spheroid Sprouting Assay and In Vitro Matrigel Tube Forming Assay

Generation of HUVEC spheroids and induction of endothelial sprouting was performed in a collagen gel using 1000 HUVECs per spheroid. Quantification was performed 16 hours after embedding. To quantify sprout growth, the number of sprouts was counted, the cumulative sprout length and the maximal sprout length was assessed. For two colour sprouting experiments, HUVECs were pre-labelled with orange and green CellTracker dyes (Invitrogen). After 24 hours spheroids were fixed in 4% formaldehyde and mounted with Vectorshield (Vector labs). Slides were imaged with an Axioskop2 microscope and AxioVision SE64 Rel4.8 software (Zeiss, Cambridge, UK).

For the Matrigel tube forming assays $1.4\times10^5$ HUVECs were seeded onto 70 μl basement membrane extract (Matrigel, BD Bioscience, Oxford, UK) in a 12 well plate. After 16 hours, images were taken of 5 fields of view per well using a Leica DM IL microscope (Leica, Milton Keynes, UK) with a USB 2.0 2M Xli digital camera (XL Imaging LLC, Carrollton, Tex., USA) at 10× magnification. Images were analysed with the Angiogenesis analyser plugin for Image J (Carpentier G. et al., Angiogenesis Analyzer for ImageJ. 4th ImageJ User and Developer Conference proceedings) and available at the NIH website (http://imagej.nih.gov/ij/macros/toolsets/Angiogenesis%20Analyzer.txt).

Protein Production

Culture media (CM) from CLEC14A-Fc expressing HEK293T cells was collected. CM was flowed over a HiTrap protein A HP column (GE healthcare, Amersham, UK) and protein eluted using a 0-100% gradient of 100 mM sodium citrate (pH 3) before neutralising with 1 M Tris base. Fractions were run on a SDS-PAG and assessed for protein purity and specificity by Coomassie staining and Western blotting. Fractions containing similar concentrations of protein were combined and dialysed in PBS prior to functional assays.

Monoclonal Antibody Generation

Mouse monoclonal antibodies were commercially prepared by Serotec Ltd (Oxford, UK) using the following protocol to break tolerance supplied by us. Purified mouse CLEC14A-Fc fusion protein was given at 50 μg in Freund's complete adjuvant subcutaneously. Two weeks later mice were given another 50 μg subcutaneously but this time in Freund's adjuvant. Mice were culled and spleens harvested for fusion two weeks later.

Generation of clec14a −/− mice

Mice were housed at the Birmingham Biomedical Services Unit (Birmingham, UK). C57BL/6N VGB6 feeder-dependent embryonic stem cells containing the CLEC14A deletion cassette (Clec14atm1(KOMP)Vlcg; project ID VG10554) were procured from the Knockout Mouse Project (University of California, Davis, USA). The Transgenic Mouse Facility at the University of Birmingham generated chimeric mice by injection of embryonic stem cells into albino C57BL/6 mice and were bred to C57BL/6 females to generate mice heterozygous for the cassette.

Aortic Ring and Murine Subcutaneous Sponge Angiogenesis Assay

Aortas were isolated and processed for aortic ring assays in collagen. Tube/sprout outgrowth, maximal endothelial migration and total endothelial outgrowth was quantitated. Male C57 black mice were implanted with a subcutaneous sterile polyether sponge disc (10×5×5 mm) under the dorsal skin of each flank at day 0. 100 μl bFGF (40 ng/ml; R&D systems) was injected through the skin directly into the sponges every other day for 14 days. Sponges were excised on day 14, fixed in 10% formalin, and paraffin embedded. Sections were stained with haematoxylin and eosin, sponge cross-sections were taken using a Leica MZ 16 microscope (Leica, Milton Keynes, UK) with a USB 2.0 2M Xli digital camera (XL Imaging LLC, Carrollton, Tex., USA) at ×1 magnification for cellular invasion analysis. Images captured by Leica DM E microscope (Leica, Milton Keynes, UK) at 40× magnification were analysed for vessel density. Vessel counts were assessed in five fields per section per sponge. All animal experimentation was carried out in accordance with Home Office License number PPL 40/3339 held by RB.

Tumour Implantation Assays $10^6$ Lewis lung carcinoma cells were injected subcutaneously into the flank of male mice at 8-10 weeks of age. Tumour growth was monitored by daily calliper measurements and after two-four weeks growth, tumour mass was determined by weight, fixed in 4% PFA, paraffin embedded and serial sections cut at 6 μm.

CLEC14A Regulates Sprouting Angiogenesis In Vitro

To investigate the role of CLEC14A in sprouting angiogenesis in vitro, HUVEC spheroids were generated from HUVECs treated with siRNA targeting clec14a or a non-complementary siRNA duplex. Knockdown of clec14a expression was confirmed at the mRNA level by qPCR with an average reduction of 74% across three experiments (FIG.

Figure 2:
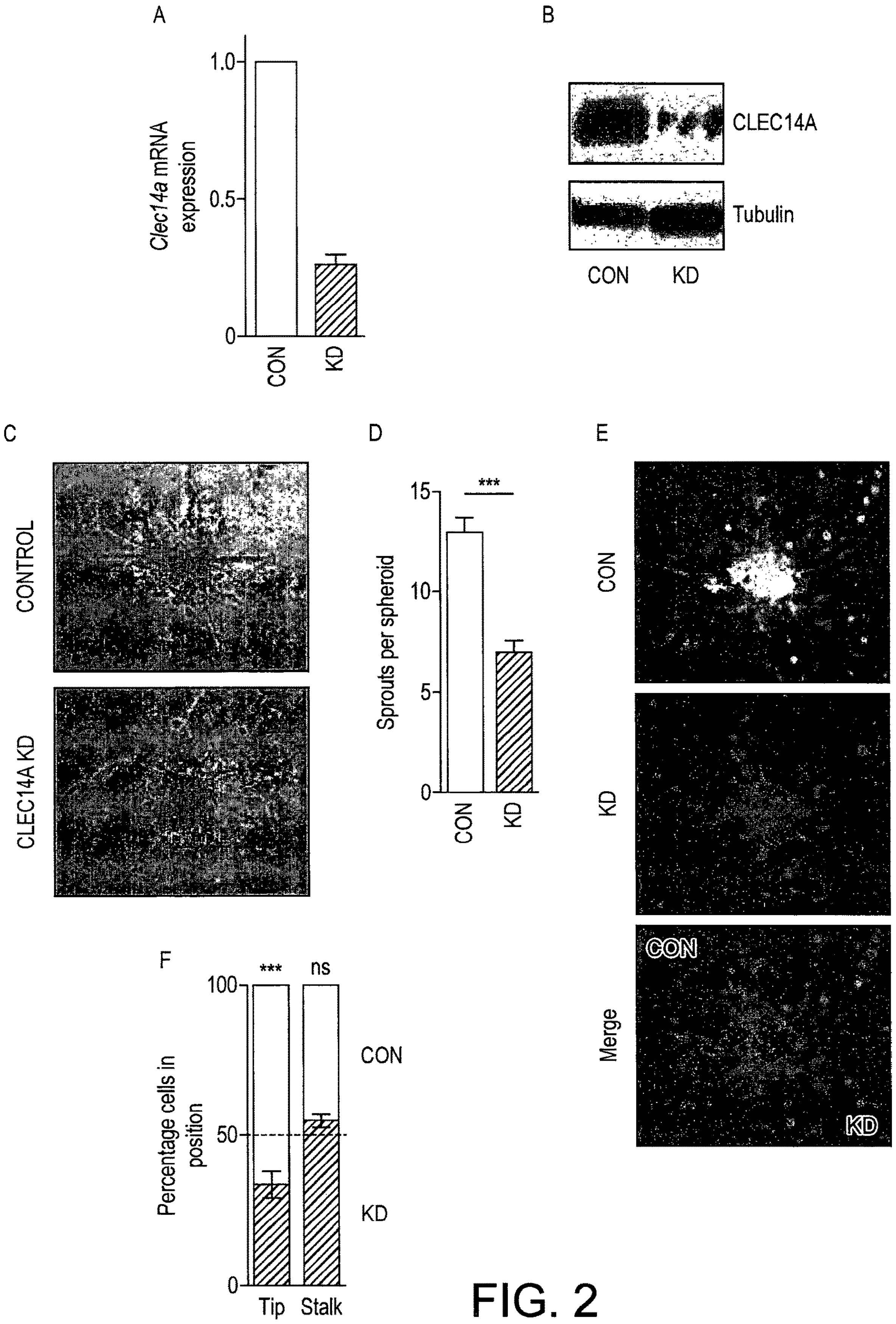

2A) and at the protein level by Western blot analysis of protein extracts probed with an anti-CLEC14A polyclonal antisera (FIG. 2B). VEGF induced sprouting from CLEC14A knockdown spheroids was impaired, knockdown spheroids produced on average 6.9 sprouts per spheroid, compared to 13.2 for control cells (FIGS. 2C and 2D). To determine the role of CLEC14A in tip/stalk cell formation, control HUVECs and knockdown HUVECs were stained either red or green and mixed, prior to spheroid formation and induced sprouting (FIG. 2E). Knockdown of CLEC14A reduced the percentage of cells at the tip position (33%) compared to control cells (67%), however, there was no effect on the percentage of stalk cells that were derived from CLEC14A knockdown HUVECs (FIG. 2F). These data suggest CLEC14A has a role in sprout initiation and migration.

CLEC14A Regulates Sprouting Angiogenesis In Vivo

Figure 3:
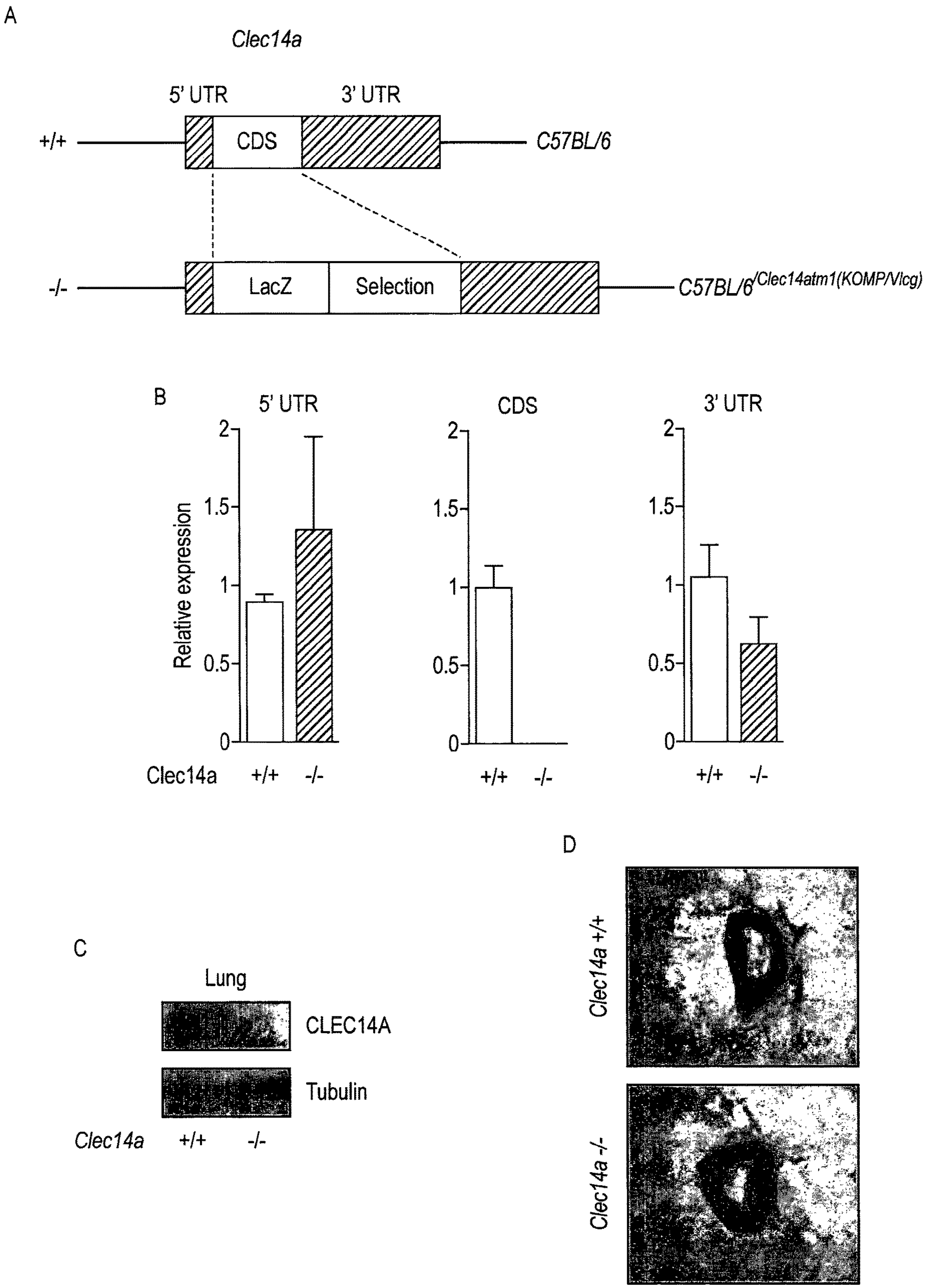
Figure 3:
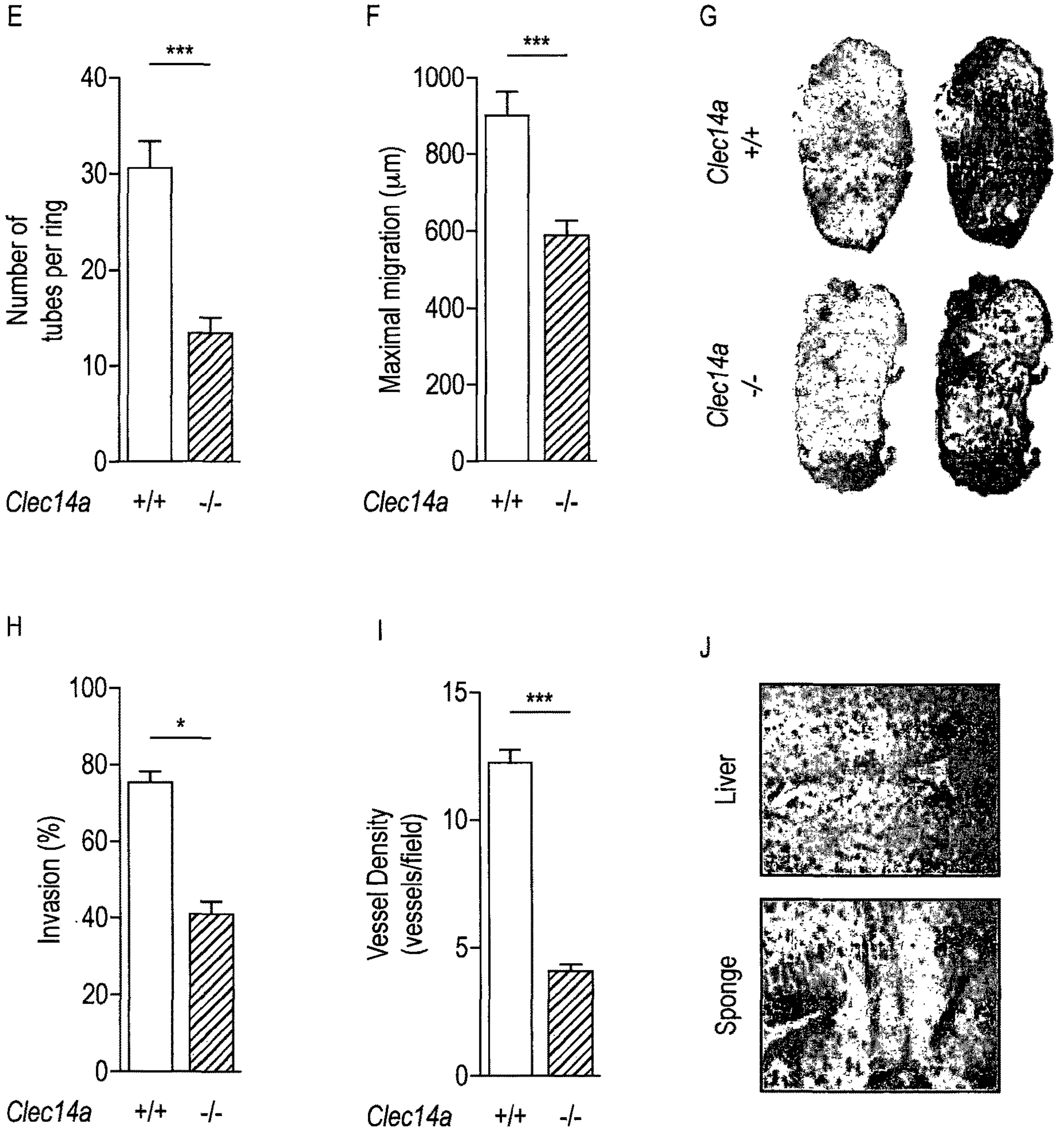

To investigate the role of CLEC14A in vivo and ex vivo, mice were generated to replace the clec14a coding sequence with a lacZ reporter (FIG. 3A). Breeding of heterozygotes (clec14a −/+) produced equal proportions of male and female mice (49.5%/50.5% respectively) and a Mendelian ratio of wildtype: heterozygote: homozygote mice (26.4%: 47.2%: 26.4% respectively). As clec14a is an endothelial-restricted gene, aortas were isolated from clec14a +/+ and clec14a −/− mice. Extracted cDNA was analysed by qPCR and confirmed loss of the clec14a coding region but expression of the 5' and 3' untranslated regions were retained (FIG. 2B). Loss of CLEC14A at the protein level was also confirmed by Western blot analysis of lung tissue lysates (FIG. 3C).

To confirm the role of CLEC14A in sprouting angiogenesis in multicellular three dimensional co-culture, aortas were isolated, cut into rings and embedded in collagen. Cellular outgrowth was stimulated by VEGF and monitored over 7 days before end-point quantitation of endothelial sprouting. Again, loss of CLEC14A impaired endothelial sprout outgrowth and migration (FIG. 3D). Aortic rings from wildtype mice produced over double the number of tubes compared to that observed for CLEC14A knockout mice (30.6 tubes compared to 13.4 tubes respectively) (FIG. 3E). In addition, the maximum migration, which is defined by the furthest distance migrated away from each aortic ring, was also reduced in knockout cultures (FIG. 3F). To assess whether CLEC14A has a similar function in vivo, sponge barrels were implanted subcutaneously into CLEC14A knockout mice. Cellular infiltration and neo-angiogenesis were stimulated using bFGF injections into the sponge every two days for two weeks. Macroscopic analysis of sponge sections stained with haematoxylin and eosin revealed impaired infiltration of cells into the sponge in clec14a −/− animals (FIGS. 3G and 3H). In addition, vascularity was significantly reduced ($p<0.01$) for clec14a −/− animals (FIG. 3I). To confirm the endothelial cells lining the neoangiogenic vessels express clec14a in this model, sponges and livers from CLEC14A KO mice were stained with x-gal. Strong x-gal staining was observed on blood vessels within the sponge compared to matched liver sections (FIG. 3J). From these data we can conclude that mouse CLEC14A expression regulates endothelial migration and angiogenic sprouting in vivo, as well as in vitro, and CLEC14A is upregulated on sprouting endothelium.

CLEC14A Promotes Tumour Growth

Figure 4:
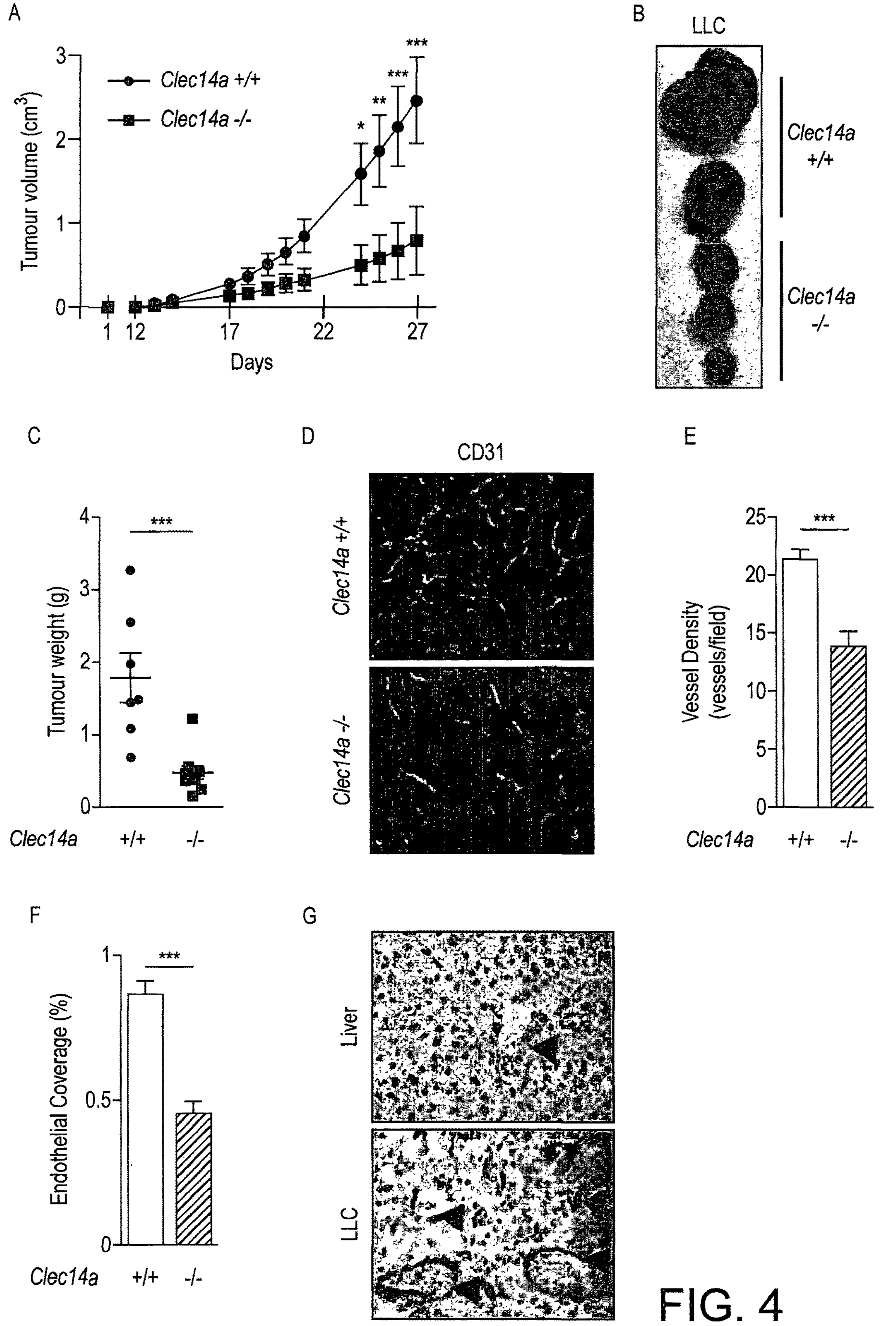

CLEC14A expression is found highly up-regulated on human tumour vessels compared to vessels from healthy tissue, suggesting that cancer therapies could be targeted against CLEC14A. Therefore, to investigate whether loss of CLEC14A effects tumour growth we used the syngeneic Lewis lung carcinoma (LLC) model. For this $1\times10^6$ LLC cells were injected subcutaneously into the right flank of either clec14a +/+ or clec14a −/− mice. Tumour growth was impaired in the clec14a −/− mice compared to clec14a +/+ littermates (FIG. 4A). This was confirmed by three independent experiments. Excised tumours taken from clec14a −/− mice were smaller in size (FIG. 4B) and smaller in weight (FIG. 4C) than clec14a +/+ littermates. To determine whether the vascular density within these tumours was also effected, tissue sections were stained with an anti-CD31 antibody. Analysis shows a reduced density of discrete vessels (FIGS. 4D and 4E) and reduced percentage endothelial coverage (FIG. 4F). Furthermore, x-gal staining of tumour and liver sections taken from clec14a −/− mice reveals high expression of clec14a on both mature vessels, with erythrocyte filled lumens (FIG. 4G, black arrows), and immature microvessels within the tumour (FIG. 4G), confirming clec14a is upregulated on tumour vessels.

Example 3

Preparation of Anti-CLEC14A Monoclonal Antibodies and Their Effect on Angiogenesis Preparation of Monoclonal Antibodies The antigens used for the preparation of monoclonal antibodies were murine CLEC14AFc (CM) and human CLEC14A-Fc (CH), optionally conjugated with adjuvant protein (AP). These four antigens (CM, CH, CM-AP, CH-AP) were used for mice immunisation using the following protocol:

Day Operation

0 Pre-immune sample taken

Immunisation of 100 ug of antigen in complete Freund's adjuvant (foot pads)

14 Immunisation of 100 ug of antigen in incomplete Freund's adjuvant (foot pads)

17 Test bleed

18 Popliteal lymph node harvest for fusion

Sera were tested by ELISA against three antigens: CM, CH and Fc. A non-immune serum was taken as a negative control.

The fusion protocol was as follows:

(1) Popliteal lymph nodes were harvested from the immune mice and homogenised.

(2) Cells were washed with warm DMEM.

(3) Cells were mixed with sp2/0 myeloma cells.

(4) The mixture was centrifuged (1000 g)

(5) The pellet was suspended in 50% PEG 500 and incubated for 1 min.

(6) The suspension was slowly diluted with warm DMEM.

(7) Suspension was centrifuged (1000 g).

(8) Cells were seeded into plates with peritoneal macrophages.

(9) Cells were cultivated at 37° C. and 5% C0 2

More than 500 HAT-resistant hybridoma clones from each mouse were obtained. All of the clone supernatants were tested twice with 4 days interval by ELISA against three absorbed antigens (CM, CH and Fc). Testing resulted in 5 clones, 2 of which, CRT-2 and CRT-3 (both subclass IgG1), were further studied and shown to react with both CM and CH and did not react with Fc. The positives were cloned 2-4 times by the limiting dilution method, propagated in culture flasks and injected into mice for ascites. One clone (CRT-3) was the result of immunisation with CLEC14a human-AP (CHAP), and the other clone (CRT-2) was the result of immunisation with CLEC14a mouse-AP (CM-AP).

Scratch Wound Healing Assay with CLEC14A Monoclonal Antibodies

A scratch with a 10 ml pipette tip was made in confluent HUVECs. New medium containing 1 g/m or 10 g/l of a monoclonal CLEC14A antibody raised in mice against the extracellular domain of CLEC14A was applied. Chemokinetic migration of HUVECs was assessed by acquiring images of wound closure at time zero, 4, 6, 12 hours with a Leica DM 1000 light microscope and USB 2.0 2M Xli camera. The open area of the wound was quantitated using Image J software.

Figure 5:
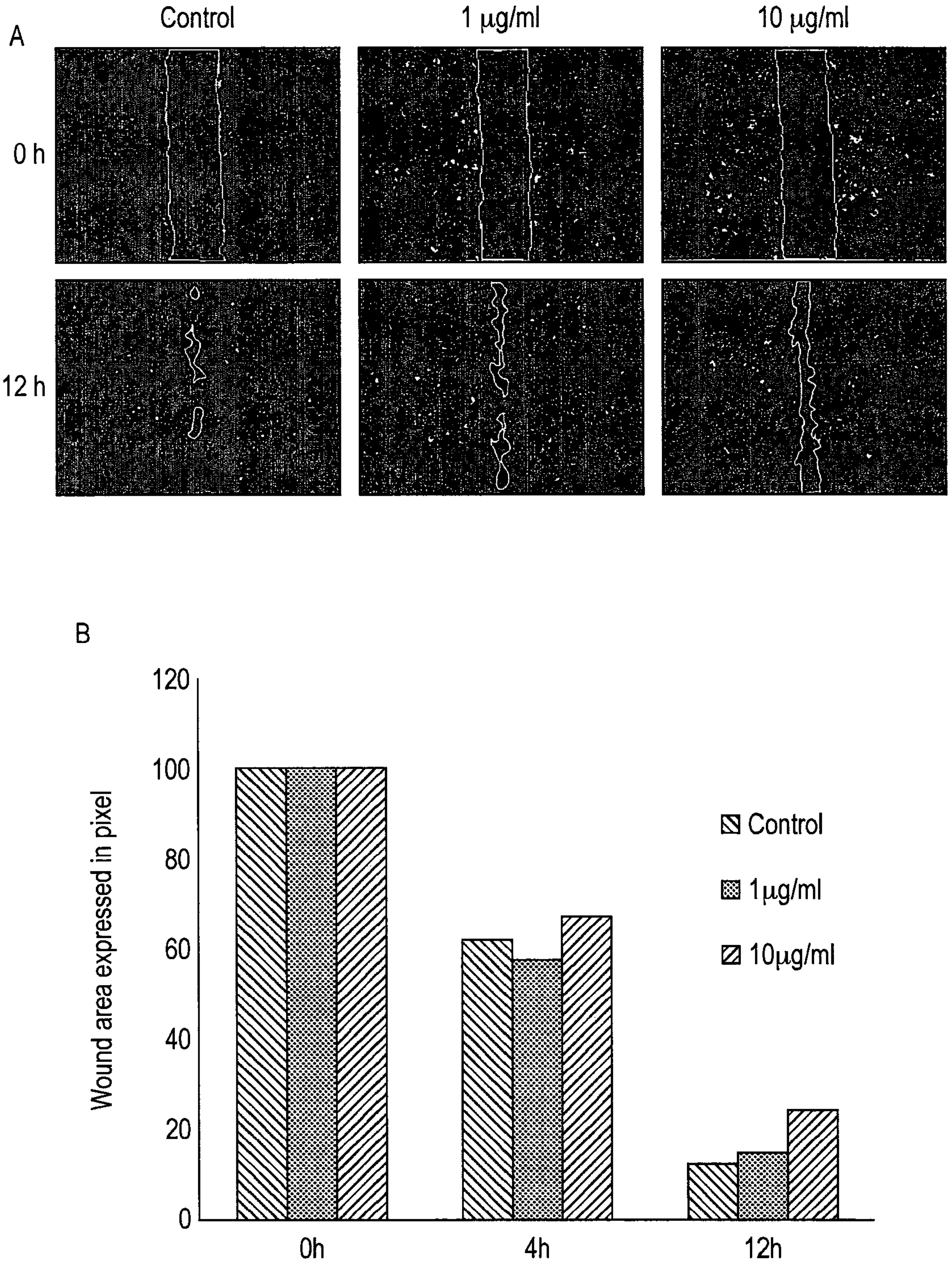
Figure 6:
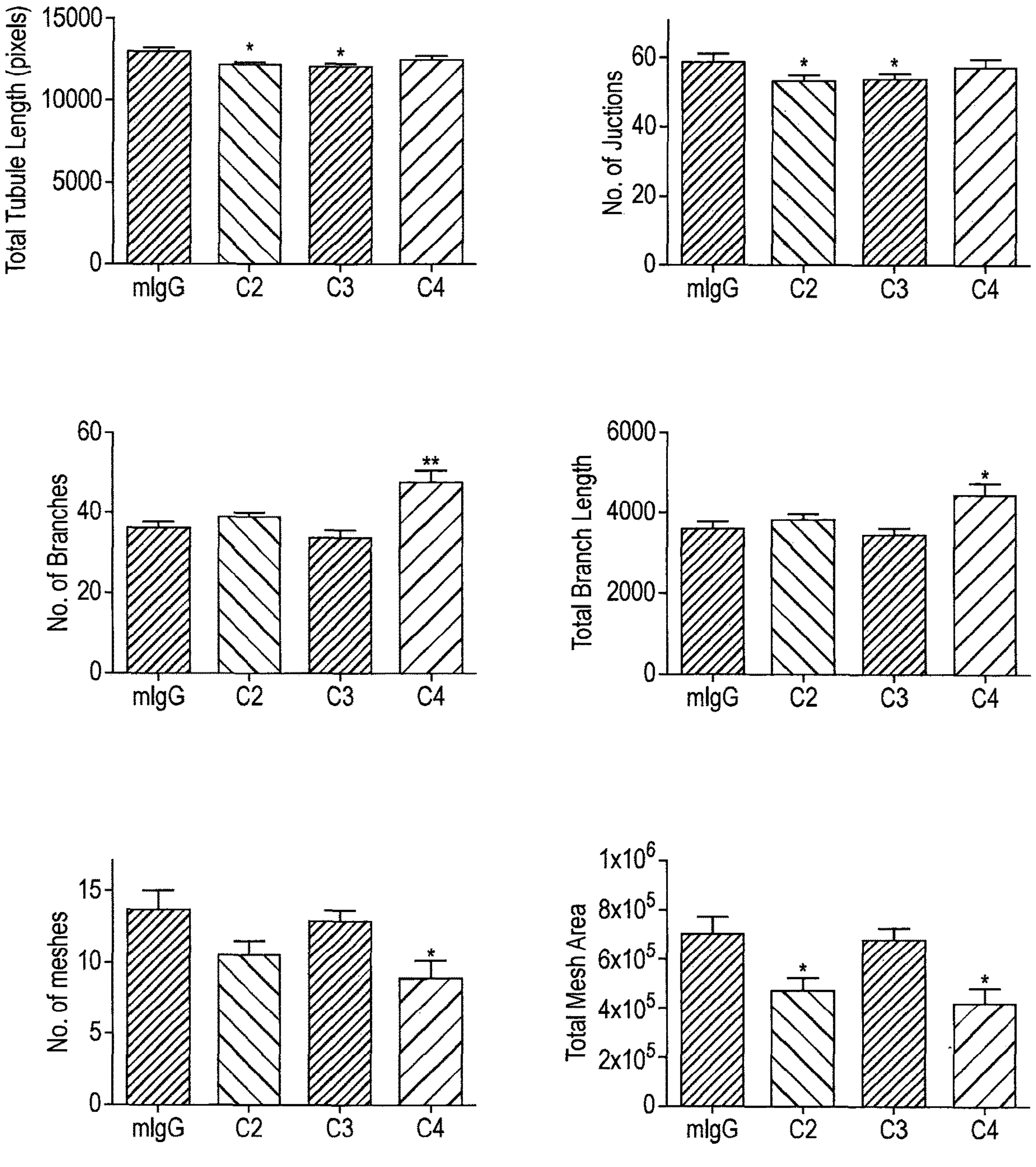

The ability of CLEC14A inhibitors to inhibit angiogenesis was examined. Scratch wound healing assays using monoclonal antibodies described above show that the anti-CLEC14A monoclonal antibodies inhibit endothelial cell migration in a HUVEC scratch wound healing assay. As shown in FIGS. 5A and B, when HUVECs were treated with 10 g/ml of monoclonal antibody CRT-3, 25% of the wound area remained open at 12 h compared to 13% in the control.

These results show that anti-CLEC14A monoclonal antibody CRT-3 has an inhibitory effect on endothelial cell migration. Endothelial cell migration is an essential feature of angiogenesis. Accordingly, these assays provide evidence that the monoclonal antibodies of the invention inhibit angiogenesis directly.

To further characterise the functional effects of CLEC14A antibody treatment on endothelial cells, tube formation assays were performed with HUVECs treated with 20 μg/ml of CRT2, CRT3 or CRT4. Treatment with CRT2 and CRT3 gave a significant reduction in tubule length and the number of junctions. CRT2 treatment also significantly reduced the mesh area per field. The results show that CRT2, 3 and 4 all have a differing negative effect on tube formation.

Example 4

Characterisation of Anti-CLEC14A Monoclonal Antibodies

Various polypeptide constructs were generated and expressed in cells to map the binding sites of the monoclonal antibodies of the invention. All constructs have a C-terminus GFP tag so green cells were gated and stained red. Binding of CRT antibodies was analysed using flow cytometry.

FIG. 7A shows that CRT-2 and CRT-3 both bind to cells expressing CLEC14A and FIG. 7B demonstrates that the antibodies do not bind to cells expressing thrombomodulin.

Figure 7:
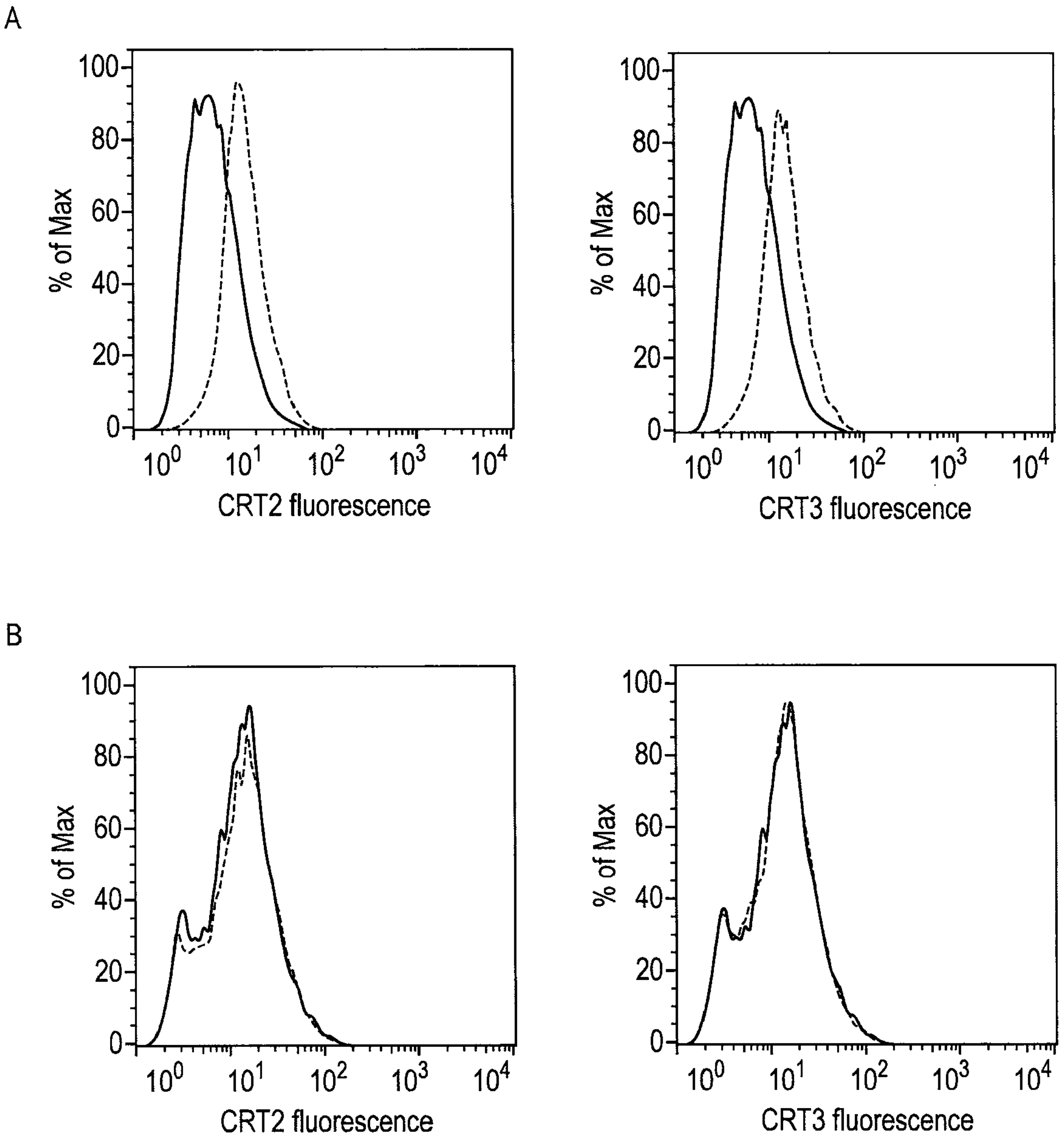
Figure 8:
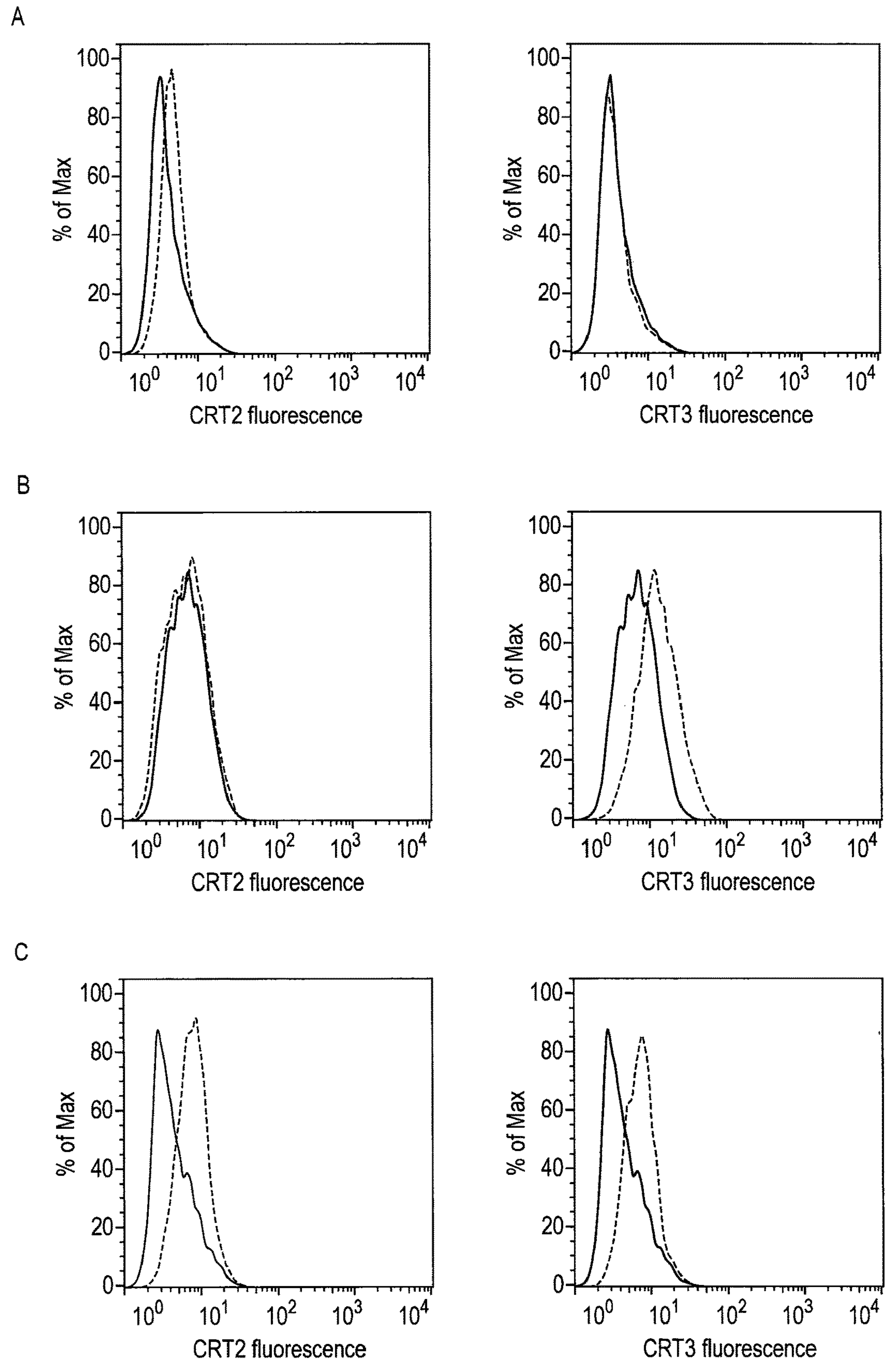

A chimera comprising the C-type lectin domain (CTLD) of thrombomodulin (CD141) and remainder of the CLEC14A molecule was produced. Cells expressing this antigen are not recognised by either of the CRT antibodies (FIG. 8A), although a slight shift in fluorescence was observed with CRT-2. A chimera comprising CLEC14A in which the Sushi-like domain has been replaced with the Sushi-like domain of thrombomodulin (CD141) (to ensure correct folding of CTLD of CLEC14A) was also generated and results in binding of CRT-3, but not CRT-2 (FIG. 8B). Both CRT antibodies bind WT CLEC14A and, as expected, neither binds to WT CD141 (FIG. 7).

These data suggest that the binding site of the antibody CRT-3 is within the C-type lectin domain and that CRT-2 binds on a region between the CTLD and sushi-like domain.

To further determine the binding regions of the antibodies, chimeric loop constructs were made. This was based on the structural predictions of CLEC14A CTLD.

CLEC14A with regions 1-42 of CD141

CD141 sequence-
(SEQ ID NO: 98)
MLGVLVLGALALAGLGFPAPAEPQPGGSQCVEHDCFALYPGP

CLEC14A with regions 97-108 of CD141

CD141 sequence-
(SEQ ID NO: 99)
QLPPGCGDPKRL

CLEC14A with regions 122-142 of CD141

CD141 sequence-
(SEQ ID NO: 100)
TSYSRWARLDLNGAPLCGPL

The alignment is shown in FIG. 9. Unfortunately 1-42 and 122-142 chimeras did not fold correctly. This is thought due to the fact they are present on the cell surface (stain positive for CLEC14A polyclonal antibodies, but they do not stain for either of the antibodies.

The 97-108 chimera does bind CRT-2 and CRT-3 showing that this mutant is correctly folded. Residues 97-108 were swapped with corresponding regions from thrombomodulin. This resulted in correct folding as CRT-2 and CRT-3 can still bind (FIG. 8C). These data suggest that CRT-2 and CRT-3 do not bind to residues 97-108 of CLEC14A.

This experiment has been repeated three times with the same result.

The CRT-2 and CRT-3 encoding sequences were clones from their respective hybridomas using standard techniques and sequenced. The CDRs have been predicted using standard software. The polypeptide and nucleotide sequences are set out in the table below. In view of different in prediction software, sequence variants, including CDR variants, are also shown (marked with a "*").

| Sequence name (sequence type) | SEQ ID NO: | Sequence |
|---|---|---|
| | | CRT-3 |
| VH CDR1 (aa) | 2 | GYTFTSYW |
| VH CDR2 (aa) | 3 | IYPGNSDT |
| VH CDR3 (aa) | 4 | THYYGSDYAMDY |
| VH CDR1* (aa) | 42 | TSYWMH |
| VH CDR2* (aa) | 43 | WIGAIYPGNSDTS |

-continued

| Sequence name (sequence type) | SEQ ID NO: | Sequence |
|---|---|---|
| VH CDR3* (aa) | 44 | THYYGSDYAMD |
| VL CDR1 (aa) | 6 | SSVSSSY |
| VL CDR2 (aa) | 7 | STS |
| VL CDR3 (aa) | 8 | HQYHRSPRT |
| VL CDR1* (aa) | 46 | SSSYLHWY |
| VL CDR2* (aa) | 47 | LWIYSTSNLA |
| VL CDR3* (aa) | 48 | HQYHRSPR |
| VH (aa) | 1 | M A E V Q L Q Q S G T V L A R P G A S V K M<br>S C K A S G Y T F T S Y W M H W V K Q R P<br>G Q G L E W I G A I Y P G N S D T S Y N Q K<br>F K G K A K L T A V T S T S T A Y M E L S S L<br>T N E D S A V F Y C T H Y Y G S D Y A M D Y<br>W G Q G T S V T V |
| VH* (aa) | 41 | MAEVQLQQSGTVLARPGASVKMSCKASGYTFTSYWMHW<br>VKQRPGQGLEWIGAIYPGNSDTSYNQKFKGKAKLTAVTST<br>STAYMELSSLTNEDSAVFYCTHYGSDYAMDYWGQGTSVTI<br>SSG |
| VL (aa) | 5 | Q I V L T Q S P A I M S A S L G E R V T M T C<br>T A S S S V S S S Y L H W Y Q Q K P G S S P<br>K L W I Y S T S N L A S G V P A R F S G S G<br>S G T S Y S L T I S S M E A E D A A T Y Y C H<br>Q Y H R S P R T F G G G T K L E I K R A A A |
| VL* (aa) | 45 | QIVLTQSPAIMSASLGERVTMTCTASSSVSSSYLHVVYQQKP<br>GSSPKLWIYSTSNLASGVPARFSGSGSGTSYSLTISSMEAE<br>DAATYYCHQYHRSPRTFGGGTKLEIKRAA |
| ScFv (aa) | 9 | M A E V Q L Q Q S G T V L A R P G A S V K M<br>S C K A S G Y T F T S Y W M H W V K Q R P<br>G Q G L E W I G A I Y P G N S D T S Y N Q K<br>F K G K A K L T A V T S T S T A Y M E L S S L<br>T N E D S A V F Y C T H Y Y G S D Y A M D Y<br>W G Q G T S V T V S S G G G G S G G G G S<br>G G G G S Q I V L T Q S P A I M S A S L G E<br>R V T M T C T A S S S V S S S Y L H W Y Q Q<br>K P G S S P K L W I Y S T S N L A S G V P A<br>R F S G S G S G T S Y S L T I S S M E A E D<br>A A T Y Y C H Q Y H R S P R T F G G G T K L<br>E I K R A A A |
| ScFv* (aa) | 49<br>(VH*) | MAEVQLQQSGTVLARPGASVKMSCKASGYTFTSYWMHW<br>VKQRPGQGLEWIGAIYPGNSDTSYNQKFKGKAKLTAVTST<br>STAYMELSSLTNEDSAVFYCTHYGSDYAMDYWGQGTSVTI<br>SSG S S G G G G S G G G G S G G G G S Q I<br>V L T Q S P A I M S A S L G E R V T M T C T<br>A S S S V S S S Y L H W Y Q Q K P G S S P K<br>L W I Y S T S N L A S G V P A R F S G S G S<br>G T S Y S L T I S S M E A E D A A T Y Y C H<br>Q Y H R S P R T F G G G T K L E I K R A A A |
| ScFv* (aa) | 50<br>(VL*) | M A E V Q L Q Q S G T V L A R P G A S V K M<br>S C K A S G Y T F T S Y W M H W V K Q R P<br>G Q G L E W I G A I Y P G N S D T S Y N Q K<br>F K G K A K L T A V T S T S T A Y M E L S S L<br>T N E D S A V F Y C T H Y Y G S D Y A M D Y<br>W G Q G T S V T V S S G G G G S G G G G S<br>G G G G<br>SQIVLTQSPAIMSASLGERVTMTCTASSSVSSSYLHVVYQQK<br>PGSSPKLWIYSTSNLASGVPARFSGSGSGTSYSLTISSMEA<br>EDAATYYCHQYHRSPRTFGGGTKLEIKRAA |
| ScFv* (aa) | 51<br>(VH*VL*) | MAEVQLQQSGTVLARPGASVKMSCKASGYTFTSYWMHW<br>VKQRPGQGLEWIGAIYPGNSDTSYNQKFKGKAKLTAVTST<br>STAYMELSSLTNEDSAVFYCTHYGSDYAMDYWGQGTSVTI<br>SSG S S G G G G S G G G G S G G G G S<br>QIVLTQSPAIMSASLGERVTMTCTASSSVSSSYLHVVYQQKP |

-continued

| Sequence name (sequence type) | SEQ ID NO: | Sequence |
|---|---|---|
| | | GSSPKLWIYSTSNLASGVPARFSGSGSGTSYSLTISSMEAE DAATYYCHQYHRSPRTFGGGTKLEIKRAA |
| VH CDR1 (nt) | 12 | ggctacacctttaccagctactgg |
| VH CDR2 (nt) | 13 | atttatcctggaaatagtgatact |
| VH CDR3 (nt) | 14 | acacattactacggtagtgactatgctatggactac |
| VL CDR1 (nt) | 16 | tcaagtgtaagttccagttac |
| VL CDR2 (nt) | 17 | agcacatcc |
| VL CDR3 (nt) | 18 | caccagtatcatcgttccccacggacg |
| VHC(nt) | 11 | atggccgaggtccagctgcagcagtctgggactgtgctggcaaggcctggggcttc agtgaagatgtcctgcaaggcttctggctacacctttaccagctactggatgcactgg gtaaaacagaggcctggacagggtctggaatggattggcgctatttatcctggaaat agtgatactagctacaaccagaagttcaagggcaaggccaaactgactgcagtc acatccaccagcactgcctacatggagctcagcagcctgacaaatgaggactctg cggtcttttactgtacacattactacggtagtgactatgctatggactactggggtcaa ggaacctcagtcactgtc |
| VL (nt) | 15 | caaattgttctcacccagtctccagcaatcatgtctgcatctctaggggaacgggtca ccatgacctgcactgccagctcaagtgtaagttccagttacttgcactggtaccagc agaagccaggatcctcccccaaactctggatttatagcacatccaacctggcttctg gagtcccagctcgcttcagtggcagtgggtctgggacctcttactctctcacaatcag cagcatggaggctgaagatgctgccacttattactgccaccagtatcatcgttcccc acggacgttcggtggaggcaccaagctggaaatcaaacgt |
| ScFv (nt) | 19 | atggccgaggtccagctgcagcagtctgggactgtgctggcaaggcctggggcttc agtgaagatgtcctgcaaggcttctggctacacctttaccagctactggatgcactgg gtaaaacagaggcctggacagggtctggaatggattggcgctatttatcctggaaat agtgatactagctacaaccagaagttcaagggcaaggccaaactgactgcagtc acatccaccagcactgcctacatggagctcagcagcctgacaaatgaggactctg cggtcttttactgtacacattactacggtagtgactatgctatggactactggggtcaa ggaacctcagtcactgtctcctcaggtggaggcggttcaggcggaggtggctctgg cggtggcggatcgcaaattgttctcacccagtctccagcaatcatgtctgcatctcta ggggaacgggtcaccatgacctgcactgccagctcaagtgtaagttccagttacttg cactggtaccagcagaagccaggatcctcccccaaactctggatttatagcacatc caacctggcttctggagtcccagctcgcttcagtggcagtgggtctgggacctcttac tctctcacaatcagcagcatggaggctgaagatgctgccacttattactgccaccag tatcatcgttccccacggacgttcggtggaggcaccaagctggaaatcaaacgtgc ggccgca |

CRT-2

| | | |
|---|---|---|
| VH CDR1 (aa) | 22 | GFTFNTYA |
| VH CDR2 (aa) | 23 | IRSKSNNYAT |
| VH CDR3 (aa) | 24 | VREGVYYYGSSGYYAMDY |
| VL CDR1 (aa) | 26 | SYMHWF |
| VL CDR2 (aa) | 27 | LWIYSTSNLA |
| VL CDR3 (aa) | 28 | QQRSSYPL |
| VH (aa) | 21 | M A E V Q G V E S G G G L V Q P K G S L K L S C A A S G F T F N T Y A M H W V C Q A P G K G L E W V A R I R S K S N N Y A T Y Y A D S V K D R F T I S R D D S Q S M L Y L Q M N N L K T E D T A M Y Y C V R E G V Y Y Y G S S G Y Y A M D Y W G Q G T S V T V S S G |
| VL (aa) | 25 | EIVLTQSPAIMSASPGEKVTITCSASSSVSYMHWFQQKPGT SPKLWIYSTSNLASGVPARFSGSGSGTSYSLTISRMEAEDA ATYYCQQRSSYPLTFGAPGKLELKRAA |
| ScFv (aa) | 29 | M A E V Q G V E S G G G L V Q P K G S L K L S C A A S G F T F N T Y A M H W V C Q A P G |

-continued

| Sequence name (sequence type) | SEQ ID NO: | Sequence |
|---|---|---|
| | | K G L E W V A R I R S K S N N Y A T Y Y A D<br>S V K D R F T I S R D D S Q S M L Y L Q M N<br>N L K T E D T A M Y Y C V R E G V Y Y Y G S<br>S G Y Y A M D Y W G Q G T S V T V S S GGGG<br>GSGGGGSGGGGSEIVLTQSPAIMSASPGEKVTITCSASSSV<br>SYMHWFQQKPGTSPKLWIYSTSNLASGVPARFSGSGSGT<br>SYSLTISRMEAEDAATYYCQQRSSYPLTFGAPGKLELKRAA |
| VH CDR1 (nt) | 32 | GGTTTCACCTTCAATACCTATGCC |
| VH CDR2 (nt) | 33 | ATAAGAAGTAAAAGTAATAATTATGCAACA |
| VH CDR3 (nt) | 34 | GTGAGAGAAGGGGTTTATTACTACGGTAGTAGTGGGTAC<br>TATGCTATGGACTAC |
| VL CDR1 (nt) | 36 | AGTTACATGCACTGGTTC |
| VL CDR2 (nt) | 37 | CTCTGGATTTATAGCACATCCAACCTGGCT |
| VL CDR3 (nt) | 38 | CAGCAAAGGAGTAGTTACCCCCTC |
| VH (nt) | 31 | GACGCTTATCGATGGCCGAGGTGCAGGGGGTGGAGTCT<br>GGTGGAGGATTGGTGCAGCCTAAAGGATCATTGAAACTC<br>TCATGTGCCGCCTCTGGTTTCACCTTCAATACCTATGCC<br>A<br>TGCACTGGGTCTGCCAGGCTCCAGGAAAGGGTTTGGAA<br>TGGGTTGCTCGCATAAGAAGTAAAAGTAATAATTATGCAA<br>CATATTATGCCGATTCAGTGAAAGACAGATTCACCATCTC<br>CAGAGATGATTCACAAAGCATGCTCTATCTGCAAATGAA<br>CAACCTGAAAACTGAGGACACAGCCATGTATTACTGTGT<br>GAGAGAAGGGGTTTATTACTACGGTAGTAGTGGGTACTA<br>TGCTATGGACTACTGGGGTCAAGGAACCTCAGTCACCGT<br>CTCCTCAGGT |
| VL (nt) | 35 | GAAATTGTTCTCACCCAGTCTCCAGCAATCATGTCTGCAT<br>CTCCAGGGGAGAAGGTCACC<br>ATAACCTGCAGTGCCAGCTCAAGTGTAAGTTACATGCAC<br>TGGTTCCAGCAGAAG<br>CCAGGCACTTCTCCCAAACTCTGGATTTATAGCACATCC<br>AACCTGGCTTCTGGAGTCCCT<br>GCTCGCTTCAGTGGCAGTGGATCTGGGACCTCTTACTCT<br>CTCACAATCAGCCGAATGGAG<br>GCTGAAGATGCTGCCACTTATTACTGCCAGCAAAGGAGT<br>AGTTACCCCCTCACGTTCGGT<br>GCTGGGACCAAGCTGGAGCTGAAACGTGCGGCCGC |
| ScFv (nt) | 39 | GACGCTTATCGATGGCCGAGGTGCAGGGGGTGGAGTCT<br>GGTGGAGGATTGGTGCAGCCTAAAGGATCATTGAAACTC<br>TCATGTGCCGCCTCTGGTTTCACCTTCAATACCTATGCC<br>ATGCACTGGGTCTGCCAGGCTCCAGGAAAGGGTTTGGA<br>ATGGGTTGCTCGCATAAGAAGTAAAAGTAATAATTATGCA<br>ACATATTATGCCGATTCAGTGAAAGACAGATTCACCATCT<br>CCAGAGATGATTCACAAAGCATGCTCTATCTGCAAATGA<br>ACAACCTGAAAACTGAGGACACAGCCATGTATTACTGTG |

-continued

| Sequence name (sequence type) | SEQ ID NO: | Sequence |
|---|---|---|
| | | TGAGAGAAGGGGTTTATTACTACGGTAGTAGTGGGTACT<br>ATGCTATGGACTACTGGGGTCAAGGAACCTCAGTCACCG<br>TCTCCTCAGGTtcctcaggtggaggcggttcaggcggaggtggctctggcg<br>gtggcggatcgGAAATTGTTCTCACCCAGTCTCCAGCAATCAT<br>GTCTGCATCTCCAGGGGAGAAGGTCACC<br>ATAACCTGCAGTGCCAGCTCAAGTGTAAGTTACATGCAC<br>TGGTTCCAGCAGAAG<br>CCAGGCACTTCTCCCAAACTCTGGATTTATAGCACATCC<br>AACCTGGCTTCTGGAGTCCCT<br>GCTCGCTTCAGTGGCAGTGGATCTGGGACCTCTTACTCT<br>CTCACAATCAGCCGAATGGAG<br>GCTGAAGATGCTGCCACTTATTACTGCCAGCAAAGGAGT<br>AGTTACCCCCTCACGTTCGGT<br>GCTGGGACCAAGCTGGAGCTGAAACGTGCGGCCGC |

Example 5

Design and Analysis of Chimeric Antigen Receptors Based on the Antigen-Binding Domains of the anti-CLEC14A Monoclonal Antibodies

Generation of CAR Constructs

Hybridomas expressing CLEC14A-specific monoclonal antibodies that cross react with human and mouse forms of the protein were obtained as described above. Gene constructs encoding an scFv were then isolated from each of the mouse hybridomas by RT-PCR using degenerate primer sets designed to amplify all mouse V-gene families. The scFv genes were then subcloned into two previously described CAR vectors pMP71.tCD34.2A.CD19ζ and pMP71.tCD34.2A.CD19.IEVζ (Cheadle et al. J Immunol. 2014; 192(8):3654-65) as a ClaI, NotI fragment, replacing the CD19-specific scFv region. These vectors were originally constructed using the MP71 retroviral expression plasmid (a kind gift from C. Baum, Hannover) and co-expressed a truncated CD34 marker gene.

Transduction of Human and Mouse T-Cells

To generate recombinant retrovirus for transducing human T cells, Phoenix amphotropic packaging cells were transfected with an MP71 retroviral vector and pCL ampho (Imgenex) using FuGENE HD (Roche) according to the manufacturer's instructions. Recombinant retrovirus for transducing mouse T cells was generated in the same way but using Phoenix ecotropic packaging cells and pCL eco. Human peripheral blood mononuclear cells (PBMCs) were isolated from heparinized blood by density gradient centrifugation on lymphoprep (Axis Shield, Oslo, Norway). PBMCs were pre-activated for 48 hours using anti-CD3 antibody (OKT3, eBioscience; 30 ng/ml), anti-CD28 antibody (R&D Systems; 30 ng/ml) and interleukin-2 (IL2; 300 U/ml; Chiron, Emeryville, Calif.) using standard medium (RPMI1640 (Sigma) containing 10% foetal bovine serum (FBS; PAA, Pasching Austria), 2 mM L-glutamine, 100 IU/ml penicillin, and 100 pg/ml streptomycin) plus 1% human AB serum (TCS Biosciences, Buckingham, UK). Transduction of mouse T cells was conducted using mouse splenocytes pre-activated for 48 hours with concanavalin A (2 ug/ml; Sigma) and mouse interleukin 7 (1 ng/ml; eBioscience) in standard medium. Preactivated human and mouse T cells were subsequently transduced (or mock-transduced with conditioned supernatant from non-transfected phoenix cells) by spinfection in retronectin (Takara)-coated plates according to the manufacturer's instructions. Human T cells were then cultured in standard medium plus 1% human AB serum with IL2 (100 U/ml). After spinfection, mouse T cells were cultured for 24 hrs in standard medium with IL2 (100 U/ml), then purified using lymphoprep (Axis Shield). Where indicated, transduced cells were enriched by immunomagnetic selection using anti-CD34 microbeads (Miltenyi Biotec, Germany) according to the manufacturer's instructions. Studies with human donors were approved by the National Research Ethics Service Committee West Midlands (Solihull) and all donors gave written informed consent.

Cell Lines and Recombinant Proteins

Phoenix A or E, CHO and Lewis lung carcinoma cells were maintained in Dulbecco's modified Eagle's medium (DMEM) containing 10% foetal bovine serum (FBS; PAA, Pasching Austria), 2 mM L-glutamine, 100 IU/ml penicillin, and 100 pg/ml streptomycin. CHO cells had been transduced with the pWPI vector (Addgene) expressing full length human CLEC14A (or vector alone). Human umbilical vein endothelial cells (HUVECs) were isolated as described above using umbilical cords obtained from Birmingham Women's Health Care NHS Trust with informed consent and with ethical approval of the south Birmingham research ethics committee. HUVECs were maintained in M199 complete medium containing 10% FBS, 4 mM L-glutamine, 10% large vessel endothelial cell growth supplement (TCS Cellworks) and cultured in plates coated with 0.1% type 1 gelatin from porcine skin (Sigma). Human and murine CLEC14A proteins with a human Fc tag were expressed in HEK293T cells and purified on a protein A column.

Flow Cytometry

HUVECs were trypsinised and stained for 1 hr on ice with CLEC14A-specific mouse monoclonal antibodies described above (10 ug/ml) or IgG1 isotype control (Dako) in 5% normal goat serum/PBS. Cells were washed and bound antibody detected by incubating with R-PE-conjugated goat-anti mouse antibody (Serotec). Dead cells were identified by staining with propidium iodide. Human T-cells were washed with PBS and stained with Live/Dead Fixable Violet Dead Cell Stain Kit (Life Technologies) for 20 mins in the dark. Cells were then washed with flow buffer (0.5% w/v BSA+2 mM EDTA in PBS; pH7.2) and stained with anti-human CD4 (PE-conjugated), anti-human CD8 (FITC-conjugated) (all from BD Pharmingen) and anti-human CD34 (Pe-Cy5) (BioLegend) for 30 mins on ice in the dark. Alternatively rather than staining for CD34, CAR expression was detected directly by firstly blocking cells with human Fc fragment (10 ug/ml), then incubating them with 10 ug/ml recombinant human CLEC14A-Fc fusion protein (or Fc control) followed by sheep anti CLEC14A polyclonal antibody (R&D systems, 10 ug/ml). Finally cells were stained with FITC-conjugated rabbit anti-sheep antibody (Invitrogen, diluted 1:10). All incubations were conducted for 1 hour on ice.

When staining mouse T cells from heparinized tail bleeds they were first subject to red blood cell lysis using BD Pharm lyse (Becton Dickinson) before staining as described above but using anti mouse CD4-FITC, CD8-PE and CD45.1 (PE-Cy7 conjugated) (all BD Biosciences). Cells were analyzed using a BD LSR II flow cytometer and FlowJo software (TreeStar Inc, Ashland, Oreg.).

CFSE Labelling

T-cells were washed twice with PBS and incubated with 2.5 μM Carboxyfluorescein succinimidyl ester (CFSE) for 10 minutes at 37° C. The labelling reaction was quenched by addition of RPMI-1640 containing 10% FBS. Cells were washed, resuspended in standard medium plus 1% human AB serum and IL2 (10 IU/ml) at $1.5\times10^6$ cells/ml and added to wells containing HUVECs to give a T-cell:HUVEC ratio of 10:1. After 5 days incubation at 37° C./5% $CO_2$, cells were analysed by flow cytometry as described above using anti-human CD34 (Pe-Cy5).

IFNγ Release Assay

Stimulator cells ($2.5\times10^4$/well) were co-cultured in triplicate with CD34+ CAR-T-cells at responder:stimulator ratios indicated. Alternatively $2\times10^4$ CD34+ CAR-T cells were incubated in wells precoated with recombinant protein (1 ug/ml). Cells were incubated at 37° C./5% $CO_2$ in 100 μl/well of standard medium supplemented with IL2 (25 U/ml). After 18 hours, culture supernatant was tested for secreted IFNγ using an ELISA (Pierce Endogen, Rockford, Ill.) according to the manufacturer's instructions.

Cytotoxicity Assays

Chromium release assays were set up at known effector: target ratios (1250 targets/well) and harvested after 7.5 hours.

Toxicity Testing

Six to eight week old C57BL6 mice (Charles River Laboratories) received 4 Gy total body irradiation (TBI). Eighteen hours later, each mouse was injected into the tail vein with $2\times10^7$ CAR- or Mock-transduced T cell preparations from CD45.1+ congenic BoyJ mice. Mice were monitored for signs of toxicity and immune monitoring was conducted by weekly tail bleeds. Mice were eventually culled 45 days later and major organs removed for histological analysis.

RipTag2 Transgenic Mouse Tumour Model

RIP-Tag2 mice are a model of pancreatic islet cell carcinogenesis. RIP-Tag2 mice were maintained on a C57BL/6J background (The Jackson Laboratory). Cryopreserved CAR-transduced and mock transduced T cells were thawed, washed and 15 million T cells/mouse injected intravenously into the tail vein on a single occasion into 12-week old mice that had been conditioned with 4 Gy TBI the day before. From 12 weeks of age, all RIP-Tag2 mice received 50% sugar food (Harlan Teklad) to relieve hypoglycaemia induced by the insulin-secreting tumours. Total tumour burden in culled CAR-T cell-treated mice was quantified at 16 weeks of age using calipers to measure individually excised macroscopic tumours (>1 mm3) using the formula: volume=a×b2×0.52, where a and b represent the longer and shorter diameter of the tumour, respectively. The volumes of all tumours from each mouse were added to give the total tumour burden per animal. There are no age-matched control comparisons for the 16-week CAR-treated mice, since untreated RIP-Tag2 mice do not survive to 16 weeks, and thus the comparison was made to 14-week old Mock-treated mice.

Lewis Lung Carcinoma (LLC) Mouse Model 6-8 week old female C57BL6 mice were inoculated subcutaneously on the flank with $10^6$ LLC cells. Three days later mice received 4 Gy TBI and 18 hrs after this each mouse was injected into the tail vein with $2\times10^7$ CAR or Mock T cell preparations from CD45.1+ congenic BoyJ mice. Tumour growth was measured with calipers (using the formula: volume=length×width2×0.5) and bioluminescence imaging (IVIS Spectrum, Caliper Life Sciences). Immune monitoring was conducted by weekly tail bleeds.

Tissue Preparation and Immunofluorescence Analysis

Tissues from mouse experiments were embedded in OCT (Bio Optica), frozen in dry ice and stored at −80° C. Tissue preparation and histology analysis were carried out with the following primary antibodies: purified rat monoclonal anti-panendothelial cell antigen (550563, clone Meca32, BD Pharmingen, USA), diluted 1:100; rabbit monoclonal anti-cleaved caspase 3 (asp175, clone 5A1, Cell Signaling, USA), diluted 1:100; rabbit polyclonal anti-Fibrinogen (A0080, Dako), diluted 1:100; and rabbit monoclonal anti-CD34 (ab174720, Abcam) diluted 1:50; sheep polyclonal anti-CLEC14A (AF4968, R&D) diluted 1:50. After incubation and washing, samples were incubated with secondary antibodies anti Rabbit Alexa Fluor-488 and Alexa Fluor-555; anti Rat Alexa Fluor-488 and Alexa Fluor-555; and anti Sheep Alexa Fluor-488 (Molecular Probes) and counterstained with DAPI Nucleic Acid Stain (Invitrogen). To detect CAR-transduced T cells tissues were stained with rabbit monoclonal anti-CD34 (ab174720, Abcam) diluted 1:50 in PBS. After incubation and washing, samples were stained with anti Rabbit Alexa Fluor-555 (Molecular Probes) and counterstained with DAPI.

Human tumour tissue arrays (SuperBiochips Inc., Seoul, Korea) were stained using sheep polyclonal anti-CLEC14A (AF4968, R&D systems) diluted 1:20 and Ulex europaeus agglutinin I conjugated to rhodamine (Vectorlabs, UK) for 1 hour, followed by anti-sheep FITC antibody (10 μg/ml, Invitrogen, UK).

For analysis of RipTag2 tumour tissue, the surface area occupied by vessels was quantified through the ImageJ software as the area occupied by Meca32-positive structures, compared with the total tissue area visualised by DAPI. For each animal, the total vessel area of at least four field/images was quantified. To determine the amount of fibrinogen extravasation (red channel) in each image, we drew a region of interest (ROI) close to each blood vessel (Meca32, green channel), and then quantified the mean fluorescence intensity (MFI) of red and green channels using the Leica Confocal Software Histogram Quantification Tool. In order to normalize the vessel number values obtained, we calculated the ratio between red and green channel MFI; values are expressed as percentage of red-green co-staining. To determine the expression levels of caspase 3 (green channel) in each analysed image, we considered 5 random ROIs of the same size. Then we measured the MFI of the green channel, and we normalized the values by comparing caspase 3-stained area with the total cells present in the tissue area. At least 10 images of five mice per treatment group were analyzed for each sample. Tissue from RipTag2 mice were analyzed using a Leica TCS SP2 AOBS confocal laser-scanning microscope (Leica Microsystems). All other tissues were analysed using an Axiovert 100M laser scanning confocal microscope (Carl Zeiss, Welwyn Garden City, UK).

Statistical Analysis

Statistical analyses of data were conducted using the tests indicated and GraphPad Prism software. A p value <0.05 was considered significant.

Results

Figure 10:
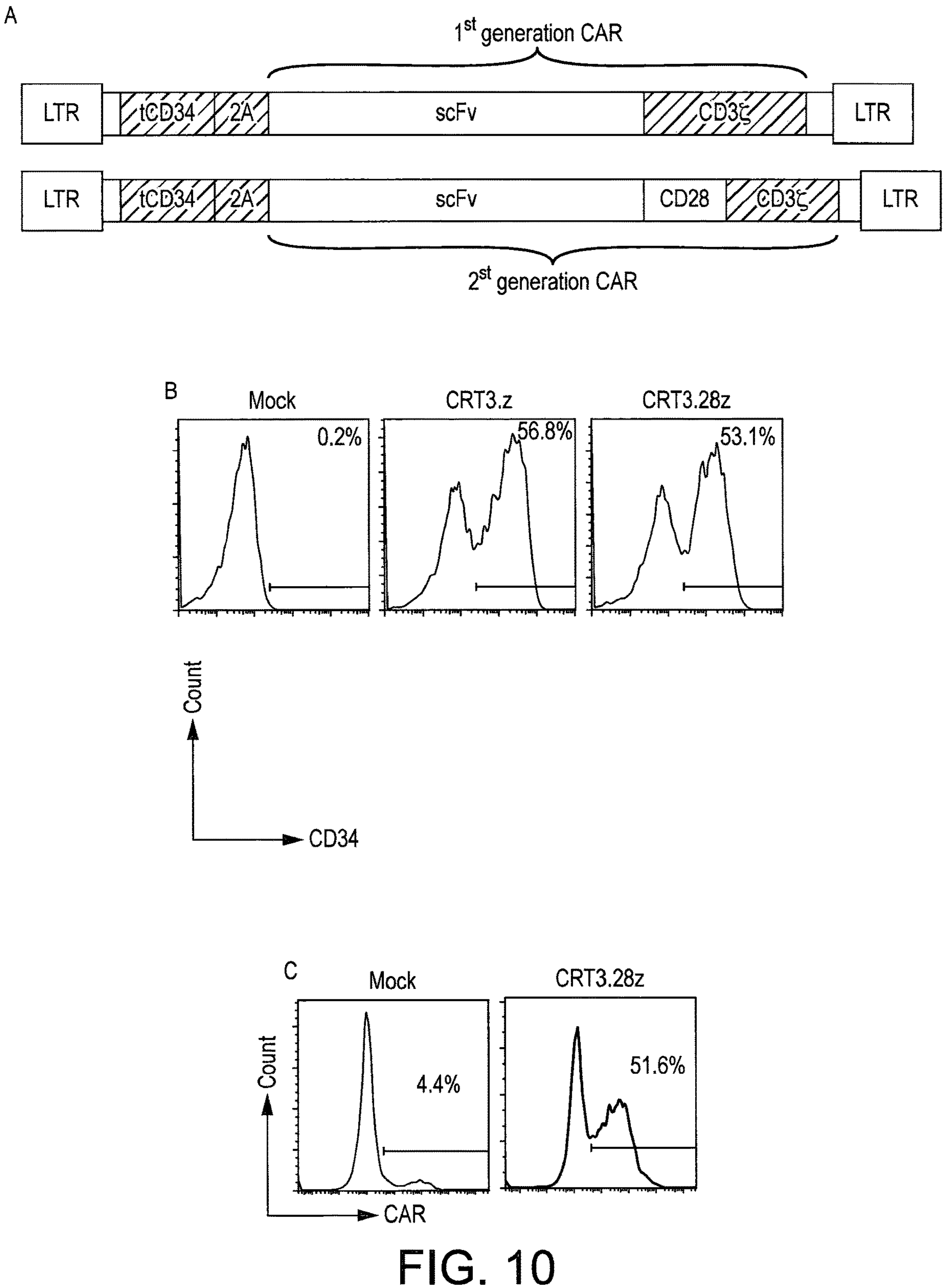

A retroviral CAR vector was generated (based on pMP71) that co-expresses a truncated CD34 marker gene and an scFv fragment/CD3 zeta chain chimeric receptor. Expression is driven from the LTR promoter and the 2A peptide linker ensures equimolar expression of both the CD34 and the CAR. Second generation CAR constructs included the CD28 co-stimulatory domain (see FIG. 10).

FIG. 10B shows CD34 staining analysed by flow cytometry demonstrated successful transduction of T cells using retroviral constructs that co-express a CLEC14A-specific CAR. A first generation CAR based on the antibody CRT-3 is referred to as CRT3.z. A second generation CAR based on the antibody CRT-3 is referred to as CRT3.28z. Note equivalent expression was seen in CD4 and CD8 T cell subsets (data not shown).

FIG. 10C shows cells stained directly for expression of CAR using CLEC14A-Fc (% values show specific binding of CLEC14A-Fc having subtracted background staining with Fc alone).

Figure 11:
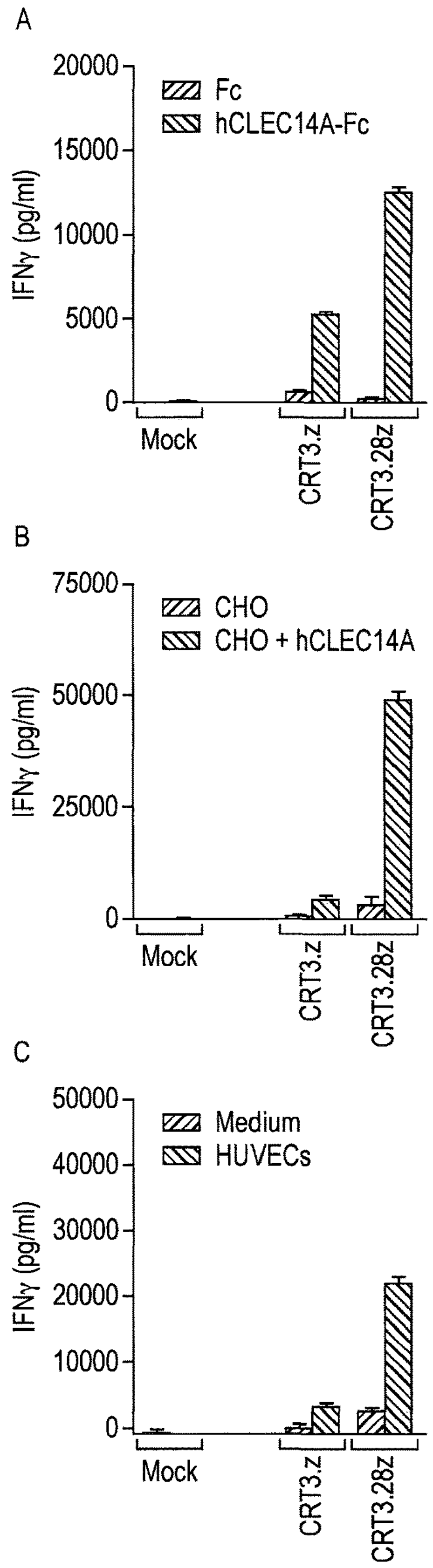

FIG. 11 shows CAR-transduced T cells respond to CLEC14A in vitro. T cells transduced to express 1st or 2nd generation CARs based on antibody CRT-3 or mock-transduced (control) T cells were tested for their ability to respond to CLEC14A expressed either as (A) plate-bound recombinant Fc fusion protein, (B) expressed on engineered CHO cells, or (C) expressed on human umbilical vein endothelial cells (HUVECs) which naturally express CLEC14A when grown in static culture. T cell response was measured using an ELISA for interferon gamma production. Data shown in FIG. 11 are representative of that obtained from 3-7 repeat experiments. T cells were adjusted to equalise the frequency of transgene expressing cells. All histograms show mean response+SD.

Figure 12:
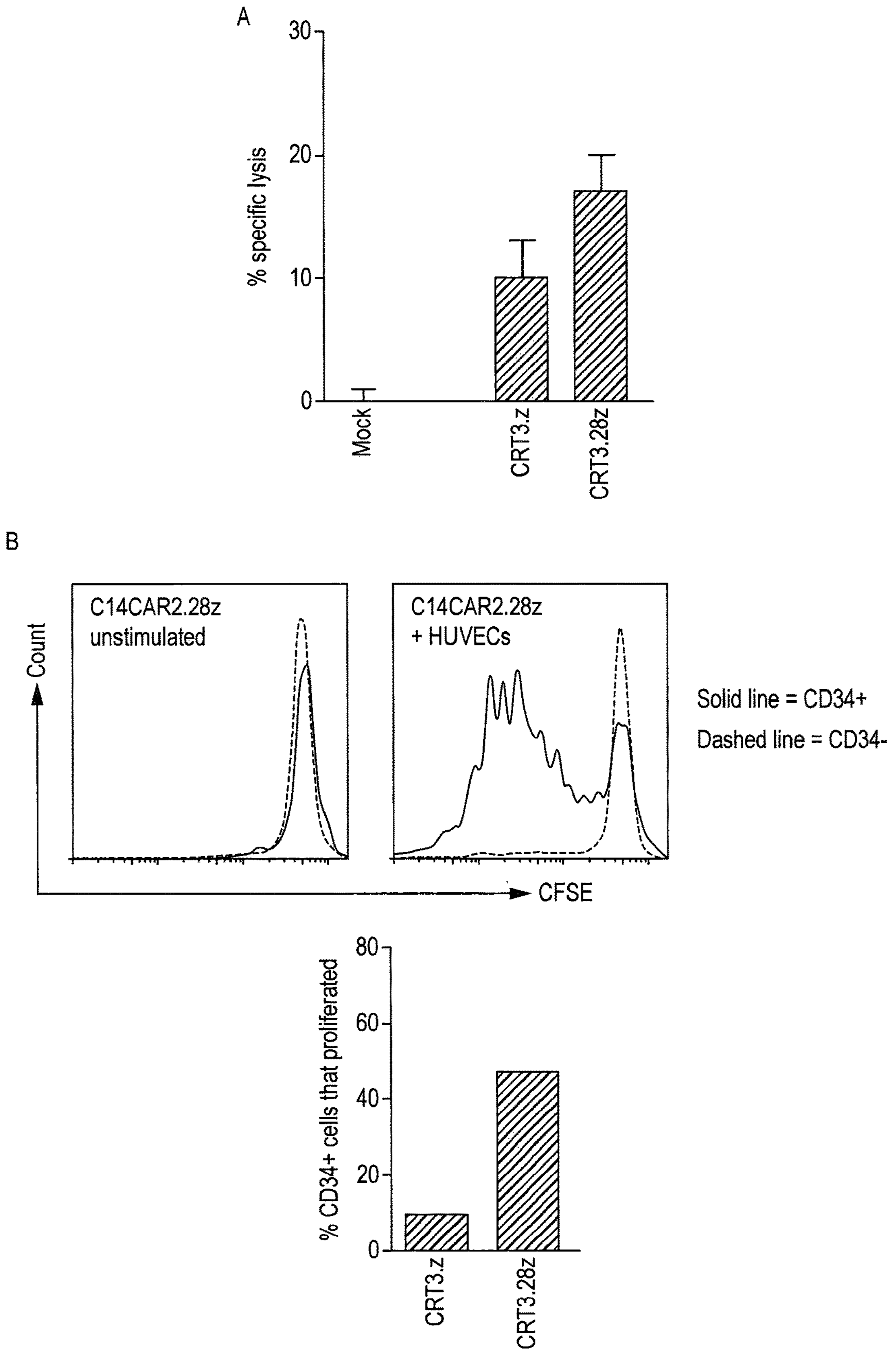
Figure 12:
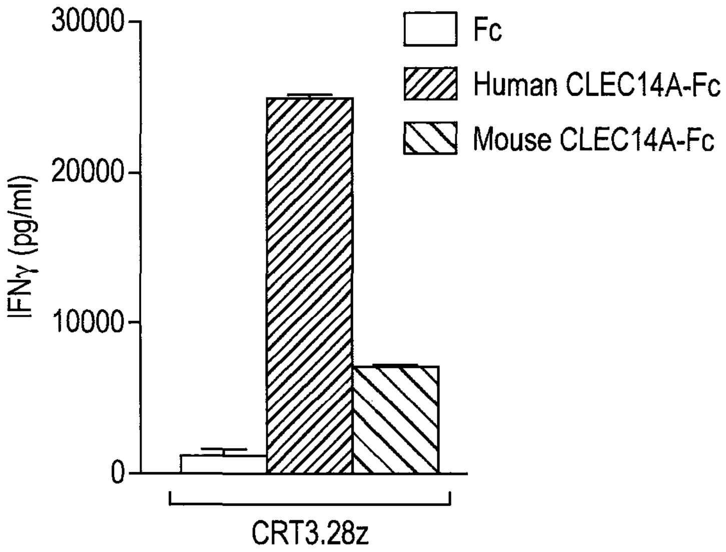

FIG. 12 shows further in vitro functional testing of CLEC14A-specific CAR-transduced T cells. T cells transduced to express 1st or 2nd generation CARs based on antibody CRT-3, or mock-transduced (control) T cells, were tested for their ability to respond to CLEC14A in the following functional assays: (A) Cytotoxicity, using CHO cells engineered to express human CLEC14A (having subtracted background levels of lysis of CHO alone (control cells)). Data shown are representative of 5 repeat experiments. (B) Proliferation, using CFSE-labelled CAR-transduced T cells we measured the proliferation of CAR+ (CD34+) and CAR− (CD34−) cell subsets when co-cultured for 4 days with HUVECs. Data shown are representative of 2 repeat experiments. (C) The response of (CLEC14A-specific CAR-transduced T cells to both human and mouse CLEC14A was assessed using interferon gamma release. T cells were adjusted to equalise the frequency of transgene expressing cells. Data shown are representative of 6 repeat experiments. All histograms show mean response+SD.

Figure 13:
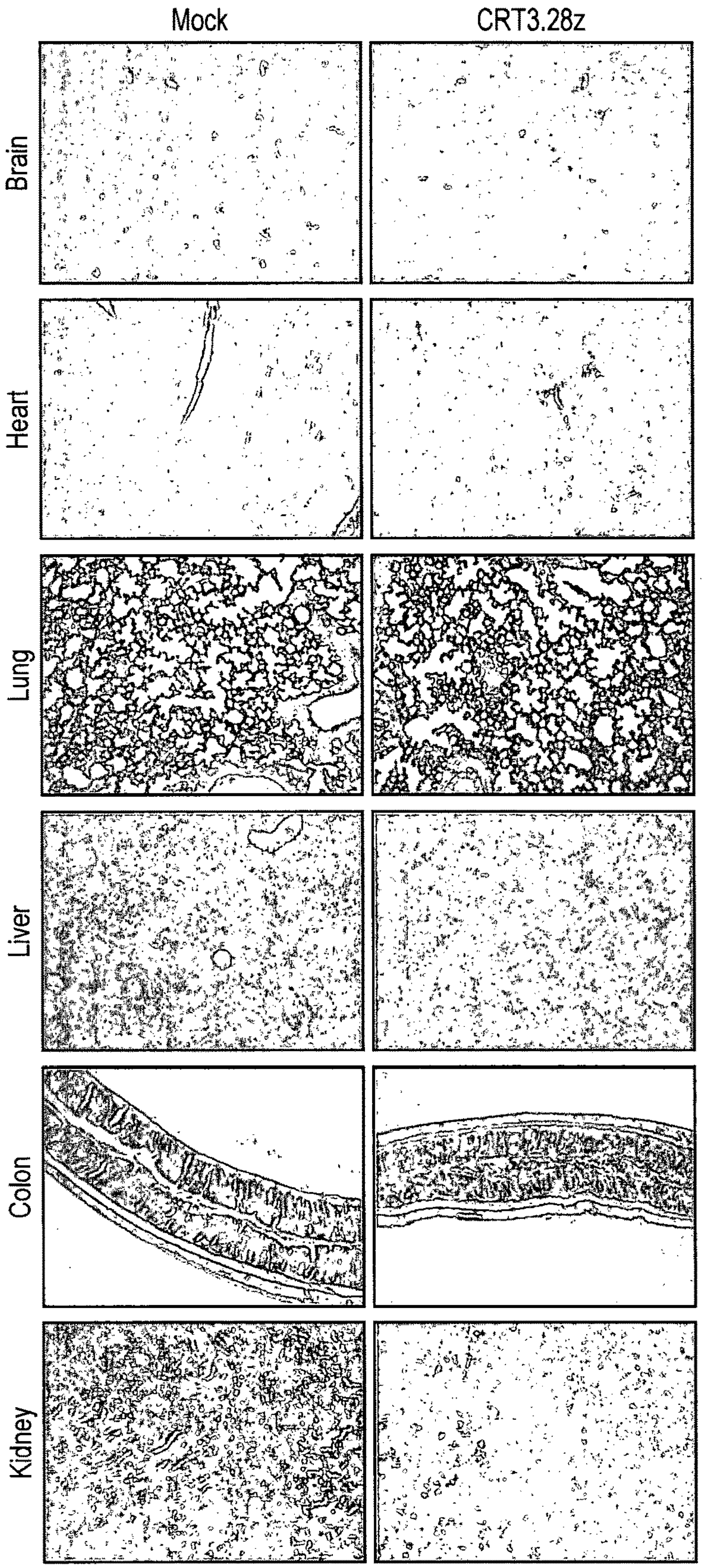

FIG. 13 shows toxicity testing in vivo using healthy C57/BL6 mice injected with CLEC14A-specific CAR-transduced mouse T cells. At the end of the experiment mice were culled and major organs harvested. Histological examination revealed no evidence of pathology.

Figure 14:
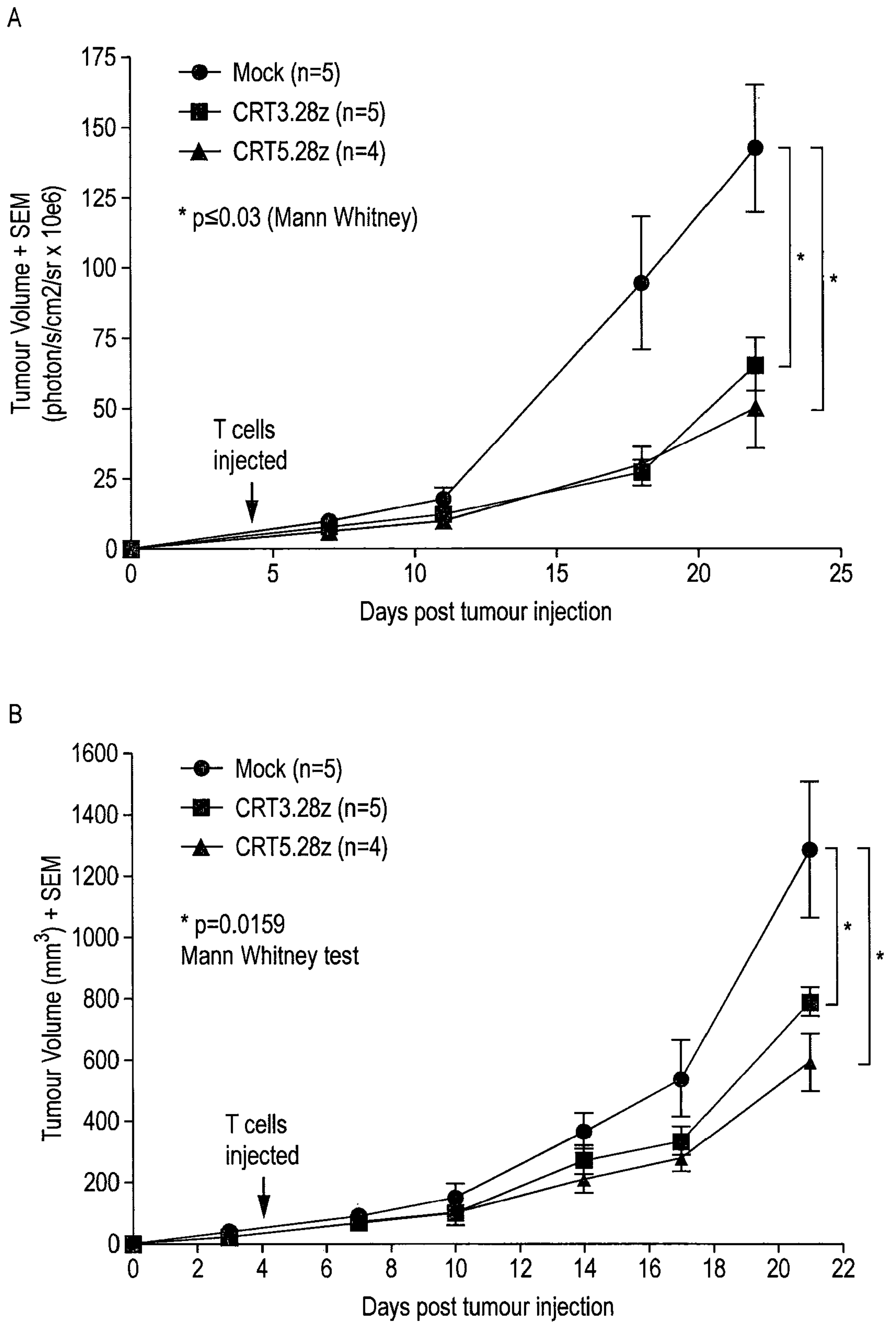

FIG. 14 shows the anti-tumour response of CLEC14A-specific CAR-transduced mouse T cells when injected into mice carrying Lewis Lung carcinoma tumours. C57BL6 mice were injected subcutaneously with Lewis Lung Carcinoma cells (1 million cells/mouse) and 4 days later mice received 4 Gy total body irradiation to aid T cell engraftment. T cells transduced to express 2nd generation CARs based on antibody CRT-3, or mock-transduced (control) T cells, were then injected into the tail vein. Mice received a total of 20 million T cells (CD8:CD4=5:2) with CRT3.28z expressed on 2.2 of these cells. Tumour growth was then monitored using (A) Bioluminescence or (B) Calipers.

Figure 15:
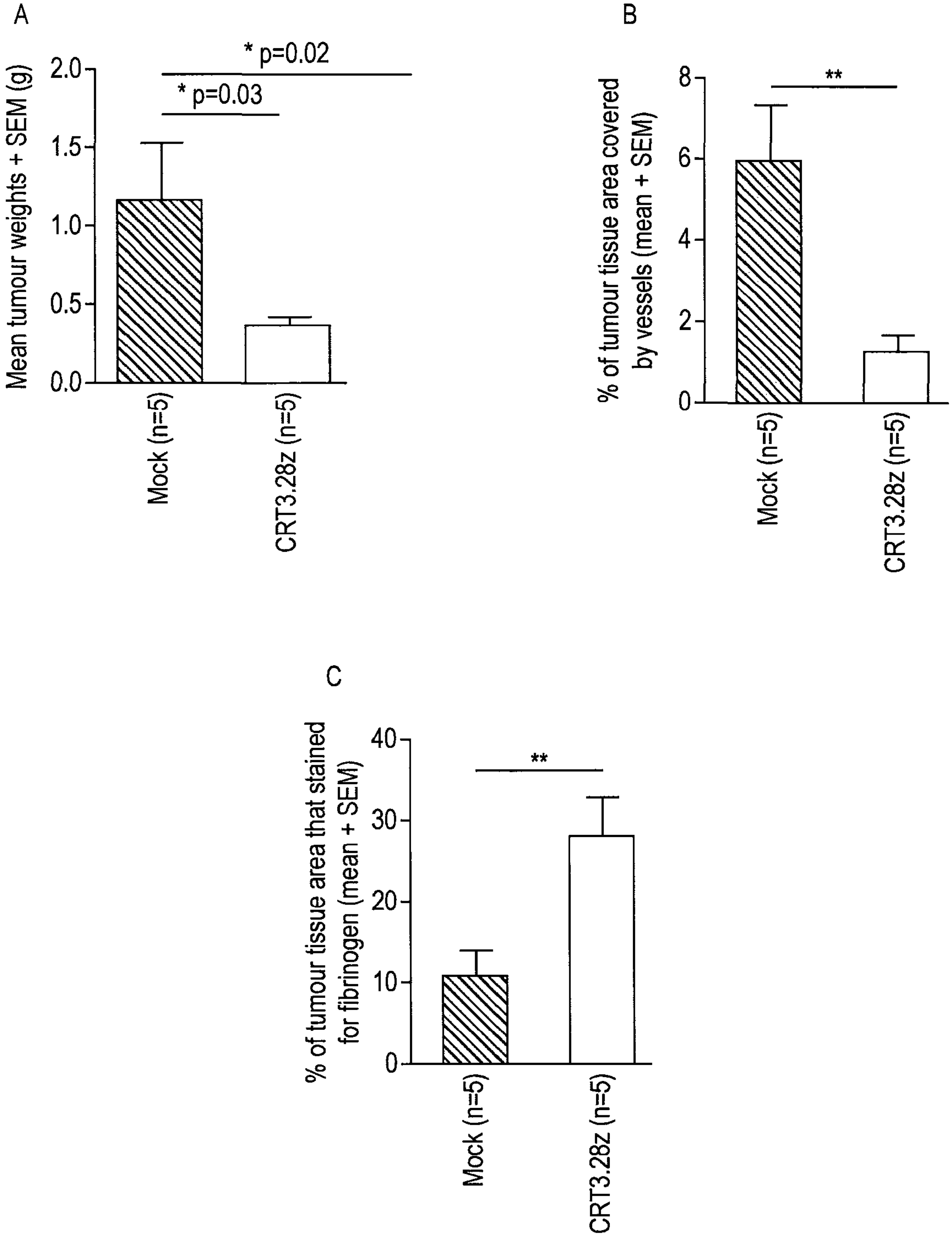
FIG. 15 shows bar charts depicting tumour weight (A), percentage of tumour tissue area covered by vessels (B) and percentage of tumour tissue that stained for fibrinogen (C) in Lewis Lung carcinoma tumours from mice injected with T cells transduced to express 2nd generation CARs based on antibody CRT-3 or mock-transduced (control) T cells.

FIG. 15 shows the anti-tumour response of CLEC14A-specific CAR-transduced mouse T cells when injected into mice carrying Lewis Lung carcinoma tumours. At the end of the experiment tumours were excised and weighed (A). Histological analysis demonstrated that tumours from mice treated with the CARs showed significantly reduced vascular density (B, staining for MECA-32) and greater levels of vascular leakage (C, staining for fibrinogen).

The polypeptide and nucleotide sequences for the CAR derived from CRT-3 are set out in the table below:

| | | |
|---|---|---|
| CAR3 full-aa | 10 | M G V L L T Q R T L L S L V L A L L F P S M A<br>S M A E V Q L Q Q S G T V L A R P G A S V K<br>M S C K A S G Y T F T S Y W M H W V K Q R<br>P G Q G L E W I G A I Y P G N S D T S Y N Q<br>K F K G K A K L T A V T S T S T A Y M E L S S<br>L T N E D S A V F Y C T H Y Y G S D Y A M D<br>Y W G Q G T S V T V S S G G G G S G G G G<br>S G G G G S Q I V L T Q S P A I M S A S L G<br>E R V T M T C T A S S S V S S S Y L H W Y Q<br>Q K P G S S P K L W I Y S T S N L A S G V P<br>A R F S G S G S G T S Y S L T I S S M E A E<br>D A A T Y Y C H Q Y H R S P R T F G G G T K<br>L E I K R A A A I E V M Y P P P Y L D N E K S<br>N G T I I H V K G K H L C P S P L F P G P S K<br>P F W V L V V V G G V L A C Y S L L V T V A<br>F I I F W V R S K R S R L L H S D Y M N M T P<br>R R P G P T R K H Y Q P Y A P P R D F A A Y<br>R S R V K F S R S A D A P A Y Q Q G Q N Q L<br>Y N E L N L G R R E E Y D V L D K R R G R D<br>P E M G G K P Q R R K N P Q E G L Y N E L Q<br>K D K M A E A Y S E I G M K G E R R R G K G<br>H D G L Y Q G L S T A T K D T Y D A L H M Q<br>A L P P R |

-continued

```
CAR3 full-nt   20   atgggcgtgctgctgacccagaggaccctgctgagcctggtgctggccctgctgttt
                    ccatctatggcatcgatggccgaggtccagctgcagcagtctgggactgtgctggc
                    aaggcctggggcttcagtgaagatgtcctgcaaggcttctggctacacctttaccag
                    ctactggatgcactgggtaaaacagaggcctggacagggtctggaatggattggc
                    gctatttatcctggaaatagtgatactagctacaaccagaagttcaagggcaaggc
                    caaactgactgcagtcacatccaccagcactgcctacatggagctcagcagcctg
                    acaaatgaggactctgcggtcttttactgtacacattactacggtagtgactatgctat
                    ggactactggggtcaaggaacctcagtcactgtctcctcaggtggaggcggttcag
                    gcggaggtggctctggcggtggcggatcgcaaattgttctcacccagtctccagca
                    atcatgtctgcatctctaggggaacgggtcaccatgacctgcactgccagctcaagt
                    gtaagttccagttacttgcactggtaccagcagaagccaggatcctcccccaaactc
                    tggatttatagcacatccaacctggcttctggagtcccagctcgcttcagtggcagtg
                    ggtctgggacctcttactctctcacaatcagcagcatggaggctgaagatgctgcca
                    cttattactgccaccagtatcatcgttccccacggacgttcggtggaggcaccaagct
                    ggaaatcaaacgtgcggccgcaattgaagttatgtatcctcctccttacctagacaat
                    gagaagagcaatggaaccattatccatgtgaaagggaaacacctttgtccaagtc
                    ccctatttcccggaccttctaagcccttttgggtgctggtggtggttggtggagtcctgg
                    cttgctatagcttgctagtaacagtggcctttattattttctgggtgaggagtaagagga
                    gcaggctcctgcacagtgactacatgaacatgactccccgccgccccgggcccac
                    ccgcaagcattaccagccctatgccccaccacgcgacttcgcagcctatcgctcca
                    gagtgaagttcagcaggagcgcagacgcccccgcgtaccagcagggccagaa
                    ccagctctataacgagctcaatctaggacgaagagaggagtacgatgttttggaca
                    agagacgtggccgggaccctgagatggggggaaagccgcagagaaggaaga
                    accctcaggaaggcctgtacaatgaactgcagaaagataagatggcggaggcct
                    acagtgagattgggatgaaaggcgagcgccggaggggcaaggggcacgatgg
                    cctttaccagggtctcagtacagccaccaaggacacctacgacgcccttcacatgc
                    aggccctgccccctcgctaataaaagcttaacacgagcca
```

Example 6

Design and Analysis of Anti-CLEC14A Monoclonal Antibody-Drug Conjugates (Immunoconjugates)

Internalisation of CRT-3 Antibody-Drug Conjugate (Immunoconjugate)

Monoclonal anti-CLEC14A antibody (CRT-3) drug conjugates (CRT-3-ADC) were generated, wherein the antibody was attached to tirapazamine.

Figure 16:
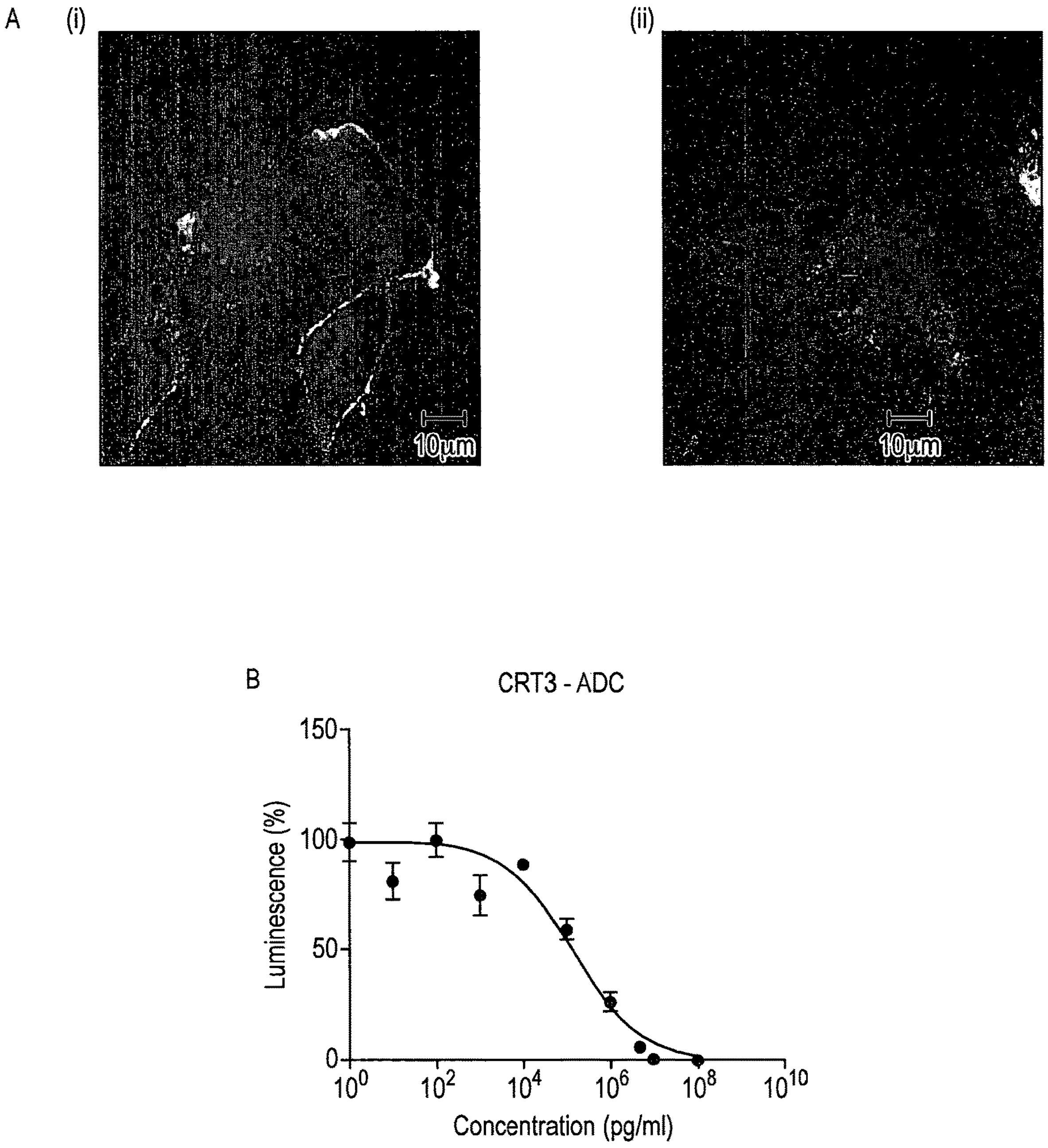
FIG. 16 shows (A) images of HUVEC treated with CRT-3 at (i) 0 minutes and (ii) 90 minutes and demonstrates that the antibody is internalised; and (B) a graph showing cell viability of HUVEC treated with a CRT-3-antibody drug conjugate (immunoconjugate).

FIG. 16A shows HUVEC cells treated with CRT-3 and shows the localisation of the antibody after 0 minutes (FIG. 16A(i)) and 90 minutes (FIG. 16A(ii)) and demonstrates that the antibody is internalised in HUVEC cells. FIG. 16B shows a graph of cytotoxicity measures by Cell Titre Glo luminescent cell viability assay in HUVEC treated CRT-3-ADC and demonstrates that the CRT-3 antibody shows cytotoxicity as an immunoconjugate.

LLC ADC 24 Hour Pilot Experiment 1 million Lewis lung carcinoma cells were injected subcutaneously into the right flank of 2 mice and allowed to grow to a visible size. Next, 1 mg/kg of CRT-3-ADC or B12-ADC (control) was administered through tail vein injections. The mice were observed for an hour and culled 24 hours later.

Results

Figure 17:
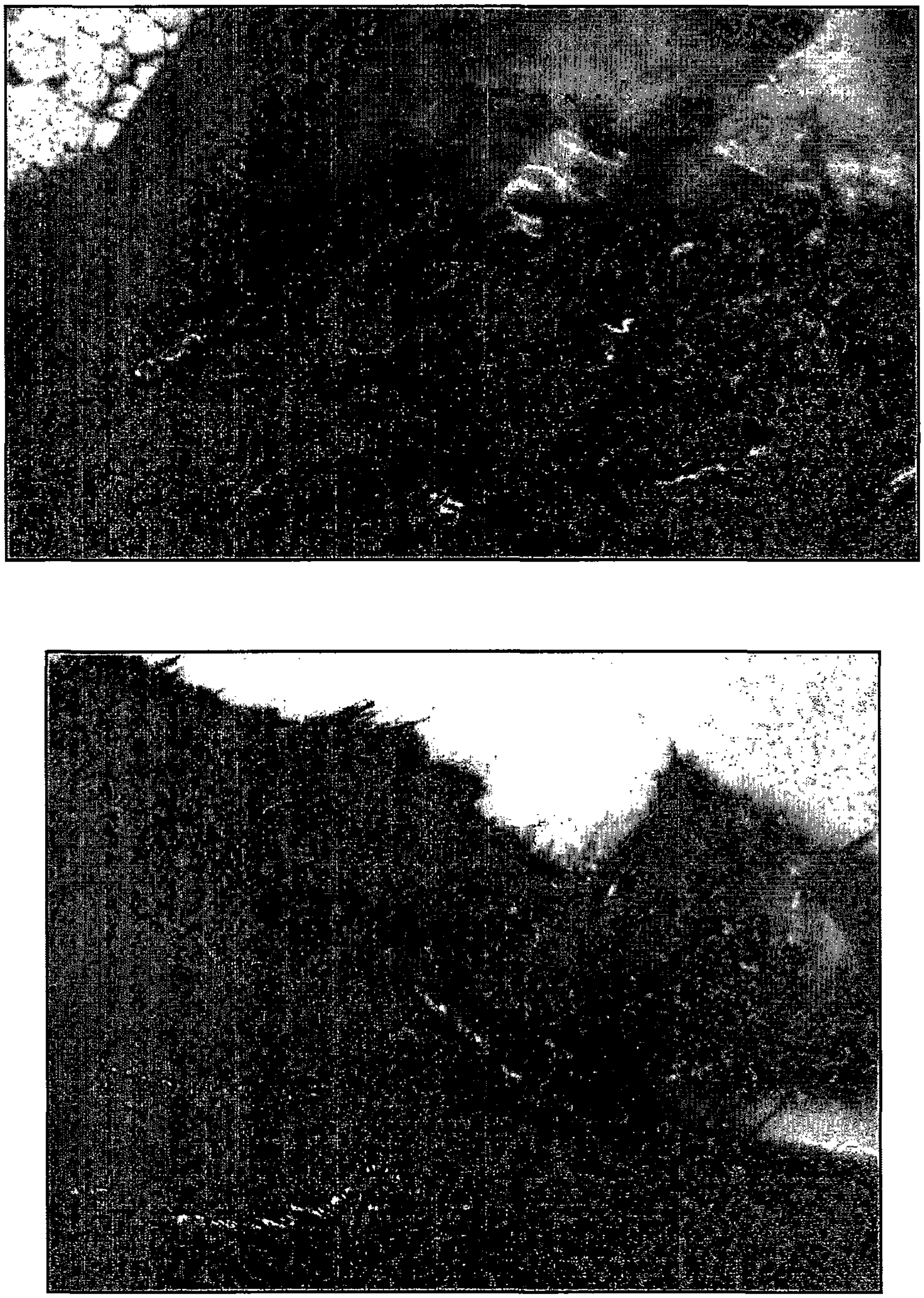
FIG. 17 shows pictures of mouse lung tissue (A) 24 hours after treatment with a control ADC (B12-ADC) and (B) 24 hours after treatment with a CRT-3-ADC.

Treatment with CRT-3-ADC for 24 h had no effect on the overall health of the mouse. Extensive haemorrhage at the site of the tumour was observed only in the CRT-3-ADC treated mouse and not the control, demonstrating tumour-specific disruption of angiogenesis (FIG. 17).

Example 7

Titration of CRT1, 3 and 5 Against CLEC14A

Figure 18:
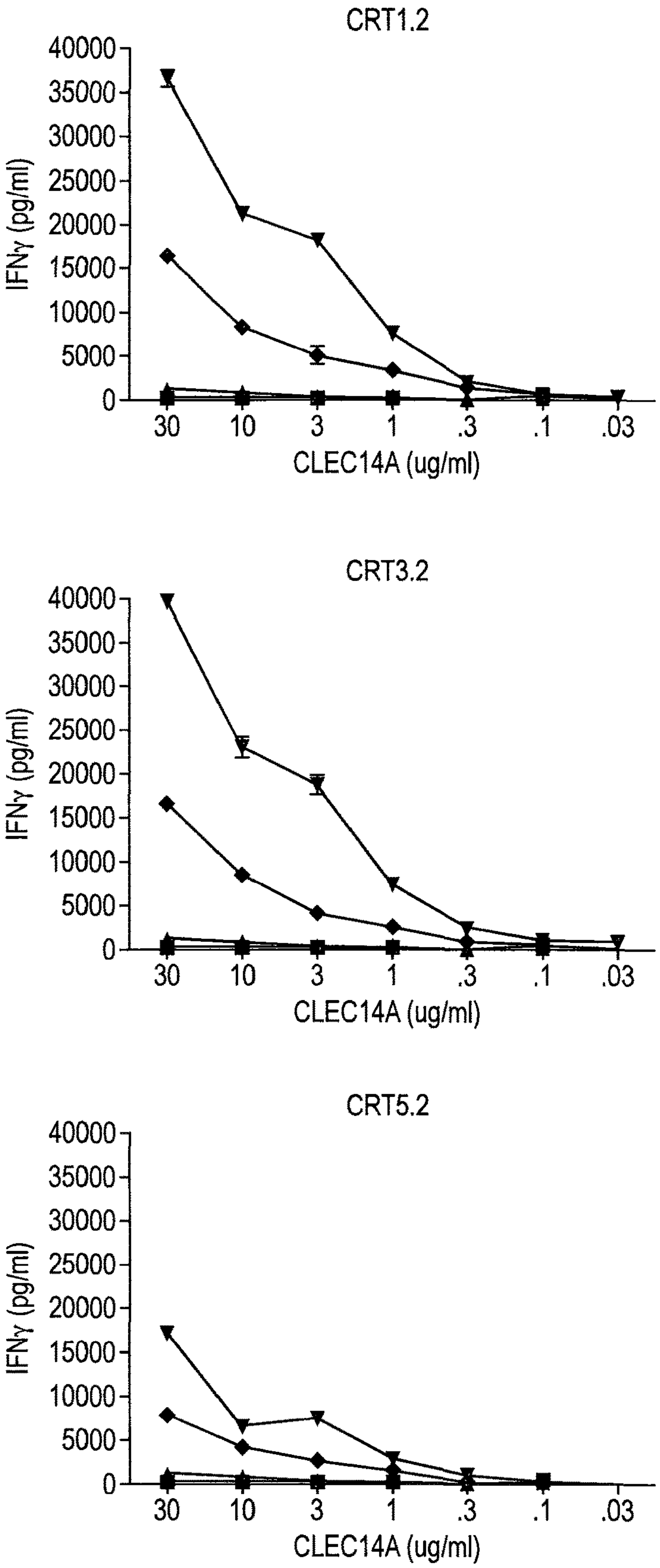
FIG. 18 shows CRT1, 3 and 5 CAR (with CD28 costimulatory domain) T cell response to titrated concentrations of human and mouse recombinant CLEC14A.

CLEC14A was expressed as an Fc fusion protein for incubation with CRT1, 3 and 5 CAR (CD28 costimulatory domain) T cells. All CAR-T cell lines were diluted with Mock T cells to equalise for transduction efficiencies. The results can be seen in FIG. 18 where it is shown that all of the tested CAR T cells respond well to CLEC14A (data shown are means of triplicate cultures +SD).

Example 8

CRT1, 3 and 5 CAR T Cell Cytotoxicity and Proliferation Assay

A cytotoxicity study was carried out using CRT1, 3 and 5 CAR (with CD28 costimulatory domain) T cells. The T cells were diluted with Mock T cells to equalise for transduction efficiencies and were incubated with mouse endothelial cells expressing human CLEC14A. The results are shown in FIG. 20 which demonstrate that all three tested CARs can mediate cytotoxicity. The data shown are means of triplicate cultures +SD.

Further, a proliferation assay was carried out (CFSE labelling) with CRT1, 3 and 5 CAR (CD28 costimulatory domain) T cells stimulated with plate-bound recombinant CLEC14A-Fc fusion proteins. All the CAR T cell lines were diluted with Mock T cells to equalise for transduction efficiencies, where all three tested CARs were capable of proliferating after stimulation.

Example 9

CARs with Different Costimulatory and Transmembrane Regions

The following CARs have been cloned and engineered into T cells from a single donor using a retroviral vector:

1) CRT3-CD28 TM-CD28 costim signal-CD3 (CRT3.28z)

2) CRT3-CD8 TM-4-1BB costim signal-CD3 (CRT3.BBz)

3) CRT3-CD28 TM-CD28 and 4-1BB costim signals-CD3 (CRT3.28BBz)

4) CRT3-CD28 TM-CD28 and OX40 costim signals-CD3 (CRT3.28Oxz)

5) CRT3-CD8 TM-4-1BB and OX40 costim signals-CD3 (CRT3.BBOxz)

All constructs generated transduced well into T cells. The function of the different constructs was assessed in vitro, analysing cytokine production, cytotoxicity and proliferative response (see FIG. 21). Cytokine release indicated strong antigen specific responses especially by T cells expressing CRT3.28z and CRT3.28Oxz. Cytokine production was analysed by measuring IFNgamma production in response to titrated numbers of CHO cells expressing human CLEC14A (or vector only control). All CAR T cell lines were diluted with Mock T cells to equalise for transduction efficiencies. Data shown are means of triplicate cultures +SD. Cytotoxic activity was measured against mouse endothelial cells (SEND) engineered to express CLEC14A and the proliferative response was measured following stimulation with plate-bound recombinant CLEC14A-Fc fusion proteins (data not shown).

Example 10

Determination of Cytokine Release from CAR T Cells Following Stimulation with Chimeric CLEC14A Chimeric forms of CLEC14A that contain the human sequence but with the transmembrane and/or intracellular domains of mouse origin were expressed in 293 and SEND cells. These cells were sorted using GFP co-expressed from a lentiviral vector to equalise for CLEC expression and then tested using CAR T cells (CRT1, 3 and 5 with CD28 costimulatory domain). The release of IFN gamma was measured after incubation of the CAR T cells with both the 293 and SEND cells. The results can be seen in FIG. 22. Additionally, the cytotoxicity of the T cells when incubated with the CLEC14A chimera expressing SEND cells was determined. All CAR T cell lines were diluted with Mock T cells to equalise for transduction efficiencies. Data shown are means of triplicate cultures.

As can be seen from FIG. 22, all of the tested CRT1, 3 and 5 CAR T cells result in the release of IFN gamma from 293 and SEND cells expressing either human CLEC14A (hu-CLEC), human CLEC14A with mouse intracellular domain (A1) and human CLEC14A with mouse transmembrane and intracellular domain (B1).

The invention claimed is:

1. An isolated antibody, which selectively binds to CLEC14A, wherein said antibody:

(a) comprises at least one heavy chain variable region that comprises three CDRs and at least one light chain variable region that comprises three CDRs, wherein said heavy chain variable region comprises:

(i) a variable heavy (VH) CDR1 that has the amino acid sequence of SEQ ID NO: 105, SEQ ID NO: 2, or SEQ ID NO: 42;

(ii) a VH CDR2 that has the amino acid sequence of SEQ ID NO: 106, SEQ ID NO: 3, or SEQ ID NO: 43; and (iii) a VH CDR3 that has the amino acid sequence of SEQ ID NO: 107, SEQ ID NO: 4, or SEQ ID NO: 44; and wherein said light chain variable region comprises:

(iv) a variable light (VL) CDR1 that has the amino acid sequence of SEQ ID NO: 108, SEQ ID NO: 6, or SEQ ID NO: 46;

(v) a VL CDR2 that has the amino acid sequence of SEQ ID NO: 109, SEQ ID NO: 7, or SEQ ID NO: 47; and (vi) a VL CDR3 that has the amino acid sequence of SEQ ID NO: 110, SEQ ID NO: 8, or SEQ ID NO: 48; or (b) comprises at least one heavy chain variable region that comprises three CDRs and at least one light chain variable region that comprises three CDRs, wherein said heavy chain variable region comprises:

(i) a variable heavy (VH) CDR1 that has the amino acid sequence of SEQ ID NO: 22;

(ii) a VH CDR2 that has the amino acid sequence of SEQ ID NO: 23; and (iii) a VH CDR3 that has the amino acid sequence of SEQ ID NO: 24; and wherein said light chain variable region comprises:

(iv) a variable light (VL) CDR1 that has the amino acid sequence of SEQ ID NO: 26;

(v) a VL CDR2 that has the amino acid sequence of SEQ ID NO: 27; and (vi) a VL CDR3 that has the amino acid sequence of SEQ ID NO: 28.

2. The antibody of claim 1, wherein said antibody:

(a) has a VH domain having the amino acid sequence of either SEQ ID NO: 1 or SEQ ID NO: 41 and/or a VL domain having the amino acid sequence of either SEQ ID NO: 5 or SEQ ID NO: 45; or (b) has a VH domain having the amino acid sequence of SEQ ID NO: 21 and/or a VL domain having the amino acid sequence of SEQ ID NO: 25.

3. The antibody of claim 1, wherein:

(a) said antibody is a mouse or humanised antibody;

(b) said antibody comprises all or a portion of an antibody heavy chain constant region and/or all or a portion of an antibody light chain constant region;

(c) said antibody is an IgG antibody;

(d) said antibody comprises:

a heavy chain that comprises the amino acid sequence of either SEQ ID NO: 1 or SEQ ID NO: 41 and a light chain that comprises the amino acid sequence of either SEQ ID NO: 5 or SEQ ID NO: 45; or (ii) a heavy chain that comprises the amino acid sequence of SEQ ID NO: 21 and a light chain that comprises the amino acid sequence of SEQ ID NO: 25;

(g) said antibody is an antigen binding fragment of an antibody; and/or (h) said antibody is an antigen binding fragment of an antibody, which is a Fab', Fab, F(ab')2, TandAbs dimer, Fv, scFv, dsFv, ds-scFv, minibody, diabody, bispecific antibody fragment, bibody, tribody, sc-diabody, BiTE, DVD-Ig or DART.

4. An immunoconjugate comprising the antibody of claim 1 conjugated to a therapeutic, diagnostic or imaging agent.

5. A composition comprising an antibody of claim 1 or an immunoconjugate comprising an antibody of claim 1, and at least one physiologically acceptable carrier or excipient, wherein said composition is a therapeutic or pharmaceutical composition.

6. The composition of claim 5, wherein said composition comprises at least one further therapeutic agent.

7. The composition of claim 5, wherein said composition is provided as a combined preparation with one or more additional therapeutic agents for separate, simultaneous or sequential use or administration.

8. The composition of claim 6, wherein said therapeutic agent is an anti-cancer and/or anti-angiogenesis agent.

9. The composition of claim 8, wherein said anti-cancer agent is an alkylating agent, topoisomerase I inhibitor, topoisomerase II inhibitor, RNA/DNA antimetabolite, DNA antimetabolite, an antimitotic agent or a cytotoxic moiety.

10. The composition of claim 9, wherein said cytotoxic moiety is a directly cytotoxic chemotherapeutic agent, a directly cytotoxic polypeptide, a moiety which is able to convert a prodrug into a cytotoxic drug, a radiosensitizer, a directly cytotoxic nucleic acid, a nucleic acid molecule that encodes a directly or indirectly cytotoxic polypeptide, or a radioactive atom.

* * * * *

UNITED STATES PATENT AND TRADEMARK OFFICE

CERTIFICATE OF CORRECTION

PATENT NO. : 11,566,075 B2
APPLICATION NO. : 16/085192
DATED : January 31, 2023
INVENTOR(S) : Roy Bicknell et al.

It is certified that error appears in the above-identified patent and that said Letters Patent is hereby corrected as shown below:

On the Title Page

Please add the following under the "(72) Inventors" field and above the "(*) Notice" field:
(73) Assignee: Cancer Research Technology LTD, London (GB)

Signed and Sealed this
Fifth Day of August, 2025

Coke Morgan Stewart
*Acting Director of the United States Patent and Trademark Office*

SEQUENCE LISTING

<160> NUMBER OF SEQ ID NOS: 121

<210> SEQ ID NO 1
<211> LENGTH: 119
<212> TYPE: PRT
<213> ORGANISM: Artificial Sequence
<220> FEATURE:
<223> OTHER INFORMATION: Variable heavy chain of CRT3 (SEQ ID NO.1)

<400> SEQUENCE: 1

Met Ala Glu Val Gln Leu Gln Gln Ser Gly Thr Val Leu Ala Arg Pro
1               5                   10                  15

Gly Ala Ser Val Lys Met Ser Cys Lys Ala Ser Gly Tyr Thr Phe Thr
            20                  25                  30

Ser Tyr Trp Met His Trp Val Lys Gln Arg Pro Gly Gln Gly Leu Glu
        35                  40                  45

Trp Ile Gly Ala Ile Tyr Pro Gly Asn Ser Asp Thr Ser Tyr Asn Gln
    50                  55                  60

Lys Phe Lys Gly Lys Ala Lys Leu Thr Ala Val Thr Ser Thr Ser Thr
65                  70                  75                  80

Ala Tyr Met Glu Leu Ser Ser Leu Thr Asn Glu Asp Ser Ala Val Phe
                85                  90                  95

Tyr Cys Thr His Tyr Tyr Gly Ser Asp Tyr Ala Met Asp Tyr Trp Gly
            100                 105                 110

Gln Gly Thr Ser Val Thr Val
        115

<210> SEQ ID NO 2
<211> LENGTH: 8
<212> TYPE: PRT
<213> ORGANISM: Artificial Sequence
<220> FEATURE:
<223> OTHER INFORMATION: CDR1 of VH of CRT3 (SEQ ID NO. 2)

<400> SEQUENCE: 2

Gly Tyr Thr Phe Thr Ser Tyr Trp
1 5

<210> SEQ ID NO 3
<211> LENGTH: 8
<212> TYPE: PRT
<213> ORGANISM: Artificial Sequence
<220> FEATURE:
<223> OTHER INFORMATION: CDR2 of VH of CRT3 (SEQ ID NO.3)

<400> SEQUENCE: 3

Ile Tyr Pro Gly Asn Ser Asp Thr
1 5

<210> SEQ ID NO 4
<211> LENGTH: 12
<212> TYPE: PRT
<213> ORGANISM: Artificial Sequence
<220> FEATURE:
<223> OTHER INFORMATION: CDR3 of VH of CRT3 (SEQ ID NO. 4)

<400> SEQUENCE: 4

Thr His Tyr Tyr Gly Ser Asp Tyr Ala Met Asp Tyr
1 5 10

<210> SEQ ID NO 5
<211> LENGTH: 112
<212> TYPE: PRT
<213> ORGANISM: Artificial Sequence
<220> FEATURE:
<223> OTHER INFORMATION: Variable light chain of CRT3 (SEQ ID NO. 5)

<400> SEQUENCE: 5

Gln Ile Val Leu Thr Gln Ser Pro Ala Ile Met Ser Ala Ser Leu Gly
1 5 10 15

Glu Arg Val Thr Met Thr Cys Thr Ala Ser Ser Ser Val Ser Ser Ser
20 25 30

Tyr Leu His Trp Tyr Gln Gln Lys Pro Gly Ser Ser Pro Lys Leu Trp
35 40 45

Ile Tyr Ser Thr Ser Asn Leu Ala Ser Gly Val Pro Ala Arg Phe Ser
50 55 60

Gly Ser Gly Ser Gly Thr Ser Tyr Ser Leu Thr Ile Ser Ser Met Glu
65 70 75 80

Ala Glu Asp Ala Ala Thr Tyr Tyr Cys His Gln Tyr His Arg Ser Pro
85 90 95

Arg Thr Phe Gly Gly Gly Thr Lys Leu Glu Ile Lys Arg Ala Ala Ala
100 105 110

<210> SEQ ID NO 6
<211> LENGTH: 7
<212> TYPE: PRT
<213> ORGANISM: Artificial Sequence
<220> FEATURE:
<223> OTHER INFORMATION: CDR1 of VL of CRT3 (SEQ ID NO. 6)

<400> SEQUENCE: 6

Ser Ser Val Ser Ser Ser Tyr
1 5

-continued

<210> SEQ ID NO 7
<211> LENGTH: 3
<212> TYPE: PRT
<213> ORGANISM: Artificial Sequence
<220> FEATURE:
<223> OTHER INFORMATION: CDR2 of VL of CRT3 (SEQ ID NO. 7)

<400> SEQUENCE: 7

Ser Thr Ser
1

<210> SEQ ID NO 8
<211> LENGTH: 9
<212> TYPE: PRT
<213> ORGANISM: Artificial Sequence
<220> FEATURE:
<223> OTHER INFORMATION: CDR3 of VL of CRT3 (SEQ ID NO. 8)

<400> SEQUENCE: 8

His Gln Tyr His Arg Ser Pro Arg Thr
1 5

<210> SEQ ID NO 9
<211> LENGTH: 248
<212> TYPE: PRT
<213> ORGANISM: Artificial Sequence
<220> FEATURE:
<223> OTHER INFORMATION: scFv of CRT3 (SEQ ID NO. 9)

<400> SEQUENCE: 9

```
Met Ala Glu Val Gln Leu Gln Gln Ser Gly Thr Val Leu Ala Arg Pro
1               5                   10                  15

Gly Ala Ser Val Lys Met Ser Cys Lys Ala Ser Gly Tyr Thr Phe Thr
            20                  25                  30

Ser Tyr Trp Met His Trp Val Lys Gln Arg Pro Gly Gln Gly Leu Glu
        35                  40                  45

Trp Ile Gly Ala Ile Tyr Pro Gly Asn Ser Asp Thr Ser Tyr Asn Gln
    50                  55                  60

Lys Phe Lys Gly Lys Ala Lys Leu Thr Ala Val Thr Ser Thr Ser Thr
65                  70                  75                  80

Ala Tyr Met Glu Leu Ser Ser Leu Thr Asn Glu Asp Ser Ala Val Phe
                85                  90                  95

Tyr Cys Thr His Tyr Tyr Gly Ser Asp Tyr Ala Met Asp Tyr Trp Gly
            100                 105                 110

Gln Gly Thr Ser Val Thr Val Ser Ser Gly Gly Gly Gly Ser Gly Gly
        115                 120                 125

Gly Gly Ser Gly Gly Gly Gly Ser Gln Ile Val Leu Thr Gln Ser Pro
    130                 135                 140

Ala Ile Met Ser Ala Ser Leu Gly Glu Arg Val Thr Met Thr Cys Thr
145                 150                 155                 160

Ala Ser Ser Ser Val Ser Ser Ser Tyr Leu His Trp Tyr Gln Gln Lys
                165                 170                 175

Pro Gly Ser Ser Pro Lys Leu Trp Ile Tyr Ser Thr Ser Asn Leu Ala
            180                 185                 190

Ser Gly Val Pro Ala Arg Phe Ser Gly Ser Gly Ser Gly Thr Ser Tyr
        195                 200                 205

Ser Leu Thr Ile Ser Ser Met Glu Ala Glu Asp Ala Ala Thr Tyr Tyr
    210                 215                 220

Cys His Gln Tyr His Arg Ser Pro Arg Thr Phe Gly Gly Gly Thr Lys
225                 230                 235                 240
```

Leu Glu Ile Lys Arg Ala Ala Ala
245

<210> SEQ ID NO 10
<211> LENGTH: 492
<212> TYPE: PRT
<213> ORGANISM: Artificial Sequence
<220> FEATURE:
<223> OTHER INFORMATION: CAR3 for CRT3 (SEQ ID NO. 10)

<400> SEQUENCE: 10

Met Gly Val Leu Leu Thr Gln Arg Thr Leu Leu Ser Leu Val Leu Ala
1 5 10 15

Leu Leu Phe Pro Ser Met Ala Ser Met Ala Glu Val Gln Leu Gln Gln
20 25 30

Ser Gly Thr Val Leu Ala Arg Pro Gly Ala Ser Val Lys Met Ser Cys
35 40 45

Lys Ala Ser Gly Tyr Thr Phe Thr Ser Tyr Trp Met His Trp Val Lys
50 55 60

Gln Arg Pro Gly Gln Gly Leu Glu Trp Ile Gly Ala Ile Tyr Pro Gly
65 70 75 80

Asn Ser Asp Thr Ser Tyr Asn Gln Lys Phe Lys Gly Lys Ala Lys Leu
85 90 95

Thr Ala Val Thr Ser Thr Ser Thr Ala Tyr Met Glu Leu Ser Ser Leu
100 105 110

Thr Asn Glu Asp Ser Ala Val Phe Tyr Cys Thr His Tyr Tyr Gly Ser
115 120 125

Asp Tyr Ala Met Asp Tyr Trp Gly Gln Gly Thr Ser Val Thr Val Ser
130 135 140

Ser Gly Gly Gly Gly Ser Gly Gly Gly Gly Ser Gly Gly Gly Gly Ser
145 150 155 160

Gln Ile Val Leu Thr Gln Ser Pro Ala Ile Met Ser Ala Ser Leu Gly
165 170 175

Glu Arg Val Thr Met Thr Cys Thr Ala Ser Ser Ser Val Ser Ser Ser
180 185 190

Tyr Leu His Trp Tyr Gln Gln Lys Pro Gly Ser Ser Pro Lys Leu Trp
195 200 205

Ile Tyr Ser Thr Ser Asn Leu Ala Ser Gly Val Pro Ala Arg Phe Ser
210 215 220

Gly Ser Gly Ser Gly Thr Ser Tyr Ser Leu Thr Ile Ser Ser Met Glu
225 230 235 240

Ala Glu Asp Ala Ala Thr Tyr Tyr Cys His Gln Tyr His Arg Ser Pro
245 250 255

Arg Thr Phe Gly Gly Gly Thr Lys Leu Glu Ile Lys Arg Ala Ala Ala
260 265 270

Ile Glu Val Met Tyr Pro Pro Pro Tyr Leu Asp Asn Glu Lys Ser Asn
275 280 285

Gly Thr Ile Ile His Val Lys Gly Lys His Leu Cys Pro Ser Pro Leu
290 295 300

Phe Pro Gly Pro Ser Lys Pro Phe Trp Val Leu Val Val Val Gly Gly
305 310 315 320

Val Leu Ala Cys Tyr Ser Leu Leu Val Thr Val Ala Phe Ile Ile Phe
325 330 335

Trp Val Arg Ser Lys Arg Ser Arg Leu Leu His Ser Asp Tyr Met Asn
340 345 350

```
Met Thr Pro Arg Arg Pro Gly Pro Thr Arg Lys His Tyr Gln Pro Tyr
        355                 360                 365

Ala Pro Pro Arg Asp Phe Ala Ala Tyr Arg Ser Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Gln Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490


<210> SEQ ID NO 11
<211> LENGTH: 357
<212> TYPE: DNA
<213> ORGANISM: Artificial Sequence
<220> FEATURE:
<223> OTHER INFORMATION: Nucleotide sequence for variable heavy chain of
      CRT3 (SEQ ID NO. 11)

<400> SEQUENCE: 11

atggccgagg tccagctgca gcagtctggg actgtgctgg caaggcctgg ggcttcagtg     60

aagatgtcct gcaaggcttc tggctacacc tttaccagct actggatgca ctgggtaaaa    120

cagaggcctg gacagggtct ggaatggatt ggcgctattt atcctggaaa tagtgatact    180

agctacaacc agaagttcaa gggcaaggcc aaactgactg cagtcacatc caccagcact    240

gcctacatgg agctcagcag cctgacaaat gaggactctg cggtctttta ctgtacacat    300

tactacggta gtgactatgc tatggactac tggggtcaag gaacctcagt cactgtc       357


<210> SEQ ID NO 12
<211> LENGTH: 24
<212> TYPE: DNA
<213> ORGANISM: Artificial Sequence
<220> FEATURE:
<223> OTHER INFORMATION: Nucleotide sequence for CDR1 of VH of CRT3 (SEQ
      ID NO. 12)

<400> SEQUENCE: 12

ggctacacct ttaccagcta ctgg                                            24


<210> SEQ ID NO 13
<211> LENGTH: 24
<212> TYPE: DNA
<213> ORGANISM: Artificial Sequence
<220> FEATURE:
<223> OTHER INFORMATION: Nucleotide sequence of CDR2 of VH of CRT3 (SEQ
      ID NO. 13)

<400> SEQUENCE: 13

atttatcctg gaaatagtga tact                                            24


<210> SEQ ID NO 14
```

```
<211> LENGTH: 36
<212> TYPE: DNA
<213> ORGANISM: Artificial Sequence
<220> FEATURE:
<223> OTHER INFORMATION: Nucleotide sequence for CDR3 of VH of CRT3 (SEQ
      ID NO. 14)

<400> SEQUENCE: 14

acacattact acggtagtga ctatgctatg gactac                              36


<210> SEQ ID NO 15
<211> LENGTH: 327
<212> TYPE: DNA
<213> ORGANISM: Artificial Sequence
<220> FEATURE:
<223> OTHER INFORMATION: Nucleotide sequence of variable light chain of
      CRT3 (SEQ ID NO. 15)

<400> SEQUENCE: 15

caaattgttc tcacccagtc tccagcaatc atgtctgcat ctctagggga acgggtcacc     60

atgacctgca ctgccagctc aagtgtaagt tccagttact tgcactggta ccagcagaag    120

ccaggatcct cccccaaact ctggatttat agcacatcca acctggcttc tggagtccca    180

gctcgcttca gtggcagtgg gtctgggacc tcttactctc tcacaatcag cagcatggag    240

gctgaagatg ctgccactta ttactgccac cagtatcatc gttccccacg gacgttcggt    300

ggaggcacca agctggaaat caaacgt                                        327


<210> SEQ ID NO 16
<211> LENGTH: 21
<212> TYPE: DNA
<213> ORGANISM: Artificial Sequence
<220> FEATURE:
<223> OTHER INFORMATION: Nucleotide sequence of CDR1 of VL of CRT3 (SEQ
      ID NO. 16)

<400> SEQUENCE: 16

tcaagtgtaa gttccagtta c                                               21


<210> SEQ ID NO 17
<211> LENGTH: 9
<212> TYPE: DNA
<213> ORGANISM: Artificial Sequence
<220> FEATURE:
<223> OTHER INFORMATION: Nucleotide sequence of CDR2 of VL of CRT3 (SEQ
      ID NO. 17)

<400> SEQUENCE: 17

agcacatcc                                                              9


<210> SEQ ID NO 18
<211> LENGTH: 27
<212> TYPE: DNA
<213> ORGANISM: Artificial Sequence
<220> FEATURE:
<223> OTHER INFORMATION: nucleotide sequence of CDR3 of VL of CRT3 (SEQ
      ID NO. 18)

<400> SEQUENCE: 18

caccagtatc atcgttcccc acggacg                                         27


<210> SEQ ID NO 19
<211> LENGTH: 744
<212> TYPE: DNA
<213> ORGANISM: Artificial Sequence
<220> FEATURE:
```

<223> OTHER INFORMATION: Nucleotide sequence of scFv for CRT3 (SEQ ID NO. 19)

<400> SEQUENCE: 19
atggccgagg tccagctgca gcagtctggg actgtgctgg caaggcctgg ggcttcagtg 60
aagatgtcct gcaaggcttc tggctacacc tttaccagct actggatgca ctgggtaaaa 120
cagaggcctg gacagggtct ggaatggatt ggcgctattt atcctggaaa tagtgatact 180
agctacaacc agaagttcaa gggcaaggcc aaactgactg cagtcacatc caccagcact 240
gcctacatgg agctcagcag cctgacaaat gaggactctg cggtctttta ctgtacacat 300
tactacggta gtgactatgc tatggactac tggggtcaag gaacctcagt cactgtctcc 360
tcaggtggag gcggttcagg cggaggtggc tctggcggtg gcggatcgca aattgttctc 420
acccagtctc cagcaatcat gtctgcatct ctaggggaac gggtcaccat gacctgcact 480
gccagctcaa gtgtaagttc cagttacttg cactggtacc agcagaagcc aggatcctcc 540
cccaaactct ggatttatag cacatccaac ctggcttctg gagtcccagc tcgcttcagt 600
ggcagtgggt ctgggacctc ttactctctc acaatcagca gcatggaggc tgaagatgct 660
gccacttatt actgccacca gtatcatcgt tccccacgga cgttcggtgg aggcaccaag 720
ctggaaatca aacgtgcggc cgca 744

<210> SEQ ID NO 20
<211> LENGTH: 1499
<212> TYPE: DNA
<213> ORGANISM: Artificial Sequence
<220> FEATURE:
<223> OTHER INFORMATION: Nucleotide sequence of CAR3 for CRT3 (SEQ ID NO. 20)

<400> SEQUENCE: 20
atgggcgtgc tgctgaccca gaggaccctg ctgagcctgg tgctggccct gctgtttcca 60
tctatggcat cgatggccga ggtccagctg cagcagtctg ggactgtgct ggcaaggcct 120
ggggcttcag tgaagatgtc ctgcaaggct tctggctaca cctttaccag ctactggatg 180
cactgggtaa aacagaggcc tggacagggt ctggaatgga ttggcgctat ttatcctgga 240
aatagtgata ctagctacaa ccagaagttc aagggcaagg ccaaactgac tgcagtcaca 300
tccaccagca ctgcctacat ggagctcagc agcctgacaa atgaggactc tgcggtcttt 360
tactgtacac attactacgg tagtgactat gctatggact actggggtca aggaacctca 420
gtcactgtct cctcaggtgg aggcggttca ggcggaggtg gctctggcgg tggcggatcg 480
caaattgttc tcacccagtc tccagcaatc atgtctgcat ctctagggga acgggtcacc 540
atgacctgca ctgccagctc aagtgtaagt tccagttact tgcactggta ccagcagaag 600
ccaggatcct cccccaaact ctggatttat agcacatcca acctggcttc tggagtccca 660
gctcgcttca gtggcagtgg gtctgggacc tcttactctc tcacaatcag cagcatggag 720
gctgaagatg ctgccactta ttactgccac cagtatcatc gttccccacg gacgttcggt 780
ggaggcacca agctggaaat caaacgtgcg gccgcaattg aagttatgta tcctcctcct 840
tacctagaca atgagaagag caatggaacc attatccatg tgaaagggaa acacctttgt 900
ccaagtcccc tatttcccgg accttctaag cccttttggg tgctggtggt ggttggtgga 960
gtcctggctt gctatagctt gctagtaaca gtggccttta ttattttctg ggtgaggagt 1020
aagaggagca ggctcctgca cagtgactac atgaacatga ctccccgccg ccccgggccc 1080
acccgcaagc attaccagcc ctatgcccca ccacgcgact tcgcagccta tcgctccaga 1140
gtgaagttca gcaggagcgc agacgccccc gcgtaccagc agggccagaa ccagctctat 1200
aacgagctca atctaggacg aagagaggag tacgatgttt tggacaagag acgtggccgg 1260
gaccctgaga tgggggaaa gccgcagaga aggaagaacc ctcaggaagg cctgtacaat 1320
gaactgcaga aagataagat ggcggaggcc tacagtgaga ttgggatgaa aggcgagcgc 1380
cggaggggca aggggcacga tggcctttac cagggtctca gtacagccac caaggacacc 1440
tacgacgccc ttcacatgca ggccctgccc cctcgctaat aaaagcttaa cacgagcca 1499

<210> SEQ ID NO 21
<211> LENGTH: 130
<212> TYPE: PRT
<213> ORGANISM: Artificial Sequence
<220> FEATURE:
<223> OTHER INFORMATION: Heavy chain variable region of CRT2 (SEQ ID NO. 21)

<400> SEQUENCE: 21

Met Ala Glu Val Gln Gly Val Glu Ser Gly Gly Gly Leu Val Gln Pro
1 5 10 15

Lys Gly Ser Leu Lys Leu Ser Cys Ala Ala Ser Gly Phe Thr Phe Asn
20 25 30

Thr Tyr Ala Met His Trp Val Cys Gln Ala Pro Gly Lys Gly Leu Glu
35 40 45

Trp Val Ala Arg Ile Arg Ser Lys Ser Asn Asn Tyr Ala Thr Tyr Tyr
50 55 60

Ala Asp Ser Val Lys Asp Arg Phe Thr Ile Ser Arg Asp Asp Ser Gln
65 70 75 80

Ser Met Leu Tyr Leu Gln Met Asn Asn Leu Lys Thr Glu Asp Thr Ala
85 90 95

Met Tyr Tyr Cys Val Arg Glu Gly Val Tyr Tyr Tyr Gly Ser Ser Gly
100 105 110

Tyr Tyr Ala Met Asp Tyr Trp Gly Gln Gly Thr Ser Val Thr Val Ser
115 120 125

Ser Gly
130

<210> SEQ ID NO 22
<211> LENGTH: 8
<212> TYPE: PRT
<213> ORGANISM: Artificial Sequence
<220> FEATURE:
<223> OTHER INFORMATION: CDR1 of VH of CRT2 (SEQ ID NO. 22)

<400> SEQUENCE: 22

Gly Phe Thr Phe Asn Thr Tyr Ala
1 5

<210> SEQ ID NO 23
<211> LENGTH: 10
<212> TYPE: PRT
<213> ORGANISM: Artificial Sequence
<220> FEATURE:
<223> OTHER INFORMATION: CDR2 of VH of CRT2 (SEQ ID NO. 23)

<400> SEQUENCE: 23

Ile Arg Ser Lys Ser Asn Asn Tyr Ala Thr
1 5 10

<210> SEQ ID NO 24

<211> LENGTH: 18
<212> TYPE: PRT
<213> ORGANISM: Artificial Sequence
<220> FEATURE:
<223> OTHER INFORMATION: CDR3 of VH of CRT2 (SEQ ID NO. 24)

<400> SEQUENCE: 24

```
Val Arg Glu Gly Val Tyr Tyr Tyr Gly Ser Ser Gly Tyr Tyr Ala Met
1               5                   10                  15

Asp Tyr
```

<210> SEQ ID NO 25
<211> LENGTH: 109
<212> TYPE: PRT
<213> ORGANISM: Artificial Sequence
<220> FEATURE:
<223> OTHER INFORMATION: Variable light chain for CRT2 (SEQ ID NO. 25)

<400> SEQUENCE: 25

```
Glu Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Leu Thr
                85                  90                  95

Phe Gly Ala Pro Gly Lys Leu Glu Leu Lys Arg Ala Ala
            100                 105
```

<210> SEQ ID NO 26
<211> LENGTH: 6
<212> TYPE: PRT
<213> ORGANISM: Artificial Sequence
<220> FEATURE:
<223> OTHER INFORMATION: CDR1 of VL of CRT2 (SEQ ID NO. 26)

<400> SEQUENCE: 26

```
Ser Tyr Met His Trp Phe
1               5
```

<210> SEQ ID NO 27
<211> LENGTH: 10
<212> TYPE: PRT
<213> ORGANISM: Artificial Sequence
<220> FEATURE:
<223> OTHER INFORMATION: CDR2 of VL of CRT2 (SEQ ID NO. 27)

<400> SEQUENCE: 27

```
Leu Trp Ile Tyr Ser Thr Ser Asn Leu Ala
1               5                   10
```

<210> SEQ ID NO 28
<211> LENGTH: 8
<212> TYPE: PRT
<213> ORGANISM: Artificial Sequence
<220> FEATURE:
<223> OTHER INFORMATION: CDR3 of VL of CRT2 (SEQ ID NO. 28)

<400> SEQUENCE: 28

Gln Gln Arg Ser Ser Tyr Pro Leu
1 5

<210> SEQ ID NO 29
<211> LENGTH: 254
<212> TYPE: PRT
<213> ORGANISM: Artificial Sequence
<220> FEATURE:
<223> OTHER INFORMATION: scFv of CRT2 (SEQ ID NO. 29)

<400> SEQUENCE: 29

Met Ala Glu Val Gln Gly Val Glu Ser Gly Gly Gly Leu Val Gln Pro
1 5 10 15

Lys Gly Ser Leu Lys Leu Ser Cys Ala Ala Ser Gly Phe Thr Phe Asn
20 25 30

Thr Tyr Ala Met His Trp Val Cys Gln Ala Pro Gly Lys Gly Leu Glu
35 40 45

Trp Val Ala Arg Ile Arg Ser Lys Ser Asn Asn Tyr Ala Thr Tyr Tyr
50 55 60

Ala Asp Ser Val Lys Asp Arg Phe Thr Ile Ser Arg Asp Asp Ser Gln
65 70 75 80

Ser Met Leu Tyr Leu Gln Met Asn Asn Leu Lys Thr Glu Asp Thr Ala
85 90 95

Met Tyr Tyr Cys Val Arg Glu Gly Val Tyr Tyr Tyr Gly Ser Ser Gly
100 105 110

Tyr Tyr Ala Met Asp Tyr Trp Gly Gln Gly Thr Ser Val Thr Val Ser
115 120 125

Ser Gly Gly Gly Gly Gly Ser Gly Gly Gly Gly Ser Gly Gly Gly Gly
130 135 140

Ser Glu Ile Val Leu Thr Gln Ser Pro Ala Ile Met Ser Ala Ser Pro
145 150 155 160

Gly Glu Lys Val Thr Ile Thr Cys Ser Ala Ser Ser Ser Val Ser Tyr
165 170 175

Met His Trp Phe Gln Gln Lys Pro Gly Thr Ser Pro Lys Leu Trp Ile
180 185 190

Tyr Ser Thr Ser Asn Leu Ala Ser Gly Val Pro Ala Arg Phe Ser Gly
195 200 205

Ser Gly Ser Gly Thr Ser Tyr Ser Leu Thr Ile Ser Arg Met Glu Ala
210 215 220

Glu Asp Ala Ala Thr Tyr Tyr Cys Gln Gln Arg Ser Ser Tyr Pro Leu
225 230 235 240

Thr Phe Gly Ala Pro Gly Lys Leu Glu Leu Lys Arg Ala Ala
245 250

<210> SEQ ID NO 30
<211> LENGTH: 841
<212> TYPE: PRT
<213> ORGANISM: Artificial Sequence
<220> FEATURE:
<223> OTHER INFORMATION: CAR CRT2 (SEQ ID NO. 30)

<400> SEQUENCE: 30

Met Pro Arg Gly Trp Thr Ala Leu Cys Leu Leu Ser Leu Leu Pro Ser
1 5 10 15

Gly Phe Met Ser Leu Asp Asn Asn Gly Thr Ala Thr Pro Glu Leu Pro
20 25 30

Thr Gln Gly Thr Phe Ser Asn Val Ser Thr Asn Val Ser Tyr Gln Glu

```
        35                  40                  45

Thr Thr Thr Pro Ser Thr Leu Gly Ser Thr Ser Leu His Pro Val Ser
    50                  55                  60

Gln His Gly Asn Glu Ala Thr Thr Asn Ile Thr Glu Thr Thr Val Lys
65                  70                  75                  80

Phe Thr Ser Thr Ser Val Ile Thr Ser Val Tyr Gly Asn Thr Asn Ser
                85                  90                  95

Ser Val Gln Ser Gln Thr Ser Val Ile Ser Thr Val Phe Thr Thr Pro
            100                 105                 110

Ala Asn Val Ser Thr Pro Glu Thr Thr Leu Lys Pro Ser Leu Ser Pro
        115                 120                 125

Gly Asn Val Ser Asp Leu Ser Thr Thr Ser Thr Ser Leu Ala Thr Ser
    130                 135                 140

Pro Thr Lys Pro Tyr Thr Ser Ser Ser Pro Ile Leu Ser Asp Ile Lys
145                 150                 155                 160

Ala Glu Ile Lys Cys Ser Gly Ile Arg Glu Val Lys Leu Thr Gln Gly
                165                 170                 175

Ile Cys Leu Glu Gln Asn Lys Thr Ser Ser Cys Ala Glu Phe Lys Lys
            180                 185                 190

Asp Arg Gly Glu Gly Leu Ala Arg Val Leu Cys Gly Glu Glu Gln Ala
        195                 200                 205

Asp Ala Asp Ala Gly Ala Gln Val Cys Ser Leu Leu Leu Ala Gln Ser
    210                 215                 220

Glu Val Arg Pro Gln Cys Leu Leu Leu Val Leu Ala Asn Arg Thr Glu
225                 230                 235                 240

Ile Ser Ser Lys Leu Gln Leu Met Lys Lys His Gln Ser Asp Leu Lys
                245                 250                 255

Lys Leu Gly Ile Leu Asp Phe Thr Glu Gln Asp Val Ala Ser His Gln
            260                 265                 270

Ser Tyr Ser Gln Lys Thr Leu Ile Ala Leu Val Thr Ser Gly Ala Leu
        275                 280                 285

Leu Ala Val Leu Gly Ile Thr Gly Tyr Phe Leu Met Asn Arg Arg Ser
    290                 295                 300

Trp Ser Pro Thr Gly Glu Arg Leu Glu Leu Glu Pro Val Asp Arg Val
305                 310                 315                 320

Lys Gln Thr Leu Asn Phe Asp Leu Leu Lys Leu Ala Gly Asp Val Glu
                325                 330                 335

Ser Asn Pro Gly Pro Gly Asn Met Gly Val Leu Leu Thr Gln Arg Thr
            340                 345                 350

Leu Leu Ser Leu Val Leu Ala Leu Leu Phe Pro Ser Met Ala Ser Met
        355                 360                 365

Ala Glu Val Gln Gly Val Glu Ser Gly Gly Gly Leu Val Gln Pro Lys
    370                 375                 380

Gly Ser Leu Lys Leu Ser Cys Ala Ala Ser Gly Phe Thr Phe Asn Thr
385                 390                 395                 400

Tyr Ala Met His Trp Val Cys Gln Ala Pro Gly Lys Gly Leu Glu Trp
                405                 410                 415

Val Ala Arg Ile Arg Ser Lys Ser Asn Asn Tyr Ala Thr Tyr Tyr Ala
            420                 425                 430

Asp Ser Val Lys Asp Arg Phe Thr Ile Ser Arg Asp Asp Ser Gln Ser
        435                 440                 445

Met Leu Tyr Leu Gln Met Asn Asn Leu Lys Thr Glu Asp Thr Ala Met
    450                 455                 460
```

```
Tyr Tyr Cys Val Arg Glu Gly Val Tyr Tyr Tyr Gly Ser Ser Gly Tyr
465                 470                 475                 480

Tyr Ala Met Asp Tyr Trp Gly Gln Gly Thr Ser Val Thr Val Ser Ser
                485                 490                 495

Gly Gly Gly Gly Gly Ser Gly Gly Gly Gly Ser Gly Gly Gly Gly Ser
            500                 505                 510

Glu Ile Val Leu Thr Gln Ser Pro Ala Ile Met Ser Ala Ser Pro Gly
        515                 520                 525

Glu Lys Val Thr Ile Thr Cys Ser Ala Ser Ser Ser Val Ser Tyr Met
    530                 535                 540

His Trp Phe Gln Gln Lys Pro Gly Thr Ser Pro Lys Leu Trp Ile Tyr
545                 550                 555                 560

Ser Thr Ser Asn Leu Ala Ser Gly Val Pro Ala Arg Phe Ser Gly Ser
                565                 570                 575

Gly Ser Gly Thr Ser Tyr Ser Leu Thr Ile Ser Arg Met Glu Ala Glu
            580                 585                 590

Asp Ala Ala Thr Tyr Tyr Cys Gln Gln Arg Ser Ser Tyr Pro Leu Thr
        595                 600                 605

Phe Gly Ala Pro Gly Lys Leu Glu Leu Lys Arg Ala Ala Ile Glu Val
    610                 615                 620

Met Tyr Pro Pro Pro Tyr Leu Asp Asn Glu Lys Ser Asn Gly Thr Ile
625                 630                 635                 640

Ile His Val Lys Gly Lys His Leu Cys Pro Ser Pro Leu Phe Pro Gly
                645                 650                 655

Pro Ser Lys Pro Phe Trp Val Leu Val Val Val Gly Gly Val Leu Ala
            660                 665                 670

Cys Tyr Ser Leu Leu Val Thr Val Ala Phe Ile Ile Phe Trp Val Arg
        675                 680                 685

Ser Lys Arg Ser Arg Leu Leu His Ser Asp Tyr Met Asn Met Thr Pro
    690                 695                 700

Arg Arg Pro Gly Pro Thr Arg Lys His Tyr Gln Pro Tyr Ala Pro Pro
705                 710                 715                 720

Arg Asp Phe Ala Ala Tyr Arg Ser Arg Val Lys Phe Ser Arg Ser Ala
                725                 730                 735

Asp Ala Pro Ala Tyr Gln Gln Gly Gln Asn Gln Leu Tyr Asn Glu Leu
            740                 745                 750

Asn Leu Gly Arg Arg Glu Glu Tyr Asp Val Leu Asp Lys Arg Arg Gly
        755                 760                 765

Arg Asp Pro Glu Met Gly Gly Lys Pro Gln Arg Arg Lys Asn Pro Gln
    770                 775                 780

Glu Gly Leu Tyr Asn Glu Leu Gln Lys Asp Lys Met Ala Glu Ala Tyr
785                 790                 795                 800

Ser Glu Ile Gly Met Lys Gly Glu Arg Arg Arg Gly Lys Gly His Asp
                805                 810                 815

Gly Leu Tyr Gln Gly Leu Ser Thr Ala Thr Lys Asp Thr Tyr Asp Ala
            820                 825                 830

Leu His Met Gln Ala Leu Pro Pro Arg
        835                 840
```

<210> SEQ ID NO 31
<211> LENGTH: 401
<212> TYPE: DNA
<213> ORGANISM: Artificial Sequence
<220> FEATURE:

<223> OTHER INFORMATION: Nucleotide sequence encoding VH of CRT2 (SEQ ID NO. 31)

<400> SEQUENCE: 31
gacgcttatc gatggccgag gtgcaggggg tggagtctgg tggaggattg gtgcagccta 60
aaggatcatt gaaactctca tgtgccgcct ctggtttcac cttcaatacc tatgccatgc 120
actgggtctg ccaggctcca ggaaagggtt tggaatgggt tgctcgcata agaagtaaaa 180
gtaataatta tgcaacatat tatgccgatt cagtgaaaga cagattcacc atctccagag 240
atgattcaca aagcatgctc tatctgcaaa tgaacaacct gaaaactgag gacacagcca 300
tgtattactg tgtgagagaa ggggtttatt actacggtag tagtgggtac tatgctatgg 360
actactgggg tcaaggaacc tcagtcaccg tctcctcagg t 401

<210> SEQ ID NO 32
<211> LENGTH: 24
<212> TYPE: DNA
<213> ORGANISM: Artificial Sequence
<220> FEATURE:
<223> OTHER INFORMATION: Nucleotide sequence encoding CDR1 of VH of CRT2 (SEQ ID NO. 32)

<400> SEQUENCE: 32
ggtttcacct tcaataccta tgcc 24

<210> SEQ ID NO 33
<211> LENGTH: 30
<212> TYPE: DNA
<213> ORGANISM: Artificial Sequence
<220> FEATURE:
<223> OTHER INFORMATION: Nucleotide sequence encoding CDR2 of VH of CRT2 (SEQ ID NO. 33)

<400> SEQUENCE: 33
ataagaagta aaagtaataa ttatgcaaca 30

<210> SEQ ID NO 34
<211> LENGTH: 54
<212> TYPE: DNA
<213> ORGANISM: Artificial Sequence
<220> FEATURE:
<223> OTHER INFORMATION: Nucleotide sequence encoding CDR3 of VH of CRT2 (SEQ ID NO. 34)

<400> SEQUENCE: 34
gtgagagaag gggtttatta ctacggtagt agtgggtact atgctatgga ctac 54

<210> SEQ ID NO 35
<211> LENGTH: 329
<212> TYPE: DNA
<213> ORGANISM: Artificial Sequence
<220> FEATURE:
<223> OTHER INFORMATION: Nucleotide sequence for Variable light chain of CRT2 (SEQ ID NO. 35)

<400> SEQUENCE: 35
gaaattgttc tcacccagtc tccagcaatc atgtctgcat ctccagggga gaaggtcacc 60
ataacctgca gtgccagctc aagtgtaagt tacatgcact ggttccagca gaagccaggc 120
acttctccca aactctggat ttatagcaca tccaacctgg cttctggagt ccctgctcgc 180
ttcagtggca gtggatctgg gacctcttac tctctcacaa tcagccgaat ggaggctgaa 240
gatgctgcca cttattactg ccagcaaagg agtagttacc ccctcacgtt cggtgctggg 300
accaagctgg agctgaaacg tgcggccgc 329

<210> SEQ ID NO 36
<211> LENGTH: 18
<212> TYPE: DNA
<213> ORGANISM: Artificial Sequence
<220> FEATURE:
<223> OTHER INFORMATION: Nucleotide sequence of CDR1 of VL of CRT2 (SEQ ID NO. 36)

<400> SEQUENCE: 36
agttacatgc actggttc 18

<210> SEQ ID NO 37
<211> LENGTH: 30
<212> TYPE: DNA
<213> ORGANISM: Artificial Sequence
<220> FEATURE:
<223> OTHER INFORMATION: Nucleotide sequence of CDR2 of VL of CRT2 (SEQ ID NO. 37)

<400> SEQUENCE: 37
ctctggattt atagcacatc caacctggct 30

<210> SEQ ID NO 38
<211> LENGTH: 24
<212> TYPE: DNA
<213> ORGANISM: Artificial Sequence
<220> FEATURE:
<223> OTHER INFORMATION: Nucleotide sequence for CDR3 of VL of CRT2 (SEQ ID NO. 38)

<400> SEQUENCE: 38
cagcaaagga gtagttaccc cctc 24

<210> SEQ ID NO 39
<211> LENGTH: 781
<212> TYPE: DNA
<213> ORGANISM: Artificial Sequence
<220> FEATURE:
<223> OTHER INFORMATION: Nucleotide sequence encoding scFv of CRT2 (SEQ ID NO. 39)

<400> SEQUENCE: 39
gacgcttatc gatggccgag gtgcaggggg tggagtctgg tggaggattg gtgcagccta 60
aaggatcatt gaaactctca tgtgccgcct ctggtttcac cttcaatacc tatgccatgc 120
actgggtctg ccaggctcca ggaaagggtt tggaatgggt tgctcgcata agaagtaaaa 180
gtaataatta tgcaacatat tatgccgatt cagtgaaaga cagattcacc atctccagag 240
atgattcaca aagcatgctc tatctgcaaa tgaacaacct gaaaactgag gacacagcca 300
tgtattactg tgtgagagaa ggggtttatt actacggtag tagtgggtac tatgctatgg 360
actactgggg tcaaggaacc tcagtcaccg tctcctcagg ttcctcaggt ggaggcggtt 420
caggcggagg tggctctggc ggtggcggat cggaaattgt tctcacccag tctccagcaa 480
tcatgtctgc atctccaggg gagaaggtca ccataacctg cagtgccagc tcaagtgtaa 540
gttacatgca ctggttccag cagaagccag gcacttctcc caaactctgg atttatagca 600
catccaacct ggcttctgga gtccctgctc gcttcagtgg cagtggatct gggacctctt 660
actctctcac aatcagccga atggaggctg aagatgctgc cacttattac tgccagcaaa 720
ggagtagtta ccccctcacg ttcggtgctg ggaccaagct ggagctgaaa cgtgcggccg 780
c 781

<210> SEQ ID NO 40
<211> LENGTH: 2549
<212> TYPE: DNA
<213> ORGANISM: Artificial Sequence
<220> FEATURE:
<223> OTHER INFORMATION: Nucleotide sequence encoding CAR CRT2 (SEQ ID NO. 40)

<400> SEQUENCE: 40

```
atgcctcgcg gctggacagc cctgtgcctg ctgtctctgc tgccatccgg cttcatgagc     60
ctggataata acggcacagc caccccagag ctgcctacac agggcacctt cagcaatgtg    120
tccacaaacg tgagctatca ggagaccaca acccottcta ccctgggatc cacaagcctg    180
caccccgtgt ctcagcacgg caacgaagcc accaccaaca tcaccgagac cacagtgaag    240
tttacctcca cctctgtgat tacctctgtg tacggaaata caaactccag cgtgcagtct    300
cagacatctg tgatctccac agtgtttaca acacctgcca atgtgtccac cccagagaca    360
accctgaagc ccagcctgtc tcctggaaat gtgtccgatc tgtctaccac ctccaccagc    420
ctggccacct ctcccaccaa gccctatacc tcctcttctc ccatcctgag cgatatcaaa    480
gccgagatca aatgcagcgg gattcgggaa gtgaaactga cacagggcat ctgcctggaa    540
cagaataaga catccagctg cgccgagttt aagaaagata gaggagaggg actggccagg    600
gtgctgtgtg gcgaagagca ggccgacgcc gatgccggcg cccaggtgtg ttccctgctg    660
ctggcccagt ctgaggtgcg cccccagtgc ctgctgctgg tgctggccaa tcggacagaa    720
attagcagca agctgcagct gatgaaaaaa caccagagcg atctgaaaaa gctgggcatc    780
ctggacttta ccgagcagga cgtggcctct caccagagct acagccagaa aacactgatc    840
gccctggtga ccagcggagc cctgctggcc gtgctgggca tcaccggata tttcctgatg    900
aataggcgca gctggagccc caccggcgag cggctggagc tggagcctgt cgaccgagtg    960
aagcagaccc tgaactttga tctgctgaag ctggccggcg acgtggagtc caaccccggg   1020
ccagggaata tgggcgtgct gctgacccag aggaccctgc tgagcctggt gctggccctg   1080
ctgtttccat ctatggcatc ggacgcttat cgatggccga ggtgcagggg gtggagtctg   1140
gtggaggatt ggtgcagcct aaaggatcat tgaaactctc atgtgccgcc tctggtttca   1200
ccttcaatac ctatgccatg cactgggtct gccaggctcc aggaaagggt ttggaatggg   1260
ttgctcgcat aagaagtaaa agtaataatt atgcaacata ttatgccgat tcagtgaaag   1320
acagattcac catctccaga gatgattcac aaagcatgct ctatctgcaa atgaacaacc   1380
tgaaaactga ggacacagcc atgtattact gtgtgagaga aggggtttat tactacggta   1440
gtagtgggta ctatgctatg gactactggg gtcaaggaac ctcagtcacc gtctcctcag   1500
gttcctcagg tggaggcggt tcaggcggag gtggctctgg cggtggcgga tcggaaattg   1560
ttctcaccca gtctccagca atcatgtctg catctccagg ggagaaggtc accataacct   1620
gcagtgccag ctcaagtgta agttacatgc actggttcca gcagaagcca ggcacttctc   1680
ccaaactctg gatttatagc acatccaacc tggcttctgg agtccctgct cgcttcagtg   1740
gcagtggatc tgggacctct tactctctca caatcagccg aatggaggct gaagatgctg   1800
ccacttatta ctgccagcaa aggagtagtt accccctcac gttcggtgct gggaccaagc   1860
tggagctgaa acgtgcggcc gcaattgaag ttatgtatcc tcctccttac ctagacaatg   1920
agaagagcaa tggaaccatt atccatgtga aagggaaaca cctttgtcca agtcccctat   1980
ttcccggacc ttctaagccc ttttgggtgc tggtggtggt tggtggagtc ctggcttgct   2040
```

```
atagcttgct agtaacagtg gcctttatta ttttctgggt gaggagtaag aggagcaggc   2100

tcctgcacag tgactacatg aacatgactc cccgccgccc cgggcccacc cgcaagcatt   2160

accagcccta tgccccacca cgcgacttcg cagcctatcg ctccagagtg aagttcagca   2220

ggagcgcaga cgcccccgcg taccagcagg gccagaacca gctctataac gagctcaatc   2280

taggacgaag agaggagtac gatgttttgg acaagagacg tggccgggac cctgagatgg   2340

ggggaaagcc gcagagaagg aagaaccctc aggaaggcct gtacaatgaa ctgcagaaag   2400

ataagatggc ggaggcctac agtgagattg ggatgaaagg cgagcgccgg aggggcaagg   2460

ggcacgatgg cctttaccag ggtctcagta cagccaccaa ggacacctac gacgcccttc   2520

acatgcaggc cctgccccct cgctaataa                                     2549
```

```
<210> SEQ ID NO 41
<211> LENGTH: 121
<212> TYPE: PRT
<213> ORGANISM: Artificial Sequence
<220> FEATURE:
<223> OTHER INFORMATION: Variable heavy chain of CRT3 variant (SEQ ID
      NO. 41)

<400> SEQUENCE: 41

Met Ala Glu Val Gln Leu Gln Gln Ser Gly Thr Val Leu Ala Arg Pro
1               5                   10                  15

Gly Ala Ser Val Lys Met Ser Cys Lys Ala Ser Gly Tyr Thr Phe Thr
            20                  25                  30

Ser Tyr Trp Met His Trp Val Lys Gln Arg Pro Gly Gln Gly Leu Glu
        35                  40                  45

Trp Ile Gly Ala Ile Tyr Pro Gly Asn Ser Asp Thr Ser Tyr Asn Gln
    50                  55                  60

Lys Phe Lys Gly Lys Ala Lys Leu Thr Ala Val Thr Ser Thr Ser Thr
65                  70                  75                  80

Ala Tyr Met Glu Leu Ser Ser Leu Thr Asn Glu Asp Ser Ala Val Phe
                85                  90                  95

Tyr Cys Thr His Tyr Gly Ser Asp Tyr Ala Met Asp Tyr Trp Gly Gln
            100                 105                 110

Gly Thr Ser Val Thr Ile Ser Ser Gly
        115                 120


<210> SEQ ID NO 42
<211> LENGTH: 6
<212> TYPE: PRT
<213> ORGANISM: Artificial Sequence
<220> FEATURE:
<223> OTHER INFORMATION: CDR1 of VH of CRT3 variant (SEQ ID NO. 42)

<400> SEQUENCE: 42

Thr Ser Tyr Trp Met His
1               5


<210> SEQ ID NO 43
<211> LENGTH: 13
<212> TYPE: PRT
<213> ORGANISM: Artificial Sequence
<220> FEATURE:
<223> OTHER INFORMATION: CDR2 of VH of CRT3 variant (SEQ ID NO. 43)

<400> SEQUENCE: 43

Trp Ile Gly Ala Ile Tyr Pro Gly Asn Ser Asp Thr Ser
1               5                   10
```

<210> SEQ ID NO 44
<211> LENGTH: 11
<212> TYPE: PRT
<213> ORGANISM: Artificial Sequence
<220> FEATURE:
<223> OTHER INFORMATION: CDR3 of VH of CRT3 variant (SEQ ID NO. 44)

<400> SEQUENCE: 44

```
Thr His Tyr Tyr Gly Ser Asp Tyr Ala Met Asp
1               5                   10
```

<210> SEQ ID NO 45
<211> LENGTH: 111
<212> TYPE: PRT
<213> ORGANISM: Artificial Sequence
<220> FEATURE:
<223> OTHER INFORMATION: Variable light chain of CRT3 variant (SEQ ID NO. 45)

<400> SEQUENCE: 45

```
Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Arg Thr Phe Gly Gly Gly Thr Lys Leu Glu Ile Lys Arg Ala Ala
            100                 105                 110
```

<210> SEQ ID NO 46
<211> LENGTH: 8
<212> TYPE: PRT
<213> ORGANISM: Artificial Sequence
<220> FEATURE:
<223> OTHER INFORMATION: CDR1 of VL of CRT3 variant (SEQ ID NO. 46)

<400> SEQUENCE: 46

```
Ser Ser Ser Tyr Leu His Trp Tyr
1               5
```

<210> SEQ ID NO 47
<211> LENGTH: 10
<212> TYPE: PRT
<213> ORGANISM: Artificial Sequence
<220> FEATURE:
<223> OTHER INFORMATION: CDR2 of VL of CRT3 variant (SEQ ID NO. 47)

<400> SEQUENCE: 47

```
Leu Trp Ile Tyr Ser Thr Ser Asn Leu Ala
1               5                   10
```

<210> SEQ ID NO 48
<211> LENGTH: 8
<212> TYPE: PRT
<213> ORGANISM: Artificial Sequence
<220> FEATURE:
<223> OTHER INFORMATION: CDR3 of VL of CRT3 variant (SEQ ID NO. 48)

<400> SEQUENCE: 48

```
His Gln Tyr His Arg Ser Pro Arg
1               5
```

<210> SEQ ID NO 49
<211> LENGTH: 250
<212> TYPE: PRT
<213> ORGANISM: Artificial Sequence
<220> FEATURE:
<223> OTHER INFORMATION: scFv comprising VH of variant CRT3 and VL of non-variant CRT3 (SEQ ID NO. 49)

<400> SEQUENCE: 49

```
Met Ala Glu Val Gln Leu Gln Gln Ser Gly Thr Val Leu Ala Arg Pro
1               5                   10                  15

Gly Ala Ser Val Lys Met Ser Cys Lys Ala Ser Gly Tyr Thr Phe Thr
            20                  25                  30

Ser Tyr Trp Met His Trp Val Lys Gln Arg Pro Gly Gln Gly Leu Glu
        35                  40                  45

Trp Ile Gly Ala Ile Tyr Pro Gly Asn Ser Asp Thr Ser Tyr Asn Gln
    50                  55                  60

Lys Phe Lys Gly Lys Ala Lys Leu Thr Ala Val Thr Ser Thr Ser Thr
65                  70                  75                  80

Ala Tyr Met Glu Leu Ser Ser Leu Thr Asn Glu Asp Ser Ala Val Phe
                85                  90                  95

Tyr Cys Thr His Tyr Gly Ser Asp Tyr Ala Met Asp Tyr Trp Gly Gln
            100                 105                 110

Gly Thr Ser Val Thr Ile Ser Ser Gly Ser Ser Gly Gly Gly Gly Ser
        115                 120                 125

Gly Gly Gly Gly Ser Gly Gly Gly Gly Ser Gln Ile Val Leu Thr Gln
    130                 135                 140

Ser Pro Ala Ile Met Ser Ala Ser Leu Gly Glu Arg Val Thr Met Thr
145                 150                 155                 160

Cys Thr Ala Ser Ser Ser Val Ser Ser Ser Tyr Leu His Trp Tyr Gln
                165                 170                 175

Gln Lys Pro Gly Ser Ser Pro Lys Leu Trp Ile Tyr Ser Thr Ser Asn
            180                 185                 190

Leu Ala Ser Gly Val Pro Ala Arg Phe Ser Gly Ser Gly Ser Gly Thr
        195                 200                 205

Ser Tyr Ser Leu Thr Ile Ser Ser Met Glu Ala Glu Asp Ala Ala Thr
    210                 215                 220

Tyr Tyr Cys His Gln Tyr His Arg Ser Pro Arg Thr Phe Gly Gly Gly
225                 230                 235                 240

Thr Lys Leu Glu Ile Lys Arg Ala Ala Ala
                245                 250
```

<210> SEQ ID NO 50
<211> LENGTH: 247
<212> TYPE: PRT
<213> ORGANISM: Artificial Sequence
<220> FEATURE:
<223> OTHER INFORMATION: scFv comprising VH of CRT3 and VL of CRT3 variant (SEQ ID NO. 50)

<400> SEQUENCE: 50

```
Met Ala Glu Val Gln Leu Gln Gln Ser Gly Thr Val Leu Ala Arg Pro
1               5                   10                  15
```

```
Gly Ala Ser Val Lys Met Ser Cys Lys Ala Ser Gly Tyr Thr Phe Thr
            20                  25                  30

Ser Tyr Trp Met His Trp Val Lys Gln Arg Pro Gly Gln Gly Leu Glu
        35                  40                  45

Trp Ile Gly Ala Ile Tyr Pro Gly Asn Ser Asp Thr Ser Tyr Asn Gln
    50                  55                  60

Lys Phe Lys Gly Lys Ala Lys Leu Thr Ala Val Thr Ser Thr Ser Thr
65                  70                  75                  80

Ala Tyr Met Glu Leu Ser Ser Leu Thr Asn Glu Asp Ser Ala Val Phe
                85                  90                  95

Tyr Cys Thr His Tyr Tyr Gly Ser Asp Tyr Ala Met Asp Tyr Trp Gly
            100                 105                 110

Gln Gly Thr Ser Val Thr Val Ser Ser Gly Gly Gly Gly Ser Gly Gly
        115                 120                 125

Gly Gly Ser Gly Gly Gly Gly Ser Gln Ile Val Leu Thr Gln Ser Pro
    130                 135                 140

Ala Ile Met Ser Ala Ser Leu Gly Glu Arg Val Thr Met Thr Cys Thr
145                 150                 155                 160

Ala Ser Ser Ser Val Ser Ser Ser Tyr Leu His Trp Tyr Gln Gln Lys
                165                 170                 175

Pro Gly Ser Ser Pro Lys Leu Trp Ile Tyr Ser Thr Ser Asn Leu Ala
            180                 185                 190

Ser Gly Val Pro Ala Arg Phe Ser Gly Ser Gly Ser Gly Thr Ser Tyr
        195                 200                 205

Ser Leu Thr Ile Ser Ser Met Glu Ala Glu Asp Ala Ala Thr Tyr Tyr
    210                 215                 220

Cys His Gln Tyr His Arg Ser Pro Arg Thr Phe Gly Gly Gly Thr Lys
225                 230                 235                 240

Leu Glu Ile Lys Arg Ala Ala
                245


<210> SEQ ID NO 51
<211> LENGTH: 249
<212> TYPE: PRT
<213> ORGANISM: Artificial Sequence
<220> FEATURE:
<223> OTHER INFORMATION: scFv comprising VH and VL of CRT3 variant (SEQ
      ID NO. 51)

<400> SEQUENCE: 51

Met Ala Glu Val Gln Leu Gln Gln Ser Gly Thr Val Leu Ala Arg Pro
1               5                   10                  15

Gly Ala Ser Val Lys Met Ser Cys Lys Ala Ser Gly Tyr Thr Phe Thr
            20                  25                  30

Ser Tyr Trp Met His Trp Val Lys Gln Arg Pro Gly Gln Gly Leu Glu
        35                  40                  45

Trp Ile Gly Ala Ile Tyr Pro Gly Asn Ser Asp Thr Ser Tyr Asn Gln
    50                  55                  60

Lys Phe Lys Gly Lys Ala Lys Leu Thr Ala Val Thr Ser Thr Ser Thr
65                  70                  75                  80

Ala Tyr Met Glu Leu Ser Ser Leu Thr Asn Glu Asp Ser Ala Val Phe
                85                  90                  95

Tyr Cys Thr His Tyr Gly Ser Asp Tyr Ala Met Asp Tyr Trp Gly Gln
            100                 105                 110

Gly Thr Ser Val Thr Ile Ser Ser Gly Ser Ser Gly Gly Gly Gly Ser
        115                 120                 125
```

Gly Gly Gly Gly Ser Gly Gly Gly Gly Ser Gln Ile Val Leu Thr Gln
    130                 135                 140

Ser Pro Ala Ile Met Ser Ala Ser Leu Gly Glu Arg Val Thr Met Thr
145                 150                 155                 160

Cys Thr Ala Ser Ser Ser Val Ser Ser Ser Tyr Leu His Trp Tyr Gln
                165                 170                 175

Gln Lys Pro Gly Ser Ser Pro Lys Leu Trp Ile Tyr Ser Thr Ser Asn
            180                 185                 190

Leu Ala Ser Gly Val Pro Ala Arg Phe Ser Gly Ser Gly Ser Gly Thr
        195                 200                 205

Ser Tyr Ser Leu Thr Ile Ser Ser Met Glu Ala Glu Asp Ala Ala Thr
    210                 215                 220

Tyr Tyr Cys His Gln Tyr His Arg Ser Pro Arg Thr Phe Gly Gly Gly
225                 230                 235                 240

Thr Lys Leu Glu Ile Lys Arg Ala Ala
                245

<210> SEQ ID NO 52
<211> LENGTH: 490
<212> TYPE: PRT
<213> ORGANISM: Homo sapiens

<400> SEQUENCE: 52

Met Arg Pro Ala Phe Ala Leu Cys Leu Leu Trp Gln Ala Leu Trp Pro
1               5                   10                  15

Gly Pro Gly Gly Gly Glu His Pro Thr Ala Asp Arg Ala Gly Cys Ser
            20                  25                  30

Ala Ser Gly Ala Cys Tyr Ser Leu His His Ala Thr Met Lys Arg Gln
        35                  40                  45

Ala Ala Glu Glu Ala Cys Ile Leu Arg Gly Gly Ala Leu Ser Thr Val
    50                  55                  60

Arg Ala Gly Ala Glu Leu Arg Ala Val Leu Ala Leu Leu Arg Ala Gly
65                  70                  75                  80

Pro Gly Pro Gly Gly Gly Ser Lys Asp Leu Leu Phe Trp Val Ala Leu
                85                  90                  95

Glu Arg Arg Arg Ser His Cys Thr Leu Glu Asn Glu Pro Leu Arg Gly
            100                 105                 110

Phe Ser Trp Leu Ser Ser Asp Pro Gly Gly Leu Glu Ser Asp Thr Leu
        115                 120                 125

Gln Trp Val Glu Glu Pro Gln Arg Ser Cys Thr Ala Arg Arg Cys Ala
    130                 135                 140

Val Leu Gln Ala Thr Gly Gly Val Glu Pro Ala Gly Trp Lys Glu Met
145                 150                 155                 160

Arg Cys His Leu Arg Ala Asn Gly Tyr Leu Cys Lys Tyr Gln Phe Glu
                165                 170                 175

Val Leu Cys Pro Ala Pro Arg Pro Gly Ala Ala Ser Asn Leu Ser Tyr
            180                 185                 190

Arg Ala Pro Phe Gln Leu His Ser Ala Ala Leu Asp Phe Ser Pro Pro
        195                 200                 205

Gly Thr Glu Val Ser Ala Leu Cys Arg Gly Gln Leu Pro Ile Ser Val
    210                 215                 220

Thr Cys Ile Ala Asp Glu Ile Gly Ala Arg Trp Asp Lys Leu Ser Gly
225                 230                 235                 240

Asp Val Leu Cys Pro Cys Pro Gly Arg Tyr Leu Arg Ala Gly Lys Cys

```
                245                 250                 255

Ala Glu Leu Pro Asn Cys Leu Asp Asp Leu Gly Gly Phe Ala Cys Glu
            260                 265                 270

Cys Ala Thr Gly Phe Glu Leu Gly Lys Asp Gly Arg Ser Cys Val Thr
        275                 280                 285

Ser Gly Glu Gly Gln Pro Thr Leu Gly Gly Thr Gly Val Pro Thr Arg
    290                 295                 300

Arg Pro Pro Ala Thr Ala Thr Ser Pro Val Pro Gln Arg Thr Trp Pro
305                 310                 315                 320

Ile Arg Val Asp Glu Lys Leu Gly Glu Thr Pro Leu Val Pro Glu Gln
                325                 330                 335

Asp Asn Ser Val Thr Ser Ile Pro Glu Ile Pro Arg Trp Gly Ser Gln
            340                 345                 350

Ser Thr Met Ser Thr Leu Gln Met Ser Leu Gln Ala Glu Ser Lys Ala
        355                 360                 365

Thr Ile Thr Pro Ser Gly Ser Val Ile Ser Lys Phe Asn Ser Thr Thr
    370                 375                 380

Ser Ser Ala Thr Pro Gln Ala Phe Asp Ser Ser Ser Ala Val Val Phe
385                 390                 395                 400

Ile Phe Val Ser Thr Ala Val Val Val Leu Val Ile Leu Thr Met Thr
                405                 410                 415

Val Leu Gly Leu Val Lys Leu Cys Phe His Glu Ser Pro Ser Ser Gln
            420                 425                 430

Pro Arg Lys Glu Ser Met Gly Pro Pro Gly Leu Glu Ser Asp Pro Glu
        435                 440                 445

Pro Ala Ala Leu Gly Ser Ser Ser Ala His Cys Thr Asn Asn Gly Val
    450                 455                 460

Lys Val Gly Asp Cys Asp Leu Arg Asp Arg Ala Glu Gly Ala Leu Leu
465                 470                 475                 480

Ala Glu Ser Pro Leu Gly Ser Ser Asp Ala
                485                 490


<210> SEQ ID NO 53
<211> LENGTH: 1380
<212> TYPE: DNA
<213> ORGANISM: Homo sapiens

<400> SEQUENCE: 53

ctcctcttgc tctaagcagg gtgtttgacc ttctagtcga ctgcgtcccc tgtacccggc      60

gccagctgtg ttcctgaccc cagaataact cagggctgca ccgggcctgg cagcgctccg     120

cacacatttc ctgtcgcggc ctaagggaaa ctgttggccg ctgggcccgc ggggggattc     180

ttggcagttg gggggtccgt cgggagcgag ggcggagggg aagggagggg gaaccgggtt     240

ggggaagcca gctgtagagg gcggtgaccg cgctccagac acagctctgc gtcctcgagc     300

gggacagatc caagttggga gcagctctgc gtgcggggcc tcagagaatg aggccggcgt     360

tcgccctgtg cctcctctgg caggcgctct ggcccgggcc gggcggcggc gaacacccca     420

ctgccgaccg tgctggctgc tcggcctcgg gggcctgcta cagcctgcac cacgctacca     480

tgaagcggca ggcggccgag gaggcctgca tcctgcgagg tggggcgctc agcaccgtgc     540

gtgcgggcgc cgagctgcgc gctgtgctcg cgctcctgcg ggcaggccca gggcccggag     600

ggggctccaa agacctgctg ttctgggtcg cactggagcg caggcgttcc cactgcaccc     660

tggagaacga gcctttgcgg ggtttctcct ggctgtcctc cgaccccggc ggtctcgaaa     720
```

gcgacacgct gcagtgggtg gaggagcccc aacgctcctg caccgcgcgg agatgcgcgg 780
tactccaggc caccggtggg gtcgagcccg caggctggaa ggagatgcga tgccacctgc 840
gcgccaacgg ctacctgtgc aagtaccagt ttgaggtctt gtgtcctgcg ccgcgccccg 900
gggccgcctc taacttgagc tatcgcgcgc ccttccagct gcacagcgcc gctctggact 960
tcagtccacc tgggaccgag gtgagtgcgc tctgccgggg acagctcccg atctcagtta 1020
cttgcatcgc ggacgaaatc ggcgctcgct gggacaaact ctcgggcgat gtgttgtgtc 1080
cctgccccgg gaggtacctc cgtgctggca aatgcgcaga gctccctaac tgcctagacg 1140
acttgggagg ctttgcctgc gaatgtgcta cgggcttcga gctggggaag gacggccgct 1200
cttgtgtgac cagtggggaa ggacagccga ccccttgggg gaccggggtg cccaccaggc 1260
gcccgccggc cactgcaacc agccccgtgc cgcagagaac atggccaatc agggtcgacg 1320
agaagctggg agagacacca cttgtccctg aacaagacaa ttcagtaaca tctattcctg 1380

<210> SEQ ID NO 54
<211> LENGTH: 363
<212> TYPE: DNA
<213> ORGANISM: Artificial Sequence
<220> FEATURE:
<223> OTHER INFORMATION: Nucleotide sequence of variable heavy chain of CRT3 variant (SEQ ID NO. 54)

<400> SEQUENCE: 54
atggccgagg tccagctgca gcagtctggg actgtgctgg caaggcctgg ggcttcagtg 60
aagatgtcct gcaaggcttc tggctacacc tttaccagct actggatgca ctgggtaaaa 120
cagaggcctg gacagggtct ggaatggatt ggcgctattt atcctggaaa tagtgatact 180
agctacaacc agaagttcaa gggcaaggcc aaactgactg cagtcacatc caccagcact 240
gcctacatgg agctcagcag cctgacaaat gaggactctg cggtctttta ctgtacacat 300
tactacggta gtgactatgc tatggactac tggggtcaag gaacctcagt cactgtctcc 360
tca 363

<210> SEQ ID NO 55
<211> LENGTH: 18
<212> TYPE: DNA
<213> ORGANISM: Artificial Sequence
<220> FEATURE:
<223> OTHER INFORMATION: Nucleotide sequence of CDR1 VH of CRT3 variant (SEQ ID NO. 55)

<400> SEQUENCE: 55
accagctact ggatgcac 18

<210> SEQ ID NO 56
<211> LENGTH: 39
<212> TYPE: DNA
<213> ORGANISM: Artificial Sequence
<220> FEATURE:
<223> OTHER INFORMATION: Nucleotide sequence of CDR2 of VH of CRT3 variant (SEQ ID NO. 56)

<400> SEQUENCE: 56
tggattggcg ctatttatcc tggaaatagt gatactagc 39

<210> SEQ ID NO 57
<211> LENGTH: 33
<212> TYPE: DNA
<213> ORGANISM: Artificial Sequence
<220> FEATURE:

<223> OTHER INFORMATION: Nucleotide sequence of CDR3 of VH of CRT3
      variant (SEQ ID NO. 57)

<400> SEQUENCE: 57
acacattact acggtagtga ctatgctatg gac                                33

<210> SEQ ID NO 58
<211> LENGTH: 335
<212> TYPE: DNA
<213> ORGANISM: Artificial Sequence
<220> FEATURE:
<223> OTHER INFORMATION: Nucleotide sequence of VL of CRT3 variant (SEQ
      ID NO. 58)

<400> SEQUENCE: 58
caaattgttc tcacccagtc tccagcaatc atgtctgcat ctctagggga acgggtcacc     60
atgacctgca ctgccagctc aagtgtaagt tccagttact tgcactggta ccagcagaag    120
ccaggatcct cccccaaact ctggatttat agcacatcca acctggcttc tggagtccca    180
gctcgcttca gtggcagtgg gtctgggacc tcttactctc tcacaatcag cagcatggag    240
gctgaagatg ctgccactta ttactgccac cagtatcatc gttccccacg gacgttcggt    300
ggaggcacca agctggaaat caaacgtgcg gccgc                               335

<210> SEQ ID NO 59
<211> LENGTH: 24
<212> TYPE: DNA
<213> ORGANISM: Artificial Sequence
<220> FEATURE:
<223> OTHER INFORMATION: Nucleotide sequence of CDR1 of VL of CRT3
      variant (SEQ ID NO. 59)

<400> SEQUENCE: 59
agttccagtt acttgcactg gtac                                           24

<210> SEQ ID NO 60
<211> LENGTH: 30
<212> TYPE: DNA
<213> ORGANISM: Artificial Sequence
<220> FEATURE:
<223> OTHER INFORMATION: Nucleotide sequence of CDR2 of VL of CRT3
      variant (SEQ ID NO. 60)

<400> SEQUENCE: 60
ctctggattt atagcacatc caacctggct                                     30

<210> SEQ ID NO 61
<211> LENGTH: 25
<212> TYPE: DNA
<213> ORGANISM: Artificial Sequence
<220> FEATURE:
<223> OTHER INFORMATION: Nucleotide sequence of CDR3 of VL of CRt3
      variant (SEQ ID NO. 61)

<400> SEQUENCE: 61
ccaccagtat catcgttccc cacgg                                          25

<210> SEQ ID NO 62
<211> LENGTH: 741
<212> TYPE: DNA
<213> ORGANISM: Artificial Sequence
<220> FEATURE:
<223> OTHER INFORMATION: Nucleotide sequence for scFv comprising VH of
      CRT3 variant and VL of CRT3 (SEQ ID NO. 62)

<400> SEQUENCE: 62

```
atggccgagg tccagctgca gcagtctggg actgtgctgg caaggcctgg ggcttcagtg     60

aagatgtcct gcaaggcttc tggctacacc tttaccagct actggatgca ctgggtaaaa    120

cagaggcctg gacagggtct ggaatggatt ggcgctattt atcctggaaa tagtgatact    180

agctacaacc agaagttcaa gggcaaggcc aaactgactg cagtcacatc caccagcact    240

gcctacatgg agctcagcag cctgacaaat gaggactctg cggtctttta ctgtacacat    300

tactacggta gtgactatgc tatggactac tggggtcaag gaacctcagt cactgtctcc    360

tcatcctcag gtggaggcgg ttcaggcgga ggtggctctg gcggtggcgg atcgcaaatt    420

gttctcaccc agtctccagc aatcatgtct gcatctctag gggaacgggt caccatgacc    480

tgcactgcca gctcaagtgt aagttccagt tacttgcact ggtaccagca gaagccagga    540

tcctccccca aactctggat ttatagcaca tccaacctgg cttctggagt cccagctcgc    600

ttcagtggca gtgggtctgg gacctcttac tctctcacaa tcagcagcat ggaggctgaa    660

gatgctgcca cttattactg ccaccagtat catcgttccc cacggacgtt cggtggaggc    720

accaagctgg aaatcaaacg t                                              741
```

<210> SEQ ID NO 63
<211> LENGTH: 743
<212> TYPE: DNA
<213> ORGANISM: Artificial Sequence
<220> FEATURE:
<223> OTHER INFORMATION: Nucleotide sequence for scFv comrprising VH of CRT3 and VL of CRT3 variant (SEQ ID NO. 63)

<400> SEQUENCE: 63

```
atggccgagg tccagctgca gcagtctggg actgtgctgg caaggcctgg ggcttcagtg     60

aagatgtcct gcaaggcttc tggctacacc tttaccagct actggatgca ctgggtaaaa    120

cagaggcctg gacagggtct ggaatggatt ggcgctattt atcctggaaa tagtgatact    180

agctacaacc agaagttcaa gggcaaggcc aaactgactg cagtcacatc caccagcact    240

gcctacatgg agctcagcag cctgacaaat gaggactctg cggtctttta ctgtacacat    300

tactacggta gtgactatgc tatggactac tggggtcaag gaacctcagt cactgtctcc    360

tcaggtggag gcggttcagg cggaggtggc tctggcggtg gcggatcgca aattgttctc    420

acccagtctc cagcaatcat gtctgcatct ctaggggaac gggtcaccat gacctgcact    480

gccagctcaa gtgtaagttc cagttacttg cactggtacc agcagaagcc aggatcctcc    540

cccaaactct ggatttatag cacatccaac ctggcttctg gagtcccagc tcgcttcagt    600

ggcagtgggt ctgggacctc ttactctctc acaatcagca gcatggaggc tgaagatgct    660

gccacttatt actgccacca gtatcatcgt tccccacgga cgttcggtgg aggcaccaag    720

ctggaaatca aacgtgcggc cgc                                            743
```

<210> SEQ ID NO 64
<211> LENGTH: 749
<212> TYPE: DNA
<213> ORGANISM: Artificial Sequence
<220> FEATURE:
<223> OTHER INFORMATION: Nucleotide sequence of scFv comrprising VH of CRT3 variant and VL of CRT3 variant (SEQ ID NO. 64)

<400> SEQUENCE: 64

```
atggccgagg tccagctgca gcagtctggg actgtgctgg caaggcctgg ggcttcagtg     60

aagatgtcct gcaaggcttc tggctacacc tttaccagct actggatgca ctgggtaaaa    120
```

```
cagaggcctg gacagggtct ggaatggatt ggcgctattt atcctggaaa tagtgatact    180

agctacaacc agaagttcaa gggcaaggcc aaactgactg cagtcacatc caccagcact    240

gcctacatgg agctcagcag cctgacaaat gaggactctg cggtctttta ctgtacacat    300

tactacggta gtgactatgc tatggactac tggggtcaag gaacctcagt cactgtctcc    360

tcatcctcag gtggaggcgg ttcaggcgga ggtggctctg gcggtggcgg atcgcaaatt    420

gttctcaccc agtctccagc aatcatgtct gcatctctag gggaacgggt caccatgacc    480

tgcactgcca gctcaagtgt aagttccagt tacttgcact ggtaccagca gaagccagga    540

tcctcccccca aactctggat ttatagcaca tccaacctgg cttctggagt cccagctcgc    600

ttcagtggca gtgggtctgg gacctcttac tctctcacaa tcagcagcat ggaggctgaa    660

gatgctgcca cttattactg ccaccagtat catcgttccc cacggacgtt cggtggaggc    720

accaagctgg aaatcaaacg tgcggccgc                                     749
```

```
<210> SEQ ID NO 65
<211> LENGTH: 15
<212> TYPE: PRT
<213> ORGANISM: Artificial Sequence
<220> FEATURE:
<223> OTHER INFORMATION: (G4S)2 linker (SEQ ID NO. 65)

<400> SEQUENCE: 65

Gly Gly Gly Gly Ser Gly Gly Gly Gly Ser Gly Gly Gly Gly Ser
1               5                   10                  15


<210> SEQ ID NO 66
<211> LENGTH: 55
<212> TYPE: PRT
<213> ORGANISM: Artificial Sequence
<220> FEATURE:
<223> OTHER INFORMATION: hinge domain of CD8alpha (SEQ ID NO. 66)

<400> SEQUENCE: 66

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp
    50                  55


<210> SEQ ID NO 67
<211> LENGTH: 13
<212> TYPE: PRT
<213> ORGANISM: Artificial Sequence
<220> FEATURE:
<223> OTHER INFORMATION: Shortened IgG hinge (SEQ ID NO. 67)

<400> SEQUENCE: 67

Ala Glu Pro Lys Ser Pro Asp Lys Thr His Thr Cys Pro
1               5                   10


<210> SEQ ID NO 68
<211> LENGTH: 4
<212> TYPE: PRT
<213> ORGANISM: Artificial Sequence
<220> FEATURE:
<223> OTHER INFORMATION: Linker sequence (SEQ ID NO. 68)

<400> SEQUENCE: 68
```

Lys Asp Pro Lys
1

<210> SEQ ID NO 69
<211> LENGTH: 17
<212> TYPE: PRT
<213> ORGANISM: Artificial Sequence
<220> FEATURE:
<223> OTHER INFORMATION: Shortened IgG hinge and linker (SEQ ID NO. 69)

<400> SEQUENCE: 69

Ala Glu Pro Lys Ser Pro Asp Lys Thr His Thr Cys Pro Lys Asp Pro
1               5                   10                  15

Lys

<210> SEQ ID NO 70
<211> LENGTH: 28
<212> TYPE: PRT
<213> ORGANISM: Artificial Sequence
<220> FEATURE:
<223> OTHER INFORMATION: CD8alpha transmembrane domain (SEQ ID NO. 70)

<400> SEQUENCE: 70

Ile Tyr Ile Trp Ala Pro Leu Ala Gly Thr Cys Gly Val Leu Leu Leu
1               5                   10                  15

Ser Leu Val Ile Thr Leu Tyr Cys Asn His Arg Asn
            20                  25

<210> SEQ ID NO 71
<211> LENGTH: 27
<212> TYPE: PRT
<213> ORGANISM: Artificial Sequence
<220> FEATURE:
<223> OTHER INFORMATION: CD28 transmembrane domain (SEQ ID NO. 71)

<400> SEQUENCE: 71

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 72
<211> LENGTH: 239
<212> TYPE: PRT
<213> ORGANISM: Artificial Sequence
<220> FEATURE:
<223> OTHER INFORMATION: CH2CH3 hinge (SEQ ID NO. 72)

<400> SEQUENCE: 72

Asp Pro Ala Glu Pro Lys Ser Pro Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
    50                  55                  60

Trp Tyr Val Asp Gly Val Glu Val His Asn Ala Lys Thr Lys Pro Arg
65                  70                  75                  80

Glu Glu Gln Tyr Asn Ser Thr Tyr Arg Val Val Ser Val Leu Thr Val
                85                  90                  95

```
Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Asp
    130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Lys Lys Asp Pro Lys
225                 230                 235


<210> SEQ ID NO 73
<211> LENGTH: 112
<212> TYPE: PRT
<213> ORGANISM: Artificial Sequence
<220> FEATURE:
<223> OTHER INFORMATION: CD3zeta domain (SEQ ID NO. 73)

<400> SEQUENCE: 73

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 74
<211> LENGTH: 47
<212> TYPE: PRT
<213> ORGANISM: Artificial Sequence
<220> FEATURE:
<223> OTHER INFORMATION: intracellular domain of 41BB (SEQ ID NO. 74)

<400> SEQUENCE: 74

Arg Phe Ser Val Val Lys Arg Gly Arg Lys Lys Leu Leu Tyr Ile Phe
1               5                   10                  15

Lys Gln Pro Phe Met Arg Pro Val Gln Thr Thr Gln Glu Glu Asp Gly
            20                  25                  30

Cys Ser Cys Arg Phe Pro Glu Glu Glu Glu Gly Gly Cys Glu Leu
        35                  40                  45


<210> SEQ ID NO 75
```

<211> LENGTH: 41
<212> TYPE: PRT
<213> ORGANISM: Artificial Sequence
<220> FEATURE:
<223> OTHER INFORMATION: intracellualr domain of human CD28 (SEQ ID NO. 75)

<400> SEQUENCE: 75

Arg Ser Lys Arg Ser Arg Leu Leu His Ser Asp Tyr Met Asn Met Thr
1 5 10 15

Pro Arg Arg Pro Gly Pro Thr Arg Lys His Tyr Gln Pro Tyr Ala Pro
20 25 30

Pro Arg Asp Phe Ala Ala Tyr Arg Ser
35 40

<210> SEQ ID NO 76
<211> LENGTH: 36
<212> TYPE: PRT
<213> ORGANISM: Artificial Sequence
<220> FEATURE:
<223> OTHER INFORMATION: OX40 costimulatory domain (SEQ ID NO. 76)

<400> SEQUENCE: 76

Arg Asp Gln Arg Leu Pro Pro Asp Ala His Lys Pro Pro Gly Gly Gly
1 5 10 15

Ser Phe Arg Thr Pro Ile Gln Glu Glu Gln Ala Asp Ala His Ser Thr
20 25 30

Leu Ala Lys Ile
35

<210> SEQ ID NO 77
<211> LENGTH: 1101
<212> TYPE: DNA
<213> ORGANISM: Artificial Sequence
<220> FEATURE:
<223> OTHER INFORMATION: Nucleotide sequence of truncated CD34 (SEQ ID NO. 77)

<400> SEQUENCE: 77
atgcctcgcg gctggacagc cctgtgcctg ctgtctctgc tgccatccgg cttcatgagc 60
ctggataata acggcacagc caccccagag ctgcctacac agggcacctt cagcaatgtg 120
tccacaaacg tgagctatca ggagaccaca accccttcta ccctgggatc cacaagcctg 180
caccccgtgt ctcagcacgg caacgaagcc accaccaaca tcaccgagac cacagtgaag 240
tttacctcca cctctgtgat tacctctgtg tacggaaata caaactccag cgtgcagtct 300
cagacatctg tgatctccac agtgtttaca acacctgcca atgtgtccac cccagagaca 360
accctgaagc ccagcctgtc tcctggaaat gtgtccgatc tgtctaccac ctccaccagc 420
ctggccacct ctcccaccaa gccctatacc tcctcttctc ccatcctgag cgatatcaaa 480
gccgagatca aatgcagcgg gattcgggaa gtgaaactga cacagggcat ctgcctggaa 540
cagaataaga catccagctg cgccgagttt aagaaagata gaggagaggg actggccagg 600
gtgctgtgtg gcgaagagca ggccgacgcc gatgccggcg cccaggtgtg ttccctgctg 660
ctggcccagt ctgaggtgcg cccccagtgc ctgctgctgg tgctggccaa tcggacagaa 720
attagcagca agctgcagct gatgaaaaaa caccagagcg atctgaaaaa gctgggcatc 780
ctggacttta ccgagcagga cgtggcctct caccagagct acagccagaa aacactgatc 840
gccctggtga ccagcggagc cctgctggcc gtgctgggca tcaccggata tttcctgatg 900
aataggcgca gctggagccc caccggcgag cggctggagc tggagcctgt cgaccgagtg 960
aagcagaccc tgaactttga tctgctgaag ctggccggcg acgtggagtc caaccccggg 1020
ccagggaata tgggcgtgct gctgacccag aggaccctgc tgagcctggt gctggccctg 1080
ctgtttccat ctatggcatc g 1101

<210> SEQ ID NO 78
<211> LENGTH: 367
<212> TYPE: PRT
<213> ORGANISM: Artificial Sequence
<220> FEATURE:
<223> OTHER INFORMATION: Truncated CD34 (SEQ ID NO. 78)

<400> SEQUENCE: 78

Met Pro Arg Gly Trp Thr Ala Leu Cys Leu Leu Ser Leu Leu Pro Ser
1 5 10 15

Gly Phe Met Ser Leu Asp Asn Asn Gly Thr Ala Thr Pro Glu Leu Pro
20 25 30

Thr Gln Gly Thr Phe Ser Asn Val Ser Thr Asn Val Ser Tyr Gln Glu
35 40 45

Thr Thr Thr Pro Ser Thr Leu Gly Ser Thr Ser Leu His Pro Val Ser
50 55 60

Gln His Gly Asn Glu Ala Thr Thr Asn Ile Thr Glu Thr Thr Val Lys
65 70 75 80

Phe Thr Ser Thr Ser Val Ile Thr Ser Val Tyr Gly Asn Thr Asn Ser
85 90 95

Ser Val Gln Ser Gln Thr Ser Val Ile Ser Thr Val Phe Thr Thr Pro
100 105 110

Ala Asn Val Ser Thr Pro Glu Thr Thr Leu Lys Pro Ser Leu Ser Pro
115 120 125

Gly Asn Val Ser Asp Leu Ser Thr Thr Ser Thr Ser Leu Ala Thr Ser
130 135 140

Pro Thr Lys Pro Tyr Thr Ser Ser Ser Pro Ile Leu Ser Asp Ile Lys
145 150 155 160

Ala Glu Ile Lys Cys Ser Gly Ile Arg Glu Val Lys Leu Thr Gln Gly
165 170 175

Ile Cys Leu Glu Gln Asn Lys Thr Ser Ser Cys Ala Glu Phe Lys Lys
180 185 190

Asp Arg Gly Glu Gly Leu Ala Arg Val Leu Cys Gly Glu Glu Gln Ala
195 200 205

Asp Ala Asp Ala Gly Ala Gln Val Cys Ser Leu Leu Leu Ala Gln Ser
210 215 220

Glu Val Arg Pro Gln Cys Leu Leu Leu Val Leu Ala Asn Arg Thr Glu
225 230 235 240

Ile Ser Ser Lys Leu Gln Leu Met Lys Lys His Gln Ser Asp Leu Lys
245 250 255

Lys Leu Gly Ile Leu Asp Phe Thr Glu Gln Asp Val Ala Ser His Gln
260 265 270

Ser Tyr Ser Gln Lys Thr Leu Ile Ala Leu Val Thr Ser Gly Ala Leu
275 280 285

Leu Ala Val Leu Gly Ile Thr Gly Tyr Phe Leu Met Asn Arg Arg Ser
290 295 300

Trp Ser Pro Thr Gly Glu Arg Leu Glu Leu Glu Pro Val Asp Arg Val
305 310 315 320

Lys Gln Thr Leu Asn Phe Asp Leu Leu Lys Leu Ala Gly Asp Val Glu
325 330 335

Ser Asn Pro Gly Pro Gly Asn Met Gly Val Leu Leu Thr Gln Arg Thr
340 345 350

Leu Leu Ser Leu Val Leu Ala Leu Leu Phe Pro Ser Met Ala Ser
355 360 365

<210> SEQ ID NO 79
<211> LENGTH: 18
<212> TYPE: DNA
<213> ORGANISM: Artificial Sequence
<220> FEATURE:
<223> OTHER INFORMATION: CLEC14A primer (SEQ ID NO. 79)

<400> SEQUENCE: 79
ctgggaccga ggtgagtg 18

<210> SEQ ID NO 80
<211> LENGTH: 20
<212> TYPE: DNA
<213> ORGANISM: Artificial Sequence
<220> FEATURE:
<223> OTHER INFORMATION: CLEC14A probe (SEQ ID NO. 80)

<400> SEQUENCE: 80
cgcgatgcaa gtaactgaga 20

<210> SEQ ID NO 81
<211> LENGTH: 24
<212> TYPE: DNA
<213> ORGANISM: Artificial Sequence
<220> FEATURE:
<223> OTHER INFORMATION: Flotillin 2 primer (SEQ ID NO. 81)

<400> SEQUENCE: 81
tgttgtggtt ccgactataa acag 24

<210> SEQ ID NO 82
<211> LENGTH: 20
<212> TYPE: DNA
<213> ORGANISM: Artificial Sequence
<220> FEATURE:
<223> OTHER INFORMATION: Flotillin 2 probe (SEQ ID NO. 82)

<400> SEQUENCE: 82
gggctgcaac gtcataatct 20

<210> SEQ ID NO 83
<211> LENGTH: 39
<212> TYPE: DNA
<213> ORGANISM: Artificial Sequence
<220> FEATURE:
<223> OTHER INFORMATION: CLEC14A fwd primer (SEQ ID NO. 83)

<400> SEQUENCE: 83
tagtaggaat tcgagagaat gaggccggcg ttcgccctg 39

<210> SEQ ID NO 84
<211> LENGTH: 39
<212> TYPE: DNA
<213> ORGANISM: Artificial Sequence
<220> FEATURE:
<223> OTHER INFORMATION: CLEC14A rev primer (SEQ ID NO. 84)

<400> SEQUENCE: 84
agaaccgcgg ccgctggagg agtcgaaagc ctgaggagt 39

<210> SEQ ID NO 85
<211> LENGTH: 39
<212> TYPE: DNA
<213> ORGANISM: Artificial Sequence
<220> FEATURE:
<223> OTHER INFORMATION: Murine CLEC14A primer (SEQ ID NO. 85)

<400> SEQUENCE: 85
tagtaggaat tcgagagaat gaggccagcg cttgccctg 39

<210> SEQ ID NO 86
<211> LENGTH: 36
<212> TYPE: DNA
<213> ORGANISM: Artificial Sequence
<220> FEATURE:
<223> OTHER INFORMATION: Murine CLEC14A primer (SEQ ID NO. 86)

<400> SEQUENCE: 86
ctactagcgg ccgctcgtgg aagaggtgtc gaaagt 36

<210> SEQ ID NO 87
<211> LENGTH: 35
<212> TYPE: DNA
<213> ORGANISM: Artificial Sequence
<220> FEATURE:
<223> OTHER INFORMATION: Human CLEC14A fwd primer (SEQ ID NO. 87)

<400> SEQUENCE: 87
tagtagttaa ttaagagaga atgaggccgg cgttc 35

<210> SEQ ID NO 88
<211> LENGTH: 35
<212> TYPE: DNA
<213> ORGANISM: Artificial Sequence
<220> FEATURE:
<223> OTHER INFORMATION: Murine CLEC14A fwd primer (SEQ ID NO. 88)

<400> SEQUENCE: 88
tagtagttaa ttaagagaga atgaggccag cgctt 35

<210> SEQ ID NO 89
<211> LENGTH: 35
<212> TYPE: DNA
<213> ORGANISM: Artificial Sequence
<220> FEATURE:
<223> OTHER INFORMATION: human Fc rev primer (SEQ ID NO. 89)

<400> SEQUENCE: 89
ctactagttt aaactcattt acccggagac aggga 35

<210> SEQ ID NO 90
<211> LENGTH: 20
<212> TYPE: DNA
<213> ORGANISM: Artificial Sequence
<220> FEATURE:
<223> OTHER INFORMATION: 5'UTR fwd (SEQ ID NO. 90)

<400> SEQUENCE: 90
ttccttttcc agggtttgtg 20

<210> SEQ ID NO 91
<211> LENGTH: 20
<212> TYPE: DNA
<213> ORGANISM: Artificial Sequence
<220> FEATURE:
<223> OTHER INFORMATION: 5'UTR rev (SEQ ID NO. 91)

<400> SEQUENCE: 91
gcctacaagg tggcttgaat 20

<210> SEQ ID NO 92
<211> LENGTH: 20
<212> TYPE: DNA
<213> ORGANISM: Artificial Sequence
<220> FEATURE:
<223> OTHER INFORMATION: CDS fwd (SEQ ID NO. 92)

<400> SEQUENCE: 92
aagctgtgct cctgctcttg 20

<210> SEQ ID NO 93
<211> LENGTH: 21
<212> TYPE: DNA
<213> ORGANISM: Artificial Sequence
<220> FEATURE:
<223> OTHER INFORMATION: CDS rev (SEQ ID NO. 93)

<400> SEQUENCE: 93
tcctgagtgc actgtgagat g 21

<210> SEQ ID NO 94
<211> LENGTH: 20
<212> TYPE: DNA
<213> ORGANISM: Artificial Sequence
<220> FEATURE:
<223> OTHER INFORMATION: 3'UTR fwd (SEQ ID NO. 94)

<400> SEQUENCE: 94
ctgtagaggg cggtgacttt 20

<210> SEQ ID NO 95
<211> LENGTH: 19
<212> TYPE: DNA
<213> ORGANISM: Artificial Sequence
<220> FEATURE:
<223> OTHER INFORMATION: 3'UTR rev (SEQ ID NO. 95)

<400> SEQUENCE: 95
agctgctccc aagtcctct 19

<210> SEQ ID NO 96
<211> LENGTH: 20
<212> TYPE: DNA
<213> ORGANISM: Artificial Sequence
<220> FEATURE:
<223> OTHER INFORMATION: mACTB fwd (SEQ ID NO. 96)

<400> SEQUENCE: 96
ctaaggccaa ccgtgaaaag 20

<210> SEQ ID NO 97
<211> LENGTH: 20
<212> TYPE: DNA
<213> ORGANISM: Artificial Sequence
<220> FEATURE:
<223> OTHER INFORMATION: mACTB rev (SEQ ID NO. 97)

<400> SEQUENCE: 97
accagaggca tacagggaca 20

<210> SEQ ID NO 98

<211> LENGTH: 42
<212> TYPE: PRT
<213> ORGANISM: Artificial Sequence
<220> FEATURE:
<223> OTHER INFORMATION: CD141 1-42 aa (SEQ ID NO. 98)

<400> SEQUENCE: 98

Met Leu Gly Val Leu Val Leu Gly Ala Leu Ala Leu Ala Gly Leu Gly
1 5 10 15

Phe Pro Ala Pro Ala Glu Pro Gln Pro Gly Gly Ser Gln Cys Val Glu
20 25 30

His Asp Cys Phe Ala Leu Tyr Pro Gly Pro
35 40

<210> SEQ ID NO 99
<211> LENGTH: 12
<212> TYPE: PRT
<213> ORGANISM: Artificial Sequence
<220> FEATURE:
<223> OTHER INFORMATION: CD141 97-108 aa (SEQ ID NO. 99)

<400> SEQUENCE: 99

Gln Leu Pro Pro Gly Cys Gly Asp Pro Lys Arg Leu
1 5 10

<210> SEQ ID NO 100
<211> LENGTH: 20
<212> TYPE: PRT
<213> ORGANISM: Artificial Sequence
<220> FEATURE:
<223> OTHER INFORMATION: CD141 122-142 aa (SEQ ID NO. 100)

<400> SEQUENCE: 100

Thr Ser Tyr Ser Arg Trp Ala Arg Leu Asp Leu Asn Gly Ala Pro Leu
1 5 10 15

Cys Gly Pro Leu
20

<210> SEQ ID NO 101
<211> LENGTH: 744
<212> TYPE: DNA
<213> ORGANISM: Artificial Sequence
<220> FEATURE:
<223> OTHER INFORMATION: CRT3 scFv codon optimised human nucleotide sequence (SEQ ID NO. 101)

<400> SEQUENCE: 101
atggccgagg tgcagctgca gcagtctggc accgtgctgg ccaggcccgg agcaagcgtg 60
aagatgtcct gcaaggcctc tggctacacc ttcacaagct attggatgca ctgggtgaag 120
cagcgcccag gacagggcct ggagtggatc ggagcaatct accccggcaa ctccgacacc 180
tcttataatc agaagttcaa gggcaaggcc aagctgacag ccgtgacctc tacaagcacc 240
gcctacatgg agctgagcag cctgaccaac gaggatagcg ccgtgtttta ttgcacacac 300
tactatggct ccgactacgc tatggactat tggggccagg gcacctccgt gacagtgtct 360
agcggaggag gaggcagcgg aggaggaggc tccggcggcg gcggctctca gatcgtgctg 420
acccagagcc ctgccatcat gtccgcctct ctgggcgagc gggtgacaat gacctgtaca 480
gcctcctcta gcgtgtcctc tagctacctg cactggtatc agcagaagcc cggctcctct 540
cctaagctgt ggatctacag cacctccaat ctggcatccg gcgtgcctgc aaggttctct 600
ggcagcggct ccggcacctc ttacagcctg acaatcagca gcatggaggc agaggacgca 660

```
gcaacatact attgtcacca gtatcaccgg agcccaagaa cctttggcgg cggcacaaag    720

ctggagatca agcgggcggc cgca                                           744
```

<210> SEQ ID NO 102
<211> LENGTH: 744
<212> TYPE: DNA
<213> ORGANISM: Artificial Sequence
<220> FEATURE:
<223> OTHER INFORMATION: CRT3 scFv murine codon optimised nucleotide sequence (SEQ ID NO. 102)

<400> SEQUENCE: 102

```
atggccgagg tgcagctgca gcagtctggc accgtgctgg ctcggcccgg agctagcgtg     60

aagatgtcct gcaaggcttc tggctacacc ttcacaagct actggatgca ctgggtgaag    120

cagcgcccag gacagggcct ggagtggatc ggcgccatct accccggaaa ctccgacacc    180

tcttacaacc agaagttcaa gggcaaggct aagctgacag ccgtgacctc tacaagcacc    240

gcttacatgg agctgagcag cctgaccaac gaggatagcg ccgtgtttta ctgcacacac    300

tactacggct ccgactacgc tatggattac tggggacagg gcacctccgt gacagtgtct    360

agcggaggag gaggaagcgg cggaggcggc agcggaggag gaggatctca gatcgtgctg    420

acccagtctc ctgctatcat gtccgcctct ctgggcgaga gggtgacaat gacctgtaca    480

gcctcctcta gcgtgtcctc tagctacctg cactggtatc agcagaagcc cggctcctct    540

cctaagctgt ggatctacag cacctccaac ctggcttccg gagtgcctgc tcggttctct    600

ggaagcggct ccggaacctc ttacagcctg acaatcagca gcatggaggc tgaggacgcc    660

gctacatact actgtcacca gtaccacagg agcccaagaa cctttggcgg aggcacaaag    720

ctggagatca agagggcggc cgca                                           744
```

<210> SEQ ID NO 103
<211> LENGTH: 762
<212> TYPE: DNA
<213> ORGANISM: Artificial Sequence
<220> FEATURE:
<223> OTHER INFORMATION: CRT2 scFv human codon optimised nucleotide sequence (SEQ ID NO. 103)

<400> SEQUENCE: 103

```
atggcagagg tgcagggagt ggagagcgga ggcggcctgg tgcagcctaa gggctccctg     60

aagctgtctt gcgccgccag cggcttcacc tttaacacat atgcaatgca ctgggtgtgc    120

caggcaccag gcaagggcct ggagtgggtg gcacggatca gaagcaagtc caacaattat    180

gccacctact atgccgacag cgtgaaggat aggttcacaa tctcccgcga cgattctcag    240

agcatgctgt acctgcagat gaacaatctg aagaccgagg acacagccat gtactattgc    300

gtgcgggagg gcgtgtacta ttacggcagc tccggctatt acgctatgga ctactggggc    360

cagggcacca gcgtgacagt gtctagcgga ggaggaggct ccggaggagg aggctctggc    420

ggcggcggca gcgagatcgt gctgacccag tccccagcaa tcatgtccgc ctctccagga    480

gagaaggtga ccatcacatg ctccgcctcc tctagcgtgt cttatatgca ctggttccag    540

cagaagcccg gcacctctcc taagctgtgg atctacagca catccaatct ggcatccggc    600

gtgcccgcaa ggttttctgg cagcggctcc ggcacctctt atagcctgac aatcagccgg    660

atggaggcag aggacgcagc aacctattac tgtcagcaga gatcctctta ccctctgacc    720

tttggcgccg gcacaaagct ggagctgaag cgcgcggccg ca                       762
```

<210> SEQ ID NO 104
<211> LENGTH: 762
<212> TYPE: DNA
<213> ORGANISM: Artificial Sequence
<220> FEATURE:
<223> OTHER INFORMATION: CRT2 scFv murine codon optimised nucleotide sequence (SEQ ID NO. 104)

<400> SEQUENCE: 104
atggctgagg tgcagggagt ggagagcgga ggaggcctgg tgcagcctaa gggctccctg 60
aagctgtctt gcgccgctag cggattcacc tttaacacat acgctatgca ctgggtgtgc 120
caggctccag gaaagggcct ggagtgggtg gccaggatca gaagcaagtc caacaactac 180
gctacctact acgccgacag cgtgaaggat cggttcacaa tctcccgcga cgattctcag 240
agcatgctgt acctgcagat gaacaacctg aagaccgagg acacagctat gtactactgc 300
gtgcgggagg gcgtgtacta ctacggcagc tccggatact acgctatgga ctactgggga 360
cagggcacct ccgtgacagt gtctagcgga ggaggaggct ccggaggagg aggctctgga 420
ggcggaggca gcgagatcgt gctgacccag tctccagcta tcatgtccgc ctctcccggc 480
gagaaggtga ccatcacatg ctccgcctcc tctagcgtgt cttacatgca ctggttccag 540
cagaagcccg gcacctctcc taagctgtgg atctacagca catccaacct ggctagcgga 600
gtgcccgctc ggttttctgg aagcggctcc ggaacctctt acagcctgac aatctccagg 660
atggaggctg aggacgccgc tacatactac tgtcagcaga gatcctctta ccctctgacc 720
tttggcgccg gaacaaagct ggagctgaag cgcgcggccg ca 762

<210> SEQ ID NO 105
<211> LENGTH: 6
<212> TYPE: PRT
<213> ORGANISM: Artificial Sequence
<220> FEATURE:
<223> OTHER INFORMATION: Consensus of CRT3 variants 1 and 2 heavy chain CDR1 (SEQ ID NO. 105)
<220> FEATURE:
<221> NAME/KEY: Xaa
<222> LOCATION: (1)..(1)
<223> OTHER INFORMATION: Xaa can represent any one of G, Y, T, F, or no amino acid
<220> FEATURE:
<221> NAME/KEY: Xaa
<222> LOCATION: (6)..(6)
<223> OTHER INFORMATION: Xaa can represent any one of M, H, or no amino acid

<400> SEQUENCE: 105

Xaa Thr Ser Tyr Trp Xaa
1               5

<210> SEQ ID NO 106
<211> LENGTH: 10
<212> TYPE: PRT
<213> ORGANISM: Artificial Sequence
<220> FEATURE:
<223> OTHER INFORMATION: Consensus of CRT3 variants 1 and 2 heavy chain CDR2 (SEQ ID NO. 106)
<220> FEATURE:
<221> NAME/KEY: Xaa
<222> LOCATION: (1)..(1)
<223> OTHER INFORMATION: Xaa can represent any one of W, I, G, A, or no amino acid
<220> FEATURE:
<221> NAME/KEY: Xaa
<222> LOCATION: (10)..(10)
<223> OTHER INFORMATION: Xaa is S or no amino acid

<400> SEQUENCE: 106

```
Xaa Ile Tyr Pro Gly Asn Ser Asp Thr Xaa
1               5                   10


<210> SEQ ID NO 107
<211> LENGTH: 12
<212> TYPE: PRT
<213> ORGANISM: Artificial Sequence
<220> FEATURE:
<223> OTHER INFORMATION: Consensus of CRT3 variants 1 and 2 heavy chain
      CDR3 (SEQ ID NO. 107)
<220> FEATURE:
<221> NAME/KEY: Xaa
<222> LOCATION: (12)..(12)
<223> OTHER INFORMATION: Xaa is Y or no amino acid

<400> SEQUENCE: 107

Thr His Tyr Tyr Gly Ser Asp Tyr Ala Met Asp Xaa
1               5                   10


<210> SEQ ID NO 108
<211> LENGTH: 6
<212> TYPE: PRT
<213> ORGANISM: Artificial Sequence
<220> FEATURE:
<223> OTHER INFORMATION: Consensus of CRT3 variants 1 and 2 light chain
      CDR1 (SEQ ID NO. 108)
<220> FEATURE:
<221> NAME/KEY: Xaa
<222> LOCATION: (1)..(1)
<223> OTHER INFORMATION: Xaa can represent any one of S, S, V, or no
      amino acid
<220> FEATURE:
<221> NAME/KEY: Xaa
<222> LOCATION: (6)..(6)
<223> OTHER INFORMATION: Xaa can represent any one of L, H, W, Y, or no
      amino acid

<400> SEQUENCE: 108

Xaa Ser Ser Ser Tyr Xaa
1               5


<210> SEQ ID NO 109
<211> LENGTH: 5
<212> TYPE: PRT
<213> ORGANISM: Artificial Sequence
<220> FEATURE:
<223> OTHER INFORMATION: Consensus of CRT3 variants 1 and 2 light chain
      CDR2 (SEQ ID NO. 109)
<220> FEATURE:
<221> NAME/KEY: Xaa
<222> LOCATION: (1)..(1)
<223> OTHER INFORMATION: Xaa can represent any one of L, W, I, Y, or no
      amino acid
<220> FEATURE:
<221> NAME/KEY: Xaa
<222> LOCATION: (5)..(5)
<223> OTHER INFORMATION: Xaa can represent any one of N, L, A, or no
      amino acid

<400> SEQUENCE: 109

Xaa Ser Thr Ser Xaa
1               5


<210> SEQ ID NO 110
<211> LENGTH: 9
<212> TYPE: PRT
<213> ORGANISM: Artificial Sequence
<220> FEATURE:
<223> OTHER INFORMATION: Consensus of CRT3 variants 1 and 2 light chain
      CDR3 (SEQ ID NO. 110)
<220> FEATURE:
```

<221> NAME/KEY: Xaa
<222> LOCATION: (9)..(9)
<223> OTHER INFORMATION: Xaa is T or no amino acid

<400> SEQUENCE: 110

His Gln Tyr His Arg Ser Pro Arg Xaa
1               5

<210> SEQ ID NO 111
<211> LENGTH: 216
<212> TYPE: DNA
<213> ORGANISM: Mus musculus

<400> SEQUENCE: 111
actactacca agccagtgct gcgaactccc tcacctgtgc accctaccgg gacatctcag 60
ccccagagac cagaagattg tcggccccgt ggctcagtga aggggaccgg attggacttc 120
gcctgtgata tttacatctg ggcacccttg gccggaatct gcgtggccct tctgctgtcc 180
ttgatcatca ctctcatctg ctaccacagg agccga 216

<210> SEQ ID NO 112
<211> LENGTH: 123
<212> TYPE: DNA
<213> ORGANISM: Mus musculus

<400> SEQUENCE: 112
aatagtagaa ggaacagact ccttcaaagt gactacatga acatgactcc ccggaggcct 60
gggctcactc gaaagcctta ccagccctac gcccctgcca gagactttgc agcgtaccgc 120
ccc 123

<210> SEQ ID NO 113
<211> LENGTH: 135
<212> TYPE: DNA
<213> ORGANISM: Mus musculus

<400> SEQUENCE: 113
aaatggatca ggaaaaaatt cccccacata ttcaagcaac catttaagaa gaccactgga 60
gcagctcaag aggaagatgc ttgtagctgc cgatgtccac aggaagaaga aggaggagga 120
ggaggctatg agctg 135

<210> SEQ ID NO 114
<211> LENGTH: 334
<212> TYPE: DNA
<213> ORGANISM: Mus musculus

<400> SEQUENCE: 114
agagcaaaat tcagcaggag tgcagagact gctgccaacc tgcaggaccc caaccagctc 60
tacaatgagc tcaatctagg gcgaagagag gaatatgacg tcttggagaa gaagcgggct 120
cgggatccag agatgggagg caaacagcag aggaggagga acccccagga aggcgtatac 180
aatgcactgc agaaagacaa gatggcagaa gcctacagtg agatcggcac aaaaggcgag 240
aggcggagag gcaaggggca cgatggcctt taccagggtc tcagcactgc caccaaggac 300
acctatgatg ccctgcatat gcagaccctg gccc 334

<210> SEQ ID NO 115
<211> LENGTH: 108
<212> TYPE: DNA
<213> ORGANISM: Mus musculus

<400> SEQUENCE: 115
cggaaggctt ggagattgcc taacactccc aaaccttgtt ggggaaacag cttcaggacc 60
ccgatccagg aggaacacac agacgcacac tttactctgg ccaagatc 108

<210> SEQ ID NO 116
<211> LENGTH: 752
<212> TYPE: DNA
<213> ORGANISM: Artificial Sequence
<220> FEATURE:
<223> OTHER INFORMATION: Murine CD8alpha hinge-CD8alpha transmembrane domain-CD28 costimulatory signal-CD3 zeta intracellular signalling domain (SEQ ID NO. 116)

<400> SEQUENCE: 116
ggaggcacca agctggaaat caaacgtgcg gccgcaacta ctaccaagcc agtgctgcga 60
actccctcac ctgtgcaccc taccgggaca tctcagcccc agagaccaga agattgtcgg 120
ccccgtggct cagtgaaggg gaccggattg gacttcgcct gtgatattta catctgggca 180
cccttggccg gaatctgcgt ggcccttctg ctgtccttga tcatcactct catctgctac 240
cacaggagcc gaaatagtag aaggaacaga ctccttcaaa gtgactacat gaacatgact 300
ccccggaggc ctgggctcac tcgaaagcct taccagccct acgcccctgc cagagacttt 360
gcagcgtacc gccccagagc aaaattcagc aggagtgcag agactgctgc caacctgcag 420
gaccccaacc agctctacaa tgagctcaat ctagggcgaa gagaggaata tgacgtcttg 480
gagaagaagc gggctcggga tccagagatg ggaggcaaac agcagaggag gaggaacccc 540
caggaaggcg tatacaatgc actgcagaaa gacaagatgg cagaagccta cagtgagatc 600
ggcacaaaag gcgagaggcg gagaggcaag gggcacgatg gcctttacca gggtctcagc 660
actgccacca aggacaccta tgatgccctg catatgcaga ccctggcccc tcgctaataa 720
aagcttaaca cgagccatag atagaataaa ag 752

<210> SEQ ID NO 117
<211> LENGTH: 764
<212> TYPE: DNA
<213> ORGANISM: Artificial Sequence
<220> FEATURE:
<223> OTHER INFORMATION: Murine CD8alpha hinge-CD8alpha transmembrane domain-41BB costimulatory domain-CD3 zeta intracellular signalling domain (SEQ ID NO. 117)

<400> SEQUENCE: 117
ggaggcacca agctggaaat caaacgtgcg gccgcaacta ctaccaagcc agtgctgcga 60
actccctcac ctgtgcaccc taccgggaca tctcagcccc agagaccaga agattgtcgg 120
ccccgtggct cagtgaaggg gaccggattg gacttcgcct gtgatattta catctgggca 180
cccttggccg gaatctgcgt ggcccttctg ctgtccttga tcatcactct catctgctac 240
cacaggagcc gaaaatggat caggaaaaaa ttcccccaca tattcaagca accatttaag 300
aagaccactg gagcagctca agaggaagat gcttgtagct gccgatgtcc acaggaagaa 360
gaaggaggag gaggaggcta tgagctgaga gcaaaattca gcaggagtgc agagactgct 420
gccaacctgc aggaccccaa ccagctctac aatgagctca atctagggcg aagagaggaa 480
tatgacgtct tggagaagaa gcgggctcgg gatccagaga tgggaggcaa acagcagagg 540
aggaggaacc cccaggaagg cgtatacaat gcactgcaga aagacaagat ggcagaagcc 600
tacagtgaga tcggcacaaa aggcgagagg cggagaggca aggggcacga tggcctttac 660
cagggtctca gcactgccac caaggacacc tatgatgccc tgcatatgca gaccctggcc 720
cctcgctaat aaaagcttaa cacgagccat agatagaata aaag 764

<210> SEQ ID NO 118
<211> LENGTH: 737
<212> TYPE: DNA
<213> ORGANISM: Artificial Sequence
<220> FEATURE:
<223> OTHER INFORMATION: Murine CD8alpha hinge-CD8alpha transmembrane domain-OX40 costimulatory domain-CD3 zeta intracellular signalling domain (SEQ ID NO. 118)

<400> SEQUENCE: 118
ggaggcacca agctggaaat caaacgtgcg gccgcaacta ctaccaagcc agtgctgcga 60
actccctcac ctgtgcaccc taccgggaca tctcagcccc agagaccaga agattgtcgg 120
ccccgtggct cagtgaaggg gaccggattg gacttcgcct gtgatattta catctgggca 180
cccttggccg gaatctgcgt ggcccttctg ctgtccttga tcatcactct catctgctac 240
cacaggagcc gacggaaggc ttggagattg cctaacactc ccaaaccttg ttggggaaac 300
agcttcagga ccccgatcca ggaggaacac acagacgcac actttactct ggccaagatc 360
agagcaaaat tcagcaggag tgcagagact gctgccaacc tgcaggaccc caaccagctc 420
tacaatgagc tcaatctagg gcgaagagag gaatatgacg tcttggagaa gaagcgggct 480
cgggatccag agatgggagg caaacagcag aggaggagga acccccagga aggcgtatac 540
aatgcactgc agaaagacaa gatggcagaa gcctacagtg agatcggcac aaaaggcgag 600
aggcggagag gcaaggggca cgatggcctt taccagggtc tcagcactgc caccaaggac 660
acctatgatg ccctgcatat gcagaccctg gcccctcgct aataaaagct taacacgagc 720
catagataga ataaaag 737

<210> SEQ ID NO 119
<211> LENGTH: 887
<212> TYPE: DNA
<213> ORGANISM: Artificial Sequence
<220> FEATURE:
<223> OTHER INFORMATION: Murine CD8alpha hinge-CD8alpha transmembrane domain-CD28 and 41BB costimulatory domains-CD3 zeta intracellular signalling domain (SEQ ID NO. 119)

<400> SEQUENCE: 119
ggaggcacca agctggaaat caaacgtgcg gccgcaacta ctaccaagcc agtgctgcga 60
actccctcac ctgtgcaccc taccgggaca tctcagcccc agagaccaga agattgtcgg 120
ccccgtggct cagtgaaggg gaccggattg gacttcgcct gtgatattta catctgggca 180
cccttggccg gaatctgcgt ggcccttctg ctgtccttga tcatcactct catctgctac 240
cacaggagcc gaaatagtag aaggaacaga ctccttcaaa gtgactacat gaacatgact 300
ccccggaggc ctgggctcac tcgaaagcct taccagccct acgcccctgc cagagacttt 360
gcagcgtacc gccccaaatg gatcaggaaa aaattccccc acatattcaa gcaaccattt 420
aagaagacca ctggagcagc tcaagaggaa gatgcttgta gctgccgatg tccacaggaa 480
gaagaaggag gaggaggagg ctatgagctg agagcaaaat tcagcaggag tgcagagact 540
gctgccaacc tgcaggaccc caaccagctc tacaatgagc tcaatctagg gcgaagagag 600
gaatatgacg tcttggagaa gaagcgggct cgggatccag agatgggagg caaacagcag 660
aggaggagga acccccagga aggcgtatac aatgcactgc agaaagacaa gatggcagaa 720
gcctacagtg agatcggcac aaaaggcgag aggcggagag gcaaggggca cgatggcctt 780

```
taccagggtc tcagcactgc caccaaggac acctatgatg ccctgcatat gcagaccctg    840

gcccctcgct aataaaagct taacacgagc catagataga ataaaag                  887


<210> SEQ ID NO 120
<211> LENGTH: 860
<212> TYPE: DNA
<213> ORGANISM: Artificial Sequence
<220> FEATURE:
<223> OTHER INFORMATION: Murine CD8alpha hinge-CD8alpha transmembrane
      domain-CD28 and OX40 costimulatory domains-CD3 zeta intracellular
      signalling domain (SEQ ID NO. 120)

<400> SEQUENCE: 120

ggaggcacca agctggaaat caaacgtgcg gccgcaacta ctaccaagcc agtgctgcga     60

actccctcac ctgtgcaccc taccgggaca tctcagcccc agagaccaga agattgtcgg    120

ccccgtggct cagtgaaggg gaccggattg gacttcgcct gtgatattta catctgggca    180

cccttggccg gaatctgcgt ggcccttctg ctgtccttga tcatcactct catctgctac    240

cacaggagcc gaaatagtag aaggaacaga ctccttcaaa gtgactacat gaacatgact    300

ccccggaggc ctgggctcac tcgaaagcct taccagccct acgcccctgc cagagacttt    360

gcagcgtacc gcccccggaa ggcttggaga ttgcctaaca ctcccaaacc ttgttgggga    420

aacagcttca ggaccccgat ccaggaggaa cacacagacg cacactttac tctggccaag    480

atcagagcaa aattcagcag gagtgcagag actgctgcca acctgcagga ccccaaccag    540

ctctacaatg agctcaatct agggcgaaga gaggaatatg acgtcttgga gaagaagcgg    600

gctcgggatc cagagatggg aggcaaacag cagaggagga ggaaccccca ggaaggcgta    660

tacaatgcac tgcagaaaga caagatggca gaagcctaca gtgagatcgg cacaaaaggc    720

gagaggcgga gaggcaaggg gcacgatggc ctttaccagg gtctcagcac tgccaccaag    780

gacacctatg atgccctgca tatgcagacc ctggcccctc gctaataaaa gcttaacacg    840

agccatagat agaataaaag                                                860


<210> SEQ ID NO 121
<211> LENGTH: 872
<212> TYPE: DNA
<213> ORGANISM: Artificial Sequence
<220> FEATURE:
<223> OTHER INFORMATION: Murine CD8alpha hinge-CD8alpha transmembrane
      domain- 41BB and Ox40 costimulatory domains and CD3 zeta
      intracelluar signalling domain (SEQ ID NO. 121)

<400> SEQUENCE: 121

ggaggcacca agctggaaat caaacgtgcg gccgcaacta ctaccaagcc agtgctgcga     60

actccctcac ctgtgcaccc taccgggaca tctcagcccc agagaccaga agattgtcgg    120

ccccgtggct cagtgaaggg gaccggattg gacttcgcct gtgatattta catctgggca    180

cccttggccg gaatctgcgt ggcccttctg ctgtccttga tcatcactct catctgctac    240

cacaggagcc gaaaatggat caggaaaaaa ttcccccaca tattcaagca accatttaag    300

aagaccactg gagcagctca agaggaagat gcttgtagct gccgatgtcc acaggaagaa    360

gaaggaggag gaggaggcta tgagctgcgg aaggcttgga gattgcctaa cactcccaaa    420

ccttgttggg gaaacagctt caggaccccg atccaggagg aacacacaga cgcacacttt    480

actctggcca agatcagagc aaaattcagc aggagtgcag agactgctgc caacctgcag    540

gaccccaacc agctctacaa tgagctcaat ctagggcgaa gagaggaata tgacgtcttg    600

gagaagaagc gggctcggga tccagagatg ggaggcaaac agcagaggag gaggaacccc    660
```

-continued

```
caggaaggcg tatacaatgc actgcagaaa gacaagatgg cagaagccta cagtgagatc    720

ggcacaaaag gcgagaggcg gagaggcaag gggcacgatg gcctttacca gggtctcagc    780

actgccacca aggacaccta tgatgccctg catatgcaga ccctggcccc tcgctaataa    840

aagcttaaca cgagccatag atagaataaa ag                                  872
```